US011559574B2

(12) United States Patent
Lacher et al.

(10) Patent No.: US 11,559,574 B2
(45) Date of Patent: Jan. 24, 2023

(54) WHOLE-CELL CANCER VACCINES AND METHODS FOR SELECTION THEREOF

(71) Applicant: BriaCell Therapeutics Corp., Philadelphia, PA (US)

(72) Inventors: Markus Daniel Lacher, Redwood City, CA (US); Joseph Paul Wagner, San Ramon, CA (US); Charles Louis Wiseman, Santa Monica, CA (US); William Valentine Williams, Havertown, PA (US)

(73) Assignee: BriaCell Therapeutics Corp., Philadelphia, PA (US)

( * ) Notice: Subject to any disclaimer, the term of this patent is extended or adjusted under 35 U.S.C. 154(b) by 1183 days.

(21) Appl. No.: 16/110,317

(22) Filed: Aug. 23, 2018

(65) Prior Publication Data
US 2019/0046624 A1 Feb. 14, 2019

Related U.S. Application Data

(63) Continuation of application No. PCT/US2017/019757, filed on Feb. 27, 2017.

(60) Provisional application No. 62/425,027, filed on Nov. 21, 2016, provisional application No. 62/299,674, filed on Feb. 25, 2016.

(51) Int. Cl.
*A61K 39/00* (2006.01)
*C07K 14/74* (2006.01)
*A61K 9/00* (2006.01)
*G01N 33/574* (2006.01)

(52) U.S. Cl.
CPC .... *A61K 39/001139* (2018.08); *A61K 9/0019* (2013.01); *A61K 39/0011* (2013.01); *A61K 39/00112* (2018.08); *A61K 39/00114* (2018.08); *A61K 39/001129* (2018.08); *C07K 14/70539* (2013.01); *G01N 33/57415* (2013.01); *G01N 33/57484* (2013.01); *A61K 2039/5152* (2013.01); *A61K 2039/5156* (2013.01); *A61K 2039/55522* (2013.01)

(58) Field of Classification Search
CPC .... A61K 2039/5152; A61K 39/001139; A61K 2039/5156; C07K 14/70539
See application file for complete search history.

(56) References Cited

U.S. PATENT DOCUMENTS

| | | | |
|---|---|---|---|
| 5,750,102 | A | 5/1998 | Eisenbach et al. |
| 6,149,905 | A | 11/2000 | Ostrand-Rosenberg et al. |
| 7,807,186 | B2 | 10/2010 | Ostrand-Rosenberg et al. |
| 9,301,998 | B2 | 4/2016 | Peretz et al. |
| 2005/0276822 | A1 | 12/2005 | Wiseman et al. |
| 2008/0020386 | A1 | 1/2008 | Chen et al. |
| 2010/0119537 | A1 | 5/2010 | Podack |
| 2013/0052215 | A9 | 2/2013 | Podack |
| 2016/0045583 | A1 | 2/2016 | Podack |

FOREIGN PATENT DOCUMENTS

| | | | |
|---|---|---|---|
| JP | 2012-505918 A | 3/2012 | |
| WO | WO-0050589 A1 * | 8/2000 | ......... C07K 14/4748 |
| WO | 2006/081629 A1 | 8/2006 | |
| WO | 2006135454 A1 | 12/2006 | |
| WO | 2010/045573 A2 | 4/2010 | |
| WO | WO-2010045573 A2 * | 4/2010 | ......... A61K 39/0011 |
| WO | 2012/156969 A1 | 11/2012 | |
| WO | 2017/147600 A1 | 8/2017 | |

OTHER PUBLICATIONS

Yamazaki et al (Cancer Research, 1999, vol. 59, pp. 4642-4650) (Year: 1999).*
Marsh et al (Tissue Antigens, 2005, vol. 65, pp. 301-369) (Year: 2005).*
Srivastava et al (International Journal of Cancer, 2010, vol. 127, pp. 2612-2621) (Year: 2010).*
Niwa et al (Gene, 1991, vol. 108, pp. 193-200) (Year: 1999).*
Cheng and Roffler (Medicinal Research Reviews, 2008, vol. 28, pp. 24-44) (Year: 2008).*
Tundis et al (Bioorganic and Medicinal chemistry Letters, 2005, vol. 15, pp. 4757-4760). (Year: 2005).*
Boegel et al., "A catalog of HLA type, HLA expression, and neoepitope candidates in human cancer cell lines", Oncoimmunology vol. 3, No. 8, 3 Aug. 1, 2014, pp. e954893-1-e954893-12, 12 pages.
Chen G, Gupta R, Petrik S, Laiko M, Leatherman JM, Asquith JM, et al. A feasibility study of cyclophosphamide, trastuzumab, and an allogeneic GM-CSF-secreting breast tumor vaccine for HER2+ metastatic breast cancer. Cancer Immunol Res (2014) 2(10):949-61. doi:10.1158/2326-6066. CIR-14-0058, 14 pages.
Creelan BC, Antonia S, Noyes D, Hunter TB, Simon GR, Bepler G, et al. Phase II trial of a GM-CSF-producing and CD40L—expressing bystander cell line combined with an allogeneic tumor cell-based vaccine for refractory lung adenocarcinoma. J Immunother (2013) 36(8):442-50. doi:10.1097/CJI.b013e3182a80237, 9 pages.
Gupta R, Emens LA. GM-CSF-secreting vaccines for solid tumors: moving forward. Discov Med (2010) 10(50):52-60, 9 pages.
Le DT, Wang-Gillam A, Picozzi V, Greten TF, Crocenzi T, Springett G, et al. Safety and survival with GVAX pancreas prime and Listeria monocytogenes-expressing mesothelin (CRS-207) boost vaccines for metastatic pancreatic cancer. J Clin Oncol (2015) 33(12):1325-33. doi:10.1200/JCO. 2014.57.4244, 12 pages.

(Continued)

*Primary Examiner* — Karen A. Canella
(74) *Attorney, Agent, or Firm* — Kilpatrick Townsend & Stockton LLP

(57) ABSTRACT

The present invention provides a modified human cancer cell comprising a recombinant polynucleotide encoding an allele of a human leukocyte antigen gene. The present invention also provides methods for selecting a whole-cell cancer vaccine for a subject having cancer and methods of treating cancer using whole-cell cancer vaccines of the present invention. In addition, the present invention provides a method of determining the HER2 status of a cell. Compositions and kits are also provided herein.

81 Claims, 24 Drawing Sheets

Specification includes a Sequence Listing.

(56) References Cited

OTHER PUBLICATIONS

Lipson EJ, Sharfman WH, Chen S, McMiller TL, Pritchard TS, Salas JT, et al. Safety and immunologic correlates of melanoma GVAX, a GM-CSF secreting allogeneic melanoma cell vaccine administered in the adjuvant setting. J Transl Med (2015) 13:214. doi:10.1186/s12967-015-0572-3, 14 pages.
Ozaki et al., "HLA-DRB 1, -DRB3, -DRB4 and -DRB5 genotyping at a super-high resolution level by long range PCR and high-throughput sequencing", Tissue Antigens vol. 83, No. 1, Jan. 2014, pp. 10-16, 7 pages.
Santegoets SJ, Stam AG, Lougheed SM, Gall H, Jooss K, Sacks N, et al. Mye loid derived suppressor and dendritic cell subsets are related to clinical outcome in prostate cancer patients treated with prostate GVAX and ipilimumab. J Immunother Cancer (2014) 2:31. doi:10.1186/s40425-014-0031-3, 12 pages.
Shiina et al., "The HLA genomic loci map: expression, interaction, diversity and disease", Journal of Human Genetics (2009), vol. 54, No. 1, Jan. 2009, pp. 15-39, 25 pages.
Srivatsan S, Patel JM, Bozeman EN, Imasuen IE, He S, Daniels D, et al. Allogeneic tumor cell vaccines: the promise and limitations in clinical trials. Hum Vaccin Immunother (2014) 10(1):52-63. doi:10.4161/hv.26568, 13 pages.
Wiseman CL, Kharazi A. Objective clinical regression of metastatic breast cancer in disparate sites after use of whole-cell vaccine genetically modified to release sargramostim. Breast J (2006) 12(5):475-80. doi:10.1111/j.1075-122X.2006.00319.x, 6 pages.
Wiseman CL, Kharazi A. Phase I study with SV-BR-1 breast cancer cell line vaccine and GM-CSF: clinical experience in 14 patients. Open Breast Cancer J (2010) 2:4-11. doi: 10.2174/1876817201002010004, 8 pages.
Keenan BP, Jaffee EM. Whole cell vaccines—past progress and future strategies. Semin Oncol (2012) 39(3):276-86. doi:10.1053/j.seminoncol.2012.02.007, 11 pages.
Soares KC, Rucki AA, Kim V, Foley K, Solt S, Wolfgang CL, et al. TGF-beta blockade depletes T regulatory cells from metastatic pancreatic tumors in a vaccine dependent manner. Oncotarget (2015) 6(40):43005-15. doi:10.18632/oncotarget.5656, 11 pages.
Emens LA, Asquith JM, Leatherman JM, Kobrin BJ, Petrik S, Laiko M, et al. Timed sequential treatment with cyclophosphamide, doxorubicin, and an allogeneic granulocyte-macrophage colony-stimulating factor-secreting breast tumor vaccine: a chemotherapy dose-ranging factorial study of safety and immune activation. J Clin Oncol (2009) 27(35):5911-18. doi:10.1200/JCO.2009.23.3494, 8 pages.
Le DT, Jaffee EM. Regulatory T-cell modulation using cyclophosphamide in vaccine approaches: a current perspective. Cancer Res (2012) 72(14). doi:10.1158/0008-5472.CAN-11-3912, 7 pages.
Arico E and Belardelli F. Interferon-alpha as antiviral and antitumor vaccine adjuvants: mechanisms of action and response signature. J Interferon Cytokine Res (2012) 32(6):235-47. doi:10.1089/jir.2011.0077, 13 pages.
Gibbert K, Schlaak JF, Yang D, Dittmer U. IFN-alpha subtypes: distinct biological activities in anti-viral therapy. Br J Pharmacol (2013) 168(5): 1048-58. doi:10.1111/bph.12010, 11 pages.
Gessani S, Conti L, Del Corno M, Belardelli F. Type I interferons as regulators of human antigen presenting cell functions. Toxins (Basel) (2014) 6(6):1696-723. doi:10.3390/toxins6061696, 28 pages.
Hillyer P, Raviv N, Gold DM, Dougherty D, Liu J, Johnson TR, et al. Subtypes of type I IFN differentially enhance cytokine expression by suboptimally stimulated CD4(+) T cells. Eur J Immunol (2013) 43(12):3197-208. doi:10.1002/eji.201243288, 12 pages.
Frangione et al. CIITA-driven MHC-II positive tumor cells: preventive vaccines and superior generators of antitumor CD41 T lymphocytes for immunotherapy. International Journal of Cancer: 127, 1614-1624 (2010), UICC, 12 pages.
Mortara et al. "CIITA-Induced MHC Class II Expression in Mammary Adenocarcinoma Leads to a Th1 Polarization of the Tumor Microenvironment, Tumor Rejection, and Specific Antitumor Memory", American Association for Cancer Research, Clinical Cancer Research 2006; 12 (11), 3435-443, Jun. 1, 2006, downloaded on Oct. 19, 2018, 10 pages.
Dissanayake et al. Activation of Tumor-specific CD4+ T Lymphocytes by Major Histocompatibility Complex Class II Tumor Cell Vaccines: A Novel Cell-based Immunotherapy. Cancer Research 64, 1867-1874, Mar. 1, 2004, Downloaded on Oct. 19, 2018, 9 pages.
Srivastava et al. MHC II lung cancer vaccines prime and boost tumor-specific CD4+ T cells that cross-react with multiple histologic subtypes of nonsmall cell lung cancer cells. International Journal of Cancer 127, 2612-2621, 2010, 10 pages.
Doonan et al., HLA Class II Antigen Presentation in Prostate Cancer Cells: A Novel Approach to Prostate Tumor Immunotherapy. The Open Cancer Immunology Journal, 2010, 3, 1-7, 7 pages.
Younger et al. HLA class II antigen presentation by prostate cancer cells. Prostates Cancer and Prostatic Diseases (2008) 11, 334-341, 8 pages.
International Preliminary Report on Patentability, dated Sep. 7, 2018 for PCT Application No. PCT/US2017/019757, 15 pages.
International Search Report and Written Opinion, dated Jul. 31, 2017, for PCT Application No. PCT/US2017/019757, 21 pages.
Invitation to Pay Additional Fees and Partial Search Report, dated May 22, 2017, for PCT Application No. PCT/US2017/019757, 3 pages.
Lacher, M. et al., "SV-BR-1-GM, a Clinically Effective GM-CSF-Secreting Breast Cancer Cell Line, Expresses an Immune Signature and Directly Activates CD4+ T Lymphocytes," Frontiers in Immunology, vol. 9:1-23, 2018.
EP 17757429.0, Extended European Search Report, dated Oct. 7, 2019, 9 pages.

* cited by examiner

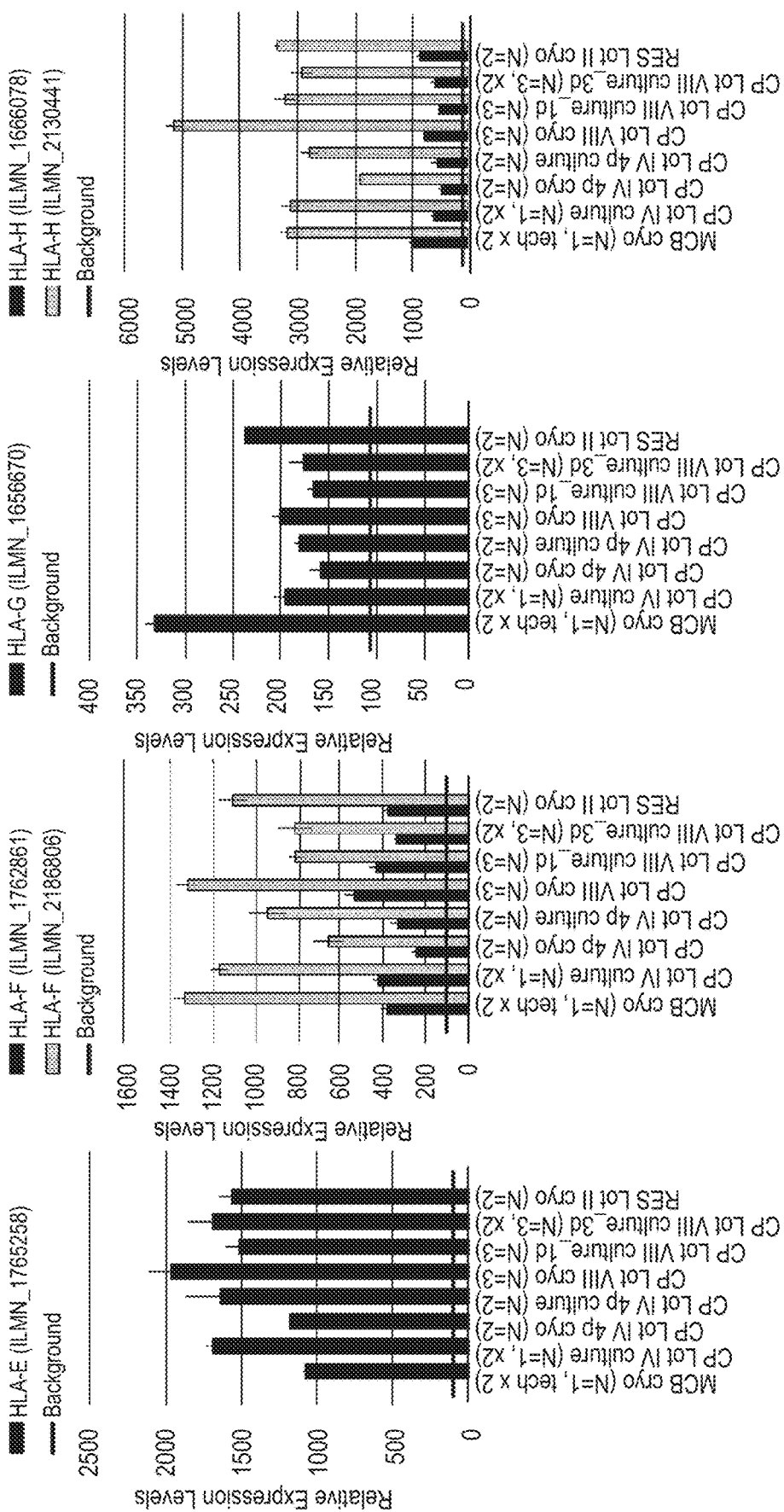

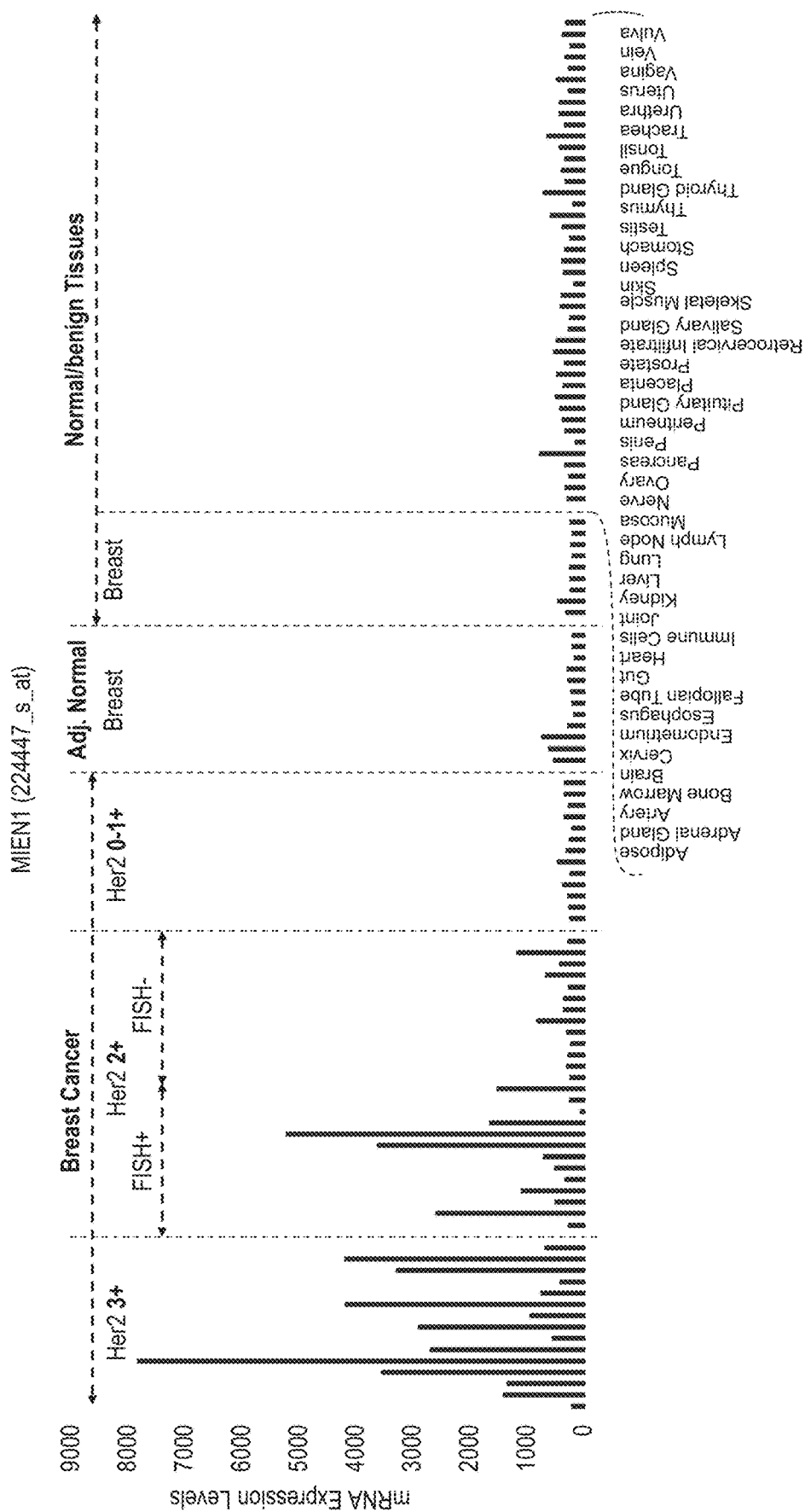

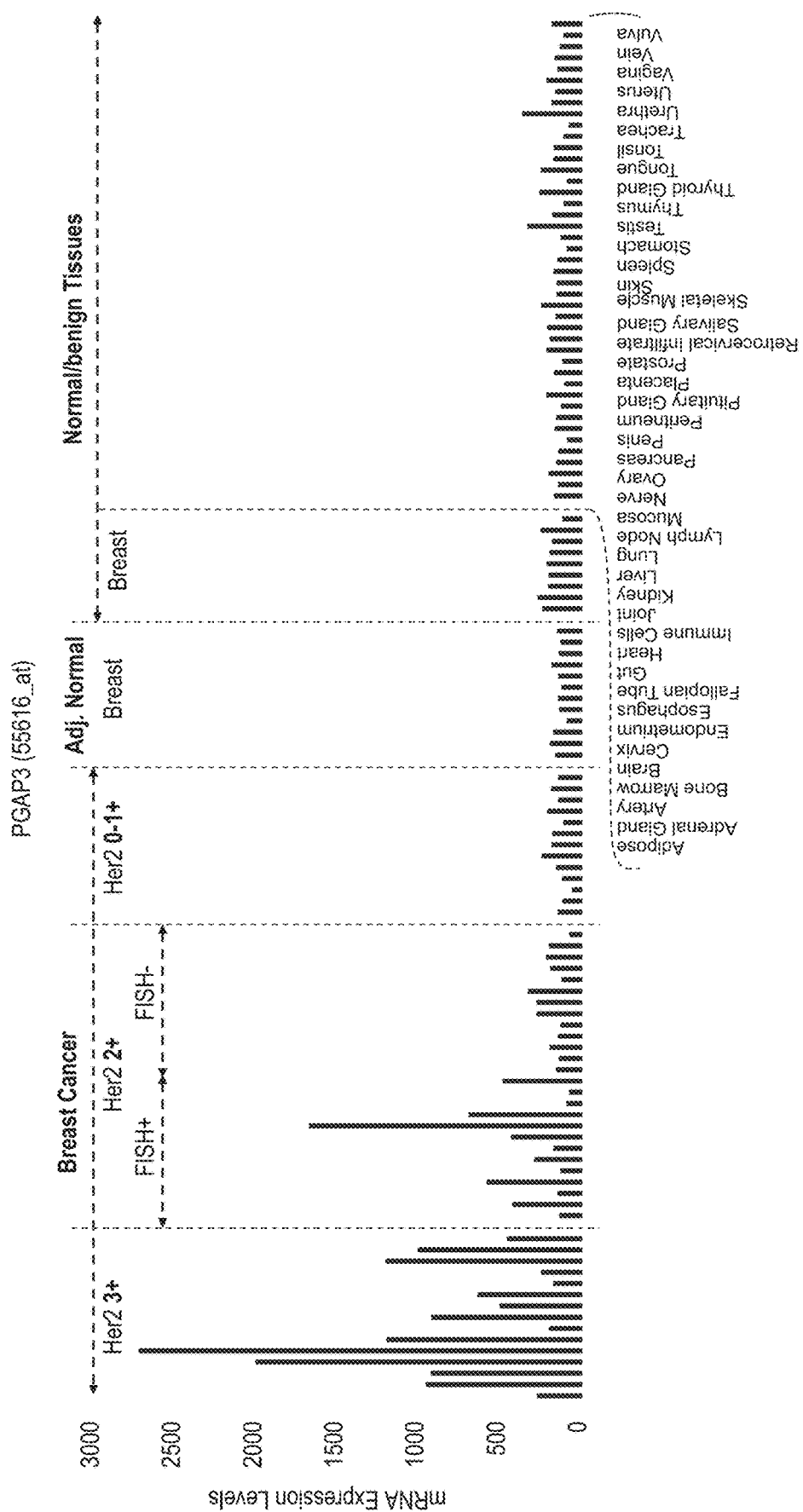

WHOLE-CELL CANCER VACCINES AND METHODS FOR SELECTION THEREOF

CROSS-REFERENCES TO RELATED APPLICATIONS

The present application is a continuation of PCT/US2017/019757 filed on Feb. 27, 2017, which claims priority to U.S. Provisional Application No. 62/299,674, filed on Feb. 25, 2016, and U.S. Provisional Application No. 62/425,027, filed on Nov. 21, 2016, the disclosures of which are incorporated herein by reference in their entirety for all purposes.

BACKGROUND OF THE INVENTION

Cancer immunotherapy with allogeneic whole-cell vaccines is a relatively simple and in many cases effective approach to reduce tumor burden. It is generally assumed that to be effective, the vaccine needs to express immunogenic antigens co-expressed in patient tumor cells; and antigen-presenting cells (APCs) such as dendritic cells (DCs) need to cross-present such antigens following uptake of vaccine cell fragments. Not only is there a need in the art for improved whole-cell vaccines, but there is also a need for the elucidation and characterization of potential diagnostic features to prospectively identify patients likely to benefit from whole-cell cancer vaccines. The present invention satisfies this need and provides related advantages as well.

BRIEF SUMMARY OF THE INVENTION

In a first aspect, the present invention provides a modified human cancer cell comprising a recombinant polynucleotide encoding an allele of a human leukocyte antigen (HLA) class I gene. In some embodiments, the modified human cancer cell further comprises a recombinant polynucleotide encoding an allele of an HLA class II gene.

In a second aspect, the present invention provides a modified human cancer cell comprising a recombinant polynucleotide encoding an allele of an HLA class II gene. In some embodiments, the modified human cancer cell further comprises a recombinant polynucleotide encoding an allele of an HLA class I gene.

In some embodiments, the recombinant polynucleotide is present on a vector in the cell. In other embodiments, the recombinant polynucleotide is integrated into the genome of the cell.

In some embodiments, the HLA class I gene is selected from the group consisting of an HLA-A gene, an HLA-B gene, an HLA-C gene, an HLA-E gene, an HLA-F gene, an HLA-G gene, a beta-2-microglobulin (B2M) gene, and a combination thereof. In some instances, the allele of the HLA-A gene is an allele selected from the group consisting of HLA-A*11:01, HLA-A*01:01, HLA-A*02:01, HLA-A*03:01, HLA-A*26:01, HLA-A*29:02, HLA-A*32:01, HLA-A*24:02, HLA-A*33:03, HLA-A*68:01, HLA-A*31:01, HLA-A*02:06, and a combination thereof. In other instances, the allele of the HLA-B gene is an allele selected from the group consisting of HLA-B*13:02, HLA-B*41:01, HLA-B*18:03, HLA-B*44:02, HLA-B*07:02, HLA-B*35:01, HLA-B*40:01, HLA-B*35:08, HLA-B*55:01, HLA-B*51:01, HLA-B*44:03, HLA-B*58:01, HLA-B*08:01, HLA-B*18:01, HLA-B*15:01, HLA-B*52:01, and a combination thereof. In some instances, the allele of the HLA-C gene is an allele selected from the group consisting of HLA-C*04:01, HLA-C*07:02, HLA-C*07:01, HLA-C*06:02, HLA-C*03:04, HLA-C*01:02, HLA-C*02:02, HLA-C*08:02, HLA-C*15:02, HLA-C*03:03, HLA-C*05:01, HLA-C*08:01, HLA-C*16:01, HLA-C*12:03, HLA-C*14:02, and a combination thereof.

In some embodiments, the HLA class II gene is selected from the group consisting of an HLA class II alpha subunit gene, an HLA class II beta subunit gene, and a combination thereof. In other embodiments, the HLA class II gene is selected from the group consisting of an HLA-DP gene, an HLA-DM gene, an HLA-DOA gene, an HLA-DOB gene, an HLA-DQ gene, an HLA-DR gene, and a combination thereof. In some embodiments, HLA-DM gene is selected from the group consisting of an HLA-DMA gene, an HLA-DMB gene, and a combination thereof. In other embodiments, the HLA-DR gene is selected from the group consisting of an HLA-DRA gene, an HLA-DRB1 gene, an HLA-DRB3 gene, an HLA-DRB4 gene, an HLA-DRB5 gene, and a combination thereof. In some instances, the allele of the HLA-DRB3 gene is an allele selected from the group consisting of HLA-DRB3*02:02, HLA-DRB3*01:01, HLA-DRB3*03:01, and a combination thereof. In particular instances, the allele of the HLA class I gene is HLA-A*11:01 or HLA-A*24:02 and the allele of the HLA class II gene is HLA-DRB3*02:02 or HLA-DRB3*01:01.

In some embodiments, the modified human cancer cell further comprises a recombinant polynucleotide encoding granulocyte-macrophage colony-stimulating factor (GM-CSF). In other embodiments, the modified human cancer cell further comprises a recombinant polynucleotide encoding interferon alpha (IFNa).

In some embodiments, the modified human cancer cell further comprises a recombinant polynucleotide encoding adenosine deaminase (ADA), adhesion G protein-coupled receptor E5 (ADGRE5), caveolin 1 (CAV1), CD58 molecule (CD58), CD74 molecule (CD74), CD83 molecule (CD83), C-X-C motif chemokine ligand 8 (CXCL8), C-X-C motif chemokine ligand 16 (CXCL16), intracellular adhesion molecule 3 (ICAM3), interleukin 6 (IL6), interleukin 10 (IL10), interleukin 15 (IL15), interleukin 18 (IL18), KIT ligand (KITLG), tumor necrosis factor superfamily member 14 (TNFSF14), preferentially expressed antigen in melanoma (PRAME), PDZ binding kinase (PBK), centrosomal protein 55 (CEP55), kinesin family member 2C (KIF2C), placenta-specific protein 1 (PLAC1), Opa interacting protein 5 (OIP5), calcium binding tyrosine phosphorylation regulated (CABYR), sperm-associated antigen 1 (SPAG1), or a combination thereof.

In some embodiments, the human cancer cell is a human cancer cell line. In some instances, the human cancer cell line is an SV-BR-1 breast cancer cell line.

In a third aspect, the present invention provides a method for selecting a whole-cell cancer vaccine for a subject having cancer, the method comprising:

(a) detecting the presence or absence of one or more alleles of one or more human leukocyte antigen (HLA) genes in a sample obtained from the subject to generate an HLA allele profile of the subject;

(b) comparing the HLA allele profile of the subject to an HLA allele profile of the whole-cell cancer vaccine based on the presence or absence of the one or more alleles of one or more of the HLA genes in the whole-cell cancer vaccine; and (c) selecting the whole-cell cancer vaccine for the subject when the HLA allele profile of the subject matches the HLA allele profile of the whole-cell cancer vaccine.

In some embodiments, the one or more HLA genes comprise an HLA class I gene, an HLA class II gene, or a combination thereof. In other embodiments, the HLA class I gene is selected from the group consisting of an HLA-A gene, an HLA-B gene, an HLA-C gene, an HLA-E gene, an HLA-F gene, an HLA-G gene, a beta-2-microglobulin (B2M) gene, and a combination thereof. In some instances, the allele of the HLA-A gene is an allele selected from the group consisting of HLA-A*11:01, HLA-A*01:01, HLA-A*02:01, HLA-A*03:01, HLA-A*26:01, HLA-A*29:02, HLA-A*32:01, HLA-A*24:02, HLA-A*33:03, HLA-A*68:01, HLA-A*31:01, HLA-A*02:06, and a combination thereof. In other instances, the allele of the HLA-B gene is an allele selected from the group consisting of HLA-B*13:02, HLA-B*41:01, HLA-B*18:03, HLA-B*44:02, HLA-B*07:02, HLA-B*35:01, HLA-B*40:01, HLA-B*35:08, HLA-B*55:01, HLA-B*51:01, HLA-B*44:03, HLA-B*58:01, HLA-B*08:01, HLA-B*18:01, HLA-B*15:01, HLA-B*52:01, and a combination thereof. In some instances, the allele of the HLA-C gene is an allele selected from the group consisting of HLA-C*04:01, HLA-C*07:02, HLA-C*07:01, HLA-C*06:02, HLA-C*03:04, HLA-C*01:02, HLA-C*02:02, HLA-C*08:02, HLA-C*15:02, HLA-C*03:03, HLA-C*05:01, HLA-C*08:01, HLA-C*16:01, HLA-C*12:03, HLA-C*14:02, and a combination thereof.

In some embodiments, the HLA class II gene is selected from the group consisting of an HLA class II alpha subunit gene, an HLA class II beta subunit gene, and a combination thereof. In other embodiments, the HLA class II gene is selected from the group consisting of an HLA-DP gene, an HLA-DM gene, an HLA-DOA gene, an HLA-DOB gene, an HLA-DQ gene, an HLA-DR gene, and a combination thereof. In some embodiments, the HLA-DM gene is selected from the group consisting of an HLA-DMA gene, an HLA-DMB gene, and a combination thereof. In other embodiments, the HLA-DR gene is selected from the group consisting of an HLA-DRA gene, an HLA-DRB1 gene, an HLA-DRB3 gene, an HLA-DRB4 gene, an HLA-DRB5 gene, and a combination thereof. In some instances, the allele of the HLA-DRB3 gene is an allele selected from the group consisting of HLA-DRB3*02:02, HLA-DRB3*01:01, HLA-DRB3*03:01, and a combination thereof. In other instances, the allele of the HLA class I gene is HLA-A*11:01 or HLA-A*24:02 and the allele of the HLA class II gene is HLA-DRB3*02:02 or HLA-DRB3*01:01.

In some embodiments, the whole-cell cancer vaccine is selected for the subject when one or more alleles in the HLA allele profile of the subject match the HLA allele profile of the whole-cell cancer vaccine. In some instances, the whole-cell cancer vaccine is selected for the subject when two or more alleles in the HLA allele profile of the subject match the HLA allele profile of the whole-cell cancer vaccine.

In a fourth aspect, the present invention provides a method for selecting a whole-cell cancer vaccine for a subject having cancer, the method comprising:

(a)(i) detecting the presence or level of one or more biomarkers in a sample obtained from the subject; and/or (a)(ii) measuring the level of activity and/or number of one or more immune cells obtained from the subject;

(b) comparing the presence or level of the one or more biomarkers detected in step (a)(i) and/or the level of activity and/or number of the one or more immune cells measured in step (a)(ii) to the presence or level of the one or more biomarkers and/or the level of activity and/or number of one or more immune cells in a control sample; and (c) selecting the whole-cell cancer vaccine for the subject based on the comparison in step (b), wherein the whole-cell cancer vaccine is derived from a breast cancer cell line or a breast cancer cell.

In some embodiments, the breast cancer cell line is an SV-BR-1 breast cancer cell line. In other instances, the one or more biomarkers is selected from the group consisting of preferentially expressed antigen in melanoma (PRAME), PDZ binding kinase (PBK), centrosomal protein 55 (CEP55), kinesin family member 2C (KIF2C), placenta-specific protein 1 (PLAC1), Opa interacting protein 5 (OIP5), calcium binding tyrosine phosphorylation regulated (CABYR), sperm-associated antigen 1 (SPAG1), alpha-1,3-glucosyltransferase (ALG8), actin-related protein 2/3 complex, subunit 5-like (ARPC5L), chromobox homolog 2 (CBX2), collagen type VIII alpha 1 chain (COL8A1), DDB1 and CUL4 associated factor 10, (DCAF10), eukaryotic translation initiation factor 3 subunit H (EIF3H), erb-b2 receptor tyrosine kinase 2 (ERBB2), histone cluster 1 H4 family member h (HIST1H4H), insulin like growth factor binding protein 5 (IGFBP5), integrator complex subunit 7 (INTS7), keratin 19 (KRT19), keratin 81 (KRT81), mannosyl (alpha-1,3-)-glycoprotein beta-1,4-N-acetylglucosaminyltransferase, isozyme A (MGAT4A), migration and invasion enhancer 1 (MIEN1), post-GPI attachment to proteins 3 (PGAP3), remodeling and spacing factor 1 (RSF1), SH2 domain containing adaptor protein B (SHB), soluble carrier family 35, member A2 (SLC35A2), spectrin repeat containing nuclear envelope family member 4 (SYNE4), transportin 1 (TNPO1), and a combination thereof. In yet other embodiments, the one or more biomarkers is selected from the group consisting of PRAME, PBK, CEP55, KIF2C, ERBB2, PGAP3, and a combination thereof. In some instances, the one or more biomarkers is PRAME. In other instances, the one or more biomarkers is selected from the group consisting of ERBB2, MIEN1, PGAP3, and a combination thereof.

In some embodiments, the vaccine is selected for the subject when the level of at least one of the one or more biomarkers is overexpressed in the sample obtained from the subject compared to the control sample, wherein the control sample comprises a normal cell or tissue obtained from the subject, from a different subject, or from a population of subjects. In some instances, the vaccine is selected for the subject when the level of at least one of the one or more biomarkers is overexpressed at least about 1.5-fold compared to the control sample.

In other embodiments, the vaccine is selected for the subject when the level of activity and/or number of the one or more immune cells obtained from the subject is higher compared to the control sample, wherein the control sample comprises one or more immune cells obtained from a different subject or population of subjects who do not have cancer. In some instances, the level of activity and/or number of the one or more immune cells obtained from the subject is at least about 1.5-fold higher compared to the control sample.

In some embodiments, the one or more immune cells in which the level of activity and/or number is measured is selected from the group consisting of a peripheral blood mononuclear cell (PBMC), a lymphocyte, a monocyte, a natural killer (NK) cell, a dendritic cell, a macrophage, a myeloid-derived suppressor cell (MDSC), and a combination thereof. In some instances, the one or more immune cells in which the level of activity and/or number is measured is selected from the group consisting of a PBMC, a lymphocyte, a dendritic cell, and a combination thereof.

In some embodiments, the presence or level of the one or more biomarkers is detected using a method selected from the group consisting of an ELISA, a multiplex assay, measuring the RNA transcript level of a gene encoding an antigen, immunohistochemistry, a Western blot, a bead-based method, and a combination thereof. In other embodiments, the level of activity and/or number of the one or more immune cells is measured using a method selected from the group consisting of an ELISA, an ELISPOT assay, a Western blot, a cytotoxic T lymphocyte (CTL) activity assay, a cytotoxicity assay, a proliferation assay, a cytokine production assay, an MHC multimer assay, a flow cytometry assay, and a combination thereof. In particular embodiments, the level of activity and/or number of the one or more immune cells is measured following stimulation with an antigen.

In some embodiments, the one or more biomarkers comprise one or more alleles of one or more human leukocyte antigen (HLA) genes. In other embodiments, the one or more HLA genes comprise an HLA class I gene, an HLA class II gene, or a combination thereof. In some other embodiments, the HLA class I gene is selected from the group consisting of an HLA-A gene, an HLA-B gene, an HLA-C gene, an HLA-E gene, an HLA-F gene, an HLA-G gene, a beta-2-microglobulin (B2M) gene, and a combination thereof. In some instances, the allele of the HLA-A gene is an allele selected from the group consisting of HLA-A*11:01, HLA-A*01:01, HLA-A*02:01, HLA-A*03:01, HLA-A*26:01, HLA-A*29:02, HLA-A*32:01, HLA-A*24:02, HLA-A*33:03, HLA-A*68:01, HLA-A*31:01, HLA-A*02:06, and a combination thereof. In other instances, the allele of the HLA-B gene is an allele selected from the group consisting of HLA-B*13:02, HLA-B*41:01, HLA-B*18:03, HLA-B*44:02, HLA-B*07:02, HLA-B*35:01, HLA-B*40:01, HLA-B*35:08, HLA-B*55:01, HLA-B*51:01, HLA-B*44:03, HLA-B*58:01, HLA-B*08:01, HLA-B*18:01, HLA-B*15:01, HLA-B*52:01, and a combination thereof. In some instances, the allele of the HLA-C gene is an allele selected from the group consisting of HLA-C*04:01, HLA-C*07:02, HLA-C*07:01, HLA-C*06:02, HLA-C*03:04, HLA-C*01:02, HLA-C*02:02, HLA-C*08:02, HLA-C*15:02, HLA-C*03:03, HLA-C*05:01, HLA-C*08:01, HLA-C*16:01, HLA-C*12:03, HLA-C*14:02, and a combination thereof.

In some embodiments, the HLA class II gene is selected from the group consisting of an HLA class II alpha subunit gene, an HLA class II beta subunit gene, and a combination thereof. In other embodiments, the HLA class II gene is selected from the group consisting of an HLA-DP gene, an HLA-DM gene, an HLA-DOA gene, an HLA-DOB gene, an HLA-DQ gene, an HLA-DR gene, and a combination thereof. In some embodiments, the HLA-DM gene is selected from the group consisting of an HLA-DMA gene, an HLA-DMB gene, and a combination thereof. In other embodiments, the HLA-DR gene is selected from the group consisting of an HLA-DRA gene, an HLA-DRB1 gene, an HLA-DRB3 gene, an HLA-DRB4 gene, an HLA-DRB5 gene, and a combination thereof. In some instances, the allele of the HLA-DRB3 gene is an allele selected from the group consisting of HLA-DRB3*02:02, HLA-DRB3*01:01, HLA-DRB3*03:01, and a combination thereof. In other instances, the allele of the HLA class I gene is HLA-A*11:01 or HLA-A*24:02 and the allele of the HLA class II gene is HLA-DRB3*02:02 or HLA-DRB3*01:01.

In some embodiments, the vaccine is selected for the subject when one or more alleles of one or more human leukocyte antigen (HLA) genes in the sample obtained from the subject match one or more alleles of one or more human leukocyte antigen (HLA) genes in the vaccine.

In other embodiments, the sample obtained from the subject is a whole blood sample, a plasma sample, a serum sample, a buccal swab sample, a tumor tissue sample, a biofluid sample, a pleural effusion sample, a urine sample, a hair sample, a skin sample, or a combination thereof. In other embodiments, the sample is obtained from a biopsy, from a surgical resection, as a fine needle aspirate (FNA), or a combination thereof. In some other embodiments, the sample comprises tumor tissue, a tumor cell, a circulating tumor cell (CTC), or a combination thereof.

In a fifth aspect, the present invention provides a composition comprising a modified human cancer cell comprising a recombinant polynucleotide encoding an allele of a human leukocyte antigen (HLA) class I gene. In some embodiments, the modified human cancer cell further comprises a recombinant polynucleotide encoding an allele of an HLA class II gene.

In a sixth aspect, the present invention provides a composition comprising a modified human cancer cell comprising a recombinant polynucleotide encoding an allele of an HLA class II gene. In some embodiments, the modified human cancer cell further comprises a recombinant polynucleotide encoding an allele of an HLA class I gene. In other embodiments, the recombinant polynucleotide is present on a vector in the cell. In some embodiments, the recombinant polynucleotide is integrated into the genome of the cell.

In some embodiments, the HLA class I gene is selected from the group consisting of an HLA-A gene, an HLA-B gene, an HLA-C gene, an HLA-E gene, an HLA-F gene, an HLA-G gene, a beta-2-microglobulin (B2M) gene, and a combination thereof. In some instances, the allele of the HLA-A*11:01, HLA-A*01:01, HLA-A*02:01, HLA-A*03:01, HLA-A*26:01, HLA-A*29:02, HLA-A*32:01, HLA-A*24:02, HLA-A*33:03, HLA-A*68:01, HLA-A*31:01, HLA-A*02:06, and a combination thereof. In other instances, the allele of the HLA-B gene is an allele selected from the group consisting of HLA-B*13:02, HLA-B*41:01, HLA-B*18:03, HLA-B*44:02, HLA-B*07:02, HLA-B*35:01, HLA-B*40:01, HLA-B*35:08, HLA-B*55:01, HLA-B*51:01, HLA-B*44:03, HLA-B*58:01, HLA-B*08:01, HLA-B*18:01, HLA-B*15:01, HLA-B*52:01, and a combination thereof. In some instances, the allele of the HLA-C gene is an allele selected from the group consisting of HLA-C*04:01, HLA-C*07:02, HLA-C*07:01, HLA-C*06:02, HLA-C*03:04, HLA-C*01:02, HLA-C*02:02, HLA-C*08:02, HLA-C*15:02, HLA-C*03:03, HLA-C*05:01, HLA-C*08:01, HLA-C*16:01, HLA-C*12:03, HLA-C*14:02, and a combination thereof.

In some embodiments, the HLA class II gene is selected from the group consisting of an HLA class II alpha subunit gene, an HLA class II beta subunit gene, and a combination thereof. In other embodiments, the HLA class II gene is selected from the group consisting of an HLA-DP gene, an HLA-DM gene, an HLA-DOA gene, an HLA-DOB gene, an HLA-DQ gene, an HLA-DR gene, and a combination thereof. In some embodiments, the HLA-DM gene is selected from the group consisting of an HLA-DMA gene, an HLA-DMB gene, and a combination thereof. In other embodiments, the HLA-DR gene is selected from the group consisting of an HLA-DRA gene, an HLA-DRB1 gene, an HLA-DRB3 gene, an HLA-DRB4 gene, an HLA-DRB5 gene, and a combination thereof. In some instances, the allele of the HLA-DRB3 gene is an allele selected from the group consisting of HLA-DRB3*02:02, HLA-DRB3*01:01, HLA-DRB3*03:01, and a combination thereof. In particular instances, the allele of the HLA class I gene is HLA-A*11:01 or HLA-A*24:02 and the allele of the HLA class II gene is HLA-DRB3*02:02 or HLA-DRB3*01:01.

In some embodiments, the modified human cancer cell further comprises a recombinant polynucleotide encoding adenosine deaminase (ADA), adhesion G protein-coupled receptor E5 (ADGRE5), caveolin 1 (CAV1), CD58 molecule (CD58), CD74 molecule (CD74), CD83 molecule (CD83), C-X-C motif chemokine ligand 8 (CXCL8), C-X-C motif chemokine ligand 16 (CXCL16), intracellular adhesion molecule 3 (ICAM3), interleukin 6 (IL6), interleukin 10 (IL10), interleukin 15 (IL15), interleukin 18 (IL18), KIT ligand (KITLG), tumor necrosis factor superfamily member 14 (TNFSF14), or a combination thereof.

In other embodiments, the composition further comprises granulocyte-macrophage colony-stimulating factor (GM-CSF). In some embodiments, the GM-CSF is encoded by a recombinant polynucleotide and expressed by a modified cell. In some instances, the GM-CSF is expressed by the same modified cell that comprises the recombinant polynucleotide encoding an allele of a human leukocyte antigen (HLA) class I and/or class II gene. In other instances, the GM-CSF is not expressed by the same modified cell that comprises the recombinant polynucleotide encoding an allele of a human leukocyte antigen (HLA) class I and/or class II gene. In other embodiments, the GM-CSF is present in a soluble form.

In some embodiments, the composition further comprises interferon alpha (IFNa). In particular embodiments, the IFNa is expressed by the same modified cell that comprises the recombinant polynucleotide encoding an allele of a human leukocyte antigen (HLA) class I and/or class II gene. In other embodiments, the IFNa is present in a soluble form.

In some embodiments, the human cancer cell is a human cancer cell line. In some instances, the human cancer cell line is an SV-BR-1 breast cancer cell line.

In a seventh aspect, the invention provides a pharmaceutical composition comprising a composition of the present invention and a pharmaceutically acceptable carrier.

In another aspect, the invention provides a method for treating cancer in a subject, the method comprising administering to the subject a therapeutically effective amount of the pharmaceutical composition of the present invention. In some embodiments, the method further comprises treating the subject with a therapy selected from the group consisting of chemotherapy, immunotherapy, radiotherapy, hormone therapy, a differentiating agent, a small-molecule drug, and a combination thereof. In some instances, the immunotherapy comprises an agent selected from the group consisting of an immune checkpoint inhibitor, a monoclonal antibody, a small-molecule drug, and a combination thereof. In other instances, the chemotherapy comprises an agent selected from the group consisting of an alkylating agent, an antimetabolite, an anti-tumor antibiotic, a topoisomerase inhibitor, a mitotic inhibitor, a corticosteroid, and a combination thereof. In some embodiments, the method further comprises selecting a whole-cell cancer vaccine for the subject according to a method of the present invention.

In some embodiments, the subject has stage I, stage II, stage III, or stage IV cancer. In other embodiments, the cancer is selected from the group consisting of breast cancer, ovarian cancer, cervical cancer, prostate cancer, pancreatic cancer, colorectal cancer, gastric cancer, lung cancer, skin cancer, liver cancer, brain cancer, eye cancer, soft tissue cancer, renal cancer, bladder cancer, head and neck cancer, mesothelioma, acute leukemia, chronic leukemia, medulloblastoma, multiple myeloma, sarcoma, and a combination thereof.

In some embodiments, the pharmaceutical composition is administered by injection. In some instances, the injection is an intradermal and/or intralymphatic injection. In other embodiments, treating the subject produces a decrease in tumor volume. In still other embodiments, treating the subject ameliorates or eliminates one or more signs or symptoms of cancer.

In other embodiments, treating the subject results in an increase in the activity and/or number of one or more immune cells. In some embodiments, the one or more immune cells in which the level of activity and/or number is increased are selected from the group consisting of a peripheral blood mononuclear cell (PBMC), a lymphocyte, a monocyte, a natural killer (NK) cell, a dendritic cell, a macrophage, a myeloid-derived suppressor cell (MDSC), and a combination thereof. In some instances, the one or more immune cells in which the level of activity and/or number is increased are selected from the group consisting of a PBMC, a lymphocyte, a dendritic cell, and a combination thereof.

In some embodiments, the level of activity and/or number of the one or more immune cells is measured using a method selected from the group consisting of an ELISA, an ELISPOT assay, a Western blot, a cytotoxic T lymphocyte (CTL) activity assay, a cytotoxicity assay, a proliferation assay, a cytokine production assay, an WIC multimer assay, a flow cytometry assay, and a combination thereof. In particular embodiments, the level of activity and/or number of the one or more immune cells is measured following stimulation with an antigen.

In some embodiments, an increase in immune cell activity and/or number indicates that the subject should be administered one or more additional doses of the pharmaceutical composition. In other embodiments, treating the subject results in an increased survival time.

In still another aspect, the present invention provides a kit for treating a subject with cancer comprising a pharmaceutical composition of the present invention. In some embodiments, the kit further comprises instructions for use. In other embodiments, the kit further comprises one or more reagents. In some instances, the one or more reagents are for isolating a sample from the subject having cancer, detecting the presence or absence of one or more alleles of one or more human leukocyte antigen (HLA) genes, detecting the presence or level of one or more biomarkers, and/or measuring the activity and/or number of one or more immune cells.

In yet another aspect, the invention provides a method for determining the HER2 status of a cell, the method comprising:

(a) detecting the presence or level of one or more biomarkers in the sample cell, wherein the one or more biomarkers comprise:
  (i) MIEN1,
  (ii) PGAP3,
  (iii) ERBB2 and MIEN1,
  (iv) ERBB2 and PGAP3,
  (v) MIEN1 and PGAP3, or
  (vi) ERBB2, MIEN1, and PGAP3;

(b) comparing the presence or level of the one or more biomarkers detected in step (a) to the presence or level of the one or more biomarkers in a reference cell; and (c) determining the HER2 status of the sample cell based upon the comparison performed in step (b).

In some embodiments, the sample cell is a cancer cell or is a cell obtained from a subject who has cancer. In other embodiments, the sample cell is determined to be HER2 positive when the one or more biomarkers is expressed at a higher level in the sample cell compared to the reference cell. In some instances, the reference cell is a non-cancer cell obtained from the same subject as the sample cell or is a non-cancer cell obtained from a different subject or population of subjects.

In some embodiments, the level of the one or more biomarkers is higher in a HER2 3+ cell than in a HER2 2+ cell. In other embodiments, the level of the one or more biomarkers is higher in a HER2 2+ cell than in a HER2 1+ or a HER2 0 cell. In some other embodiments, detecting the presence or level of the one or more biomarkers comprises measuring mRNA expression, protein abundance, or a combination thereof.

In some embodiments, the determination is made with a sensitivity of at least about 60%. In some instances, the determination is made with a sensitivity of at least about 87%. In other instances, the determination is made with a sensitivity of at least about 100%. In other embodiments, the steps of (a), (b), and/or (c) are automated.

Other objects, features, and advantages of the present invention will be apparent to one of skill in the art from the following detailed description and figures.

BRIEF DESCRIPTION OF THE DRAWINGS

FIG. 1A shows a schematic depicting development of the SV-BR-1-GM (BriaVax) cell line. The SV-BR-1-GM cell line was derived from SV-BR-1 breast cancer cells following stable transfection with CSF2 (which encodes human GM-CSF). The SV-BR-1 cell line itself was established from a chest lesion of a metastatic breast cancer patient (16,17). An SV-BR-1-GM master cell bank (MCB) was previously generated, and several "clinical product" (CP) lots were manufactured therefrom for actual or potential clinical use. Additionally, MCB-independent research (RES) banks were generated. The depicted developmental stages of SV-BR-1-GM represent samples for which gene expression profiles were generated in the context of Example 1. RNA for gene expression analysis was extracted from cells taken directly from cryogenic vials ("cryo") or following a culturing step ("culture"). FIG. 1B shows morphologies of SV-BR-1-GM cells after serum starvation, as exemplified by 40× and 100× magnifications of cultured SV-BR-1-GM Lot 11 cells. Of note, SV-BR-1-GM cells grow in monolayers but can also loosely attach or form aggregates following low-density seeding. FIGS. 1C and 1D depict quality control (QC) measures. FIG. 1C shows hierarchical clustering of SV-BR-1-GM samples based on their microarray expression profiles. Normalized gene expression levels of samples belonging to the same sample type were averaged (i.e., the arithmetic mean was computed) prior to clustering. FIG. 1D shows that only samples with a RIM value of at least 7.5 were used for this study. Notably, the CP Lot V cryo sample clustered separately. Additionally, the CP Lot V cryo sample did not pass the minimal variability QC metric (see, section titled "Methods" of Example 1) and was thus excluded from additional analyses.

FIG. 2A shows hierarchical clustering of both samples and genes (i.e., probes) with minimum expression values among all samples greater than 1.5 times the background cutoff value. The SV-BR-1-GM samples clustered separately from the MDA-MB-231, MDA-MB-468, MCF7, and MCF10A samples. FIG. 2B shows hierarchical clustering of both samples and genes (i.e., probes) with maximum expression values among the different sample groups (i.e., SV-BR-1-GM, MDA-MB-231, MDA-MB-468, MCF7, MCF10A, ALDH NEG, ALDH POS, ERBB3 NEG, NCL, BASAL, STROMAL, HMEC early proliferating, HMEC deep senescence) greater than 1.5 times the background cutoff value. Cell lines and noncultured breast cells built separate clusters; the SV-BR-1-GM samples built their own subcluster within the cell line group. FIG. 2C shows the ERBB2 cluster. ALDH3B2, EIF4E3, SYBU, and TMC6 clustered tightly with ERBB2 across the samples indicated. The heat map shown represents an enlarged section of the heat map displayed in FIG. 2B. "Global" vs. "Relative" refer to intensities based on all of the expression values represented ("Global") or based on only those of the corresponding gene ("Relative"). As evidenced from the "Global" display, ERBB2, in both SV-BR-1-GM and normal breast cells, was expressed at higher levels than the other genes. "Chr. Location" denotes chromosomal location as indicated on the respective NCBI Gene sites.

FIG. 4A depicts the expression of HLA-DRA, which encodes an HLA-DR alpha chain. FIG. 4B depicts the expression of HLA-DMA and HLA-DMB, which encode components of HLA-DM, a non-classical MEW II which chaperones peptide-free MHC II against inactivation and catalysis of the exchange of the CLIP peptide with peptides from endocytosed or endogenous antigens (71). FIG. 4C depicts the expression of CD74, which encodes the invariant chain and CLIP.

FIG. 5A depicts the expression of HLA-DRA and HLA-DRB. FIG. 5B depicts the expression of HLA-DMA and HLA-DMB. FIG. 5C depicts the expression of CD74.

FIGS. 6A-6G show that SV-BR-1-GM expressed both "classical" HLA-Ia and "nonclassical" HLA-Ib components. "Relative Expression Levels" refers to quantile-normalized mRNA levels obtained via microarray hybridization. FIG. 6A shows expression of B2M, encoding b2-microglobulin. FIG. 6B shows expression of HLA-A. FIG. 6C shows expression of HLA-B. FIG. 6D shows expression of HLA-E. FIG. 6E shows expression of HLA-F. FIG. 6F shows expression of HLA-G. FIG. 6G shows expression of HLA-H.

FIG. 7A shows data for CP Lot IV 4p. FIG. 7B shows data for CP Lot VIII.

FIG. 9A depicts RNA expression levels of 279 confirmed or putative CTAs (Table 7) in SV-BR-1-GM cells, several other established breast cancer cell lines, and several normal human breast cell types. FIG. 9B depicts transcript levels of PRAME. FIG. 9C depicts transcript levels of KIF2C. FIG. 9D depicts transcript levels of CEP55. FIG. 9E depicts transcript levels of PBK.

FIGS. 10A-10C depict in silico screening results for immunogen candidates. SV-BR-1-GM RNA samples were hybridized onto Illumina® HumanHT-12 v4 Expression BeadChip arrays. SV-BR-1-GM expression data were compared to those of normal human breast cells provided in the Gene Expression Omnibus (GEO, NCBI) database as datasets GSE35399 (81), GSE56718 (80) and GSE48398 (MCF10A only). Two serial filters (FIGS. 13 and 14) were applied to the quantile-normalized expression values to enrich for genes likely differentiating SV-BR-1-GM cells from normal breast cells. Such genes represented candidate immunogens for mediating SV-BR-1-GM's anti-cancer effect. After the first (i.e., low-stringency) filter was applied, 455 different genes were retained, of which 352 remained after the second (i.e., medium-stringency) filter was applied. The latter genes were in silico validated on GEO datasets GSE29431 (i.e., breast cancer tissues) and GSE7307 (i.e., nonmalignant tissues representing various organs; see, Table 11). By means of this high-stringency filtration/validation step, twenty genes were identified with expression levels that were higher in breast cancer than in a variety of nonmalignant tissues. Strikingly, among these 20 genes were 3 that mapped to chromosome 17q12 (Table 12), namely ERBB2, MIEN1, and PGAP3. FIG. 10A depicts expression of ERBB2 (HER2/neu, Illumina® probe 216836_s_at). FIG. 10B depicts expression of MIEN1 (Illumina® probe 224447_s_at). FIG. 10C depicts expression of PGAP3 (Illumina® probe 55616_at).

FIG. 11A depicts immune modulators expressed in BriaVax (SV-BR-1-GM). Shown are a subset of the factors having immune modulating roles expressed in SV-BR-1-GM. Additional factors are listed in Table 5. FIG. 11B depicts cross-dressing (trogocytosis) of DCs with SV-BR-1-GM peptide-MHCs. In this mechanism, allogeneic SV-BR-1-GM cell surface MHCs loaded with SV-BR-1-GM antigens are directly transferred onto the cell surface of patient DCs by trogocytosis. FIG. 11C depicts cross-presentation. In this mechanism, SV-BR-1-GM cells are degraded (i.e., by apoptosis and other mechanisms), then fragments of degraded cells are taken up by dendritic cells (DCs) from the patient. Inside DCs, SV-BR-1-GM antigens are proteolytically degraded and presented on cell surface MHCs to patient T cells.

DETAILED DESCRIPTION OF THE INVENTION

I. Introduction

Figure 1A:
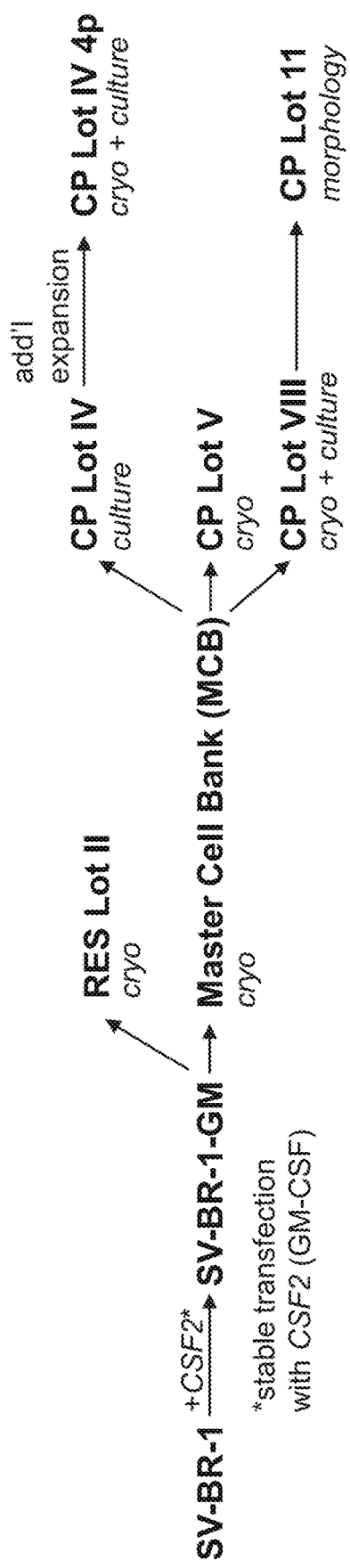
FIGS. 1A-1D show the development of SV-BR-1-GM.

It has been previously reported that in a clinical study a subject with stage IV breast cancer (the "special clinical responder") experienced substantial regression of breast, lung and brain lesions following inoculation with the whole-cell vaccine SV-BR-1-GM (referred to as BriaVax). The present invention is based, in part, on the discovery that SV-BR-1-GM cells not only express tumor-associated antigens (TAAs), but also a set of biomarkers including HLA class I and II alleles known for their immune-stimulatory roles in antigen-presenting cells (APCs). The present invention is also based, in part, on the discovery that human leukocyte antigen (HLA) allele matches between SV-BR-1-GM and the special clinical responder enabled patient T lymphocytes to directly recognize TAAs as presented by the vaccine's MHC system. Furthermore, the present invention is based, in part, on the discovery of biomarkers than enable superior identification and discrimination of HER2 positive cells.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The terms "subject," "individual," and "patient" are used interchangeably herein to refer to a vertebrate, preferably a mammal, more preferably a human. Mammals include, but are not limited to, murines, rats, simians, humans, farm animals, sport animals, and pets. Tissues, cells and their progeny of a biological entity obtained in vivo or cultured in vitro are also encompassed.

As used herein, the term "administering" includes oral administration, topical contact, administration as a suppository, intravenous, intraperitoneal, intramuscular, intralesional, intratumoral, intradermal, intralymphatic, intrathecal, intranasal, or subcutaneous administration to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The term "treating" refers to an approach for obtaining beneficial or desired results including, but not limited to, a therapeutic benefit and/or a prophylactic benefit. By therapeutic benefit is meant any therapeutically relevant improvement in or effect on one or more diseases, conditions, or symptoms under treatment. Therapeutic benefit can also mean to effect a cure of one or more diseases, conditions, or symptoms under treatment.

The term "effective amount" or "sufficient amount" refers to the amount of a modified cancer cell or other composition that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The specific amount may vary depending on one or more of: the particular agent chosen, the target cell type, the location of the target cell in the subject, the dosing regimen to be followed, whether it is administered in combination with other compounds, timing of administration, and the physical delivery system in which it is carried.

For the purposes herein an effective amount is determined by such considerations as may be known in the art. The amount must be effective to achieve the desired therapeutic effect in a subject suffering from cancer. The desired therapeutic effect may include, for example, amelioration of undesired symptoms associated with cancer, prevention of the manifestation of such symptoms before they occur, slowing down the progression of symptoms associated with cancer, slowing down or limiting any irreversible damage caused by cancer, lessening the severity of or curing a cancer, or improving the survival rate or providing more rapid recovery from a cancer.

The effective amount depends, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the distribution profile of a therapeutic agent (e.g., a whole-cell cancer vaccine) or composition within the body, the relationship between a variety of pharmacological parameters (e.g., half-life in the body) and undesired side effects, and other factors such as age and gender, etc.

The term "pharmaceutically acceptable carrier" refers to a substance that aids the administration of an active agent to a cell, an organism, or a subject. "Pharmaceutically acceptable carrier" refers to a carrier or excipient that can be included in the compositions of the invention and that causes no significant adverse toxicological effect on the subject. Non-limiting examples of pharmaceutically acceptable carriers include water, NaCl, normal saline solutions, lactated Ringer's, normal sucrose, normal glucose, binders, fillers, disintegrants, lubricants, coatings, sweeteners, flavors and colors, liposomes, dispersion media, microcapsules, cationic lipid carriers, isotonic and absorption delaying agents, and the like. The carrier may also be substances for providing the formulation with stability, sterility and isotonicity (e.g. antimicrobial preservatives, antioxidants, chelating agents and buffers), for preventing the action of microorganisms (e.g. antimicrobial and antifungal agents, such as parabens, chlorobutanol, sorbic acid and the like) or for providing the formulation with an edible flavor etc. In some instances, the carrier is an agent that facilitates the delivery of a modified cancer cell to a target cell or tissue. One of skill in the art will recognize that other pharmaceutical carriers are useful in the present invention.

The term "nucleic acid" or "nucleotide" as used herein refers to a polymer containing at least two deoxyribonucleotides or ribonucleotides in either single- or double-stranded form and includes DNA, RNA, and hybrids thereof. DNA may be in the form of, e.g., antisense molecules, plasmid DNA, DNA-DNA duplexes, pre-condensed DNA, PCR products, vectors (P1, PAC, BAC, YAC, artificial chromosomes), expression cassettes, chimeric sequences, chromosomal DNA, or derivatives and combinations of these groups. RNA may be in the form of small interfering RNA (siRNA), Dicer-substrate dsRNA, small hairpin RNA (shRNA), asymmetrical interfering RNA (aiRNA), microRNA (miRNA), mRNA, tRNA, rRNA, tRNA, viral RNA (vRNA), and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.,* 19:5081 (1991); Ohtsuka et al., *J. Biol. Chem.,* 260: 2605-2608 (1985); Rossolini et al., *Mol. Cell. Probes,* 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "gene" means the segment of DNA involved in producing a polypeptide chain. The DNA segment may include regions preceding and following the coding region (leader and trailer) involved in the transcription/translation of the gene product and the regulation of the transcription/translation, as well as intervening sequences (introns) between individual coding segments (exons).

The terms "vector" and "expression vector" refer to a nucleic acid construct, generated recombinantly or synthetically, with a series of specified nucleic acid elements that permit transcription of a particular polynucleotide sequence in a host cell. An expression vector may be part of a plasmid, viral genome, or nucleic acid fragment. Typically, an expression vector includes a polynucleotide to be transcribed, operably linked to a promoter. The term "promoter" is used herein to refer to an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. Other elements that may be present in an expression vector include those that enhance transcription (e.g., enhancers) and terminate transcription (e.g., terminators).

"Recombinant" refers to a genetically modified polynucleotide, polypeptide, cell, tissue, or organism. For example, a recombinant polynucleotide (or a copy or complement of a recombinant polynucleotide) is one that has been manipulated using well known methods. A recombinant expression cassette comprising a promoter operably linked to a second polynucleotide (e.g., a coding sequence) can include a promoter that is heterologous to the second polynucleotide as the result of human manipulation (e.g., by methods described in Sambrook et al., *Molecular Cloning—A Laboratory Manual,* Cold Spring Harbor Laboratory, Cold Spring Harbor, N.Y., (1989) or Current Protocols in Molecular Biology Volumes 1-3, John Wiley & Sons, Inc. (1994-1998)). A recombinant expression cassette (or expression vector) typically comprises polynucleotides in combinations that are not found in nature. For instance, human manipulated restriction sites or plasmid vector sequences can flank or separate the promoter from other sequences. A recombinant protein is one that is expressed from a recombinant polynucleotide, and recombinant cells, tissues, and organisms are those that comprise recombinant sequences (polynucleotide and/or polypeptide). A recombinant cell is one that has been modified (e.g., transfected or transformed), with a recombinant nucleotide, expression vector or cassette, or the like.

The term "cancer" is intended to include any member of a class of diseases characterized by the uncontrolled growth of aberrant cells. The term includes all known cancers and neoplastic conditions, whether characterized as malignant, benign, recurrent, soft tissue, or solid, and cancers of all stages and grades including advanced, pre- and post-metastatic cancers. Examples of different types of cancer include, but are not limited to, gynecological cancers (e.g., ovarian, cervical, uterine, vaginal, and vulvar cancers); lung cancers (e.g., non-small cell lung cancer; small cell lung cancer, mesothelioma, carcinoid tumors, lung adenocarcinoma); breast cancers (e.g., triple-negative breast cancer, ductal carcinoma in situ, invasive ductal carcinoma, tubular carcinoma, medullary carcinoma, mucinous carcinoma, papillary carcinoma, cribriform carcinoma, invasive lobular carcinoma, inflammatory breast cancer, lobular carcinoma in situ, Paget's disease, Phyllodes tumors); digestive and gastrointestinal cancers such as gastric cancer (e.g., stomach cancer); colorectal cancer, gastrointestinal stromal tumors (GIST), gastrointestinal carcinoid tumors, colon cancer, rectal cancer, anal cancer, bile duct cancer, small intestine cancer, and esophageal cancer; thyroid cancer; gallbladder cancer; liver cancer; pancreatic cancer; appendix cancer; prostate cancer (e.g., prostate adenocarcinoma); renal cancer (e.g., renal cell carcinoma); cancer of the central nervous system (e.g., glioblastoma, neuroblastoma, medulloblastoma); skin cancer (e.g., melanoma); bone and soft tissue sarcomas (e.g., Ewing's sarcoma); lymphomas; choriocarcinomas; urinary cancers (e.g., urothelial bladder cancer); head and neck cancers; and bone marrow and blood cancers (e.g., acute leukemia, chronic leukemia (e.g., chronic lymphocytic leukemia), lymphoma, multiple myeloma). As used herein, a "tumor" comprises one or more cancerous cells.

In the context of cancer, the term "stage" refers to a classification of the extent of cancer. Factors that are considered when staging a cancer include but are not limited to tumor size, tumor invasion of nearby tissues, and whether the tumor has metastasized to other sites. The specific criteria and parameters for differentiating one stage from another can vary depending on the type of cancer. Cancer staging is used, for example, to assist in determining a prognosis and/or identifying the most appropriate treatment option(s).

One non-limiting example of a cancer staging system is referred to as the "TNM" system. In the TNM system, "T" refers to the size and extent of the main tumor, "N" refers to the number of nearby lymph nodes to which the cancer has spread, and "M" refers to whether the cancer has metastasized. "TX" denotes that the main tumor cannot be measured, "TO" denotes that the main tumor cannot be found, and "T1," "T2," "T3," and "T4" denote the size and/or extent of the main tumor, wherein a larger number corresponds to a larger tumor and/or a tumor that has grown into nearby tissues. "NX" denotes that cancer in nearby lymph nodes cannot be measured, "N0" denotes that there is no cancer in nearby lymph nodes, and "N1," "N2," "N3," and "N4" denote the number and location of lymph nodes to which the cancer has spread, wherein a larger number corresponds to a greater number of lymph nodes containing the cancer. "MX" denotes that metastasis cannot be measured, "M0" denotes that no metastasis has occurred, and "M1" denotes that the cancer has metastasized to other parts of the body.

In another non-limiting example of a cancer staging system, cancers are classified or graded as having one of five stages: "Stage 0," "Stage I," "Stage II," "Stage III," and "Stage IV." Stage 0 denotes that abnormal cells are present, but have not spread to nearby tissue. This is also commonly called carcinoma in situ (CIS). CIS is not cancer, but may subsequently develop into cancer. Stages I, II, and III denote that cancer is present. Higher numbers correspond to larger tumor sizes and/or tumors that have spread to nearby tissues. Stage IV denotes that the cancer has metastasized. One of skill in the art will be familiar with different cancer staging systems and readily be able to apply and/or interpret them.

The term "biopsy" refers to the process of removing a tissue sample for diagnostic or prognostic evaluation, and to the tissue specimen itself. Any biopsy technique known in the art can be applied to the methods and compositions of the present invention. The biopsy technique applied will generally depend on the tissue type to be evaluated and the size and type of the tumor (i.e., solid or suspended (i.e., blood, thoracentesis aspirate, or ascites)), among other factors. Representative biopsy techniques include excisional biopsy, incisional biopsy, needle biopsy (e.g., core needle biopsy, fine-needle aspiration biopsy, etc.), surgical biopsy, and bone marrow biopsy. Biopsy techniques are discussed, for example, in *Harrison's Principles of internal Medicine*, Kasper, et al., eds., 16th ed., 2005, Chapter 70, and throughout Part V. One skilled in the art will appreciate that biopsy techniques can be performed to identify cancerous and/or precancerous cells in a given tissue sample.

The term "allele" refers to a particular form or variant of a gene, typically arising through a mutation event. Alleles can result from, for example, nucleotide substitutions, additions, or deletions, or can represent a variable number of short nucleotide repeats. In the context of human leukocyte antigen (HLA) genes, HLA alleles are named by the World Health Organization Naming Committee for Factors of the HLA system. Under this system, an HLA gene name is followed by a series of numerical fields. At a minimum, two numerical fields are included. As a non-limiting example, HLA-A*02:101 denotes a specific allele of the HLA-A gene. The first field, separated from the gene name by an asterisk, denotes an allele group. The second field, separated from the first field by a colon, denotes the specific HLA protein that is produced. In some instances, a longer name is used (e.g., HLA-A*02:101:01:02N). In this example, the third numerical field denotes whether a synonymous DNA substitution is present within the coding region, and the fourth numerical field denotes differences between alleles that exist in the non-coding region. In some other instances, an HLA allele name is contains a letter at the end. Under the HLA allele naming system, "N" denotes that the allele is a null allele (i.e., the allele produces a non-functional protein), "L" denotes that the allele results in lower than normal cell surface expression of the particular HLA protein, "S" denotes that the allele produces a soluble protein not found on the cell surface, "Q" denotes a questionable allele (i.e., an allele that nay not affect normal expression), "C" denotes that the allele produces a protein that is present in cell cytoplasm but is not present at the cell surface, and "A" denotes an allele that results in aberrant expression (i.e., it is uncertain whether the particular HLA protein is expressed). One of skill in the art will be familiar with the various gene alleles and their naming conventions.

The term "allele profile" refers to a collection of alleles of one or more genes in a particular sample. The sample may be obtained from a subject, a particular cell or cell type (e.g., a breast cell or breast cancer cell), or from an engineered cell (e.g., a cancer cell that has been engineered to express one or more proteins). In some instances, an allele profile describes the alleles of a single gene that are present in a sample (e.g., in a cell obtained from a subject or a cancer vaccine cell), or may describe the alleles that are present for two or more genes in a sample. As a non-limiting example, an allele profile may list the alleles that are present for the HLA-A gene in a particular sample. For a diploid cell, only one allele may be present (e.g., if both chromosomes contain the same allele, such as HLA-A*02:01). Alternatively, two different alleles may be present (e.g., the allele profile contains HLA-A*02:01 and HLA-A*24:02, or HLA-A*02:01 and HLA-A*03:01). In other instances, the allele profile enumerates the alleles that are present for two or more genes. As a non-limiting example, an allele profile may describe the alleles of the HLA-A and HLA-DRB3 genes that are present in a patient sample.

For purposes of illustration only, an allele profile of a subject may indicate that the HLA-A*02:01 and HLA-A*24:02 alleles of the HLA-A gene are present, and that the HLA-DRB3*03:01 allele of the HLA-DRB3 gene is present. Furthermore, allele profiles can be compared. As a non-limiting example, a subject can have an allele profile containing the HLA-A*02:01 and HLA-A*24:02 alleles, while a cancer vaccine cell can have a profile containing the HLA-A*02:01 and HLA-A*03:01 alleles. In this example, if the two allele profiles are compared, then there is a partial match between the profiles (i.e., the HLA-A*02:01 allele is present in both profiles). As another non-limiting example, if the vaccine cell has an allele profile containing HLA-A*02:01 and HLA-A*24:02, then the subject and vaccine cell profiles are a complete match with respect to this particular gene.

The term "human leukocyte antigen (HLA)" refers to a gene complex that encodes human major histocompatibility complex (MEW) proteins, which are a set of cell surface proteins that are essential for recognition of foreign molecules by the adaptive immune system. The HLA complex is found within a 3 Mbp stretch of chromosome 6p21. Class I MEW proteins, which present peptides from inside the cell, are encoded by the HLA-A, HLA-B, HLA-C, HLA-E, HLA-F, and HLA-G genes. HLA-A, HLA-B, and HLA-C genes are more polymorphic, while HLA-E, HLA-F, and HLA-G genes are less polymorphic. HLA-K and HLA-L are also known to exist as pseudogenes. In addition, beta-2-microglobulin is an MHC class I protein, encoded by the (B2M) gene. Non-limiting examples of HLA-A nucleotide sequences are set forth under GenBank reference numbers NM 001242758 and NM_002116. A non-limiting example of an HLA-B nucleotide sequence is set forth under Gen- Bank reference number NM_005514. Non-limiting examples of HLA-C nucleotide sequences are set forth under GenBank reference numbers NM_001243042 and NM_002117. A non-limiting example of an HLA-E nucleotide sequence is set forth under GenBank reference number NM_005516. A non-limiting example of an HLA-F nucleotide sequence is set forth under GenBank reference number NM_018950. A non-limiting example of an HLA-G nucleotide sequence is set forth under GenBank reference number NM_002127. A non-limiting example of a B2M nucleotide sequence is set forth under GenBank reference number NM_004048.

Class II MHC proteins, which present antigens from the outside of the cell to T lymphocytes, are encoded by the HLA-DP, HLA-DM, HLA-DO, HLA-DQ, and HLA-DR genes. HLA-DM genes include HLA-DMA and HLA-DMB. HLA-DO genes include HLA-DOA and HLA-DOB. HLA-DP genes include HLA-DPA1 and HLA-DPB1. HLA-DQ genes include HLA-DQA1, HLA-DQA2, HLA-DQB1, and HLA-DQB2. HLA-DR genes include HLA-DRA, HLA-DRB1, HLA-DRB3, HLA-DRB4, and HLA-DRB5. Non-limiting examples of HLA-DMA and HLA-DMB nucleotide sequences are set forth under GenBank reference numbers NM_006120 and NM_002118, respectively. Non-limiting examples of HLA-DRA, HLA-DRB1, HLA-DRB3, HLA-DRB4, and HLA-DRB5 nucleotide sequences are set forth in GenBank reference numbers NM_01911, NM_002124, NM_022555, NM_021983, NM_002125, respectively.

The term "vaccine" refers to a biological composition that, when administered to a subject, has the ability to produce an acquired immunity to a particular pathogen or disease in the subject. Typically, one or more antigens, or fragments of antigens, that are associated with the pathogen or disease of interest are administered to the subject. Vaccines can comprise, for example, inactivated or attenuated organisms (e.g., bacteria or viruses), cells, proteins that are expressed from or on cells (e.g., cell surface proteins), proteins that are produced by organisms (e.g., toxins), or portions of organisms (e.g., viral envelope proteins. In some instances, cells are engineered to express proteins such that, when administered as a vaccine, they enhance the ability of a subject to acquire immunity to that particular cell type (e.g., enhance the ability of a subject to acquire immunity to a cancer cell). As used herein, the term "vaccine" or "whole-cell cancer vaccine" includes but is not limited to modified cancer cell(s) of the present invention.

The term "granulocyte macrophage colony-stimulating factor (GM-CSF)" refers to a monomeric glycoprotein also known as "colony stimulating factor (CSF2)" that is secreted by cells such as macrophages, T cells, mast cells, natural killer (NK) cells, endothelial cells, and fibroblasts. GM-CSF functions as a cytokine that affects a number of cell types, in particular macrophages and eosinophils. As part of the immune/inflammatory cascade, GM-CSF stimulates stem cells to produce granulocytes (i.e., neutrophils, eosinophils, and basophils) and monocytes. The monocytes subsequently mature into macrophages and dendritic cells after tissue infiltration. A non-limiting example of a CSF2 nucleotide sequence (the gene that encodes GM-CSF) in humans is set forth under GenBank reference number NM_000758.

The term "interferon alpha (IFNa)" or "IFN-α" refers to a group of proteins that are part of a larger class of proteins known as interferons, which are signaling proteins that are synthesized and released by host cells in response to a pathogen (e.g., viruses, bacteria, parasites, tumor cells). Interferon alpha proteins are produced by leukocytes and are mainly involved in the innate immune response. Type I interferon proteins include IFN-α, IFN-β, IFN-ε, IFN-κ, IFN-τ, IFN-δ, IFN-ζ, IFN-ω, and IFN-ν. Genes that encode IFN-α proteins include IFNA1, IFNA2, IFNA4, IFNA5, IFNA6, IFNA7, IFNA8, IFNA10, IFNA13, IFNA14, IFNA16, IFNA17, and IFNA21. Non-limiting examples of IFNA1, IFNA2, IFNA4, IFNA5, IFNA6, IFNA7, IFNA8, IFNA10, IFNA13, IFNA14, IFNA16, IFNA17, and IFNA21 human nucleotide sequences are set forth in Gene Bank reference numbers NM_024013, NM_000605, NM_021068, NM_002169, NM_021002, NM_021057, NM_002170, NM_002171, NM_006900, NM_002172, NM_002173, NM_021268, and NM_002175, respectively.

The term "survival" refers to a length of time following the diagnosis of a disease and/or beginning or completing a particular course of therapy for a disease (e.g., cancer). The term "overall survival" includes the clinical endpoint describing patients who are alive for a defined period of time after being diagnosed with or treated for a disease, such as cancer. The term "disease-free survival" includes the length of time after treatment for a specific disease (e.g., cancer) during which a patient survives with no sign of the disease (e.g., without known recurrence). In certain embodiments, disease-free survival is a clinical parameter used to evaluate the efficacy of a particular therapy, which is usually measured in units of 1 or 5 years. The term "progression-free survival" includes the length of time during and after treatment for a specific disease (e.g., cancer) in which a patient is living with the disease without additional symptoms of the disease. In some embodiments, survival is expressed as a median or mean value.

The terms "HER2," "HER2/neu," and "ERBB2" (also known as CD340, receptor tyrosine-protein kinase erbB-2, proto-oncogene Neu, and human epidermal growth factor receptor 2) refer to a member of the human epidermal growth factor receptor (HER/EGFR/ERBB) family. Amplification or overexpression of this biomarker plays a significant role in the development and progression of certain aggressive types of cancer, including breast cancer. As such, HER2 has become an important biomarker and therapeutic target for at least about 30% of breast cancer patients. Non-limiting examples of HER2 nucleotide sequences are set forth in GenBank reference numbers NP_001005862, NP_001289936, NP_001289937, NP_001289938, and NP_004448. Non-limiting examples of HER2 peptide sequences are set forth in GenBank reference numbers NP_001005862, NP_001276865, NP_001276866, NP_001276867, and NP_004439.

HER2 testing methods include immunohistochemistry (IHC), fluorescence in situ hybridization (FISH), ELISAs, and RNA quantification (e.g., of HER2 expression) methods such as RT-PCR and microarray analysis. HER2 testing is performed on patients who are being considered for trastuzumab therapy, as patients who are HER2 positive are more likely to respond to trastuzumab therapy.

When HER2 is amplified or overexpressed in a cell, the cell is referred to as being "HER2 positive" The level of HER2 amplification or overexpression in HER2 positive cells is commonly expressed as a score ranging from 0 to 3 (i.e., HER2 0, HER2 1+, HER2 2+, or HER2 3+), with higher scores corresponding to greater degrees of expression.

III. Detailed Description of the Embodiments

A. Modified Human Cancer Cells

In one aspect the present invention provides a modified human cancer cell comprising a recombinant polynucleotide that encodes one more alleles of a human leukocyte antigen (HLA) gene. In some embodiments, the recombinant polynucleotide encodes one or more alleles of an HLA class I gene. In other embodiments, the recombinant polynucleotide encodes one or more alleles of an HLA class II gene. In particular embodiments, the recombinant polynucleotide encodes one or more alleles of an HLA class I gene and one or more alleles of an HLA class II gene.

In some embodiments, the recombinant polynucleotide is integrated into the genome of the cell. In other embodiments, the recombinant polynucleotide is present on a vector in the cell. In embodiments where more than one recombinant polynucleotide is present, all of the recombinant polynucleotides can be present on the same vector, or each recombinant polynucleotide can be present on a separate vector. Any number of combinations are permitted. As a non-limiting example, all of the recombinant polynucleotides encoding HLA class I gene alleles can be present on one vector, and all of the recombinant polynucleotides encoding HLA class II gene alleles can be present on another vector. As another non-limiting example all of the recombinant polynucleotides encoding HLA-A gene alleles can be present on one vector, and all of the recombinant polynucleotides encoding HLA-B gene alleles can be present on another vector.

In some embodiments, the HLA class I gene is an HLA-A gene, an HLA-B gene, an HLA-C gene, an HLA-E gene, an HLA-F gene, an HLA-G gene, or a B2M gene. In other embodiments, the HLA class I gene is a combination of an HLA-A gene, an HLA-B gene, an HLA-C gene, an HLA-E gene, an HLA-F gene, an HLA-G gene, and/or a B2M gene. In some embodiments, the modified cancer cell comprises recombinant polynucleotide(s) encoding alleles of one or more (e.g., 1, 2, 3, 4, 5, 6, or 7) HLA class I genes.

Examples of suitable HLA-A alleles include but are not limited to HLA-A*11:01, HLA-A*01:01, HLA-A*02:01, HLA-A*03:01, HLA-A*26:01, HLA-A*29:02, HLA-A*32:01, HLA-A*24:02, HLA-A*33:03, HLA-A*68:01, HLA-A*31:01, and HLA-A*02:06. Modified human cancer cells of the present invention can comprise one or more (e.g., 1, 2, 3, 4, 5, 6, 7, 8, 9, 10, 11, 12, or more) recombinant polynucleotides encoding HLA-A alleles. In some embodiments, the one or more HLA-A alleles are each present at a median frequency of at least about 2% in a population. In other embodiments, the one or more HLA-A alleles are each present at a maximum frequency of at least about 5% in a population. In still other embodiments, the one or more HLA-A alleles are each present at a median frequency of at least about 2% and a maximum frequency of at least about 5% in a population.

Examples of suitable HLA-B alleles include but are not limited to HLA-B*13:02, HLA-B*41:01, HLA-B*18:03, HLA-B*44:02, HLA-B*07:02, HLA-B*35:01, HLA-B*40:01, HLA-B*35:08, HLA-B*55:01, HLA-B*51:01, HLA-B*44:03, HLA-B*58:01, HLA-B*08:01, HLA-B*18:01, HLA-B*15:01, and HLA-B*52:01. Modified human cancer cells of the present invention can comprise one or more (e.g., 1, 2, 3, 4, 5, 6, 7, 8, 9, 10, 11, 12, 13, 14, 15, 16, or more) recombinant polynucleotide(s) encoding HLA-B alleles. In some embodiments, the one or more HLA-B alleles are each present at a median frequency of at least about 2% in a population. In other embodiments, the one or more HLA-B alleles are each present at a maximum frequency of at least about 5% in a population. In still other embodiments, the one or more HLA-B alleles are each present at a median frequency of at least about 2% and a maximum frequency of at least about 5% in a population.

Examples of suitable HLA-C alleles include but are not limited to HLA-C*04:01, HLA-C*07:02, HLA-C*07:01, HLA-C*06:02, HLA-C*03:04, HLA-C*01:02, HLA-C*02:02, HLA-C*08:02, HLA-C*15:02, HLA-C*03:03, HLA-C*05:01, HLA-C*08:01, HLA-C*16:01, HLA-C*12:03, and HLA-C*14:02. Modified human cancer cells of the present invention can comprise one or more (e.g., 1, 2, 3, 4, 5, 6, 7, 8, 9, 10, 11, 12, 13, 14, 15, or more) recombinant polynucleotide(s) encoding HLA-C alleles. In some embodiments, the one or more HLA-C alleles are each present at a median frequency of at least about 2% in a population. In other embodiments, the one or more HLA-C alleles are each present at a maximum frequency of at least about 5% in a population. In still other embodiments, the one or more HLA-C alleles are each present at a median frequency of at least about 2% and a maximum frequency of at least about 5% in a population.

In some embodiments, the HLA class II gene is an HLA class II alpha subunit gene. In other embodiments, the HLA class II gene is an HLA class II beta subunit gene. In particular embodiments, the HLA class II gene is a combination of HLA class II alpha subunit and HLA class II beta subunit genes.

In other embodiments, the HLA class II gene is an HLA-DP gene, an HLA-DM gene, an HLA-DO gene, an HLA-DQ gene, and/or an HLA-DR gene. In some instances, the HLA-DO gene is an HLA-DOA gene. In other instances, the HLA-DO gene is an HLA-DOB gene. In particular instances, the modified cancer cell comprises recombinant nucleotides encoding both HLA-DOA and HLA-DOB gene alleles. In some instances, the HLA-DM gene is an HLA-DMA gene. In other instances, the HLA-DM gene is an HLA-DMB gene. In particular instances, the modified cancer cell comprises recombinant nucleotides encoding both HLA-DMA and HLA-DMB gene alleles.

In some embodiments, the HLA-DR gene is an HLA-DRA gene, an HLA-DRB1 gene, an HLA-DRB3 gene, an HLA-DRB4 gene, and/or an HLA-DRB5 gene. In particular embodiments, the modified cancer cell comprises recombinant polynucleotides encoding alleles of one or more (e.g., 1, 2, 3, 4, 5, or more) HLA-DR gene(s).

Examples of suitable HLA-DRB3 alleles include but are not limited to HLA-DRB3*02:02, HLA-DRB3*01:01, and HLA-DRB3*03:01. Modified human cancer cells of the present invention can comprise one or more (e.g., 1, 2, 3, or more) recombinant polynucleotide(s) encoding HLA-DRB3 alleles. In some embodiments, the one or more HLA-DRB3 alleles are each present at a median frequency of at least about 2% in a population. In other embodiments, the one or more HLA-DRB3 alleles are each present at a maximum frequency of at least about 5% in a population. In still other embodiments, the one or more HLA-DRB3 alleles are each present at a median frequency of at least about 2% and a maximum frequency of at least about 5% in a population.

In some embodiments, the modified cancer cell comprises a recombinant polynucleotide encoding the HLA-DRB3*01:01 allele. In some embodiments, the modified cancer cell comprises a recombinant polynucleotide encoding the HLA-DRB3*02:02 allele. In some embodiments, the modified cancer cell comprises a recombinant polynucleotide encoding the HLA-DRB3*03:01 allele. In some embodiments, the modified cancer cell comprises a recombinant polynucleotide encoding the HLA-A*01:01 allele. In some embodiments, the modified cancer cell comprises a recombinant polynucleotide encoding the HLA-A*02:01 allele. In some embodiments, the modified cancer cell comprises a recombinant polynucleotide encoding the HLA-A*03:01 allele. In some embodiments, the modified cancer cell comprises a recombinant polynucleotide encoding the HLA-A*26:01 allele. In some embodiments, the modified cancer cell comprises a recombinant polynucleotide encoding the HLA-A*29:02 allele. In some embodiments, the modified cancer cell comprises a recombinant polynucleotide encoding the HLA-A*32:01 allele.

In some embodiments, the modified cancer cell comprises recombinant polynucleotides encoding the HLA-DRB3*01:01 and HLA-A*01:01 alleles. In some embodiments, the modified cancer cell comprises recombinant polynucleotides encoding the HLA-DRB3*02:02 and HLA-A*01:01 alleles. In some embodiments, the modified cancer cell comprises recombinant polynucleotides encoding the HLA-DRB3*03:01 and HLA-A*01:01 alleles.

In some embodiments, the modified cancer cell comprises recombinant polynucleotides encoding the HLA-DRB3*01:01 and HLA-A*02:01 alleles. In some embodiments, the modified cancer cell comprises recombinant polynucleotides encoding the HLA-DRB3*02:02 and HLA-A*02:01 alleles. In some embodiments, the modified cancer cell comprises recombinant polynucleotides encoding the HLA-DRB3*03:01 and HLA-A*02:01 alleles.

In some embodiments, the modified cancer cell comprises recombinant polynucleotides encoding the HLA-DRB3*01:01 and HLA-A*03:01 alleles. In some embodiments, the modified cancer cell comprises recombinant polynucleotides encoding the HLA-DRB3*02:02 and HLA-A*03:01 alleles. In some embodiments, the modified cancer cell comprises recombinant polynucleotides encoding the HLA-DRB3*03:01 and HLA-A*03:01 alleles.

In some embodiments, the modified cancer cell comprises recombinant polynucleotides encoding the HLA-DRB3*01:01 and HLA-A*26:01 alleles. In some embodiments, the modified cancer cell comprises recombinant polynucleotides encoding the HLA-DRB3*02:02 and HLA-A*26:01 alleles. In some embodiments, the modified cancer cell comprises recombinant polynucleotides encoding the HLA-DRB3*03:01 and HLA-A*26:01 alleles.

In some embodiments, the modified cancer cell comprises recombinant polynucleotides encoding the HLA-DRB3*01:01 and HLA-A*29:02 alleles. In some embodiments, the modified cancer cell comprises recombinant polynucleotides encoding the HLA-DRB3*02:02 and HLA-A*29:02 alleles. In some embodiments, the modified cancer cell comprises recombinant polynucleotides encoding the HLA-DRB3*03:01 and HLA-A*29:02 alleles.

In some embodiments, the modified cancer cell comprises recombinant polynucleotides encoding the HLA-DRB3*01:01 and HLA-A*32:01 alleles. In some embodiments, the modified cancer cell comprises recombinant polynucleotides encoding the HLA-DRB3*02:02 and HLA-A*32:01 alleles. In some embodiments, the modified cancer cell comprises recombinant polynucleotides encoding the HLA-DRB3*03:01 and HLA-A*32:01 alleles.

In some embodiments, the modified cancer cell comprises recombinant polynucleotides encoding the HLA-DRB3*01:01 allele and GM-CSF. In some embodiments, the modified cancer cell comprises recombinant polynucleotides encoding the HLA-DRB3*02:02 allele and GM-CSF. In some embodiments, the modified cancer cell comprises recombinant polynucleotides encoding the HLA-DRB3*03:01 allele and GM-CSF. In some embodiments, the modified cancer cell comprises recombinant polynucleotides encoding the HLA-A*01:01 allele and GM-CSF. In some embodiments, the modified cancer cell comprises recombinant polynucleotides encoding the HLA-A*02:01 allele and GM-CSF. In some embodiments, the modified cancer cell comprises recombinant polynucleotides encoding the HLA-A*03:01 allele and GM-CSF. In some embodiments, the modified cancer cell comprises recombinant polynucleotides encoding the HLA-A*26:01 allele and GM-CSF. In some embodiments, the modified cancer cell comprises recombinant polynucleotides encoding the HLA-A*29:02 allele and GM-CSF. In some embodiments, the modified cancer cell comprises recombinant polynucleotides encoding the HLA-A*32:01 allele and GM-CSF.

In some embodiments, the modified cancer cell comprises recombinant polynucleotides encoding the HLA-DRB3*01:01 and HLA-A*01:01 alleles and GM-CSF. In some embodiments, the modified cancer cell comprises recombinant polynucleotides encoding the HLA-DRB3*02:02 and HLA-A*01:01 alleles and GM-CSF. In some embodiments, the modified cancer cell comprises recombinant polynucleotides encoding the HLA-DRB3*03:01 and HLA-A*01:01 alleles and GM-CSF.

In some embodiments, the modified cancer cell comprises recombinant polynucleotides encoding the HLA-DRB3*01:01 and HLA-A*02:01 alleles and GM-CSF. In some embodiments, the modified cancer cell comprises recombinant polynucleotides encoding the HLA-DRB3*02:02 and HLA-A*02:01 alleles and GM-CSF. In some embodiments, the modified cancer cell comprises recombinant polynucleotides encoding the HLA-DRB3*03:01 and HLA-A*02:01 alleles and GM-CSF.

In some embodiments, the modified cancer cell comprises recombinant polynucleotides encoding the HLA-DRB3*01:01 and HLA-A*03:01 alleles and GM-CSF. In some embodiments, the modified cancer cell comprises recombinant polynucleotides encoding the HLA-DRB3*02:02 and HLA-A*03:01 alleles and GM-CSF. In some embodiments, the modified cancer cell comprises recombinant polynucleotides encoding the HLA-DRB3*03:01 and HLA-A*03:01 alleles and GM-CSF.

In some embodiments, the modified cancer cell comprises recombinant polynucleotides encoding the HLA-DRB3*01:01 and HLA-A*26:01 alleles and GM-CSF. In some embodiments, the modified cancer cell comprises recombinant polynucleotides encoding the HLA-DRB3*02:02 and HLA-A*26:01 alleles and GM-CSF. In some embodiments, the modified cancer cell comprises recombinant polynucleotides encoding the HLA-DRB3*03:01 and HLA-A*26:01 alleles and GM-CSF.

In some embodiments, the modified cancer cell comprises recombinant polynucleotides encoding the HLA-DRB3*01:01 and HLA-A*29:02 alleles and GM-CSF. In some embodiments, the modified cancer cell comprises recombinant polynucleotides encoding the HLA-DRB3*02:02 and HLA-A*29:02 alleles and GM-CSF. In some embodiments, the modified cancer cell comprises recombinant polynucleotides encoding the HLA-DRB3*03:01 and HLA-A*29:02 alleles and GM-CSF.

In some embodiments, the modified cancer cell comprises recombinant polynucleotides encoding the HLA-DRB3*01:01 and HLA-A*32:01 alleles and GM-CSF. In some embodiments, the modified cancer cell comprises recombinant polynucleotides encoding the HLA-DRB3*02:02 and HLA-A*32:01 alleles and GM-CSF. In some embodiments, the modified cancer cell comprises recombinant polynucleotides encoding the HLA-DRB3*03:01 and HLA-A*32:01 alleles and GM-CSF.

In some embodiments, the modified cancer cell comprises recombinant polynucleotides encoding the HLA-DRB3*01:01 allele and IFNa. In some embodiments, the modified cancer cell comprises recombinant polynucleotides encoding the HLA-DRB3*02:02 allele and IFNa. In some embodiments, the modified cancer cell comprises recombinant polynucleotides encoding the HLA-DRB3*03:01 allele and IFNa. In some embodiments, the modified cancer cell comprises recombinant polynucleotides encoding the HLA-A*01:01 allele and IFNa. In some embodiments, the modified cancer cell comprises recombinant polynucleotides encoding the HLA-A*02:01 allele and IFNa. In some embodiments, the modified cancer cell comprises recombinant polynucleotides encoding the HLA-A*03:01 allele and IFNa. In some embodiments, the modified cancer cell comprises recombinant polynucleotides encoding the HLA-A*26:01 allele and IFNa. In some embodiments, the modified cancer cell comprises recombinant polynucleotides encoding the HLA-A*29:02 allele and IFNa. In some embodiments, the modified cancer cell comprises recombinant polynucleotides encoding the HLA-A*32:01 allele and IFNa.

In some embodiments, the modified cancer cell comprises recombinant polynucleotides encoding the HLA-DRB3*01:01 and HLA-A*01:01 alleles and IFNa. In some embodiments, the modified cancer cell comprises recombinant polynucleotides encoding the HLA-DRB3*02:02 and HLA-A*01:01 alleles and IFNa. In some embodiments, the modified cancer cell comprises recombinant polynucleotides encoding the HLA-DRB3*03:01 and HLA-A*01:01 alleles and IFNa.

In some embodiments, the modified cancer cell comprises recombinant polynucleotides encoding the HLA-DRB3*01:01 and HLA-A*02:01 alleles and IFNa. In some embodiments, the modified cancer cell comprises recombinant polynucleotides encoding the HLA-DRB3*02:02 and HLA-A*02:01 alleles and IFNa. In some embodiments, the modified cancer cell comprises recombinant polynucleotides encoding the HLA-DRB3*03:01 and HLA-A*02:01 alleles and IFNa.

In some embodiments, the modified cancer cell comprises recombinant polynucleotides encoding the HLA-DRB3*01:01 and HLA-A*03:01 alleles and IFNa. In some embodiments, the modified cancer cell comprises recombinant polynucleotides encoding the HLA-DRB3*02:02 and HLA-A*03:01 alleles and IFNa. In some embodiments, the modified cancer cell comprises recombinant polynucleotides encoding the HLA-DRB3*03:01 and HLA-A*03:01 alleles and IFNa.

In some embodiments, the modified cancer cell comprises recombinant polynucleotides encoding the HLA-DRB3*01:01 and HLA-A*26:01 alleles and IFNa. In some embodiments, the modified cancer cell comprises recombinant polynucleotides encoding the HLA-DRB3*02:02 and HLA-A*26:01 alleles and IFNa. In some embodiments, the modified cancer cell comprises recombinant polynucleotides encoding the HLA-DRB3*03:01 and HLA-A*26:01 alleles and IFNa.

In some embodiments, the modified cancer cell comprises recombinant polynucleotides encoding the HLA-DRB3*01:01 and HLA-A*29:02 alleles and IFNa. In some embodiments, the modified cancer cell comprises recombinant polynucleotides encoding the HLA-DRB3*02:02 and HLA-A*29:02 alleles and IFNa. In some embodiments, the modified cancer cell comprises recombinant polynucleotides encoding the HLA-DRB3*03:01 and HLA-A*29:02 alleles and IFNa.

In some embodiments, the modified cancer cell comprises recombinant polynucleotides encoding the HLA-DRB3*01:01 and HLA-A*32:01 alleles and IFNa. In some embodiments, the modified cancer cell comprises recombinant polynucleotides encoding the HLA-DRB3*02:02 and HLA-A*32:01 alleles and IFNa. In some embodiments, the modified cancer cell comprises recombinant polynucleotides encoding the HLA-DRB3*03:01 and HLA-A*32:01 alleles and IFNa.

In some embodiments, the modified cancer cell comprises recombinant polynucleotides encoding the HLA-DRB3*01:01 allele, GM-CSF, and IFNa. In some embodiments, the modified cancer cell comprises recombinant polynucleotides encoding the HLA-DRB3*02:02 allele, GM-CSF, and IFNa. In some embodiments, the modified cancer cell comprises recombinant polynucleotides encoding the HLA-DRB3*03:01 allele, GM-CSF, and IFNa. In some embodiments, the modified cancer cell comprises recombinant polynucleotides encoding the HLA-A*01:01 allele, GM-CSF, and IFNa. In some embodiments, the modified cancer cell comprises recombinant polynucleotides encoding the HLA-A*02:01 allele, GM-CSF, and IFNa. In some embodiments, the modified cancer cell comprises recombinant polynucleotides encoding the HLA-A*03:01 allele, GM-CSF, and IFNa. In some embodiments, the modified cancer cell comprises recombinant polynucleotides encoding the HLA-A*26:01 allele, GM-CSF, and IFNa. In some embodiments, the modified cancer cell comprises recombinant polynucleotides encoding the HLA-A*29:02 allele, GM-CSF, and IFNa. In some embodiments, the modified cancer cell comprises recombinant polynucleotides encoding the HLA-A*32:01 allele, GM-CSF, and IFNa.

In some embodiments, the modified cancer cell comprises recombinant polynucleotides encoding the HLA-DRB3*01:01 and HLA-A*01:01 alleles, GM-CSF, and IFNa. In some embodiments, the modified cancer cell comprises recombinant polynucleotides encoding the HLA-DRB3*02:02 and HLA-A*01:01 alleles, GM-CSF, and IFNa. In some embodiments, the modified cancer cell comprises recombinant polynucleotides encoding the HLA-DRB3*03:01 and HLA-A*01:01 alleles, GM-CSF, and IFNa.

In some embodiments, the modified cancer cell comprises recombinant polynucleotides encoding the HLA-DRB3*01:01 and HLA-A*02:01 alleles, GM-CSF, and IFNa. In some embodiments, the modified cancer cell comprises recombinant polynucleotides encoding the HLA-DRB3*02:02 and HLA-A*02:01 alleles, GM-CSF, and IFNa. In some embodiments, the modified cancer cell comprises recombinant polynucleotides encoding the HLA-DRB3*03:01 and HLA-A*02:01 alleles, GM-CSF, and IFNa.

In some embodiments, the modified cancer cell comprises recombinant polynucleotides encoding the HLA-DRB3*01:01 and HLA-A*03:01 alleles, GM-CSF, and IFNa. In some embodiments, the modified cancer cell comprises recombinant polynucleotides encoding the HLA-DRB3*02:02 and HLA-A*03:01 alleles, GM-CSF, and IFNa. In some embodiments, the modified cancer cell comprises recombinant polynucleotides encoding the HLA-DRB3*03:01 and HLA-A*03:01 alleles, GM-CSF, and IFNa.

In some embodiments, the modified cancer cell comprises recombinant polynucleotides encoding the HLA-DRB3*01:01 and HLA-A*26:01 alleles, GM-CSF, and IFNa. In some embodiments, the modified cancer cell comprises recombinant polynucleotides encoding the HLA-DRB3*02:02 and HLA-A*26:01 alleles, GM-CSF, and IFNa. In some embodiments, the modified cancer cell comprises recombinant polynucleotides encoding the HLA-DRB3*03:01 and HLA-A*26:01 alleles, GM-CSF, and IFNa.

In some embodiments, the modified cancer cell comprises recombinant polynucleotides encoding the HLA-DRB3*01:

01 and HLA-A*29:02 alleles, GM-CSF, and IFNa. In some embodiments, the modified cancer cell comprises recombinant polynucleotides encoding the HLA-DRB3*02:02 and HLA-A*29:02 alleles, GM-CSF, and IFNa. In some embodiments, the modified cancer cell comprises recombinant polynucleotides encoding the HLA-DRB3*03:01 and HLA-A*29:02 alleles, GM-CSF, and IFNa.

In some embodiments, the modified cancer cell comprises recombinant polynucleotides encoding the HLA-DRB3*01:01 and HLA-A*32:01 alleles, GM-CSF, and IFNa. In some embodiments, the modified cancer cell comprises recombinant polynucleotides encoding the HLA-DRB3*02:02 and HLA-A*32:01 alleles, GM-CSF, and IFNa. In some embodiments, the modified cancer cell comprises recombinant polynucleotides encoding the HLA-DRB3*03:01 and HLA-A*32:01 alleles, GM-CSF, and IFNa.

In some embodiments, the modified cancer cell comprises recombinant polynucleotides encoding the HLA-A*11:01 allele of HLA-A and the HLA-DRB3*02:02 allele of HLA-DRB3. In some embodiments, the modified cancer cell comprises recombinant polynucleotides encoding the HLA-A*11:01 allele of HLA-A and the HLA-DRB3*01:01 allele of HLA-DRB3. In some embodiments, the modified cancer cell comprises recombinant polynucleotides encoding the HLA-A*24:02 allele of HLA-A and the HLA-DRB3*02:02 allele of HLA-DRB3. In some embodiments, the modified cancer cell comprises recombinant polynucleotides encoding the HLA-A*24:02 allele of HLA-A and the HLA-DRB3*01:01 allele of HLA-DRB3.

In some embodiments, the modified cancer cell comprises recombinant polynucleotides encoding the HLA-A*11:01 allele of HLA-A, the HLA-DRB3*02:02 allele of HLA-DRB3, and GM-CSF. In some embodiments, the modified cancer cell comprises recombinant polynucleotides encoding the HLA-A*11:01 allele of HLA-A, the HLA-DRB3*01:01 allele of HLA-DRB3, and GM-CSF. In some embodiments, the modified cancer cell comprises recombinant polynucleotides encoding the HLA-A*24:02 allele of HLA-A, the HLA-DRB3*02:02 allele of HLA-DRB3, and GM-CSF. In some embodiments, the modified cancer cell comprises recombinant polynucleotides encoding the HLA-A*24:02 allele of HLA-A, the HLA-DRB3*01:01 allele of HLA-DRB3, and GM-CSF.

In some embodiments, the modified cancer cell comprises recombinant polynucleotides encoding the HLA-A*11:01 allele of HLA-A, the HLA-DRB3*02:02 allele of HLA-DRB3, and IFNa. In some embodiments, the modified cancer cell comprises recombinant polynucleotides encoding the HLA-A*11:01 allele of HLA-A, the HLA-DRB3*01:01 allele of HLA-DRB3, and IFNa. In some embodiments, the modified cancer cell comprises recombinant polynucleotides encoding the HLA-A*24:02 allele of HLA-A, the HLA-DRB3*02:02 allele of HLA-DRB3, and IFNa. In some embodiments, the modified cancer cell comprises recombinant polynucleotides encoding the HLA-A*24:02 allele of HLA-A, the HLA-DRB3*01:01 allele of HLA-DRB3, and IFNa.

In some embodiments, the modified cancer cell comprises recombinant polynucleotides encoding the HLA-A*11:01 allele of HLA-A, the HLA-DRB3*02:02 allele of HLA-DRB3, GM-CSF, and IFNa. In some embodiments, the modified cancer cell comprises recombinant polynucleotides encoding the HLA-A*11:01 allele of HLA-A, the HLA-DRB3*01:01 allele of HLA-DRB3, GM-CSF, and IFNa. In some embodiments, the modified cancer cell comprises recombinant polynucleotides encoding the HLA-A*24:02 allele of HLA-A, the HLA-DRB3*02:02 allele of HLA-DRB3, GM-CSF, and IFNa. In some embodiments, the modified cancer cell comprises recombinant polynucleotides encoding the HLA-A*24:02 allele of HLA-A, the HLA-DRB3*01:01 allele of HLA-DRB3, GM-CSF, and IFNa.

In some embodiments, the modified human cancer cell further comprises a recombinant polynucleotide encoding granulocyte-macrophage colony-stimulating factor (GM-CSF). In some instances, the recombinant polynucleotide encoding GM-CSF is integrated into the genome of the cell. In other instances, the recombinant polynucleotide encoding GM-CSF is present on a vector. The recombinant polynucleotide encoding GM-CSF can be present on the same vector as the recombinant polynucleotides encoding one or more HLA alleles, or can be present on a different vector.

In some embodiments, the modified human cancer cell further comprises a recombinant polynucleotide encoding interferon alpha (IFNa). In some instances, the recombinant polynucleotide encoding IFNa is integrated into the genome of the cell. In other instances, the recombinant polynucleotide encoding IFNa is present on a vector. The recombinant polynucleotide encoding IFNa can be present on the same vector as the recombinant polynucleotides encoding one or more HLA alleles, or can be present on a different vector.

In some embodiments, the modified human cancer cell further comprises recombinant polynucleotides encoding GM-CSF and IFNa. In some instances, the recombinant polynucleotides encoding GM-CSF and/or IFNa are integrated into the genome of the cell. In other instances, the recombinant polynucleotides encoding GM-CSF and/or IFNa are present on a vector. The recombinant polynucleotides encoding GM-CSF and/or IFNa can be present on the same vector as the recombinant polynucleotides encoding one or more HLA alleles, or can be present on a different vector.

In some embodiments, the modified cancer cell further comprises a recombinant polypeptide encoding one or more immune-stimulatory genes. In some embodiments, the modified cancer cell further comprises a recombinant polynucleotide encoding an immune-stimulatory gene selected from the group consisting of adenosine deaminase (ADA), adhesion G protein-coupled receptor E5 (ADGRE5), caveolin 1 (CAV1), CD58 molecule (CD58), CD74 molecule (CD74), CD83 molecule (CD83), C-X-C motif chemokine ligand 8 (CXCL8), C-X-C motif chemokine ligand 16 (CXCL16), intracellular adhesion molecule 3 (ICAM3), interleukin 6 (IL6), interleukin 10 (IL10), interleukin 15 (IL15), interleukin 18 (IL18), KIT ligand (KITLG), tumor necrosis factor superfamily member 14 (TNFSF14), and a combination thereof. In particular embodiments, the modified cancer cell further comprises one or more (e.g., 1, 2, 3, 4, 5, 6, 7, 8, 9, 10, 11, 12, 13, 14, 15, or more) recombinant polynucleotides encoding an immune-stimulatory gene.

In some embodiments, the modified cancer cell further comprises a recombinant polypeptide encoding one or more cancer/testis antigen (CTA) genes. In some embodiments, the modified cancer cell further comprises a recombinant polynucleotide encoding a CTA gene selected from the group consisting of preferentially expressed antigen in melanoma (PRAME), PDZ binding kinase (PBK), centrosomal protein 55 (CEP55), kinesin family member 2C (KIF2C), placenta-specific protein 1 (PLAC1), Opa interacting protein 5 (OIP5), calcium binding tyrosine phosphorylation regulated (CABYR), sperm-associated antigen 1 (SPAG1), and a combination thereof. In particular embodiments, the modified cancer cell further comprises one or more (e.g., 1, 2, 3, 4, 5, 6, 7, 8, or more) recombinant polynucleotides encoding a CTA gene.

In some embodiments, the modified cancer cell further comprises one or more (e.g., 1, 2, 3, 4, 5, 6, 7, 8, 9, 10, 11, 12, 13, 14, 15, 16, 17, 18, 19, 20, 21, 22, 23, or more) recombinant polynucleotides encoding an immune-stimulatory and/or a CTA gene. In some embodiments, the modified cancer cell further comprises one or more polynucleotides encoding a gene selected from the group consisting of ADA, ADGRE5, CAV1, CD58, CD74, CD83, CXCL8, CXCL16, ICAM3, IL6, IL10, IL15, IL18, KITLG, TNFSF14, PRAME, PBK, CEP55, KIF2C, PLAC1, OIP5, CABYR, SPAG1, and a combination thereof. The recombinant polynucleotides encoding the immune-stimulatory and/or CTA genes can be integrated into the genome of the modified cancer cell, or can be present on one or more vectors.

In some embodiments, the modified cancer cell further comprises one or more recombinant polynucleotides encoding one or more genes set forth in Tables 1, 2, 5, 7, 8, 9, 10, 12, 13, and 14. In some instances, the modified cancer cell further comprises recombinant polynucleotide(s) In particular embodiments, the modified cancer cell comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, or more recombinant polynucleotides encoding genes set forth in Tables 1, 2, 5, 7, 8, 9, 10, 12, 13, and 14. In some instances, the modified cancer cell further comprises polynucleotides encoding PRAME, PBK, CEP55, KIF2C, ERBB2, MIEN1, PGAP3, or a combination thereof. The recombinant polynucleotides can be integrated into the genome of the modified cancer cell, or located on one or more vectors.

In preferred embodiments, the one or more HLA alleles, one or more CTA genes, one or more immune-stimulatory genes, GM-CSF-encoding gene, IFNa-encoding gene, and/or one or more additional biomarkers described herein are encoded by the recombinant polynucleotides are expressed by the cell. Expression can be transient, or in preferred embodiments expression is permanent. In some embodiments, expression of the HLA allele, CTA gene, immune-stimulatory gene, GM-CSF, IFNa, and/or additional biomarker is inducible.

In some embodiments, the human cancer cell is a human cancer cell line. Any number of human cancer cells or cancer cell lines are suitable for the present invention. Non-limiting examples of suitable human cancer cell lines include the SV-BR-1, SVCT, MDA-MB-231, MDA-MB-157, ZR-75-30, ZR-75-1, Hs 578T, MCF7, T47D, MTSV1-7 CE1, 1-7HB2, VP303, VP267, and VP229 breast cancer cell lines, the UM-UC-3, T24/83, ECV304, RT4, and HT 1197 bladder cancer cell lines, the MDST8, C170, GP5d, GP2d, and LS 123 colon cancer cell lines, the SHP-77, COR-L23/R, COR-L23/5010, MOR/0.2R, NCI-H69/LX20, ChaGo-K-1, and Meta 7 lung cancer cell lines, the MFE-280 and MFE-296 endometrial cancer cell lines, the CAKI 2, A.704, G-402, ACHN, G-401, UM-RC-7, and RCC4plusVHL renal cancer cell lines, the SK-HEP-1, Hep 3B, PLC/PRF/5, Hep G2, and Huh-7D12 liver cancer cell lines, the HL60, Eos-HL-60, JVM-13, Sci-1, and Ri-1 leukemia cell lines, the BHL-89, COR-L24, U937(CD59+), My-La CD8+, and HGC-27 lymphoma cell lines, the A375-C6, GR-M, VA-ES-BJ, MEWO, and COLO 818 skin cancer cell lines, the AsPC-1, HuP-T4, HuP-T3, BxPC-3, and CFPAC-1 pancreatic cancer cell lines, the 8505C, 8305C, FTC-238, TT, R082-W-1, and K1 thyroid cancer cell lines, the HeLa DH, HR5-CL11, HtTA-1, HR5, X1/5, HeLa, C-41, C-4 II, HeLa S3, Ca Ski, HeLa229, Hep2 (HeLa derivative), HeLa B, Bu25 TK-HeLa Ohio, and HeLa (AC-free) cervical cancer cell lines, the NB69, BE(2)-C, BE(2)-M17, SK-N-BE(2), and SK-N-DZ brain cancer cell lines, the OV7, OV17R, OV58, OV56, A2780ADR, A2780, COLO 720 E, SW 626, SK-OV-3, PA-1, 59M, OAW28, TO14, PEO23, and COV362 ovarian cancer cell lines, the IMR 32 abdominal cancer cell line, the SW 13 adrenal cortex cancer cell line, the TR146 buccal mucosa cancer cell line, the SK-GT-4 esophageal cancer cell line, the TE 671 embryonic cancer cell line, the FLYRD18 fibrosarcoma cell line, the 1411H germ cell tumor cell line, the MFM-223 mammary gland cancer cell line, the H-EMC-SS muscle cancer cell line, the Detroit 562 pharyngeal cancer cell line, the BeWo placental cancer cell line, the Mero-95 pleural cavity cancer cell line, the PC-3, LNCap clone FGC, Shmac 5, P4E6, and VCaP prostate cancer cell lines, the SW 837, SW 1463, CMT 93, HRT-18, and HRA-19 rectal cancer cell lines, the Y79, WERI, and RB247C retinal cancer cell line, the CHP-100 spinal cancer cell line, the KARPAS 1718 splenic lymphoma cell line, the AGS and KATO-III stomach cancer cell lines, the NTERA-2 clone D1 testicular cancer cell line, the SCC-9, H357, H103, BICR 56, and PE/CA-PJ49 tongue cancer cell lines, the MES-SA/Dx-5, MES-SA, COLO 685, and COLO 684 uterine cancer cell lines, and the HMVII vaginal cancer cell line. In particular embodiments, the human cancer cell line is an SV-BR-1 breast cancer cell line. In some instances, the human cancer cell line is a modified SV-BR-1-GM cancer cell line. The cell lines described herein and others are available, for example, from Sigma-Aldrich (www.sigmaaldrich.com). In some other embodiments, the modified cancer cell is obtained from a subject who is to be treated for cancer prior to modification of the cancer cell.

In some embodiments, the expression of the HLA allele(s), biomarker(s), GM-CSF, and/or IFNa are under the control of two or more different promoters. In some instances, the expression of each allele, biomarker, GM-CSF, and/or IFNa is under the control of a separate promoter. In some embodiments, the expression of the HLA allele(s), biomarker(s), GM-CSF, and/or IFNa are under the control of a single promoter. In some instances, the HLA allele(s), biomarker(s), GM-CSF, and/or IFNa are expressed as a polycistronic mRNA. In particular instances, one or more cistrons are separated by internal ribosomal entry sites.

B. Methods for Selecting Whole-Cell Cancer Vaccines

In another aspect, the present invention provides a method for selecting a whole-cell cancer vaccine for a subject having cancer. In some embodiments, the method comprises:

(a) detecting the presence or absence of one or more alleles of one or more human leukocyte antigen (HLA) genes in a sample obtained from the subject to generate an HLA allele profile of the subject;

(b) comparing the HLA allele profile of the subject to an HLA allele profile of the whole-cell cancer vaccine based on the presence or absence of the one or more alleles of one or more of the HLA genes in the whole-cell cancer vaccine; and (c) selecting the whole-cell cancer vaccine for the subject when the HLA allele profile of the subject matches the HLA allele profile of the whole-cell cancer vaccine.

In some embodiments, one or more alleles of one or more HLA class I genes are detected and are used to generate an allele profile. In other embodiments, one or more alleles of one or more HLA class II genes are detected and are used to generate an allele profile. In still other embodiments, one or more alleles of one or more HLA class I genes and one or more alleles of one or more HLA class II genes are detected and used to generate an allele profile.

In some embodiments, the HLA class I gene is an HLA-A gene, an HLA-B gene, an HLA-C gene, an HLA-E gene, an HLA-F gene, an HLA-G gene, or a B2M gene. In other embodiments, the HLA class I gene is a combination of an HLA-A gene, an HLA-B gene, an HLA-C gene, an HLA-E gene, an HLA-F gene, an HLA-G gene, and/or a B2M gene. In some embodiments, one or more (e.g., 1, 2, 3, 4, 5, 6, or 7) HLA class I genes are detected.

Examples of suitable HLA-A alleles include but are not limited to HLA-A*11:01, HLA-A*01:01, HLA-A*02:01, HLA-A*03:01, HLA-A*26:01, HLA-A*29:02, HLA-A*32:01, HLA-A*24:02, HLA-A*33:03, HLA-A*68:01, HLA-A*31:01, and HLA-A*02:06. In some embodiments, one or more (e.g., 1, 2, 3, 4, 5, 6, 7, 8, 9, 10, 11, 12, or more) HLA-A alleles are detected. In some embodiments, the one or more HLA-A alleles selected for detection are each present at a median frequency of at least about 2% in a population. In other embodiments, the one or more HLA-A alleles selected for detection are each present at a maximum frequency of at least about 5% in a population. In still other embodiments, the one or more HLA-A alleles selected for detection are each present at a median frequency of at least about 2% and a maximum frequency of at least about 5% in a population.

Examples of suitable HLA-B alleles include but are not limited to HLA-B*13:02, HLA-B*41:01, HLA-B*18:03, HLA-B*44:02, HLA-B*07:02, HLA-B*35:01, HLA-B*40:01, HLA-B*35:08, HLA-B*55:01, HLA-B*51:01, HLA-B*44:03, HLA-B*58:01, HLA-B*08:01, HLA-B*18:01, HLA-B*15:01, and HLA-B*52:01. In some embodiments, one or more (e.g., 1, 2, 3, 4, 5, 6, 7, 8, 9, 10, 11, 12, 13, 14, 15, 16, or more) HLA-B alleles are detected. In some embodiments, the one or more HLA-B alleles selected for detection are each present at a median frequency of at least about 2% in a population. In other embodiments, the one or more HLA-B alleles selected for detection are each present at a maximum frequency of at least about 5% in a population. In still other embodiments, the one or more HLA-B alleles selected for detection are each present at a median frequency of at least about 2% and a maximum frequency of at least about 5% in a population.

Examples of suitable HLA-C alleles include but are not limited to HLA-C*04:01, HLA-C*07:02, HLA-C*07:01, HLA-C*06:02, HLA-C*03:04, HLA-C*01:02, HLA-C*02:02, HLA-C*08:02, HLA-C*15:02, HLA-C*03:03, HLA-C*05:01, HLA-C*08:01, HLA-C*16:01, HLA-C*12:03, and HLA-C*14:02. In some embodiments, one or more (e.g., 1, 2, 3, 4, 5, 6, 7, 8, 9, 10, 11, 12, 13, 14, 15, or more) HLA-C alleles are detected. In some embodiments, the one or more HLA-C alleles selected for detection are each present at a median frequency of at least about 2% in a population. In other embodiments, the one or more HLA-C alleles selected for detection are each present at a maximum frequency of at least about 5% in a population. In still other embodiments, the one or more HLA-C alleles selected for detection are each present at a median frequency of at least about 2% and a maximum frequency of at least about 5% in a population.

In some embodiments, the HLA class II gene is an HLA class II alpha subunit gene. In other embodiments, the HLA class II gene is an HLA class II beta subunit gene. In particular embodiments, the HLA class II gene is a combination of HLA class II alpha subunit and HLA class II beta subunit genes.

In other embodiments, the HLA class II gene is an HLA-DP gene, an HLA-DM gene, an HLA-DO gene, an HLA-DQ gene, and/or an HLA-DR gene. In some instances, the HLA-DO gene is an HLA-DOA gene. In other instances, the HLA-DO gene is an HLA-DOB gene. In particular instances, both HLA-DOA and HLA-DOB gene alleles are detected. In some instances, the HLA-DM gene is an HLA-DMA gene. In other instances, the HLA-DM gene is an HLA-DMB gene. In particular instances, both HLA-DMA and HLA-DMB gene alleles are detected.

In some embodiments, the HLA-DR gene is an HLA-DRA gene, an HLA-DRB1 gene, an HLA-DRB3 gene, an HLA-DRB4 gene, and/or an HLA-DRB5 gene. In particular embodiments, alleles of one or more (e.g., 1, 2, 3, 4, 5, or more) HLA-DR gene(s) are detected.

Examples of suitable HLA-DRB3 alleles include but are not limited to HLA-DRB3*02:02, HLA-DRB3*01:01, and HLA-DRB3*03:01. In some embodiments, one or more (e.g., 1, 2, 3, or more) recombinant polynucleotide(s) encoding HLA-DRB3 alleles are detected. In some embodiments, the one or more HLA-DRB3 alleles selected for detection are each present at a median frequency of at least about 2% in a population. In other embodiments, the one or more HLA-DRB3 alleles selected for detection are each present at a maximum frequency of at least about 5% in a population. In still other embodiments, the one or more HLA-DRB3 alleles selected for detection are each present at a median frequency of at least about 2% and a maximum frequency of at least about 5% in a population.

In some embodiments, the allele profile comprises HLA-A*11:01 or HLA-A*24:02 alleles of HLA-A and HLA-DRB3*02:02 or HLA-DRB3*01:01 of HLA-DRB3.

In some embodiments, a whole-cell cancer vaccine is selected for the subject when there is a complete match between the HLA allele profile of the subject and the HLA allele profile of the vaccine. In some instances, all of the HLA alleles present in the profile of the subject are present in the profile of the vaccine. In other instances, all of the HLA alleles present in the profile of the vaccine are present in the profile of the subject. In other embodiments, a whole-cell cancer vaccine is selected for the subject when there is a partial match between the HLA allele profile of the subject and the HLA allele profile of the vaccine. In some instances, a partial match is present when one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, or more) alleles present in the profile of the subject are present in the profile of the vaccine. In some instances, a partial match is present when one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, or more) alleles present in the profile of the vaccine are present in the profile of the subject. In some instances, a partial match is present when there is at least about a 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% match between the allele profile of the subject and the allele profile of the vaccine.

In other embodiments, the method comprises:
 detecting the presence or level of one or more biomarkers in a sample obtained from the subject;
 comparing the presence or level of the one or more biomarkers detected in the sample obtained from the subject to the presence or level of the one or more biomarkers in a control sample; and selecting the whole-cell cancer vaccine for the subject based on the comparison, wherein the whole-cell cancer vaccine is derived from a breast cancer cell line or a breast cancer cell. In some instances, the breast cancer cell line is an SV-BR-1 breast cancer cell line.

In some other embodiments, the method comprises:
measuring the level of activity and/or number of one or more immune cells obtained from the subject;
comparing the activity and/or number of the one or more immune cells obtained from the subject to the activity and/or number of one or more immune cells in a control sample; and
selecting the whole-cell cancer vaccine for the subject based on the comparison, wherein the whole-cell cancer vaccine is derived from a breast cancer cell line or a breast cancer cell. In some instances, the breast cancer cell line is an SV-BR-1 breast cancer cell line.

In yet other embodiments, the method comprises:
detecting the presence or level of one or more biomarkers in a sample obtained from the subject; and/or
measuring the level of activity and/or number of one or more immune cells obtained from the subject;
comparing the presence or level of the one or more biomarkers detected in the sample obtained from the subject and/or the level of activity and/or number of the one or more immune cells obtained from the subject to the presence or level of the one or more biomarkers and/or the level of activity and/or number of one or more immune cells in a control sample; and
selecting the whole-cell cancer vaccine for the subject based on the comparison, wherein the whole-cell cancer vaccine is derived from a breast cancer cell line or a breast cancer cell. In some instances, the breast cancer cell line is an SV-BR-1 breast cancer cell line.

Biomarkers suitable for methods of the present invention include, but are not limited to, those set forth in Tables 1, 2, 5, 7, 8, 9, 10, 12, 13, and 14. In some embodiments, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, or biomarkers set forth in Tables 1, 2, 5, 7, 8, 9, 10, 12, 13, and 14 are detected.

In some embodiments, the presence or level of one or more immune-stimulatory genes are detected. In particular embodiments, the one or more immune-stimulatory genes are selected from the group consisting of adenosine deaminase (ADA), adhesion G protein-coupled receptor E5 (ADGRE5), caveolin 1 (CAV1), CD58 molecule (CD58), CD74 molecule (CD74), CD83 molecule (CD83), C-X-C motif chemokine ligand 8 (CXCL8), C-X-C motif chemokine ligand 16 (CXCL16), intracellular adhesion molecule 3 (ICAM3), interleukin 6 (IL6), interleukin 10 (IL10), interleukin 15 (IL15), interleukin 18 (IL18), KIT ligand (KITLG), tumor necrosis factor superfamily member 14 (TNFSF14), and a combination thereof. In particular embodiments, one or more (e.g., 1, 2, 3, 4, 5, 6, 7, 8, 9, 10, 11, 12, 13, 14, 15, or more) immune-stimulatory genes are detected.

In some embodiments, one or more cancer/testis antigen (CTA) genes are detected. In some embodiments, the one or more CTA genes are selected from the group consisting of preferentially expressed antigen in melanoma (PRAME), PDZ binding kinase (PBK), centrosomal protein 55 (CEP55), kinesin family member 2C (KIF2C), placenta-specific protein 1 (PLAC1), Opa interacting protein 5 (OIP5), calcium binding tyrosine phosphorylation regulated (CABYR), sperm-associated antigen 1 (SPAG1), and a combination thereof. In particular embodiments, one or more (e.g., 1, 2, 3, 4, 5, 6, 7, 8, or more) CTA genes are detected.

In some embodiments, one or more (e.g., 1, 2, 3, 4, 5, 6, 7, 8, 9, 10, 11, 12, 13, 14, 15, 16, 17, 18, 19, 20, 21, 22, 23, or more) immune-stimulatory and/or a CTA genes are detected. In some embodiments, one or more genes selected from the group consisting of ADA, ADGRE5, CAV1, CD58, CD74, CD83, CXCL8, CXCL16, ICAM3, IL6, IL10, IL15, IL18, KITLG, TNFSF14, PRAME, PBK, CEP55, KIF2C, PLAC1, OIP5, CABYR, SPAG1, are detected.

In some embodiments, the one or more biomarkers that are detected are selected from the group consisting of preferentially expressed antigen in melanoma (PRAME), PDZ binding kinase (PBK), centrosomal protein 55 (CEP55), kinesin family member 2C (KIF2C), placenta-specific protein 1 (PLAC1), Opa interacting protein 5 (OIP5), calcium binding tyrosine phosphorylation regulated (CABYR), sperm-associated antigen 1 (SPAG1), alpha-1,3-glucosyltransferase (ALG8), actin-related protein 2/3 complex, subunit 5-like (ARPC5L), chromobox homolog 2 (CBX2), collagen type VIII alpha 1 chain (COL8A1), DDB1 and CUL4 associated factor 10, (DCAF10), eukaryotic translation initiation factor 3 subunit H (EIF3H), erb-b2 receptor tyrosine kinase 2 (ERBB2), histone cluster 1 H4 family member h (HIST1H4H), insulin like growth factor binding protein 5 (IGFBP5), integrator complex subunit 7 (INTS7), keratin 19 (KRT19), keratin 81 (KRT81), mannosyl (alpha-1,3-)-glycoprotein beta-1,4-N-acetylglucosaminyltransferase, isozyme A (MGAT4A), migration and invasion enhancer 1 (MIEN1), post-GPI attachment to proteins 3 (PGAP3), remodeling and spacing factor 1 (RSF1), SH2 domain containing adaptor protein B (SHB), soluble carrier family 35, member A2 (SLC35A2), spectrin repeat containing nuclear envelope family member 4 (SYNE4), transportin 1 (TNPO1), and a combination thereof. In some instances, the one or more biomarkers that are selected are selected from the group consisting of PRAME, PBK, CEP55, KIF2C, ERBB2, MIEN1, PGAP3, and a combination thereof. In particular instances, the one or more biomarkers is PRAME. In other instances, the one or more biomarkers is selected from the group consisting of ERBB2, MIEN1, PGAP3, and a combination thereof.

Some serum/plasma biomarkers ("analytes") associated with the present invention are provided below in Table 1. The levels of the analytes in fluids such as serum or plasma can be measured via Luminex multiplex assays. Recommended dilutions for polystyrene and magnetic bead assays can be obtained from www.rndsystems.com/luminex/analytes. It should be noted that while the analytes associated with the present invention are classified as "serum/plasma biomarkers" in Table 1, the levels of these biomarkers may also be assessed in other biofluids, such as urine.

TABLE 1

| Serum/Plasma Biomarkers |
|---|
| Analyte |
| 4-1BB/CD137 |
| NAGLU |
| ADAMTS13 |
| Adiponectin |
| alpha-Fetoprotein |

TABLE 1-continued

Serum/Plasma Biomarkers

Analyte

Aggrecan
AgRP/ART
ALDH1A1
alpha 1-Microglobulin
Amphiregulin
Angiogenin
Angiopoietin-1
Angiopoietin-2
ANGPTL3
ANGPTL4
Angiopoietin-like 6 (ANGPTL6)
ApoA1
APP
APRIL
NT-Pro-ANP
beta 2-Microglobulin
B7-H1/PD-L1
BAFF/BLyS
BCMA
BDNF
BMP-2
BMP-4
BMP-9
CRP
CA125/MUC16
CA15-3
N-Cadherin
Calbindin D
Carbonic Anhydrase IX/CA9
Cathepsin D
Total Cathepsin S
CCL1/I-309
CCL2/MCP-1
CCL3/MIP-1 alpha
CCL4/MIP-1 beta
CCL5/RANTES
CCL7/MCP-3
CCL8/MCP-2
CCL11/Eotaxin
CCL13/MCP-4
CCL14/HCC-1/HCC-3
CCL17/TARC
CCL18/PARC
CCL19/MIP-3 beta
CCL20/MIP-3 alpha
CCL21/6Ckine
CCL22/MDC
CCL24/Eotaxin-2
CCL25/TECK
CCL26/Eotaxin-3
CCL27/CTACK
CCL28
CD14
CD23/Fc epsilon RII
CD27
CD30
CD31/PECAM-1
CD40
CD40 Ligand
CD44
CD117/c-kit
CD163
CD25/IL-2 R alpha
CEACAM-1/CD66a
CEA/CEACAM-5
Chemerin
CHI3L1/YKL-40
Factor XIV/Protein C
Collagen I alpha 1/COL1A1
Collagen IV alpha 1
C5/C5a
C9
Factor D/Adipsin
Contactin-1
Cripto-1
CX3CL1/Fractalkine TABLE 1-continued Serum/Plasma Biomarkers Analyte CXCL1/GRO alpha
CXCL2/Gro beta
CXCL4/PF4
CXCL5/ENA-78
CXCL6/GCP-2
CXCL7/NAP-2
CXCL8/IL-8
CXCL9/MIG
CXCL10/IP-10
CXCL11/I-TAC
CXCL12/SDF-1 alpha
CXCL13/BLC/BCA-1
CXCL14/BRAK
CXCL16
Cystatin C
D-dimer
DcR3
Dkk-1
DPPIV
DR3
EGF
EMMPRIN
EN-RAGE/S100A12
Endocan/ESM-1
Endoglin
Endostatin
Endothelin-1
Enolase 2/NSE
ENPP-2/Autotaxin
EpCAM/TROP-1
EphA2
ErbB2/Her2
ErbB3/Her3
Epo
ESAM
FABP1/L-FABP
FABP3/H-FABP
FABP4/A-FABP
Fas
Fas Ligand
Ferritin
Fetuin A/AHSG
FGF acidic
FGF basic
FGF-13 1B
FGF-21
FGF-23
Fibroblast Activation Protein
Fibronectin
Flt-3 Ligand
Follistatin
Follistatin-like 1
FLRG
G-CSF
Galectin-1
Galectin-3
Galectin-3BP
Galectin-9
Gas6
GDF-15
GDNF
GFAP
GITR
Glucagon
GM-CSF
gp130
Granzyme A
Granzyme B
Growth Hormone
HB-EGF
HE4/WFDC-2
HGF
HGF R/c-MET
HTRA2/Omi
ICAM-1
IFN-beta TABLE 1-continued Serum/Plasma Biomarkers Analyte IFN-gamma
IFN-gamma R1
IGFBP-1
IGFBP-2
IGFBP-3
IGFBP-4
IGFBP-6
IGFBP-rp1/IGFBP-7
IL-1 alpha
IL-1 beta
IL-1ra
IL-1 RI
IL-1 RII
IL-2
IL-3
IL-4
IL-4 R alpha
IL-5
IL-6
IL-6 R alpha
IL-7
IL-9
IL-10
IL-11
IL-12 p70
IL-12/23 p40
IL-13
IL-15
IL-16
IL-17A
IL-17C
IL-17E/IL-25
IL-17F
IL-18
IL-18 BPa
IL-19
IL-21
IL-22
IL-23
IL-27
IL-28A/IFN-lambda 2
IL-28B/IFN-lambda 3
IL-31
IL-33
IL-34
IL-36 beta/IL-1F8
Total Inhibin
Insulin
Insulin C-Peptide
ITIH4
Kallikrein 3/PSA
Kallikrein 5
Kallikrein 6/Neurosin
Lactoferrin
LBP
Leptin
LIF
LIGHT
Lipocalin-2/NGAL
LRG1
Lumican
Lymphotoxin-alpha/TNF-beta
M-CSF
MAdCAM-1
MBL
MCAM/CD146
Mesothelin
MFG-E8
MIA
MICA
MICB
Midkine
MIF
MMP-1
MMP-2
MMP-3

TABLE 1-continued

Serum/Plasma Biomarkers

Analyte

MMP-7
MMP-8
MMP-9
MMP-10
MMP-12
MMP-13
MSP/MST1
MPO
Cardiac Myoglobin
NCAM-1/CD56
Nectin-4
Nephrin
NRG1 beta 1
Neuropilin-1
NT-4
OSM
Osteopontin
Osteoprotegerin
Park7/DJ-1
PBEF/Visfatin
PDGF-AA
PDGF-AB
PDGF-BB
PDGF-CC
PDGF-DD
Pentraxin 3
Periostin/OSF-2
PLA2G7/Lp-PLA2
PlGF
PP14/Glycodelin
Procalcitonin
Progranulin
Prolactin
Properdin
PCSK9
Protein S/PROS1
Proteinase 3/PRTN3
RAGE
RBP4
Reg3A
Relaxin-2
Renin
Resistin
ROBO4
S100A8
S100B
SCF
SCGF/CLEC11a
E-Selectin
L-Selectin
P-Selectin
Serpin A7/TBG
Serpin A10/ZPI
Serpin A12/Vaspin
Serpin B3/SCCA1
Serpin C1/Antithrombin-III
Serpin E1/PAI-1
Serpin F1/PEDF
Serum Amyloid A1
SHBG
SLPI
SOST
SP-D
SPARC/Osteonectin
ST2
Syndecan-1/CD138
Syndecan-4
Synuclein-alpha
TACI
Tau
Tenascin C
TFF3
TFPI
TGF-alpha
Tpo
Thrombospondin-2

TABLE 1-continued

Serum/Plasma Biomarkers

Analyte

Thymidine Kinase 1/TK1
Tie-1
Tie-2
TIM-1/KIM-1
TIMP-1
TNF-alpha
TNF RI
TNF RII
TRAIL
TRAIL R2/DR5
TRAIL R3
TRANCE/RANK L
TfR
TREM-1
Cardiac Troponin I/cTNI
TWEAK
uPA/Urokinase
PARK5/UCH-L1
ULBP-1
ULBP-2/5/6
ULBP-3
ULBP-4
uPAR
Uromodulin
Uteroglobin
VAP-1
VCAM-1
VEGF
VEGF-C
VEGF-D
VEGF R1/FLT1
VEGF R2/KDR
VEGF R3
Vitamin D BP
vWF-A2
XCL1/Lymphotactin In some embodiments, the vaccine is selected for the subject when the level of at least one of the one or more biomarkers is overexpressed in the sample obtained from the subject compared to the control sample. In some instances the control sample comprises a normal cell or tissue obtained from the subject. In other instances, the control sample comprises a normal cell or tissue obtained from a different subject or from a population of subjects. Populations of subjects can be used to establish reference ranges for comparisons.

In some embodiments, the vaccine is selected for the subject when one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, or more) biomarkers are overexpressed compared to the control sample. In other embodiments, the vaccine is selected for the subject when the level(s) of the one or more biomarkers are at least about 1.5-fold (e.g., about 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, 17-fold, 18-fold, 19-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold, or more) higher compared to the control sample. In some instances, the vaccine is selected for the subject when at least one of the one or more biomarkers is overexpressed at least about 1.5-fold compared to the control sample.

In some embodiments, the vaccine is selected for the subject when the level of activity and/or number of the one or more immune cells obtained from the subject is higher compared to the control sample. In some instances, the control sample comprises one or more immune cells obtained from a different subject who does not have cancer or a population of subjects who do not have cancer. Populations of subjects can be used to establish reference ranges for use in comparisons. In other embodiments, the vaccine is selected for the subject when the level of activity and/or number of the immune cells obtained from the subject is at least about 1.5-fold (e.g., about 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, 17-fold, 18-fold, 19-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold, or more) higher compared to the control sample. In some instances, the vaccine is selected for the subject when the level(s) of activity and/or number of the one or more immune cells obtained from the subject are at least about 1.5-fold higher compared to the control sample.

Any number of immune cell types can be used to select a whole-cell cancer vaccine for a subject according to methods of the present invention. Non-limiting examples of suitable cells include peripheral blood mononuclear cells (PBMCs), lymphocytes (e.g., T lymphocytes, B lymphocytes, natural killer (NK) cells), monocytes, dendritic cells, macrophages, and myeloid-derived suppressor cells (MDSCs). In some embodiments, the one or more immune cells in which the level of activity and/or number is measured is selected from the group consisting of PBMCs, lymphocytes (e.g., T lymphocytes, B lymphocytes, natural killer (NK) cells), and/or dendritic cells.

Methods of detecting the presence or level of the biomarkers of the present invention will be known to one of skill in the art. Detecting the presence or level of biomarkers can comprise, for example, measuring DNA levels (e.g., genomic DNA copy number, mRNA or cDNA quantification) or protein levels (e.g., quantifying the amount of protein that is present in a sample, measuring the amount of protein activation or modification, or detecting antibodies). In some embodiments, the presence or level of biomarkers are detected using a method selected from the group consisting of quantitative PCR, microarray analysis, an ELISA, a radioimmunoassay (MA), immunoprecipitation, immunofluorescence, FACS analysis, electrochemiluminescence, a multiplex bead assay (e.g., using Luminex or fluorescent microbeads), immunohistochemistry, a Western blot, a dot blot, and a combination thereof.

Methods of detecting the level of immune cell activity and/or number will be known to one of skill in the art. Non-limiting examples of suitable methods include antibody detection (e.g., using an ELISA or Western blot), a cytotoxic T lymphocyte (CTL) activity assay (e.g., chromium release assay, IFN-γ ELISpot assay, or a multifactor flow cytometry-based assay), a cytotoxicity assay, a proliferation assay (e.g., a thymidine incorporation assay, a colorimetric assay (e.g., an MTT assay, a WST1 assay, or a resazurin assay), or an ATP quantification assay (e.g., a bioluminescent-based ATP detection assay)), a cytokine production assay (e.g., an ELISpot assay or an ELISA (e.g., on culture supernatant or serum)), a flow cytometry assay, and an MHC multimer assay. In an MHC multimer assay, a multimer of fluorescently-labeled peptide-MHC complexes are used to stain cells such as peptide-specific T cells. The peptide can be, for example, a tumor-associated antigen (TAA) such as PRAME or other biomarker. Typically, the multimer is a tetramer or pentamer, although other configurations are possible. In some instances, the conjugation of fluorophores or beads (e.g., magnetic beads) allows isolation and/or sorting of the T lymphocytes (e.g., using flow cytometry).

In some embodiments, an antibody or plurality thereof used to detect the biomarker(s), measure immune cell activity or number, or perform HLA typing can be immobilized on a solid support. The solid support can be, for example, a multiwell plate, a microarray, a chip, a bead, a porous strip, or a nitrocellulose filter. In some instances, the bead comprises chitin. The immobilization can be via covalent or non-covalent binding.

Labeled secondary antibodies can be used to detect binding between antibodies and biomarkers, immune cells, and/or HLA antigens. Secondary antibodies bind to the constant or "C" regions of different classes or isotypes of immunoglobulins IgM, IgD, IgG, IgA, and IgE. Usually, a secondary antibody against an IgG constant region is used in the present methods. Secondary antibodies against the IgG subclasses, for example, IgG1, IgG2, IgG3, and IgG4, also find use in the present methods. Secondary antibodies can be labeled with any directly or indirectly detectable moiety, including a fluorophore (e.g., fluorescein, phycoerythrin, quantum dot, Luminex bead, fluorescent bead), an enzyme (e.g., peroxidase, alkaline phosphatase), a radioisotope (e.g., $^3$H, $^{32}$P, $^{125}$I) or a chemiluminescent moiety. Labeling signals can be amplified using a complex of biotin and a biotin binding moiety (e.g., avidin, streptavidin, neutravidin). Fluorescently labeled anti-human IgG antibodies are commercially available, e.g., from Molecular Probes (Eugene, Oreg.). Enzyme-labeled anti-human IgG antibodies are commercially available, e.g., from Sigma-Aldrich (St. Louis, Mo.) and Chemicon (Temecula, Calif.).

General immunoassay techniques are well known in the art. Guidance for optimization of parameters can be found in, for example, Wu, Quantitative Immunoassay: A Practical Guide for Assay Establishment, Troubleshooting, and Clinical Application, 2000, AACC Press; Principles and Practice of Immunoassay, Price and Newman, eds., 1997, Groves Dictionaries, Inc.; The Immunoassay Handbook, Wild, ed., 2005, Elsevier Science Ltd.; Ghindilis, Pavlov and Atanassov, Immunoassay Methods and Protocols, 2003, Humana Press; Harlow and Lane, Using Antibodies: A Laboratory Manual, 1998, Cold Spring Harbor Laboratory Press; and Immunoassay Automation: An Updated Guide to Systems, Chan, ed., 1996, Academic Press.

In certain embodiments, the presence or decreased or increased presence of one or more biomarkers, immune cells, and/or HLA antigens is indicated by a detectable signal (e.g., a blot, fluorescence, chemiluminescence, color, radioactivity) in an immunoassay. This detectable signal can be compared to the signal from a control sample or to a threshold value In some embodiments, the results of the biomarker presence or level determinations, immune cell measurements, and/or HLA typing are recorded in a tangible medium. For example, the results can be recorded, e.g., on paper or on electronic media (e.g., audio tape, a computer disk, a CD, a flash drive, etc.).

In some embodiments, immune cells are stimulated (e.g., in vitro stimulation of isolated immune cells) before the activity and/or number is measured. In some instances, the immune cells are stimulated with an antigenic protein such as a TAA (e.g., PRAME) or other biomarker protein described herein. In particular instances, the immune cells are stimulated by being exposed to whole cells (e.g., cancer cells or modified cancer cells).

In some embodiments, the one or more biomarkers comprise one or more alleles of one or more HLA genes, as described herein. In particular embodiments, the vaccine is selected for the subject when one or more alleles of one or more HLA genes in the sample obtained from the subject match one or more alleles of one or more HLA genes in the vaccine. The match can be a complete match or a partial match, as described herein.

HLA typing methods, which will be known to one of skill in the art, are generally divided into phenotyping and genotyping methods. Typically, phenotyping methods involve the use of monoclonal antibodies to detect HLA antigens, although serological methods (e.g., complement-dependent cytotoxicity assays) are also known. Genotyping methods typically involve PCR amplification of HLA alleles. Following amplification, high-resolution sequence-based typing methods or low-resolution methods such as sequence-specific primer typing or sequence-specific oligonucleotide probe methods can be used.

In some embodiments, the sample obtained from the subject comprises whole blood, plasma, serum, cerebrospinal fluid, tissue, saliva, buccal cells, tumor tissue, a biofluid (e.g., urine, a pleural effusion sample), hair, skin, or a combination thereof. For HLA typing, any cell, tissue, or biofluid type is suitable, as long as it contains a sufficient amount of DNA or RNA to allow typing. In some instances, the sample comprises circulating tumor cells (CTCs). The sample can also be made up of a combination of normal and cancer cells.

Samples can be obtained by biopsy, from a surgical resection, as a fine needle aspirate, or any other method that yields a sufficient number of cells or amount of tissue such that detection of biomarkers, measurement of immune cell activity and/or number, or HLA typing is enabled.

C. Compositions

In another aspect, the present invention provides a composition comprising a modified human cancer cell of the present invention described herein. The modified cancer cell can comprise one or more alleles of one or more HLA class I genes, one or more alleles of one or more HLA class II genes, or a combination thereof, as described herein. In some embodiments, the modified cancer cell further comprises one or more recombinant polynucleotides encoding one or more biomarkers described herein. In some instances, the one or more biomarkers comprise one or more CTA genes and/or one or more immune-stimulatory genes. In some embodiments, the HLA allele(s) and/or biomarkers are expressed by the modified human cancer cell. Expression can be transient or permanent. In some cases, expression is inducible.

In some embodiments, the composition further comprises granulocyte-macrophage colony-stimulating factor (GM-CSF). In particular embodiments, the GM-CSF is encoded by a recombinant polynucleotide and expressed by a modified cell. In particular instances, the GM-CSF is expressed by the same modified cell (i.e., modified cancer cell) that comprises the recombinant polynucleotide encoding an allele of a human leukocyte antigen (HLA) class I and/or class II gene. In other instances, the GM-CSF is not expressed by the same modified cell (e.g., modified cancer cell) that comprises the recombinant polynucleotide encoding an allele of a human leukocyte antigen (HLA) class I and/or class II gene. In some embodiments, the GM-CSF is present in the composition in a soluble form.

In some embodiments, the composition further comprises interferon alpha (IFNa). In particular embodiments, the IFNa is expressed by the same modified cell (e.g., modified cancer cell) that comprises the recombinant polynucleotide encoding an allele of a human leukocyte antigen (HLA) class I and/or class II gene. In other embodiments, the IFNa is expressed by different cells that have been modified to express IFNa. In some embodiments, the IFNa is present in a soluble form.

In some embodiments, the human cancer cell is a human cancer cell line. Any number of human cancer cell lines are suitable for the present invention, as described herein. In particular embodiments, the human cancer cell line is an SV-BR-1 breast cancer cell line. In some instances, the human cancer cell line is a modified SV-BR-1-GM cancer cell line In another aspect, the present invention provides a pharmaceutical composition. In some embodiments, the pharmaceutical composition comprises a composition described herein and a pharmaceutically acceptable carrier. The formulation of pharmaceutical compositions is generally known in the art (see, e.g., REMINGTON'S PHARMACEUTICAL SCIENCES, 18TH ED., Mack Publishing Co., Easton, Pa. (1990)). Prevention against microorganism contamination can be achieved through the addition of one or more of various antibacterial and antifungal agents.

Pharmaceutical forms suitable for administration include sterile aqueous solutions or dispersions and sterile powders for the extemporaneous preparation of sterile injectable solutions or dispersions. Typical carriers include a solvent or dispersion medium containing, for example, water-buffered aqueous solutions (i.e., biocompatible buffers, non-limiting examples of which include Lactated Ringer's solution and CryoStor cryopreservation media (e.g., CS2, CS5, and CS10, containing 2%, 5%, and 10%, respectively of DMSO; available from BioLife Solutions, Bothell, Wash.)), ethanol, polyols such as glycerol, propylene glycol, polyethylene glycol, suitable mixtures thereof, surfactants, or vegetable oils.

Sterilization can be accomplished by an art-recognized technique, including but not limited to addition of antibacterial or antifungal agents, for example, paraben, chlorobutanol, sorbic acid or thimerosal. Further, isotonic agents such as sugars or sodium chloride may be incorporated in the subject compositions.

Production of sterile injectable solutions containing modified cancer cell(s), and/or other composition(s) of the present invention can be accomplished by incorporating the compound(s) in the required amount(s) in the appropriate solvent with various ingredients enumerated above, as required, followed by sterilization. To obtain a sterile powder, the above sterile solutions can be vacuum-dried or freeze-dried as necessary.

In some embodiments, the modified cancer cell(s), and/or other composition(s) provided herein are formulated for administration, e.g., intradermal injection, intralymphatic injection, oral, nasal, topical, or parental administration in unit dosage form for ease of administration and uniformity of dosage. Unit dosage forms, as used herein, refers to physically discrete units suited as unitary dosages for the subjects, e.g., humans or other mammals to be treated, each unit containing a predetermined quantity of active material calculated to produce the desired therapeutic effect in association with the required pharmaceutical carrier. In some instances, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the modified cancer cell(s), and/or other composition(s).

A dose may include, for example, about 50,000 to 50,000,000 (e.g., about 50,000, 60,000, 70,000, 80,000, 90,000, 100,000, 110,000, 120,000, 130,000, 140,000, 150,000, 160,000, 170,000, 180,000, 190,000, 200,000, 250,000, 300,000, 350,000, 400,000, 450,000, 500,000, 550,000, 600,000, 650,000, 700,000, 750,000, 800,000, 850,000, 900,000, 950,000, 1,000,000, 1,500,000, 2,000,000, 2,500,000, 3,000,000, 3,500,000, 4,000,000, 4,500,000, 5,000,000, 5,500,000, 6,000,000, 6,500,000, 7,000,000, 7,500,000, 8,000,000, 8,500,000, 9,000,000, 9,500,000, 10,000,000, 11,000,000, 12,000,000, 13,000,000, 14,000,000, 15,000,000, 16,000,000, 17,000,000, 18,000,000, 19,000,000, 20,000,000, 25,000,000, 30,000,000, 35,000,000, 40,000,000, 45,000,000, 50,000,000, or more) modified cancer cells. In some embodiments, a dose may contain about 5,000,000 modified cancer cells.

A dose may also include, for example, at least about 5,000,000 to 100,000,000 (e.g., about 5,000,000, 6,000,000, 7,000,000, 8,000,000, 9,000,000, 10,000,000, 15,000,000, 20,000,000, 25,000,000, 30,000,000, 35,000,000, 40,000,000, 45,000,000, 50,000,000, 55,000,000, 60,000,000, 65,000,000, 70,000,000, 75,000,000, 80,000,000, 85,000,000, 90,000,000, 95,000,000, 100,000,000, or more) modified cancer cells.

A dose may alternatively include, for example, at least about 100,000,000 to 1,000,000,000 (e.g., about 100,000,000, 150,000,000, 200,000,000, 250,000,000, 300,000,000, 350,000,000, 400,000,000, 450,000,000, 500,000,000, 550,000,000, 600,000,000, 650,000,000, 700,000,000, 750,000,000, 800,000,000, 850,000,000, 900,000,000, 950,000,000, 1,000,000,000, or more) modified cancer cells.

In some embodiments, the modified cancer cells are irradiated. The irradiation dose may be, for example, between about 2 and 2,000 Gy (e.g., about, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150, 160, 170, 180, 190, 200, 210, 220, 230, 240, 250, 260, 270, 280, 290, 300, 350, 400, 450, 500, 550, 600, 650, 700, 750, 800, 850, 900, 950, 1,000, 1,100, 1,200, 1,300, 1,400, 1,500, 1,600, 1,700, 1,800, 1,900, or 2,000 Gy). In particular embodiments, the modified cancer cells are irradiated with a dose of about 200 Gy.

Methods for preparing such dosage forms are known to those skilled in the art (see, e.g., REMINGTON'S PHARMACEUTICAL SCIENCES, supra). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., REMINGTON'S PHARMACEUTICAL SCIENCES, supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

In some embodiments, the composition for administration may be an oral delivery vehicle such as a capsule, cachet or tablet, each of which contains a predetermined amount of the composition to provide the correct incremental dose to the patient. Oral delivery vehicles may be useful, for example, in avoiding contact between the composition and the mouth and upper gastrointestinal tract. For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the therapeutically effective dose takes the form of a pill, tablet, or capsule, and thus, the dosage form can contain, along with the modified cancer cell(s), and/or other composition(s) described herein, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof.

In some embodiments, a suitable carrier masks the composition, e.g., the modified cancer cell(s), and/or other composition(s) from the mouth and upper gastrointestinal (GI) tract and reduces or prevents local itching/swelling reactions in these regions during administration. For example, a carrier may contain one or more lipid, polysaccharide or protein constituents. In some cases, the carrier is a food product.

For topical administration, the therapeutically effective dose can be in the form of emulsions, lotions, gels, foams, creams, jellies, solutions, suspensions, ointments, and transdermal patches. For administration by inhalation, the modified cancer cell(s), and/or other composition(s) described herein can be delivered as a dry powder or in liquid form via a nebulizer. Aerosol formulations can be placed into pressurized acceptable propellants such as dichlorodifluoromethane. For parenteral administration, the therapeutically effective dose can be in the form of sterile injectable solutions and sterile packaged powders. Preferably, injectable solutions are formulated at a pH of from about 4.5 to about 7.5.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to an individual.

In some embodiments, the therapeutically effective dose may further comprise other components, for example, anti-allergy drugs, such as antihistamines, steroids, bronchodilators, leukotriene stabilizers and mast cell stabilizers. Suitable anti-allergy drugs are well known in the art.

D. Methods for Treating Cancer

In another aspect, the present invention provides a method for treating cancer in a subject. In some embodiments, the method comprises administering to the subject a therapeutically effective amount of a pharmaceutical composition of the present invention (e.g., a pharmaceutical composition comprising modified cancer cells of the present invention) described herein.

In some embodiments, the method further comprises administering to the subject one or more additional therapies. Examples of suitable additional types include, but are not limited to, chemotherapy, immunotherapy, radiotherapy, hormone therapy, a differentiating agent, and a small-molecule drug. One of skill in the art will readily be able to select an appropriate additional therapy.

Chemotherapeutic agents that can be used in the present invention include but are not limited to alkylating agents (e.g., nitrogen mustards (e.g., mechlorethamine, chlorambucil, cyclophosphamide, ifosfamide, melphalan), nitrosoureas (e.g., streptozocin, carmustine (BCNU), lomustine), alkyl sulfonates (e.g., busulfan), triazines (e.g., dacarbazine (DTIC), temozlomide), ethylenimines (e.g., thiotepa, altretamine (hexamethylmelamine))), platinum drugs (e.g., cisplatin, carboplatin, oxalaplatin), antimetabolites (e.g., 5-fluorouracil (5-FU), 6-mercaptopurine (6-MP), capecitabine, cytarabine, floxuridine, fludarabine, gemcitabine, hydroxyurea, methotrexate, pemetrexed), anthracycline anti-tumor antibiotics (e.g., daunorubicin, doxorubicin, epirubicin, idarubicin), non-anthracycline anti-tumor antibiotics (e.g., actinomycin-D, bleomycin, mitomycin-C, mitoxantrone), mitotic inhibitors (e.g., taxanes (e.g., paclitaxel, docetaxel), epothilones (e.g., ixabepilone), vinca alkaloids (e.g., vinblastine, vincristine, vinorelbine), estramustine), corticosteroids (e.g., prednisone, methylprednisolone, dexamethasone), L-asparaginase, bortezomib, and topoisomerase inhibitors. Combinations of chemotherapeutic agents can be used.

Topoisomerase inhibitors are compounds that inhibit the activity of topoisomerases, which are enzymes that facilitate changes in DNA structure by catalyzing the breaking and rejoining of phosphodiester bonds in the backbones of DNA strands. Such changes in DNA structure are necessary for DNA replication during the normal cell cycle. Topoisomerase inhibitors inhibit DNA ligation during the cell cycle, leading to an increased number of single- and double-stranded breaks and thus a degradation of genomic stability. Such a degradation of genomic stability leads to apoptosis and cell death.

Topoisomerases are often divided into type I and type II topoisomerases. Type I topoisomerases are essential for the relaxation of DNA supercoiling during DNA replication and transcription. Type I topoisomerases generate DNA single-strand breaks and also religate said breaks to re-establish an intact duplex DNA molecule. Examples of inhibitors of topoisomerase type I include irinotecan, topotecan, camptothecin, and lamellarin D, which all target type IB topoisomerases.

Type II topoisomerase inhibitors are broadly classified as topoisomerase poisons and topoisomerase inhibitors. Topoisomerase poisons target topoisomerase-DNA complexes, while topoisomerase inhibitors disrupt enzyme catalytic turnover. Examples of type II topoisomerase inhibitors include amsacrine, etoposide, etoposide phosphate, teniposide, doxorubicin, and fluoroquinolones.

In some embodiments, the chemotherapeutic agent is a topoisomerase inhibitor. In some instances, the topoisomerase inhibitor is a topoisomerase I inhibitor, a topoisomerase II inhibitor, or a combination thereof. In particular embodiments, the topoisomerase inhibitor is selected from the group consisting of doxorubicin, etoposide, teniposide, daunorubicin, mitoxantrone, amsacrine, an ellipticine, aurintricarboxylic acid, HU-331, irinotecan, topotecan, camptothecin, lamellarin D, resveratrol, genistein, quercetin, epigallocatechin gallate (EGCG), and a combination thereof. EGCG is one example of a plant-derived natural phenol that serves as a suitable topoisomerase inhibitor. In some instances, the topoisomerase inhibitor is doxorubicin.

Immunotherapy refers to any treatment that uses the subject's immune system to fight a disease (e.g., cancer). Immunotherapy methods can be directed to either enhancing or suppressing immune function. In the context of cancer therapies, immunotherapy methods are typically directed to enhancing or activating immune function. In some instances, an immunotherapeutic agent comprises a monoclonal antibody that targets a particular type or part of a cancer cell. In some cases, the antibody is conjugated to a moiety such as a drug molecule or a radioactive substance. Antibodies can be derived from mouse, chimeric, or humanized, as non-limiting examples. Non-limiting examples of therapeutic monoclonal antibodies include alemtuzumab, bevacizumab, cetuximab, daratumumab, ipilimumab (MDX-101), nivolumab, ofatumumab, panitumumab, pembrolizumab, rituximab, tositumomab, and trastuzumab.

Immunotherapeutic agents can also comprise an immune checkpoint inhibitor, which modulates the ability of the immune system to distinguish between normal and "foreign" cells. Programmed cell death protein 1 (PD-1) and protein death ligand 1 (PD-L1) are common targets of immune checkpoint inhibitors, as disruption of the interaction between PD1 and PD-L1 enhance the activity of immune cells against foreign cells such as cancer cells. Examples of PD-1 inhibitors include pembrolizumab and nivolumab. An example of a PD-L1 inhibitor is atezolizumab.

Another immune checkpoint target for the treatment of cancer is cytotoxic T lymphocyte-associated protein 4 (CTLA-4), which is a receptor that downregulates immune cell responses. Therefore, drugs that inhibit CTLA-4 can increase immune function. An example of such a drug is ipilimumab, which is a monoclonal antibody that binds to and inhibits CTLA-4.

The term "radiotherapy" refers to the delivery of high-energy radiation to a subject for the treatment of a disease (e.g., cancer). Radiotherapy can comprise the delivery of X-rays, gamma rays, and/or charged particles. Radiotherapy can be delivered locally (e.g. to the site or region of a tumor), or systemically (e.g., a radioactive substance such as radioactive iodine is administered systemically and travels to the site of the tumor).

The term "hormone therapy" can refer to an inhibitor of hormone synthesis, a hormone receptor antagonist, or a hormone supplement agent. Inhibitors of hormone synthesis include but are not limited to aromatase inhibitors and gonadotropin releasing hormone (GnRH) analogs. Hormone receptor antagonists include but are not limited to selective receptor antagonists and antiandrogen drugs. Hormone supplement agents include but are not limited to progestogens, androgens, estrogens, and somatostatin analogs. Aromatase inhibitors are used, for example, to treat breast cancer. Non-limiting examples include letrozole, anastrozole, and aminoglutethimide. GnRH analogs can be used, for example, to induce chemical castration. Selective estrogen receptor antagonists, which are commonly used for the treatment of breast cancer, include tamoxifen, raloxifene, toremifene, and fulvestrant. Antiandrogen drugs, which bind to and inhibit the androgen receptor, are commonly used to inhibit the growth and survival effects of testosterone on prostate cancer. Non-limiting examples include flutamide, apalutamide, and bicalutamide.

The term "differentiating agent" refers to any substance that promotes cell differentiation, which in the context of cancer can promote malignant cells to assume a less stem cell-like state. A non-limiting example of an anti-cancer differentiating agent is retinoic acid.

Small molecule drugs generally are pharmacological agents that have a low molecular weight (i.e., less than about 900 daltons). Non-limiting examples of small molecule drugs used to treat cancer include bortezomib (a proteasome inhibitor), imatinib (a tyrosine kinase inhibitor), and seliciclib (a cyclin-dependent kinase inhibitor), and epacadostat (an indoleamine 2,3-dioxygenase (IDO1) inhibitor).

In some embodiments, the method of treating cancer of the present invention further comprises selecting a whole-cell cancer vaccine for the subject according to a method of the present invention described herein. In particular embodiments, the subject has stage I, stage II, stage III, and/or stage IV cancer. In other embodiments, the cancer is transitioning between stages. In some embodiments, the subject has a pre-cancerous lesion. In some embodiments, the subject does not have cancer.

In some embodiments, treating the subject comprises inhibiting cancer cell growth, inhibiting cancer cell proliferation, inhibiting cancer cell migration, inhibiting cancer cell invasion, ameliorating or eliminating the symptoms of cancer, reducing the size (e.g., volume) of a cancer tumor, reducing the number of cancer tumors, reducing the number of cancer cells, inducing cancer cell necrosis, pyroptosis, oncosis, apoptosis, autophagy, or other cell death, or enhancing the therapeutic effects of a composition or pharmaceutical composition. In some embodiments, treating the subject results in an increased survival time. In some instances, overall survival is increased. In other instances, disease-free survival is increased. In some instances, progression-free survival is increased. In particular embodiments, treating the subject results in a reduction in tumor volume and/or increased survival time.

In particular embodiments, treating the subject enhances the therapeutic effects of an anti-cancer therapy such as a chemotherapeutic agent, an immunotherapeutic agent, radiotherapy, hormone therapy, a differentiating agent, and/or a small-molecule drug.

Therapy such as modified cancer cell(s), composition(s), and pharmaceutical composition(s) of the present invention can be administered using routes, dosages, and protocols that will readily be known to one of skill in the art. Administration can be conducted once per day, once every two days, once every three days, once every four days, once every five days, once every six days, or once per week. Therapy can be administered 1, 2, 3, 4, 5, 6, 7, 8, 9, 10, 11, 12, 13, 14, or more times per week. In some cases, modified cancer cell(s), composition(s), and/or pharmaceutical composition(s) of the present invention are administered as a single dose, co-administered (e.g., administered in separate doses or by different routes, but close together in time), or administered separately (e.g., administered in different doses, including the same or different route, but separated by about 1, 2, 3, 4, 5, 6, 7, 8, 9, 10, 11, 12, or more hours). In cases where multiple doses are to be administered in the same day, or where a single dose comprises one or more components (e.g., the modified cancer cell(s) and IFNa are administered separately), administration can occur, for example, 1, 2, 3, 4, 5, 6, 7, 8, 9, 10, 11, 12, or more times in a day.

In some cases, therapeutic administration can occur about once per week, about every two weeks, abpit every three weeks, or about once per month. In other cases, therapeutic administration can occur about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more times per month. Treatment can continue for about 1, 2, 3, 4, 5, 6, 7, 8, 9, 10, 11, 12, or more weeks; about 1, 2, 3, 4, 5, 6, 7, 8, 9, 10, 11, 12 or more months; or longer. At any time during treatment, the therapeutic plan can be adjusted as necessary. For example, depending on the response to modified cancer cell(s), compositions, or pharmaceutical composition(s) of the present invention, a different vaccine may be selected, one or more additional therapeutic agents or drugs may be chosen, or any aspect of the therapeutic plan can be discontinued. One of skill in the art will readily be able to make such decisions, which can be informed by, for example, the results of allele profile comparison, changes in the activity and/or number of an immune cell, and/or changes in the the presence or level of one or more biomarkers.

The modified cancer cell(s), composition(s), and pharmaceutical composition(s) of the present invention can be administered by any suitable route, including those described herein. In some embodiments, the administration is by intradermal or intralymphatic injection. In some embodiments, the whole-cell cancer vaccine (e.g., comprising modified cancer cells of the present invention) is given separately from interferon alpha (IFNa). In some instances, the IFNa is injected locally. IFNa can be given before and/or after the vaccine is administered. Timing of the separate injections can be any suitable interval, including those described herein.

One of skill in the art will readily be able to administer the number of appropriate modified cancer cells to include in a particular dose. A dose may include, for example, about 50,000 to 50,000,000 (e.g., about 50,000, 60,000, 70,000, 80,000, 90,000, 100,000, 110,000, 120,000, 130,000, 140,000, 150,000, 160,000, 170,000, 180,000, 190,000, 200,000, 250,000, 300,000, 350,000, 400,000, 450,000, 500,000, 550,000, 600,000, 650,000, 700,000, 750,000, 800,000, 850,000, 900,000, 950,000, 1,000,000, 1,500,000, 2,000,000, 2,500,000, 3,000,000, 3,500,000, 4,000,000, 4,500,000, 5,000,000, 5,500,000, 6,000,000, 6,500,000, 7,000,000, 7,500,000, 8,000,000, 8,500,000, 9,000,000, 9,500,000, 10,000,000, 11,000,000, 12,000,000, 13,000,000, 14,000,000, 15,000,000, 16,000,000, 17,000,000, 18,000,000, 19,000,000, 20,000,000, 25,000,000, 30,000,000, 35,000,000, 40,000,000, 45,000,000, 50,000,000, or more) modified cancer cells. In some embodiments a dose may contain about 5,000,000 modified cancer cells.

A dose may also include, for example, at least about 5,000,000 to 100,000,000 (e.g., about 5,000,000, 6,000,000, 7,000,000, 8,000,000, 9,000,000, 10,000,000, 15,000,000, 20,000,000, 25,000,000, 30,000,000, 35,000,000, 40,000,000, 45,000,000, 50,000,000, 55,000,000, 60,000,000, 65,000,000, 70,000,000, 75,000,000, 80,000,000, 85,000,000, 90,000,000, 95,000,000, 100,000,000, or more) modified cancer cells.

A dose may alternatively include, for example, at least about 100,000,000 to 1,000,000,000 (e.g., about 100,000,000, 150,000,000, 200,000,000, 250,000,000, 300,000,000, 350,000,000, 400,000,000, 450,000,000, 500,000,000, 550,000,000, 600,000,000, 650,000,000, 700,000,000, 750,000,000, 800,000,000, 850,000,000, 900,000,000, 950,000,000, 1,000,000,000, or more) modified cancer cells.

In some embodiments, the modified cancer cells are irradiated. The irradiation dose may be, for example, between about 2 and 2,000 Gy (e.g., about, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150, 160, 170, 180, 190, 200, 210, 220, 230, 240, 250, 260, 270, 280, 290, 300, 350, 400, 450, 500, 550, 600, 650, 700, 750, 800, 850, 900, 950, 1,000, 1,100, 1,200, 1,300, 1,400, 1,500, 1,600, 1,700, 1,800, 1,900, or 2,000 Gy). In particular embodiments, the modified cancer cells are irradiated with a dose of about 200 Gy.

In some embodiments, treating the subject results in a decrease in the presence or level of one or more biomarkers measured or detected in a sample obtained from the subject. In some embodiments, treating the subject results in an increase in the presence or level of one or more biomarkers measured or detected in a sample obtained from the subject. In particular embodiments, treating the subject results in no change the presence or level of the one or more biomarkers.

In some embodiments, treating the subject results in an increase in the activity and/or number of one or more immune cells. In some instances, the increase is produced in one cell type. In other instances, the increase is produced in multiple cell types. In some embodiments, the cell in which the level of activity and/or number is increased is selected from the group consisting of a peripheral blood mononuclear cell (PBMC), a lymphocyte (e.g. T lymphocyte, B lymphocyte, NK cell), a monocyte, a dendritic cell, a macrophage, a myeloid-derived suppressor cell (MDSC), and a combination thereof. In particular embodiments, the level of activity and/or number of immune cell(s) is measured using methods of the present invention described herein.

In some embodiments, an increase in immune cell activity and/or number indicates that the subject should be administered one or more additional doses of the pharmaceutical composition (e.g., comprising modified cancer cells of the present invention). In some instances, a different vaccine is administered. One of skill in the art will recognize that an increase in immune cell activity and/or number will occur, in some instances, after 1, 2, 3, 4, 5, 6, 7, 8, 9, 10, 11, 12, 13, 14, or more doses of the vaccine have been administered.

In some embodiments, a sample is obtained from the subject. In other embodiments, a sample is obtained from a different subject or a population of subjects. Samples can be used for the purposes of selecting an appropriate cancer vaccine of the present invention, monitoring the response to vaccine therapy, and/or predicting how the subject will respond to vaccine therapy. Samples obtained from a different subject and/or a population of subjects can be used, for example, to establish reference ranges to facilitate comparisons that are part of the methods of the present invention. Samples can be obtained at any time, including before and/or after administration of the modified cancer cell(s), pharmaceutical composition(s), and/or other composition(s) of the present invention. In some embodiments, the sample comprises whole blood, plasma, serum, cerebrospinal fluid, tissue, saliva, buccal cells, tumor tissue, urine, fluid obtained from a pleural effusion, hair, skin, or a combination thereof. In general, the sample can comprise any biofluid. For HLA typing, any cell, tissue, or biofluid type is suitable, as long as it contains a sufficient amount of DNA or RNA to allow typing. In some instances, the sample comprises circulating tumor cells (CTCs). The sample can also be made up of a combination of normal and cancer cells. In particular embodiments, the sample comprises circulating tumor cells (CTCs). The sample can be obtained, for example, from a biopsy, from a surgical resection, and/or as a fine needle aspirate (FNA). Samples can be used to determine, measure, or detect HLA allele(s), immune cell activity and/or number, and/or biomarker(s), as described herein.

In some embodiments, the results of the HLA typing (e.g., the alleles present in an allele profile, the results of a comparison of allele profiles), immune cell activity and/or number measurement, and/or biomarker presence or level determinations are recorded in a tangible medium. For example, the results of assays (e.g., the alleles present in an allele profile, the results of a comparison of allele profiles, the activity level and/or number of immune cells, the presence or level (e.g., expression) of one or more biomarkers) and/or a prognosis or diagnosis (e.g., of whether or not there is the presence of cancer, the prediction of whether the subject will respond to a vaccine, or whether the subject is responding to a vaccine) can be recorded, e.g., on paper or on electronic media (e.g., audio tape, a computer disk, a CD, a flash drive, etc.).

In other embodiments, the methods further comprise the step of providing the results of assays, prognosis, and/or diagnosis to the patient (i.e., the subject) and/or the results of treatment.

E. Kits

In another aspect, the invention provides a kit for treating a subject with cancer. In some embodiments, the kit comprises a modified cancer cell, a composition, and/or a pharmaceutical composition of the present invention described herein. The kits are useful for treating any cancer, some non-limiting examples of which include breast cancer, ovarian cancer, cervical cancer, prostate cancer, pancreatic cancer, colorectal cancer, gastric cancer, lung cancer, skin cancer, liver cancer, brain cancer, eye cancer, soft tissue cancer, renal cancer, bladder cancer, head and neck cancer, mesothelioma, acute leukemia, chronic leukemia, medulloblastoma, multiple myeloma, sarcoma, and any other cancer described herein, including a combination thereof.

Materials and reagents to carry out the various methods of the present invention can be provided in kits to facilitate execution of the methods. As used herein, the term "kit" includes a combination of articles that facilitates a process, assay, analysis, or manipulation. In particular, kits of the present invention find utility in a wide range of applications including, for example, diagnostics, prognostics, therapy, and the like.

Kits can contain chemical reagents as well as other components. In addition, the kits of the present invention can include, without limitation, instructions to the kit user, apparatus and reagents for sample collection and/or purification, apparatus and reagents for product collection and/or purification, apparatus and reagents for administering modified cancer cell(s) or other composition(s) of the present invention, apparatus and reagents for determining the level(s) of biomarker(s) and/or the activity and/or number of immune cells, apparatus and reagents for detecting HLA alleles, sample tubes, holders, trays, racks, dishes, plates, solutions, buffers or other chemical reagents, suitable samples to be used for standardization, normalization, and/or control samples. Kits of the present invention can also be packaged for convenient storage and safe shipping, for example, in a box having a lid.

In some embodiments, the kits also contain negative and positive control samples for detection of HLA alleles, immune cell activity and/or number, and/or the presence or level of biomarkers. In some embodiments, the negative control samples are non-cancer cells, tissue, or biofluid obtained from the subject who is to be treated or is already undergoing treatment. In other embodiments, the negative control samples are obtained from individuals or groups of individuals who do not have cancer. In other embodiments, the positive control samples are obtained from the subject, or other individuals or groups of individuals, who have cancer. In some embodiments, the kits contain samples for the preparation of a titrated curve of one or more biomarkers in a sample, to assist in the evaluation of quantified levels of the activity and/or number of one or more immune cells and/or biomarkers in a biological sample.

F. Methods for Determining HER2 Status

In another aspect, the present invention provides a method for determining the HER2 status of a sample cell. In some embodiments, the method comprises:

(a) detecting the presence or level of one or more biomarkers in the sample cell, wherein the one or more biomarkers comprise:

(i) MIEN1,
(ii) PGAP3,
(iii) ERBB2 and MIEN1,
(iv) ERBB2 and PGAP3,
(v) MIEN1 and PGAP3, or
(vi) ERBB2, MIEN1, and PGAP3;

(b) comparing the presence or level of the one or more biomarkers detected in step (a) to the presence or level of the one or more biomarkers in a reference cell; and (c) determining the HER2 status of the sample cell based upon the comparison performed in step (b).

In some embodiments, the sample cell is a cancer cell. In some instances, the sample cell is obtained from a subject who has cancer. The sample cell can be obtained as a biopsy specimen, by surgical resection, or as a fine needle aspirate (FNA). In some embodiments, the sample cell is a circulating tumor cell (CTC).

In some embodiments, the sample cell is determined to be HER2 positive when the one or more biomarkers is expressed at a higher level in the sample cell compared to the reference cell. In other embodiments, the cell is determined to be HER2 positive when the expression of the one or more biomarkers is overexpressed at least about 1.5-fold (e.g., about 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, 17-fold, 18-fold, 19-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold, or more) compared to the reference cell. In particular embodiments, the cell is determined to be HER2 positive when the expression of the one or more biomarkers is overexpressed at least about 1.5-fold compared to the reference cell.

In some embodiments, the cell is determined to be overexpressing or not overexpressing HER2. In particular embodiments, the cell is determined to be HER2 3+, HER2 2+, HER2 1+, or HER2 0 (i.e., HER is not overexpressed). In some embodiments, the level of the one or more biomarkers is higher in a HER2 3+ cell than in a HER2 2+ cell. In other embodiments, the level of the one or more biomarkers is higher in a HER2 2+ cell than in a HER2 1+ cell or HER2 0 cell.

In some embodiments, the reference cell is a non-cancer cell obtained from the same subject as the sample cell. In other embodiments, the reference cell is a non-cancer cell obtained from a different subject or a population of subjects. In some embodiments, measuring expression comprises, for example, measuring mRNA expression, protein abundance, or a combination thereof. Some examples of suitable methods for measuring expression are described herein.

In some embodiments, the determination of HER2 status is made with a sensitivity of at least about 60% (e.g., about 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100%). In other embodiments, the determination of HER2 status is made with a sensitivity of at least about 80% (e.g., about 80%, 81%, 82%, 83%, 84%, 85%, 86%, 87%, 88%, 89%, 90%, 91%, 92%, 93%, 94%, 95%, 96%, 97%, 98%, 99%, or 100%). In still other embodiments, the determination of HER2 status is made with a sensitivity of at least about 90% (e.g., about 90%, 91%, 92%, 93%, 94%, 95%, 96%, 97%, 98%, 99%, or 100%). In some instances, the sensitivity is at least about 60%. In other instances, the sensitivity is at least about 87%. In some instances, the sensitivity is about 100%.

In some embodiments, one or more aspects of the detection step are automated. In other embodiments, one or more aspects of the comparison step are automated. In still other embodiments, one or more aspects of the determining step are automated. Non-limiting examples of aspects or steps that can be automated include sample gathering, sample isolation, sample processing, one or more methods of mRNA detection, one or more methods of protein detection, quantification and/or comparison of the levels of one or more biomarkers to reference values, and processing of expression level values to determine the HER2 status of the cell.

IV. Examples

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1: SV-BR-1-GM (BriaVax), a GM-CSF-Secreting Whole-Cell Vaccine, Expresses an Immune Signature and Matches at Both HLA I and II Alleles with a Stage IV Breast Cancer Patient with Systemic Tumor Regression Following SV-BR-1-GM Inoculation Abstract
Background
Cancer immunotherapy with allogeneic whole-cell vaccines is an effective approach to reduce tumor burden. It is generally assumed that to be effective, the vaccine needs to express immunogenic antigens co-expressed in patient tumor cells, and that antigen-presenting cells (APC) such as dendritic cells (DCs) need to cross-present such antigens following uptake of vaccine cell fragments. It has been previously reported that in a phase I/pilot study a subject with stage IV breast cancer experienced substantial regression of breast, lung and brain lesions following inoculation with the whole-cell vaccine SV-BR-1-GM (referred to as BriaVax). In order to identify potential diagnostic features permitting the prospective identification of patients likely to benefit from SV-BR-1-GM, a molecular analysis was conducted of the vaccine and of patient-derived blood as well as tumor specimens.

Results
SV-BR-1-GM cells expressed sets of genes predicting the presence of both major histocompatibility complex (MHC) class I (i.e., B2M, HLA-A, HLA-B) and class II (i.e., HLA-DRA, HLA-DRB3, HLA-DMA, HLA-DMB) molecules. Additionally, the vaccine expressed several other factors with immune-modulatory functions including ADGRE5 (CD97), CD58 (LFA3), CD74 (invariant chain and CLIP), CD83, CXCL16, HLA-F, IL6, IL10, IL15, IL18, CXCL16, and TNFSF14 (LIGHT). Surprisingly, SV-BR-1-GM and the study subject with the most pronounced clinical response both carried HLA-A*11:01 and HLA-DRB3*02:02 alleles. Furthermore, compared to normal human breast cells, SV-BR-1-GM cells overexpressed several genes known to encode tumor-associated antigens (TAAs) such as PRAME, a cancer/testis antigen. Additionally, genes encoding potentially novel TAAs were identified.

Discussion
Despite their breast origin, SV-BR-1-GM cells not only expressed TAAs but also a set of biomarkers including HLA class I and II alleles known for their immune-stimulatory roles in APCs. This suggests that the partial HLA allele match between SV-BR-1-GM and the special clinical responder enabled patient T lymphocytes to directly recognize TAAs as presented by the vaccine's MHC system.

Conclusion
These findings indicate that SV-BR-1-GM cells can act directly as APCs, and/or that APCs such as DCs can cross-dress by means of trogocytosis with peptide-loaded MHCs from SV-BR-1-GM cells.

Background
In contrast to traditional chemo- or radiation therapies that kill fast-dividing cells irrespective of whether they are cancerous or normal, the goal of cancer immunotherapy is to eradicate tumors based on the malignant cells' antigenic makeup. Tumor-selectivity of the latter approach is variable and depends on the antigens targeted. For instance, while cancer/testis antigens (CTAs) such as MAGE-A and NY-ESO-1 may be specifically expressed in certain tumors but not in the corresponding normal tissues, the prototypical target for the chimeric antigen receptor (CAR)-T cell approach, CD19 is expressed in both malignant and normal B cells. To compensate for the loss of normal B cells, B cell aplasia following CAR-T cell-based targeting of CD19 is treated with immunoglobulin replacement (1).

Developments in cancer immunotherapy have shown that not only are there several viable ways to induce an immune response against tumor-associated antigens (TAAs), but also that such TAAs can be localized intra- and/or extracellularly. For instance, whereas CARs (1, 2) and bispecific antibodies that crosslink cytotoxic T cells with cancer cells (3) rely on the presence of cell surface antigens, ectopic T cell receptor (TCR); 4), tumor-infiltrating lymphocyte (TIL; 5, 6), and vaccine-based approaches (7-18) require the display of antigenic peptides by major histocompatibility complexes (MHCs), regardless of whether the peptides represent intra- or extracellular TAAs. Similarly, immune checkpoint inhibitors such as the anti-PD-1 antibodies nivolumab and pembrolizumab and the anti-CTLA-4 antibody ipilimumab are designed to prevent inhibition of effector T cells without discriminating between T cells recognizing MHC-bound peptides from intra-versus from extracellular antigens (19).

Whole-cell vaccines comprising live but irradiated cancer cells express a very large number of antigens, of which some may be co-expressed in the tumor. Whereas a tumor shielded by an immune-suppressive microenvironment may not elicit an immune response, whole-cell vaccines (20), if injected into immune-permissive sites, may do so. However, even though an immune response induced by the vaccine may have a tumor-directed component, the exact nature of the antigens mediating that effect may not be known.

Two main categories of whole-cell vaccines have been studied (i.e., autologous and allogeneic vaccines). Autologous vaccines, derived from the tumor of the patient to be treated, are expected to express relevant antigens including patient-specific neoepitopes, but may not be effective in overcoming immunosuppression to evoke an effective immune response. On the other hand, while allogeneic vaccines that are engineered to express granulocyte-macrophage colony-stimulating factor (GM-CSF) may induce strong immune responses by promoting antigen display on dendritic cells (DCs), they may lack key antigens (15). With variable success, allogeneic whole-cell vaccines engineered to express GM-CSF ("GVAX" vaccines) have been clinically tested against a variety of malignancies representing both hematologic and solid cancers such as leukemia, melanoma, and pancreatic, prostate, breast, lung, and colorectal cancers (7, 8, 10, 11, 14, 16, 18, 21-24). Notably, it has been demonstrated using a mouse model that the GVAX approach may be suitable to prevent tumor establishment (i.e., prophylactic treatment may not be effective in reducing the tumor burden of already existing disease (25).

A cell line from a chest wall lesion of a metastatic breast cancer patient (17) has been previously established. The cell line, referred to as SV-BR-1, is estrogen receptor (ER)/progesterone receptor (PR) negative and very strongly HER2/neu (ERBB2) positive (17). To enhance the cells' immune reactivity, SV-BR-1 cells were genetically engineered to stably overexpress GM-CSF, yielding the SV-BR-1-GM (BriaVax) line. Several advanced-stage HER2+ cancer patients were treated in two early stage clinical trial settings with irradiated parental SV-BR-1 (BB-IND 2749) or SV-BR-1-GM (BB-IND 10312) cells (16, 17). Both studies employed a pretreatment step with low-dose cyclophosphamide, which has been used in many vaccine studies to blunt the activity of regulatory T cells. Additionally, for the SV-BR-1-GM study, 2 and 4 days after the application of the vaccine, interferon-alpha was injected locally into each inoculation site to provide an additional "danger signal". One subject responded to the regimen with a near-complete regression of multiple breast lesions and a complete remission of a lung metastasis after only 3 inoculations, but then experienced disease regression 3 months after the last cycle, with lesions developing in the lung, soft tissues, breast, and brain. After obtaining FDA permission, vaccinations resumed. Consequently, a systemic response was observed whereby tumors in sites including those in the brain responded with a prompt tumor remission (16).

Described herein is a molecular fingerprint of SV-BR-1-GM established with samples representing developmental intermediates or final product, such as the master cell bank or clinical product lots, respectively. Two lines of evidence are further presented that demonstrate that SV-BR-1-GM cells directly and/or indirectly act as antigen-presenting cells (APCs) and thereby mount an effective tumor-directed immune response. First, despite their presumptive breast epithelial origin, SV-BR-1-GM cells express a set of genes including HLA class I and II components associated with immune cells rather than with epithelial cells. Second, a robust clinical response occurred in a clinical trial subject with HLA alleles matching those of SV-BR-1-GM at both class I and II loci. This indicates that in this patient, fully assembled TAA-MHC complexes expressed on the cell surface of SV-BR-1-GM cells directly interacted with patient T cells, or that they were first transferred onto dendritic cells (DCs) by means of trogocytosis ("cross-dressing") and then encountered corresponding T cells.

Results
Biomarkers Indicative of Clinical Response

Given the strong clinical effects of the BriaVax vaccine (SV-BR-1-GM cell line) reported previously (16), it was hypothesized that the vaccine's mechanism of action (MoA) might at least in part be mediated by the expression of a set of genes whose protein products act as immunogens, mediating the breaking of immune tolerance. In addition to genes overexpressed in SV-BR-1-GM cells, it was also investigated whether the special clinical responder and SV-BR-1-GM exhibited a partial overlap in their HLA types (16). Both immunogen candidates and HLA alleles have utility for predicting which patients will respond best to BriaVax and thus are of prognostic and diagnostic importance.

SV-BR-1-GM Samples Used for this Study

The polyclonal SV-BR-1 cell line was established from a chest wall lesion of a female metastatic breast cancer patient. As depicted in FIG. 1A, the SV-BR-1-GM cell line was derived from SV-BR-1 cells following stable transfection with the CSF2 gene that encodes human GM-CSF and zeocin-selection (see, e.g., U.S. Pat. No. 7,674,456, U.S. patent application Ser. No. 10/868,094, both of which are hereby incorporated by reference in their entirety for all purposes and (16, 17)). Since it was not clonally selected, it had likely experienced substantial clonal drift during expansion. However, even though other parameters were expected to contribute to the potency of the vaccine as well, GM-CSF was expected to be a major factor (15). Therefore, for clinical use of the cell line as a vaccine, GM-CSF production was assessed by ELISA using culture supernatant as assay input.

GM-CSF signaling involves GM-CSF binding to the a subunit of its receptor and recruitment of the receptor's a subunit (26). Whereas a restricted region in GM-CSF's first α helix was suggested to interact with the receptor's a subunit, several regions further downstream contact the a subunit (27). Compared to the NCBI Reference Sequence of GM-CSF (see, NCBI Reference No. NP_000749.2), SV-BR-1-GM's ectopic GM-CSF sequence varied at positions 53 (i.e., Thr instead of Met) and 117 (i.e., Thr instead of Ile). Whereas position 53 mapped between the first β-pleated sheet (i.e., amino acids 39-43) and the second a helix (i.e., amino acids 55-64), and was not implicated in binding of GM-CSF to the receptor's a subunit, position 117 mapped to a region associated with receptor binding (27), thus raising the question of whether receptor binding and thereby signaling could still occur with the threonine at position 117. In agreement with signaling activity and thus GM-CSF bioactivity, cell culture supernatant from irradiated SV-BR-1-GM cells supported the proliferation of MUTZ-3 cells, a cell line reported to depend on cytokines such as GM-CSF (28), whereas supernatant from parental SV-BR-1 cells (i.e., not engineered to express GM-CSF) had at most a minimal effect.

Figure 1B:
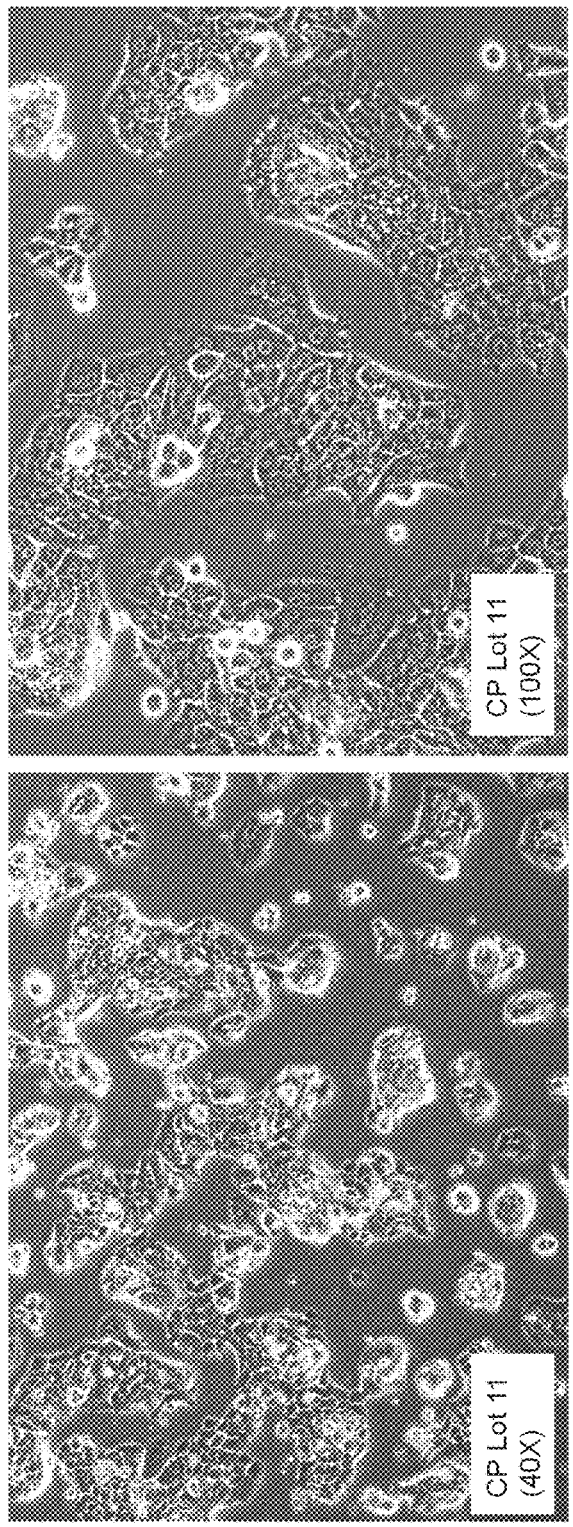
Figure 1C:
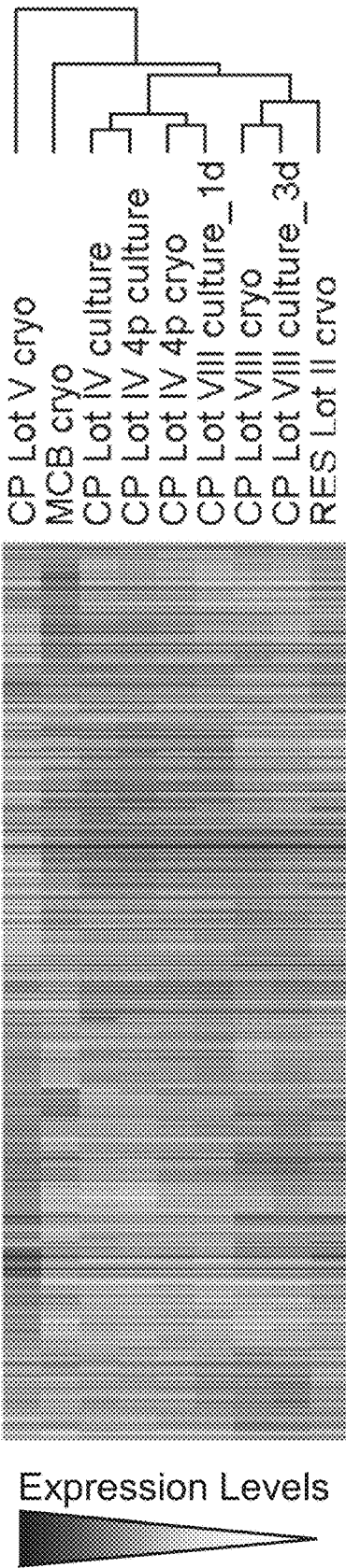
Figure 1D:
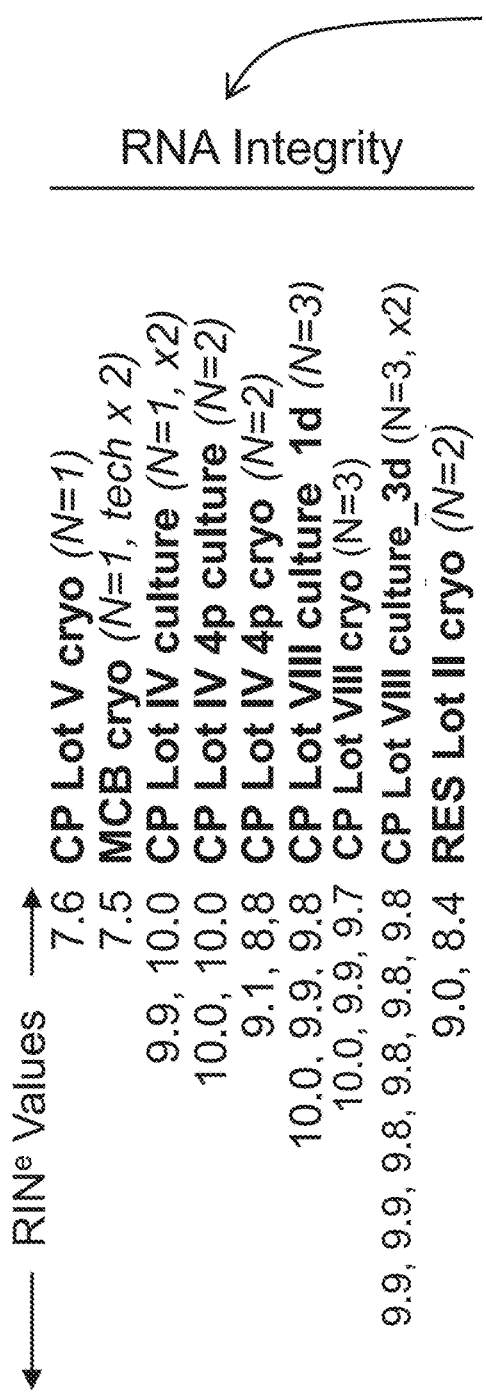
Figure 2A:
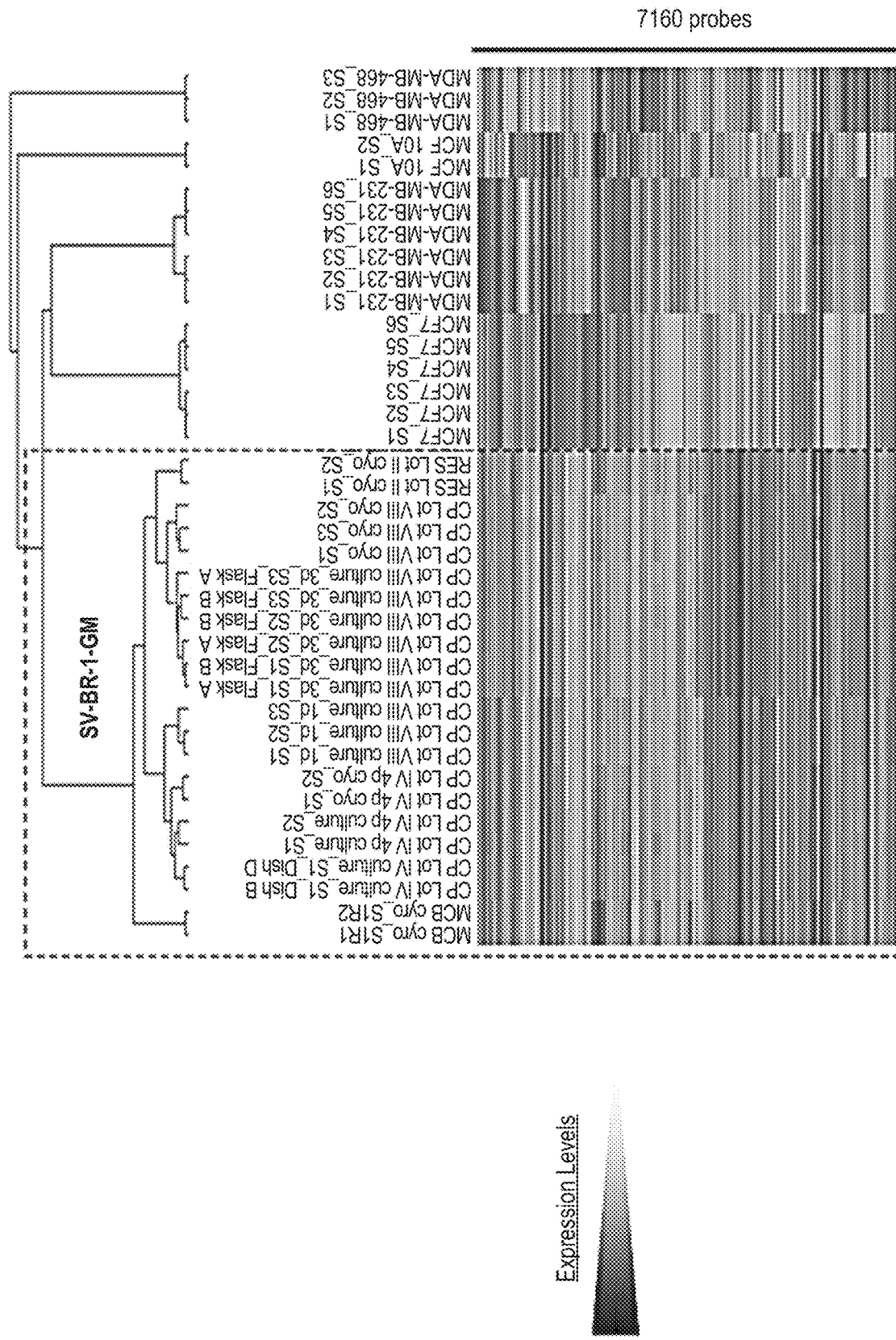
FIGS. 2A-2C show hierarchical clustering. MCF7, MDA-MB-231, and MDA-MB-468 are human breast cancer cell lines. MCF10A is a "normal" human epithelial cell line. HMEC denotes human mammary epithelial cells. Data sets other than of SV-BR-1-GM were obtained from GEO (NCBI) and are as follows: noncultured breast cells from GSE35399 (Shehata et al., *Breast Cancer Res.* 2012; 14(5): R134), HMECs from GSE56718 (Lowe et al., *Genome Biol.* 2015 Sep. 17; 16:194), and MCF7, MCF10A, MDA-MB-231, and MDA-MB-468 from GSE48398.
Figure 2B:
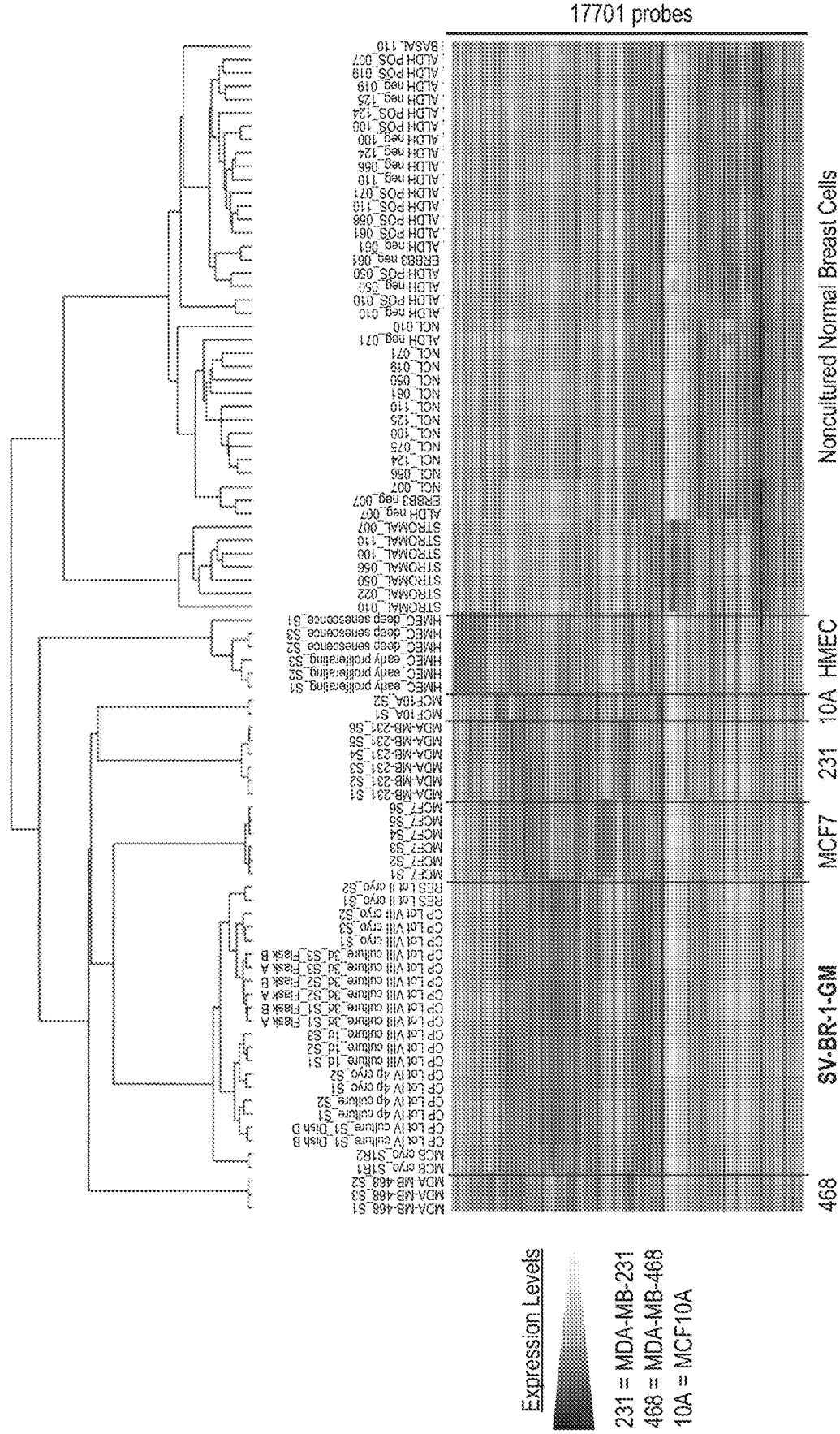
Figure 2C:
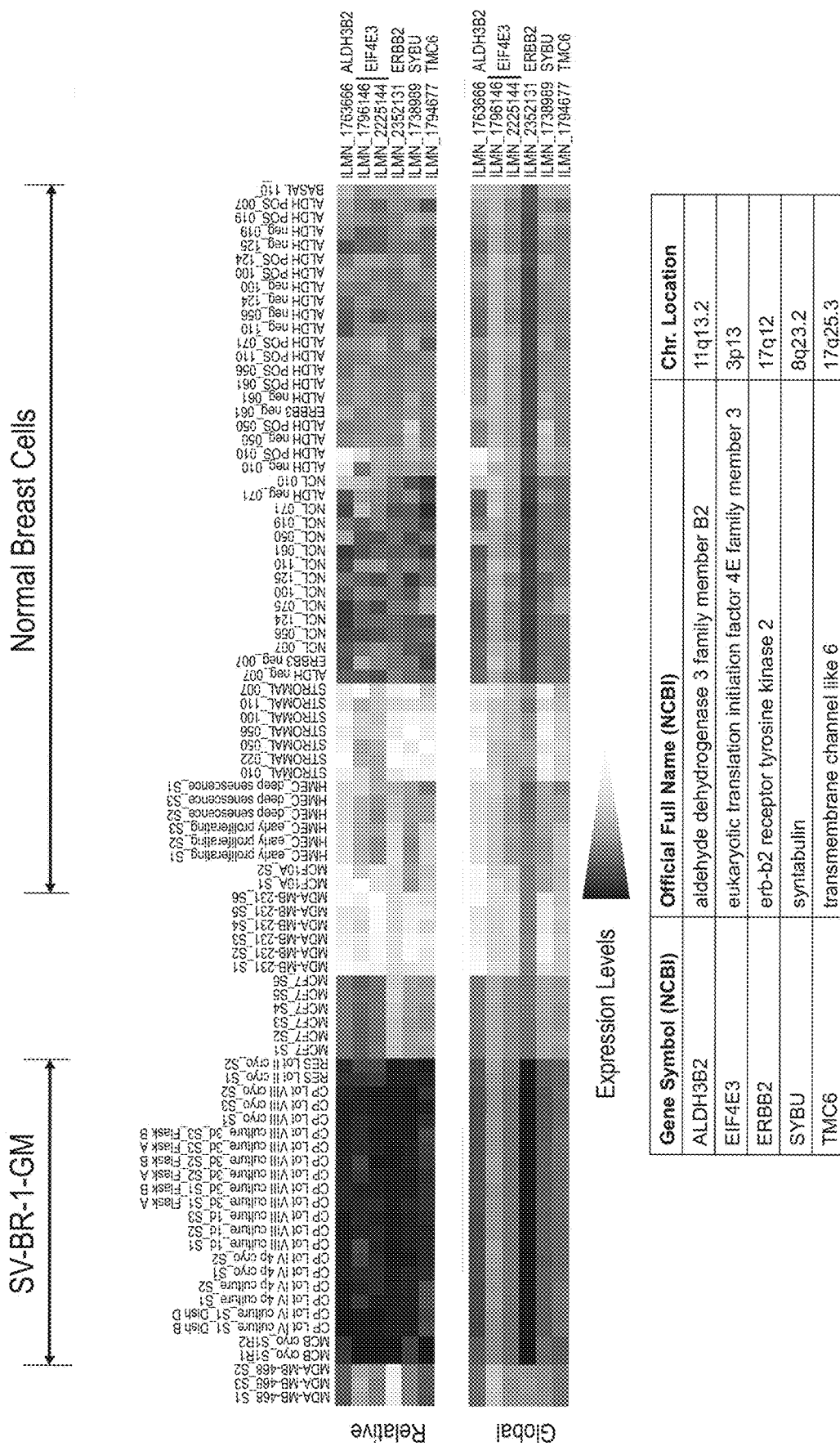

Since the excision of the original tumor specimen in 1999 several lots of both SV-BR-1 and SV-BR-1-GM have been manufactured. FIG. 1A depicts SV-BR-1-GM samples for which gene expression profiles were generated and their genealogy. Lots derived from the master cell bank (MCB) were designated "Clinical Product" (CP) lots. Additionally, MCB-independent research (RES) banks were generated. Morphologies of SV-BR-1-GM cells after serum starvation are shown in FIG. 1B. Gene expression profiles were generated on Illumina® HumanHT-12 v.4 Bead Chips from RNA either directly obtained from cryopreserved cell suspensions (denoted as "cryo" tag in sample names) or from recent cultures (denoted as "culture" tag in sample names). Whereas a certain degree of gene expression variability was apparent among different SV-BR-1-GM sample types (FIG. 1C), overall, SV-BR-1-GM cells exhibited substantially different gene expression profiles than other established breast cancer cell lines and normal breast cell types (FIG. 2). Samples with RNA integrity number equivalent (RIN$^e$) values of less than 7.5 were excluded from the analyses. Similarly, some samples (e.g., CP Lot V cryo) that failed another quality control test (see, section titled "Methods" below) were not used in further comparative analyses even if their RING values were greater than or equal to 7.5 (FIG. 1D).

SV-BR-1-GM Expresses a 24-Gene Signature Associated with Immune-Stimulatory Functions SV-BR-1-GM cells expressed several genes with known immune system-associated roles (e.g., genes involved in MHC class II-based antigen presentation by APCs such as dendritic cells (DCs)). Among these genes were HLA-DMA, HLA-DRA, and CD74, which gives rise to invariant chain (Ii) and class II-associated invariant chain peptide (CLIP).

Figure 3:
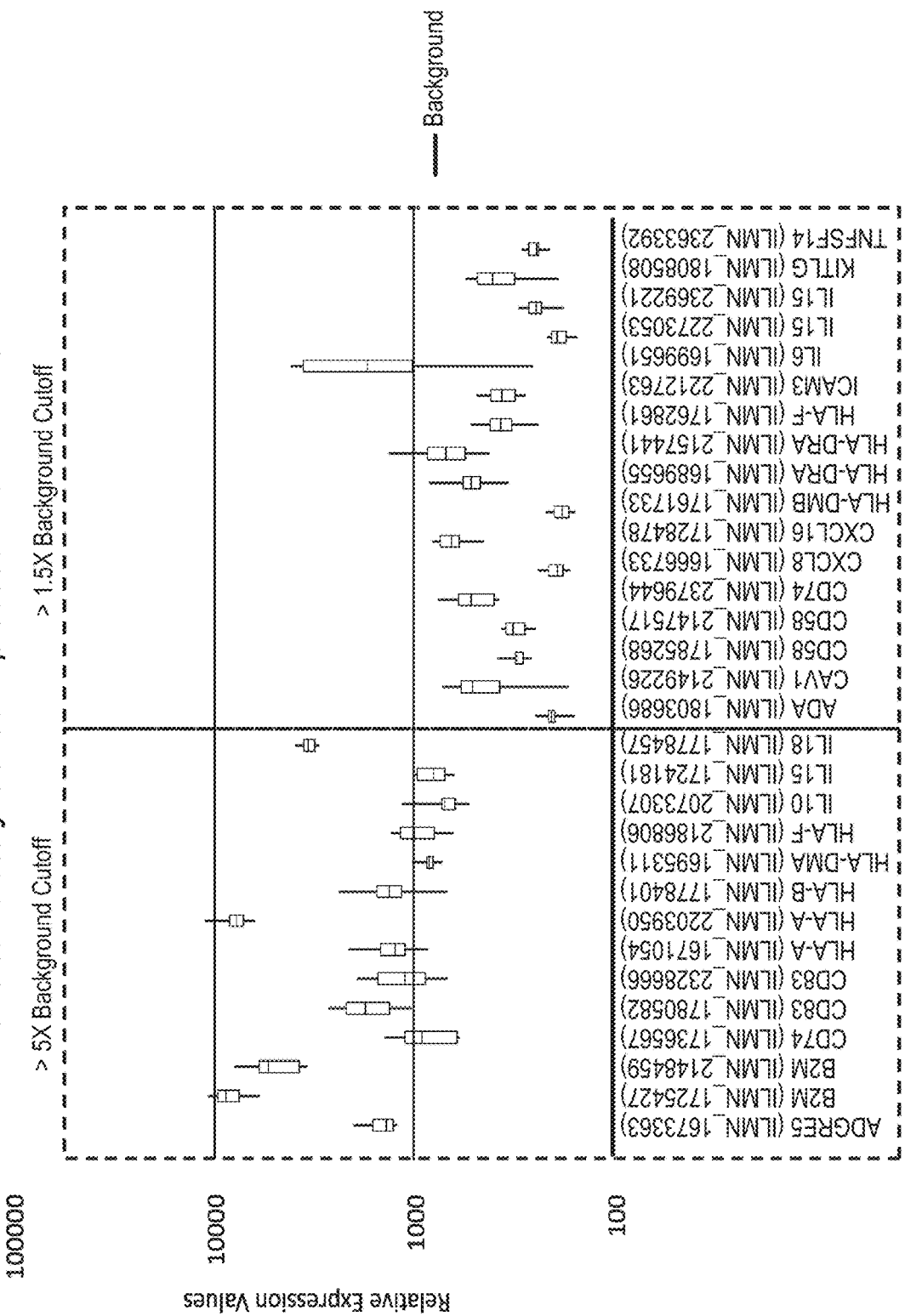
FIG. 3 depicts the expression of immune stimulators in SV-BR-1-GM cells. 111 genes with known immune-stimulatory roles were identified in published reports (29-70) (Table 2) and their microarray-based mRNA expression levels were determined. The 22 genes shown in this plot presented with transcript levels greater than 1.5 times the background cutoff value in each of the SV-BR-1-GM samples. The term "Relative Expression Values" refers to quantile-normalized mRNA levels.
Figure 4C:
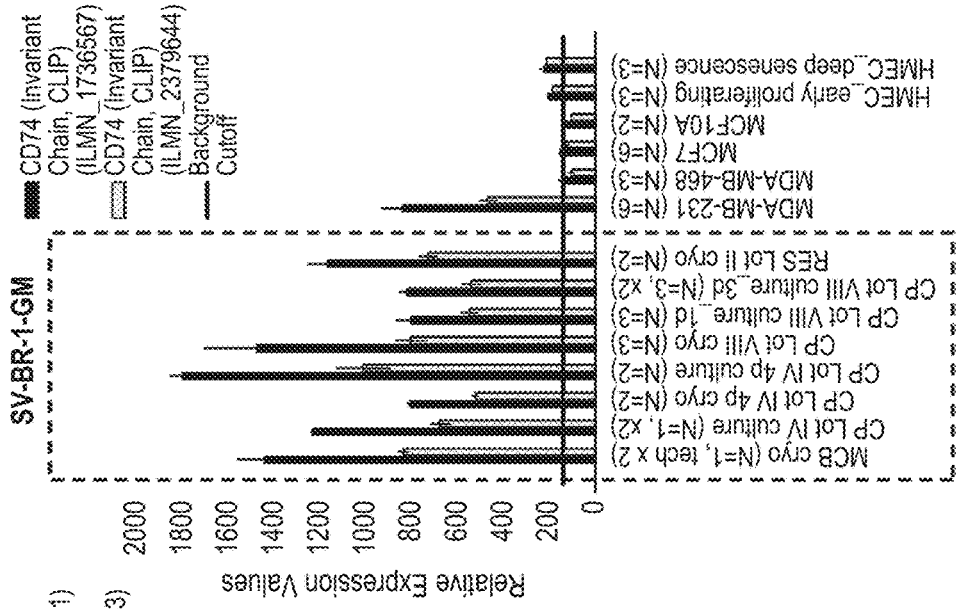
FIGS. 4A-4C depict HLA class II components in SV-BR-1-GM cells. SV-BR-1-GM cells expressed components that were predictive for functional HLA-DR complex formation. The term "Relative Expression Values" refers to quantile-normalized mRNA levels obtained via microarray hybridization.
Figure 4B:
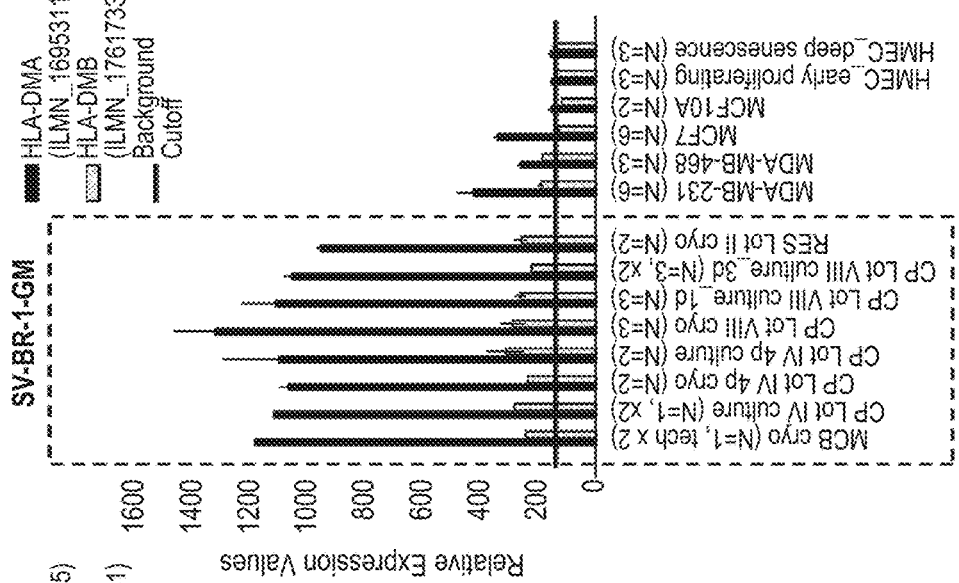
Figure 4A:
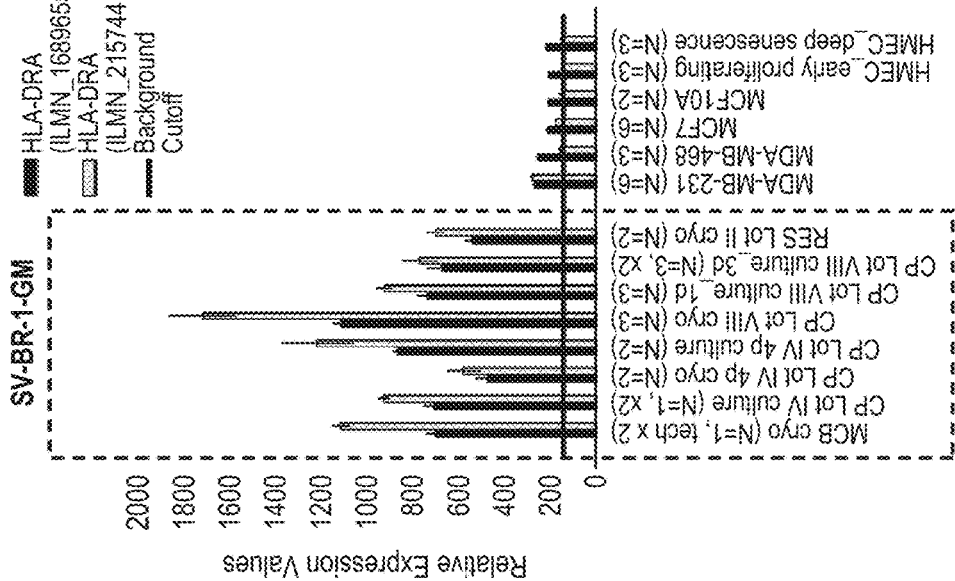
Figure 5C:
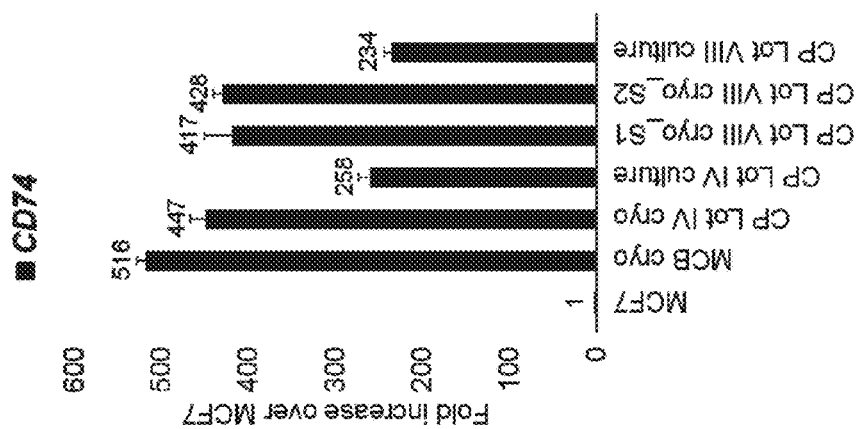
FIGS. 5A-5C depict validation of HLA class II gene expression by quantitative RT-PCR. In order to validate the expression of several critical HLA class II components, a confirmatory experiment was conducted on a subset of the SV-BR-1-GM samples (Table 4) used for Illumina® microarray analysis and with RNA from MCF7 cells (i.e., breast cancer cell line carrying the HLA-DRB3*0202 allele (72)) as a calibrator sample. The MEW II-related transcripts analyzed were not expressed only in SV-BR-1-GM cells, but were expressed at substantially higher levels than in MCF7 cells.
Figure 5B:
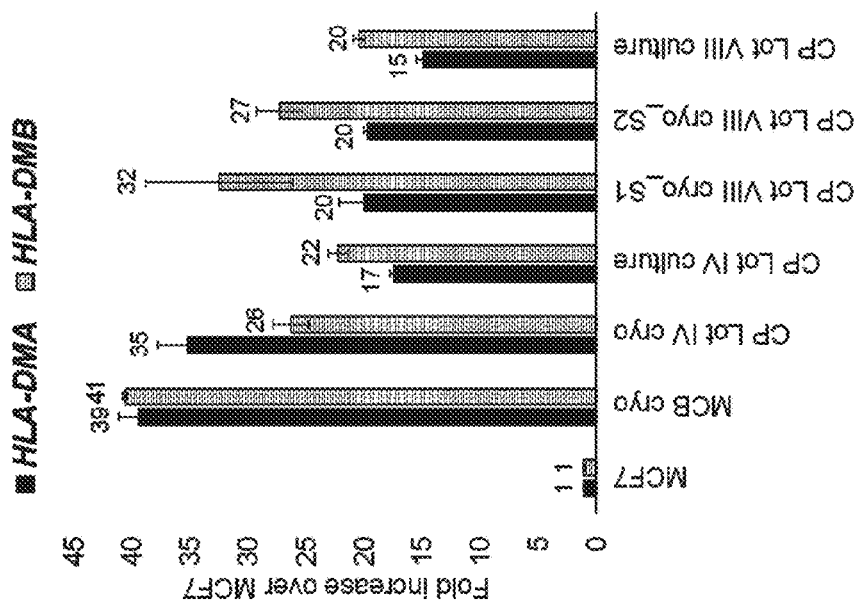
Figure 5A:
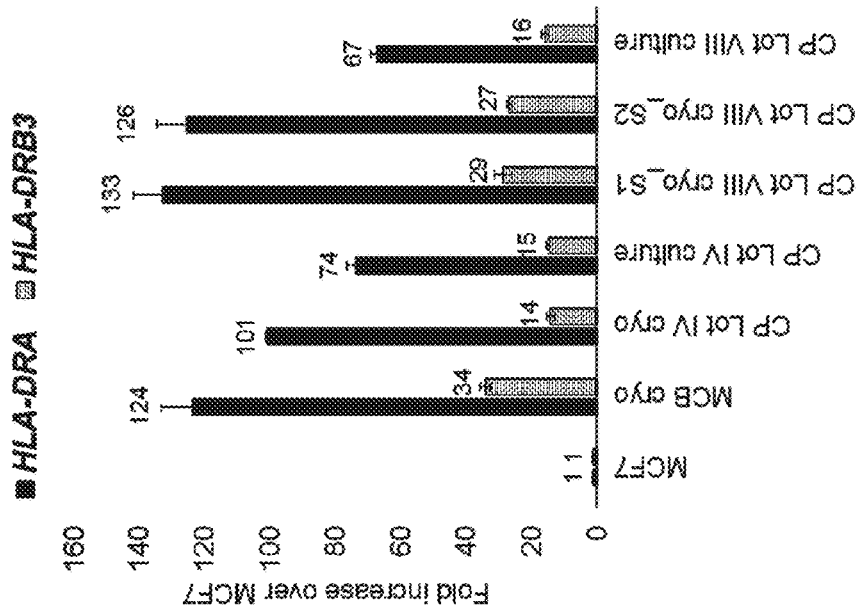

A database was generated that contained 111 genes with known immune-stimulatory roles (29-70) (Table 2). In particular, genes were included that encode (a) cell surface ligands for T cell co-stimulatory receptors or other cell surface-associated factors known to positively stimulate T cells (i.e., those that support T cell activation rather than inhibition), (b) cytokines and other soluble (i.e., free) factors that have positive T cell-stimulatory functions such as supporting activation, promoting survival, and/or inducing chemotaxis, (c) factors that promote the maturation, survival, chemotaxis, and/or in vitro generation of DCs, and (d) factors that promote antigen presentation. Of the 111 genes, 22 had quantile-normalized expression levels in all SV-BR-1-GM samples of more than 1.5 times the background cutoff value (see, the section titled "Methods" below for definition). 11 out of these 22 biomarkers expressed at levels more than 5 times the background cutoff value as demonstrated by at least one Illumina® probe (FIGS. 3 and 4). Nevertheless, HLA-DRB3 is expressed in SV-BR-1-GM cells as assessed by quantitative RT-PCR (qRT-PCR) (FIG. 5).

Figure 6A:
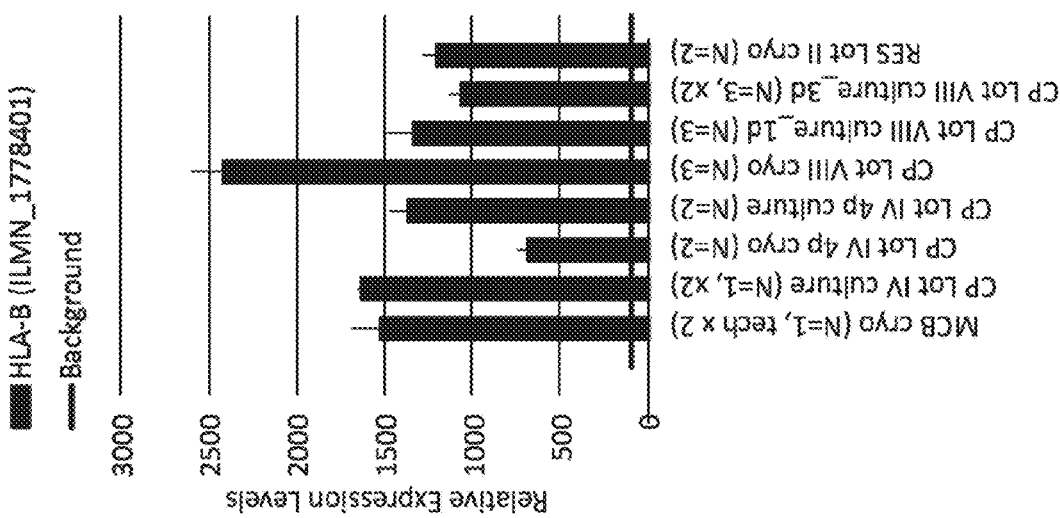
Figure 6B:
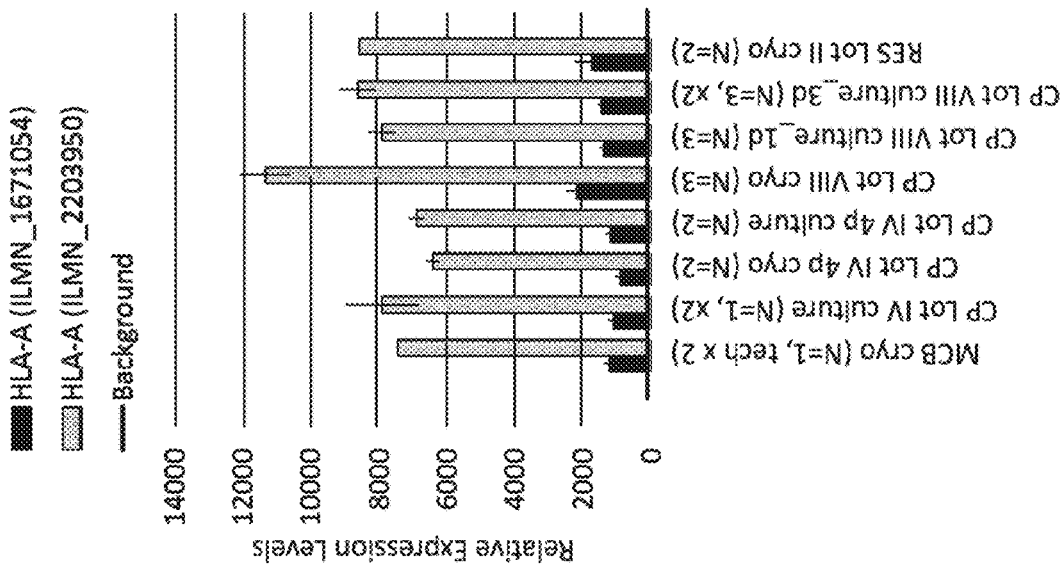
Figure 6C:
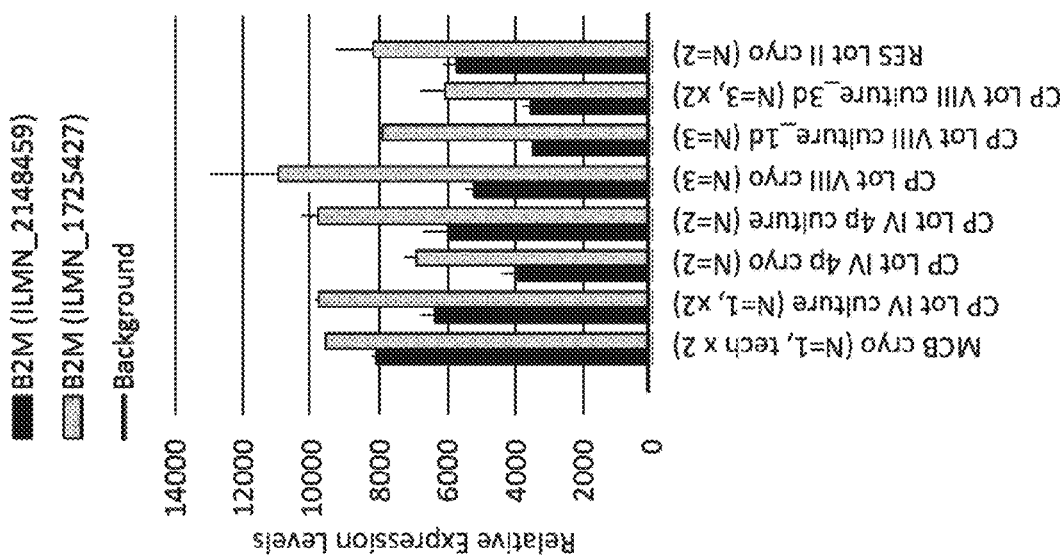

Surprisingly, among the 22 genes were several that encode HLA class I (B2M, HLA-A, HLA-B, HLA-F) or class II (HLA-DMA, HLA-DRA) components. As shown in FIG. 6, the genes HLA-E and HLA-H were also strongly expressed in SV-BR-1-GM cells. However, as they are not clearly associated with immune-stimulatory roles, they were not considered to be genes that contributed to the efficacy of SV-BR-1-GM as a cancer vaccine.

Figure 7A:
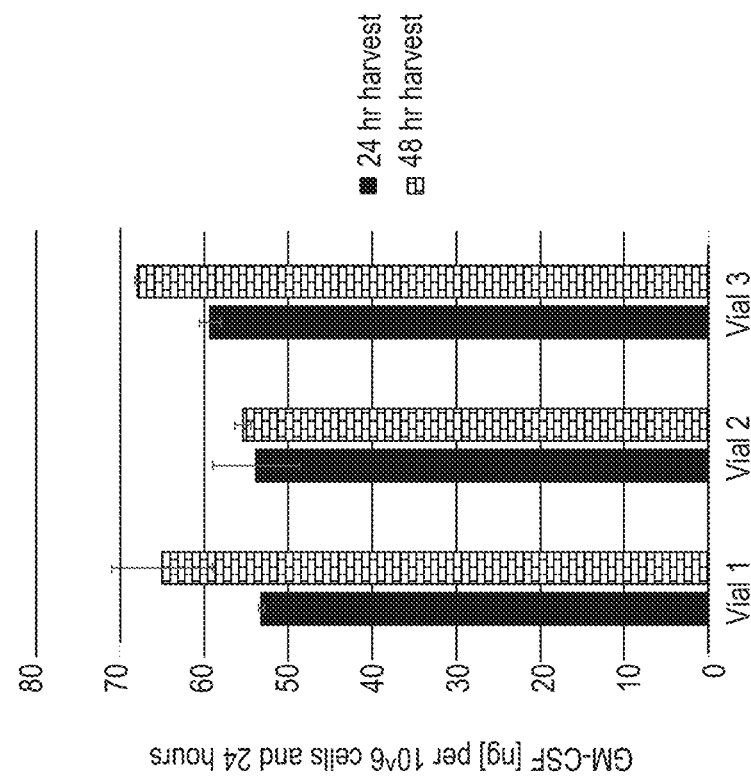
FIGS. 7A and 7B depict GM-CSF secretion by SV-BR-1-GM cells. For each sample type, GM-CSF production from cells in three cryovials (vials 1-3) was assessed. From each cryovial, cells were seeded into three T-75 flasks (approx. 4 million/flask). Two days later (t=0 hours), the medium of two flasks per cryovial was replaced with 14 mL of RPMI-1640 supplemented with 10% FBS and GlutaMAX™ (obtained from Thermo Fisher Scientific, Waltham, Mass.) and the number of cells from the third flask was determined. 24 and 48 hours after the medium change, aliquots of the culture supernatants were harvested and cryopreserved. GM-CSF secretion was assessed from the supernatants by ELISA (Human GM-CSF Quantikine ELISA Kit; obtained from R&D Systems/bio-techne, Minneapolis, Minn.). Data is expressed as ng GM-CSF per 1 million cells and 24 hours (relative to cell numbers at t=0 hours).
Figure 7B:
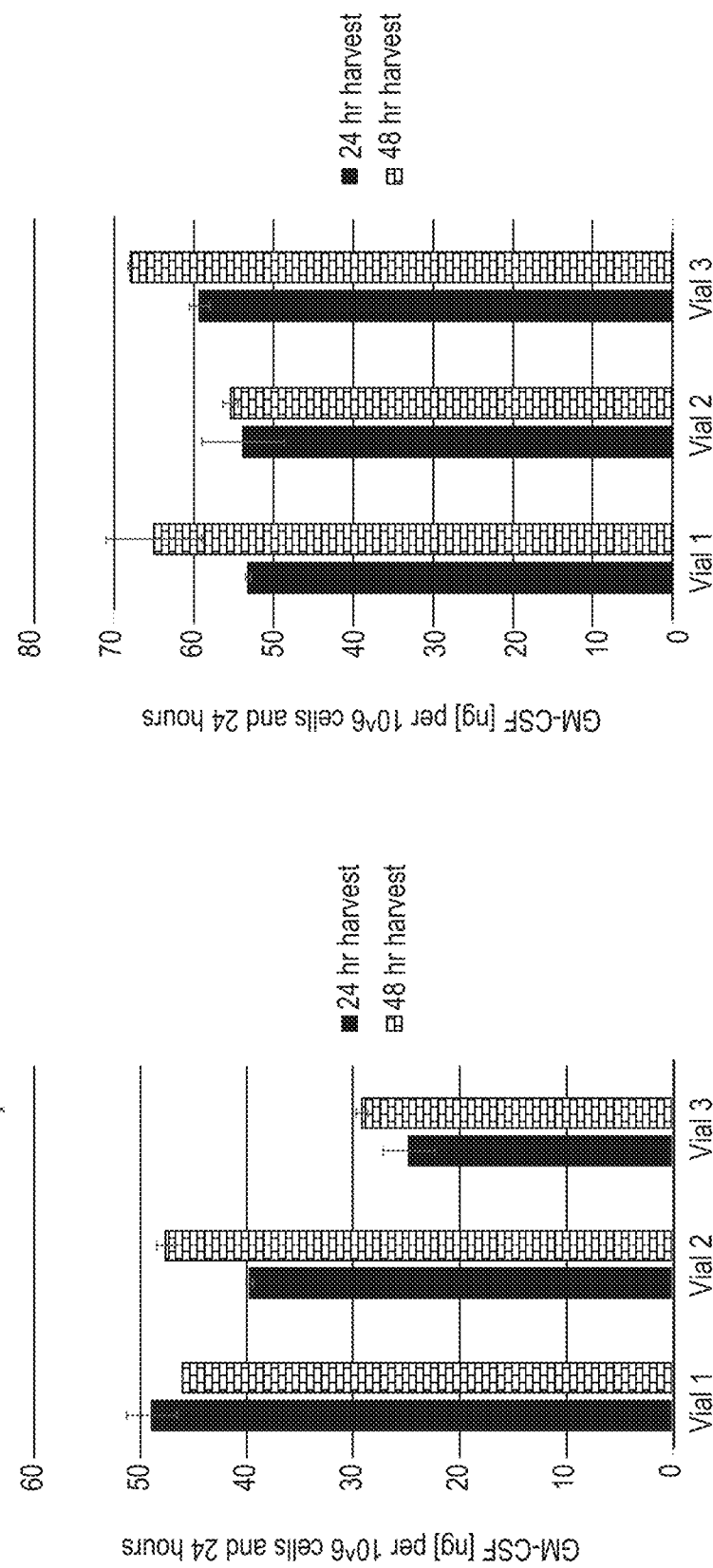

In order to further investigate the idea that SV-BR-1-GM exhibits direct immune-stimulatory effects, the expression of several genes with known immune-activating functions was confirmed by qRT-PCR. This gene set also included HLA-DRB3 and HLA-DMB, with the latter only barely expressed at more than 1.5 times the background cutoff value but being functionally tied to HLA-DMA (71), which is another immune-stimulatory biomarker expressed in SV-BR-1-GM cells (FIG. 3). The confirmatory experiment was conducted on a subset of the SV-BR-1-GM samples used for Illumina® microarray analysis and with RNA from MCF7 cells (i.e., a breast cancer cell line carrying the HLA-DRB3*0202 allele (72)) as a calibrator sample. Commercially available TaqMan® primer/probe sets were employed (Tables 3 and 4). As demonstrated in FIG. 5, all MHC class II-related transcripts analyzed (e.g., HLA-DRA, HLA-DRB3, HLA-DMA, HLA-DMB, CD74) were expressed at substantially higher levels than in MCF7 cells. This data justifies inclusion of both HLA-DRB3 and HLA-DMB in the gene signature associated with immune-stimulatory functions (Table 5). Furthermore, even though SV-BR-1-GM cells were engineered to express CSF2 (i.e., which encodes GM-CSF), CSF2 transcripts were not detected by Illumina® microarray gene expression profiling. However, this finding was not surprising because the Illumina probe sequence for CSF2 (ILMN_1661861) was not predicted to be represented in the ectopic CSF2 mRNA. Importantly, by ELISA, exogenous GM-CSF protein expression was demonstrated in medium conditioned by both irradiated and non-irradiated SV-BR-1-GM cells (FIG. 7).

Taken together, in addition to the 22 genes with transcript representation in FIG. 3, HLA-DRB3 and CSF2 (GM-CSF) were also considered to be relevant immune-stimulatory factors contributing to the efficacy of the SV-BR-1-GM (BriaVax) cancer vaccine. The complete 24-gene "immune signature" is shown in Table 5.

TABLE 5

Genes with immune-stimulatory roles that were expressed in SV-BR-1-GM cells (BriaVax)

| Gene Symbol | Official Full Name/Description | Aliases |
| --- | --- | --- |
| ADA | adenosine deaminase | |
| ADGRE5 | adhesion G protein-coupled receptor E5 | CD97, TM7LN1 |
| B2M | beta-2-microglobulin | IMD43 |
| CAV1 | caveolin 1 | BSCL3, CGL3, LCCNS, MSTP085, PPH3, VIP21 |
| CD58 | CD58 molecule | LFA-3, LFA3, ag3 |
| CD74 | CD74 molecule; invariant chain and CLIP | DHLAG, HLADG, II, Ia-GAMMA |
| CD83 | CD83 molecule | BL11, HB15 |
| CSF2 | colony stimulating factor 2 | GMCSF |
| CXCL8 | C-X-C motif chemokine ligand 8 | GCP-1, GCP1, IL8, LECT, LUCT, LYNAP, MDNCF, MONAP, NAF, NAP-1, NAP1 |
| CXCL16 | C-X-C motif chemokine ligand 16 | CXCLG16, SR-PSOX, SRPSOX |
| HLA-A | major histocompatibility complex, class I, A | HLAA |
| HLA-B | major histocompatibility complex, class I, B | AS, B-4901, HLAB |
| HLA-DMA | major histocompatibility complex, class II, DM alpha | D6S222E, DMA, HLADM, RING6 |
| HLA-DMB | major histocompatibility complex, class II, DM beta | D6S221E, RING7 |
| HLA-DRA | major histocompatibility complex, class II, DR alpha | HLA-DRA1, MLRW |

TABLE 5-continued

Genes with immune-stimulatory roles that were expressed in SV-BR-1-GM cells (BriaVax)

| Gene Symbol | Official Full Name/Description | Aliases |
|---|---|---|
| HLA-DRB3 | major histocompatibility complex, class II, DR beta 3 | HLA-DR1B, HLA-DR3B |
| HLA-F | major histocompatibility complex, class I, F | CDA12, HLA-5.4, HLA-CDA12, HLAF |
| ICAM3 | intercellular adhesion molecule 3 | CD50, CDW50, ICAM-R |
| IL6 | interleukin 6 | BSF-2, BSF2, CDF, HGF, HSF, IFN-beta-2, IFNB2, IL-6 |
| IL10 | interleukin 10 | CSIF, GVHDS, IL-10A, TGIF |
| IL15 | interleukin 15 | IL-15 |
| IL18 | interleukin 18 | IGIF, IL-18, IL-1g, IL1F4 |
| KITLG | KIT ligand | DCUA, DFNA69, FPH2, FPHH, KL-1, Kitl, MGF, SCF, SF, SHEP7 |
| TNFSF14 | tumor necrosis factor superfamily member 14 | CD258, HVEML, LIGHT, LTg |

In Table 5 above, gene symbols refer to the NCBI designations and HUGO Gene Nomenclature Committee (HGNC) recommendations. Gene symbols, official full names and descriptions, and aliases are indicated as shown on the respective NCBI Gene sites.

HLA Allele Matches Between SV-BR-1-GM and a Robust Clinical Responder

By serotyping, it was previously established that the robust clinical responder (referred to herein as subject A002) and SV-BR-1-GM cells had similarities in their HLA phenotypes (16). To determine whether such similarities were further reflected at the allele level, peripheral blood cells from patients and SV-BR-1-GM cells were subjected to high resolution HLA typing for HLA-A, -B, and -DRB3. Indeed, whereas the three clinical trial subjects who did not experience SV-BR-1-GM-induced tumor regression had only an HLA-A allele match with SV-BR-1-GM, subject A002 matched both at HLA-A (*11:01) and HLA-DRB3 (*02:02). See, Table 6. This finding agreed with a mechanism of action in which tumor antigens displayed on SV-BR-1-GM MHCs contribute to the therapeutic efficacy of the vaccine.

Figure 8:
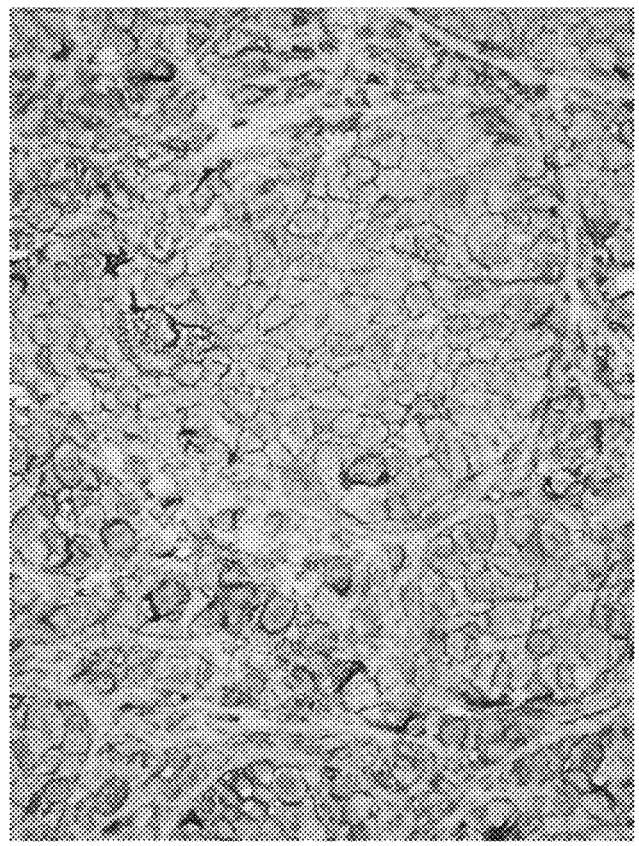
FIG. 8 shows HLA-DRB3 expression in a tumor specimen of a strong clinical responder. In order to assess whether the strong clinical responder (16), referred to as subject A002 in Example 1, presented with tumor expression of HLA-DRB3, paraffin-embedded A002 tumor material was stained with a rabbit polyclonal antibody raised against an N-terminal region of human HLA-DRB3. As demonstrated, HLA-DRB3 immunoreactivity was apparent.
Figure 8:
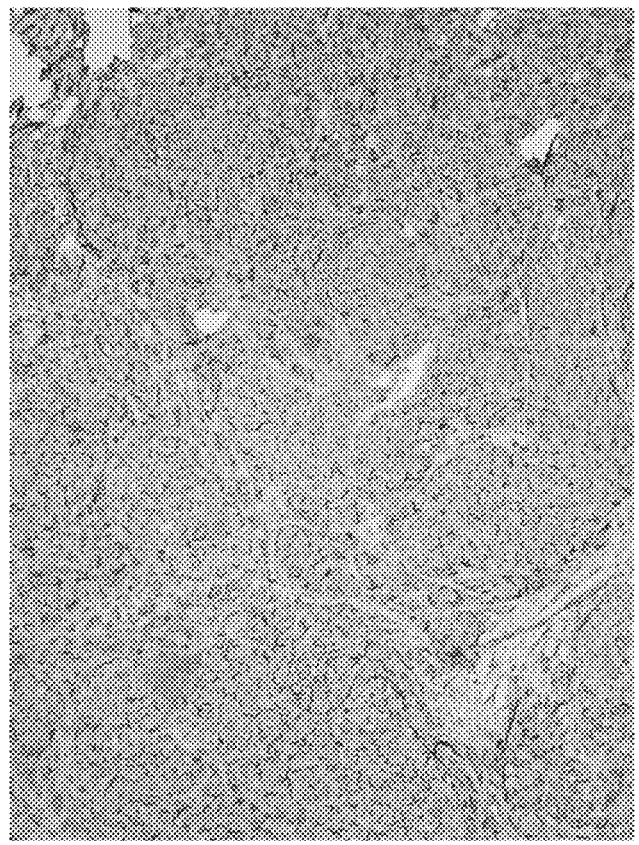

Since HLA typing was conducted using peripheral blood cells, and because vaccine-based cancer immunotherapy requires cancer cell MHC expression, the level of HLA-DRB3 protein was identified in a paraffin-embedded tumor specimen from clinical trial subject A002. As shown in FIG. 8, HLA-DRB3 immunoreactivity was indeed apparent, thus further demonstrating the role of HLA class II in the MoA of SV-BR-1-GM (BriaVax).

SV-BR-1-GM inoculation. "+" indicates allele level and "(+)" indicates allele group level identity with SV-BR-1-GM.

Cancer/Testis Antigens Expressed in SV-BR-1-GM

Cancer/testis antigens (CTAs) represent a class of antigens with physiological expression predominantly restricted to testicular or placental tissue and, for a subset, brain tissue. However, in some instances CTAs will become upregulated following malignant conversion of cells from a variety of organs. For many of such CTAs, immune-stimulatory roles have been established (6,73-79).

Given such features, the mRNA expression levels of 279 confirmed or putative CTAs (Table 7) were assessed in SV-BR-1-GM cells and compared to expression in several other breast cancer cell lines and normal breast cells. GEO datasets of both cultured (i.e., GSE56718 (80) and GSE48398 (MCF10A)) and noncultured (i.e., GSE35399 (81)) normal breast cells were utilized. The CTA genes chosen for the analysis were selected from those described by (79) and (78), those listed in the CT database (77), and those represented by the nCounter® Human PanCancer Immune Profiling Panel (obtained from NanoString Technologies®, Seattle, Wash.).

Figure 9A:
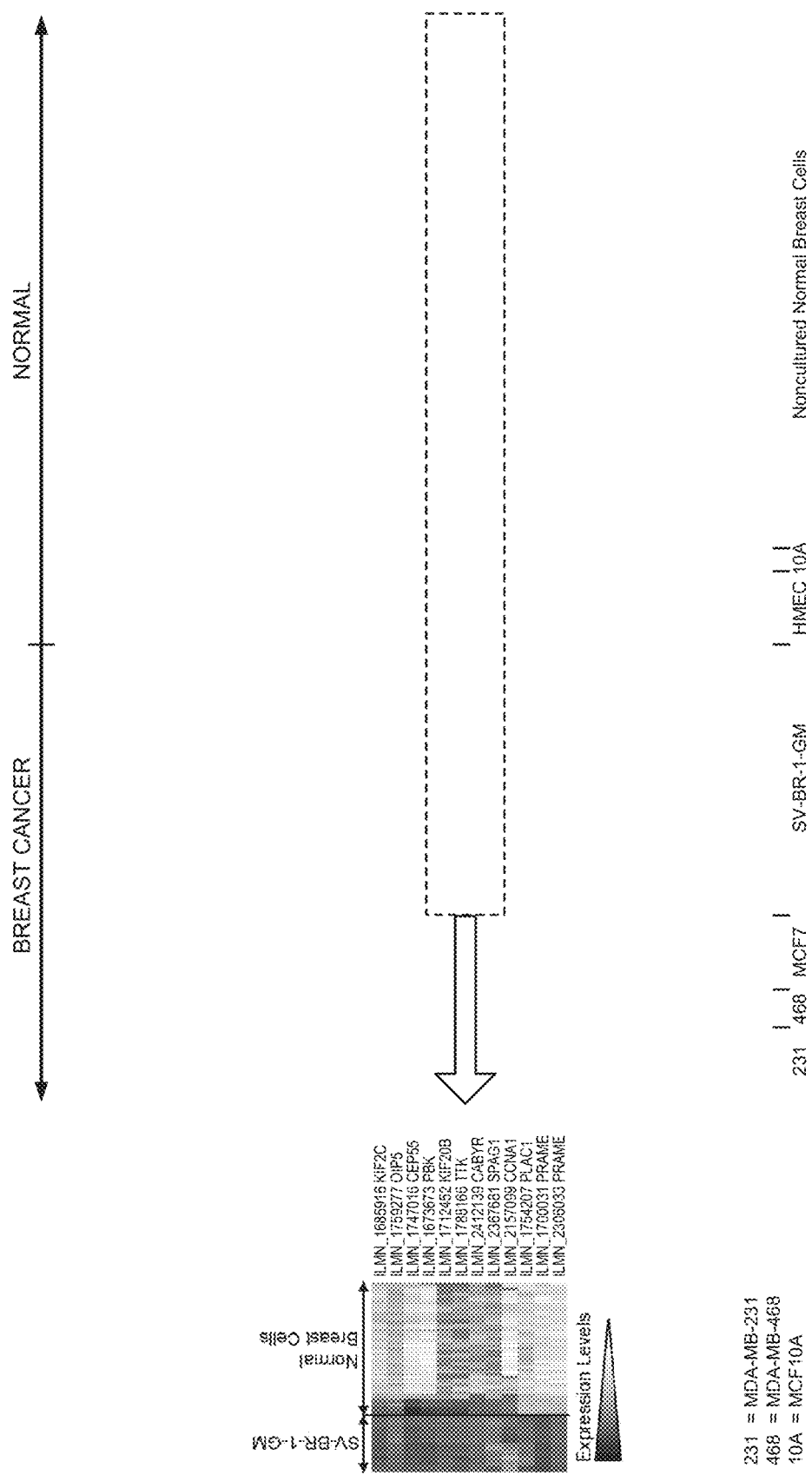
FIGS. 9A-9E depict cancer/testis antigen (CTA) expression in SV-BR-1-GM cells.

Following hierarchical clustering on both genes and samples, a group of CTA genes (i.e., KIF2C, OIP5, CEP55, PBK, KIF20B, TTK, CABYR, SPAG1, CCNA1, PLAC1, and PRAME) emerged as having a particularly good ability to discriminate between SV-BR-1-GM and normal breast cells (FIG. 9A). The genes PRAME, KIF2C, CEP55, and

TABLE 6

HLA alleles

| Subject ID | Cancer Dx | Dx to Vac (yrs) | Survival (months) | Tumor regression | HLA-A | | HLA-B | | HLA-DRB3 |
|---|---|---|---|---|---|---|---|---|---|
| A001 | Breast | 6 | 40.7 | No | 02:01 | 24:02+ | 13:02 | 41:01 | 03:01 | — |
| A002 | Breast | 2 | 33.7 | Yes | 02:01 | 11:01+ | 18:03 | 44:02 | 02:02+ | — |
| A003 | Ovarian | 33 | 35.6 | No | 02:01 | 03:01 | 07:02 | 13:02 | Neg. | — |
| B001 | Breast | 10 | 7.0 | No | 11:01+ | — | 35:01(+) | 40:01 | Neg. | — |
| SV-BR-1-GM | N/A | N/A | N/A | N/A | 11:01 | 24:02 | 35:08 | 55:01 | 01:01 | 02:02 |

Table 6 above lists HLA alleles of SV-BR-1-GM (BriaVax) and peripheral blood cells from 4 study subjects (ClinicalTrials.gov Identifier: NCT00095862) that were identified. Subject A002, with both HLA-A and HLA-DRB3 matches, responded to SV-BR-1-GM inoculation with substantial tumor regression. The "Dx to Vac" column shows the time intervals from the initial cancer diagnosis to the first SV-BR-1-GM inoculation.

Figure 9B:
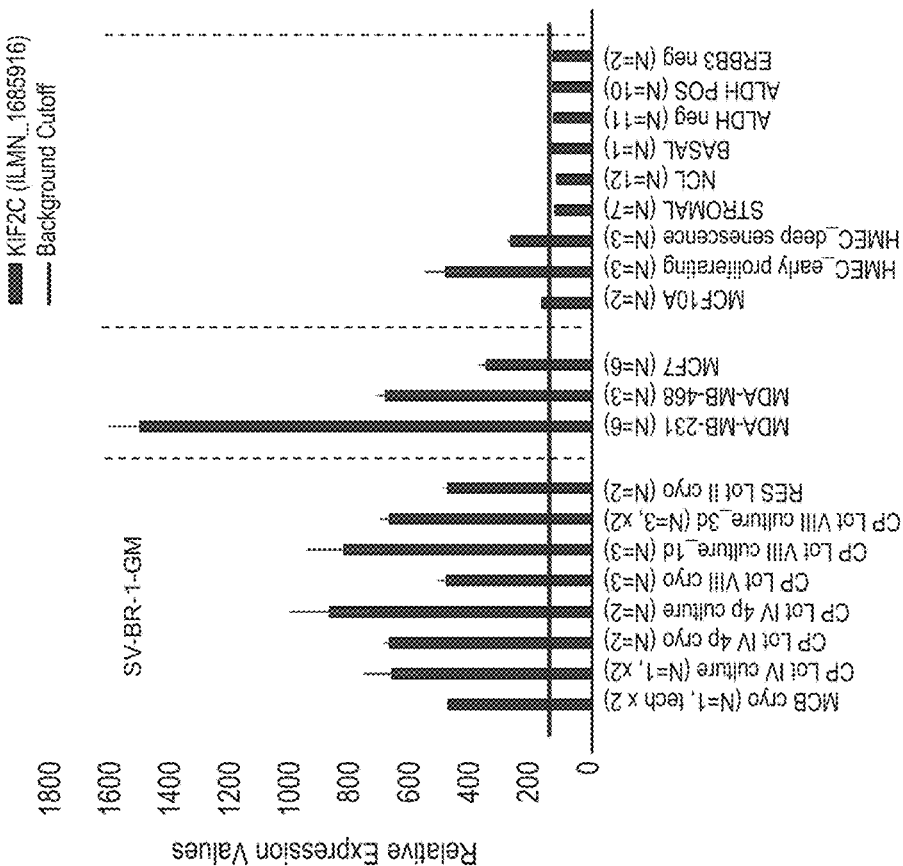
Figure 9C:
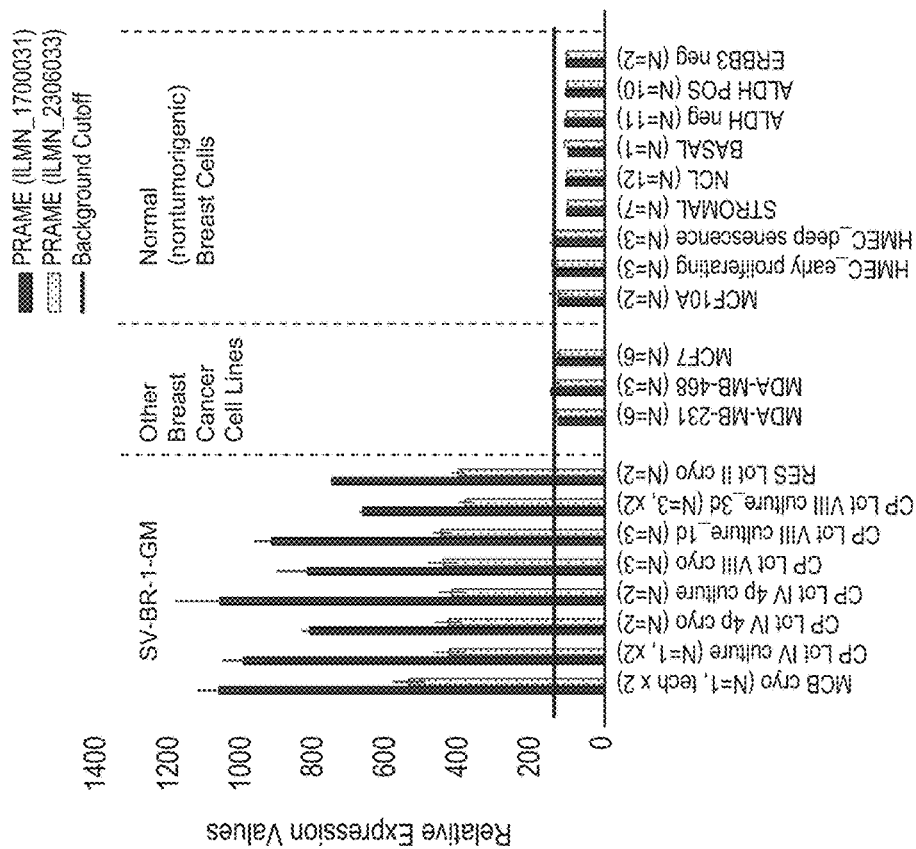
Figure 9D:
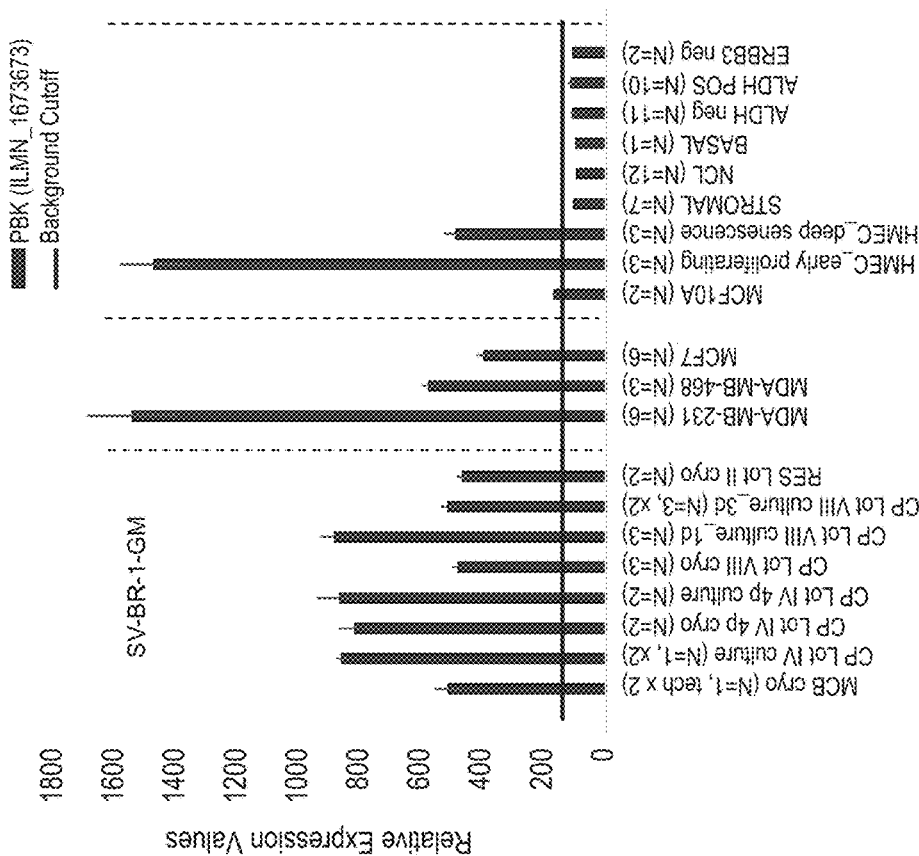
Figure 9E:
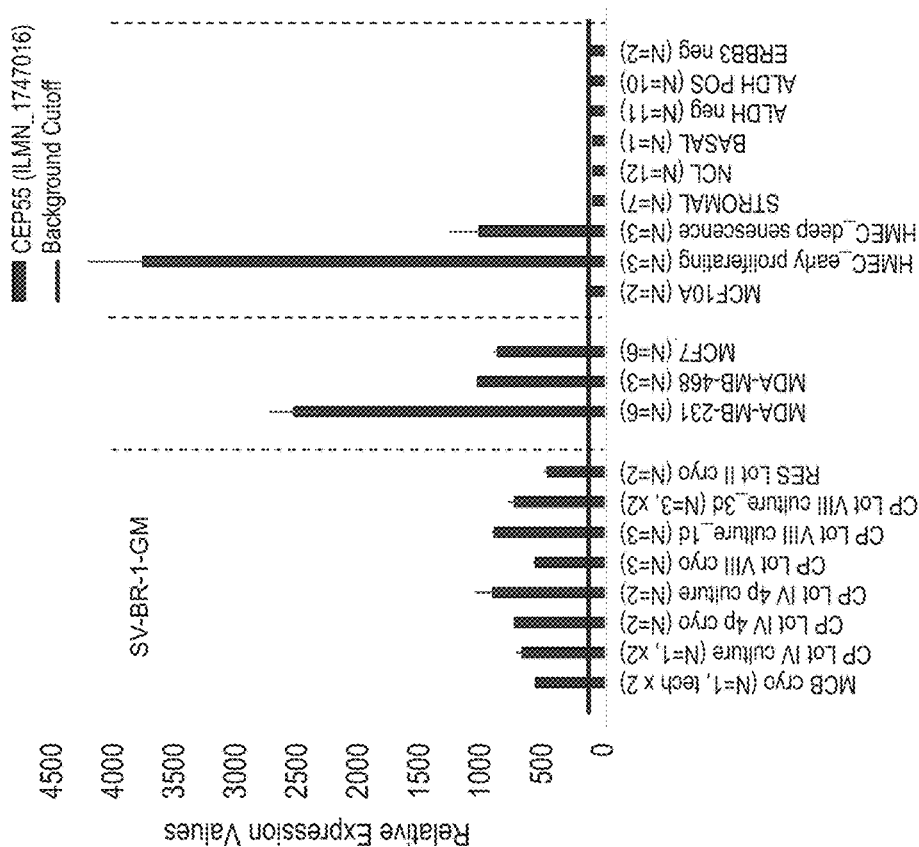

PBK were robustly expressed in SV-BR-1-GM cells (FIGS. 9B-9E), with PRAME exhibiting the highest fold-change ratio between the SV-BR-1-GM expression level and the maximal expression level among the normal breast samples (Table 8). In contrast to PRAME (FIG. 9B), KIF2C, CEP55, and PBK were also expressed in cultured human mammary epithelial cells (HMECs). Interestingly, as shown in FIGS.

9C-9E, the expression values of the latter three genes were higher in "early proliferating" than in senescent HMECs (80). This indicates that proliferating breast epithelial cells also express these genes in vivo. A list of CTAs with transcript expression values that were greater in SV-BR-1-GM cells than in normal breast cell types is shown in Table 8.

TABLE 8

CTA expression in SV-BR-1-GM cells

| Gene Symbol | Probe Identifier | SV-BR-1-GM | Max. expression values (among nonmalignant cells) | | SV-BR-1-GM/Max | |
|---|---|---|---|---|---|---|
| | | | C + NC | NC | C + NC | NC |
| PRAME | ILMN_1700031 | 869.1 | 142.8 | 114.7 | 6.1 | 7.6 |
| PRAME | ILMN_2306033 | 431.9 | 145.1 | 112.5 | 3.0 | 3.8 |
| PBK | ILMN_1673673 | 663.0 | 1465.5 | 107.2 | 0.5 | 6.2 |
| CEP55 | ILMN_1747016 | 708.4 | 3756.0 | 126.2 | 0.2 | 5.6 |
| KIF2C | ILMN_1685916 | 668.0 | 484.9 | 130.8 | 1.4 | 5.1 |
| PLAC1 | ILMN_1754207 | 415.4 | 150.1 | 144.9 | 2.8 | 2.9 |
| OIP5 | ILMN_1759277 | 405.9 | 372.3 | 167.3 | 1.1 | 2.4 |
| CABYR | ILMN_2412139 | 369.6 | 533.8 | 179.0 | 0.7 | 2.1 |
| SPAG1 | ILMN_1712773 | 289.1 | 203.7 | 181.6 | 1.4 | 1.6 |

Listed in Table 8 above are CTAs fulfilling all of the following criteria: 1) representative transcript level in SV-BR-1-GM cells greater than 1.5 times the background cutoff value, 2) representative transcript level in SV-BR-1-GM cells greater than 1.5 times the maximal transcript level among the noncultured (NC) normal breast cell types (SV-BR-1-GM/Max), 3) maximal transcript level among the NC normal breast cell types less than 1.5 times the background cutoff value, whereby the maximal NC transcript level was established among the representative values of each sample type (see, section titled "Sample Representation" in "Methods" section below). For PBK, CEP55, and CABYR, SV-BR-1-GM/Max was greater than 1 with the NC cell types alone, but was less than 1 when including the cultured (C) breast cells (C+NC). This may indicated that culturing upregulated expression of these genes. "C" denotes cultured normal cell types (i.e., MCF10A from GEO dataset GSE48398, and "early_proliferating" and "deep_senescence" human mammary epithelial cells (HMECs) from GSE56718 (80)). "NC" denotes noncultured normal cell types (i.e., ALDH NEG, ALDH POS, ERBB3 NEG, NCL, BASAL, STROMAL from GSE35399 (81)). The background cutoff value was 141.16.

Other Candidate Immunogens Expressed in SV-BR-1-GM Vaccine Cells

Even though the SV-BR-1-GM vaccine expresses an "immune signature" (Table 5), the latter alone was unlikely sufficient to induce a strong tumor-directed immune response as it does not provide cancer specificity. It was reasonable to hypothesize that for patients responding to whole-cell cancer vaccines with tumor regression, such missing directionality was provided by the vaccine through overexpression of TAAs that were co-expressed in the tumors. Candidate TAAs for the SV-BR-1-GM vaccine included the CTAs described above and illustrated in FIG. 9.

To systematically search for SV-BR-1-GM antigens with potential to break immune tolerance by overexpression, a two-tier microarray-based approach was employed. First, genes that were upregulated in SV-BR-1-GM cells relative to normal breast cells were identified. For this, gene expression levels in SV-BR-1-GM cells were compared to those of a variety of normal human breast cell types described by Shehata et al., 2012 (GEO dataset GSE35399, (81)), Lowe et al., 2015 (GEO dataset GSE56718, (80)), and MCF10A from GEO dataset GSE48398. Two serial filters were applied to quantile-normalized gene expression values to enrich for genes that differentiated SV-BR-1-GM cells from normal breast cells. After low-stringency filtration, 455 different genes (including non-coding RNA) were retained, of which, after medium-stringency filtration, 352 remained (Tables 9 and 10).

Second, among the 352 genes retained after medium-stringency filtration, those not only upregulated relative to normal breast cells but also relative to tissues other than breast were considered to be validated immunogen candidates. This second criterion was sought to enrich for genes with a potential to break immune tolerance, since physiologically high levels of gene expression not only in breast but also in tissues of other organs may prevent breakage of tolerance. The high-stringency filter applied in this step compared GEO dataset GSE29431 (i.e., breast cancer tissues) to a subset of samples represented by GEO dataset GSE7307 (i.e., nonmalignant tissues) (Table 11) and was conducted on 327 genes retained after medium-stringency filtration. Of note, the filter cutoff criteria (see, section titled "Methods" below) were selected to retain ERBB2 (HER2/neu), whose immunogenic properties are being exploited in several clinical trials (13,82). Twenty genes were validated as TAA candidates using this strategy (Table 12). Interestingly, three of them mapped to chromosome 17q12 (i.e., ERBB2 (HER2/neu), MIEN1, and PGAP3 (FIG. 10)).

TABLE 12 in silico validated candidate TAAs

| Gene Symbol | Description/Official Full Name | Location | Affymetrix Probe ID | Score |
|---|---|---|---|---|
| ALG8 | alpha-1,3-glucosyltransferase | 11q14.1 | 203545_at | 3.86 |
| ARPC5L | actin related protein 2/3 complex, subunit 5 like | 9q33.3 | 226914_at | 4.91 |
| CBX2 | chromobox homolog 2 | 17q25.3 | 226473_at | 5.72 |
| COL8A1 | collagen type VIII alpha 1 chain | 3q12.1 | 226237_at | 11.73 |
| DCAF10 | DDB1 and CUL4 associated factor 10 | 9p13.2 | 226511_at | 3.85 |
| | | | 230679_at | 8.76 |
| EIF3H | eukaryotic translation initiation factor 3 subunit H | 8q23.3-q24.11 | 230570_at | 7.28 |
| ERBB2 | erb-b2 receptor tyrosine kinase 2 | 17q12 | 216836_s_at | 3.74 |
| | | | 234354_x_at | 11.92 |
| HIST1H4H | histone cluster 1 H4 family member h | 6p22.2 | 208180_s_at | 7.71 |
| | | | 232035_at | 11.78 |

TABLE 12-continued in silico validated candidate TAAs

| Gene Symbol | Description/Official Full Name | Location | Affymetrix Probe ID | Score |
|---|---|---|---|---|
| IGFBP5 | insulin like growth factor binding protein 5 | 2q35 | 1555997_s_at | 3.87 |
| INTS7 | integrator complex subunit 7 | 1q32.3 | 218783_at | 4.49 |
| KRT19 | keratin 19 | 17q21.2 | 228491_at | 9.36 |
| KRT81 | keratin 81 | 12q13.13 | 213711_at | 7.01 |
| MGAT4A | mannosyl (alpha-1,3-)-glycoprotein beta-1,4-N-acetylglucosaminyltransferase, isozyme A | 2q11.2 | 231283_at | 5.92 |
| MIEN1 | migration and invasion enhancer 1 | 17q12 | 224447_s_at | 6.66 |
| PGAP3 | post-GPI attachment to proteins 3 | 17q12 | 221811_at | 6.05 |
|  |  |  | 55616_at | 5.24 |
| RSF1 | remodeling and spacing factor 1 | 11q14.1 | 222541_at | 8.95 |
|  |  |  | 229885_at | 4.33 |
| SHB | SH2 domain containing adaptor protein B | 9p13.1 | 1557458_s_at | 4.31 |
| SLC35A2 | solute carrier family 35 member A2 | Xp11.23 | 209326_at | 5.38 |
| SYNE4 | spectrin repeat containing nuclear envelope family member 4 | 19q13.12 | 235515_at | 4.02 |
| TNPO1 | transportin 1 | 5q13.2 | 225765_at | 3.74 |

Tables 13 and 14 provide further evidence of the importance of the 20 in silico validated TAAs. ERBB2, MIEN1, and PGAP3 (bolded entries), which are all localized to chromosome 17q12, exhibited a trend in which they were most highly expressed in Her2 3+ tumors, less so in Her2 2+ tumors, and the least in Her2 0-1+ tumors. Table 14 provides comparisons within Her2 2+ tumors (i.e., overall, FISH positive and negative samples), and shows that the 95% confidence intervals (CIs) of ERBB2, MIEN1, and PGAP3 were higher for the Her2 FISH+ than for the Her2 FISH− cancer group.

Discussion

Allogeneic whole-cell cancer vaccines express a wide variety of antigens, of which some may be TAAs co-expressed in patient tumors. However, whether or not an effective immune response is mounted against such TAAs depends on numerous factors. This example indicated that HLA allele identity between the vaccine and the patient was a significant factor.

Figure 11A:
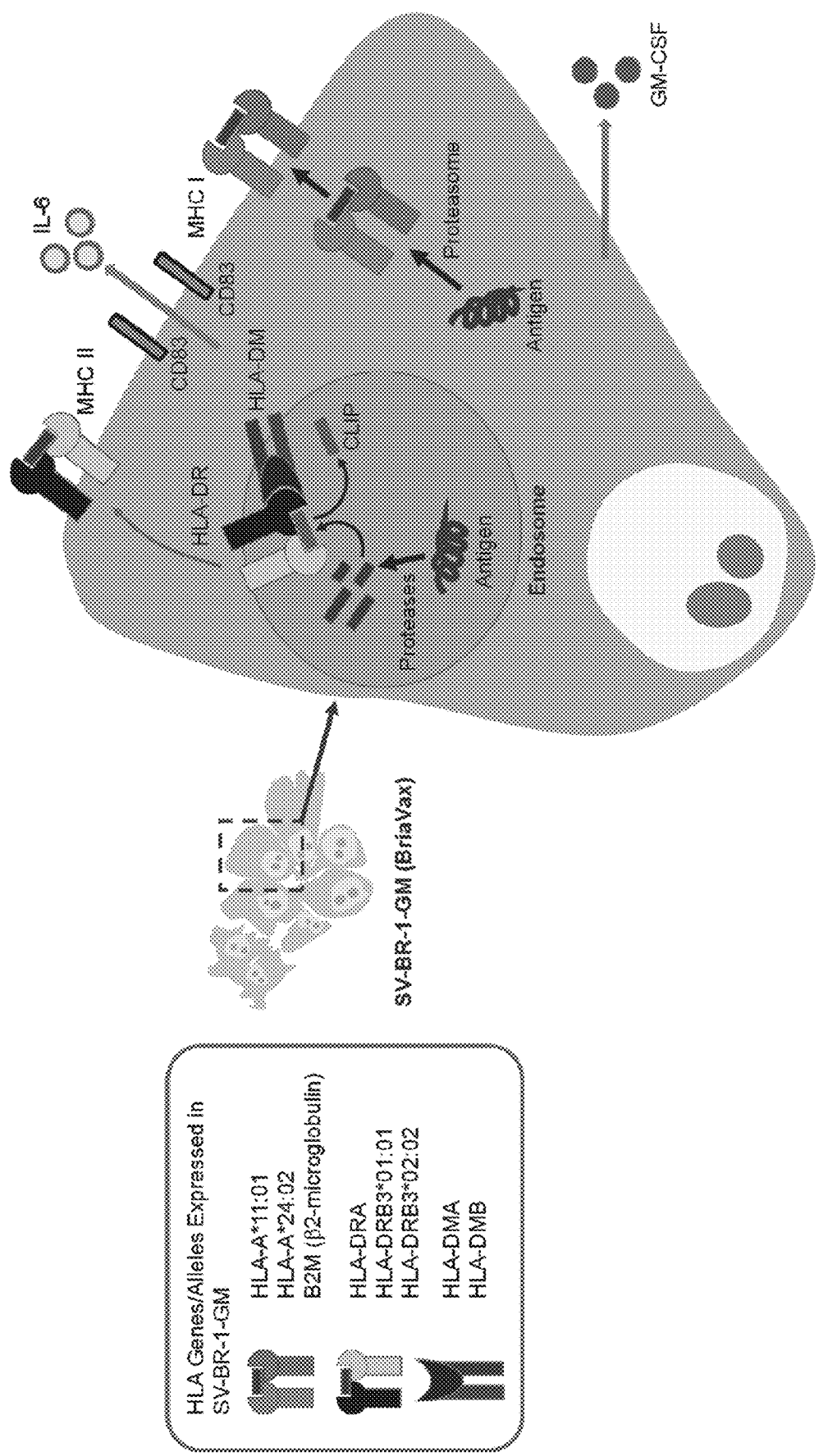
FIGS. 11A-11C depicts mechanisms of action for SV-BR-1-GM.
Figure 11B:
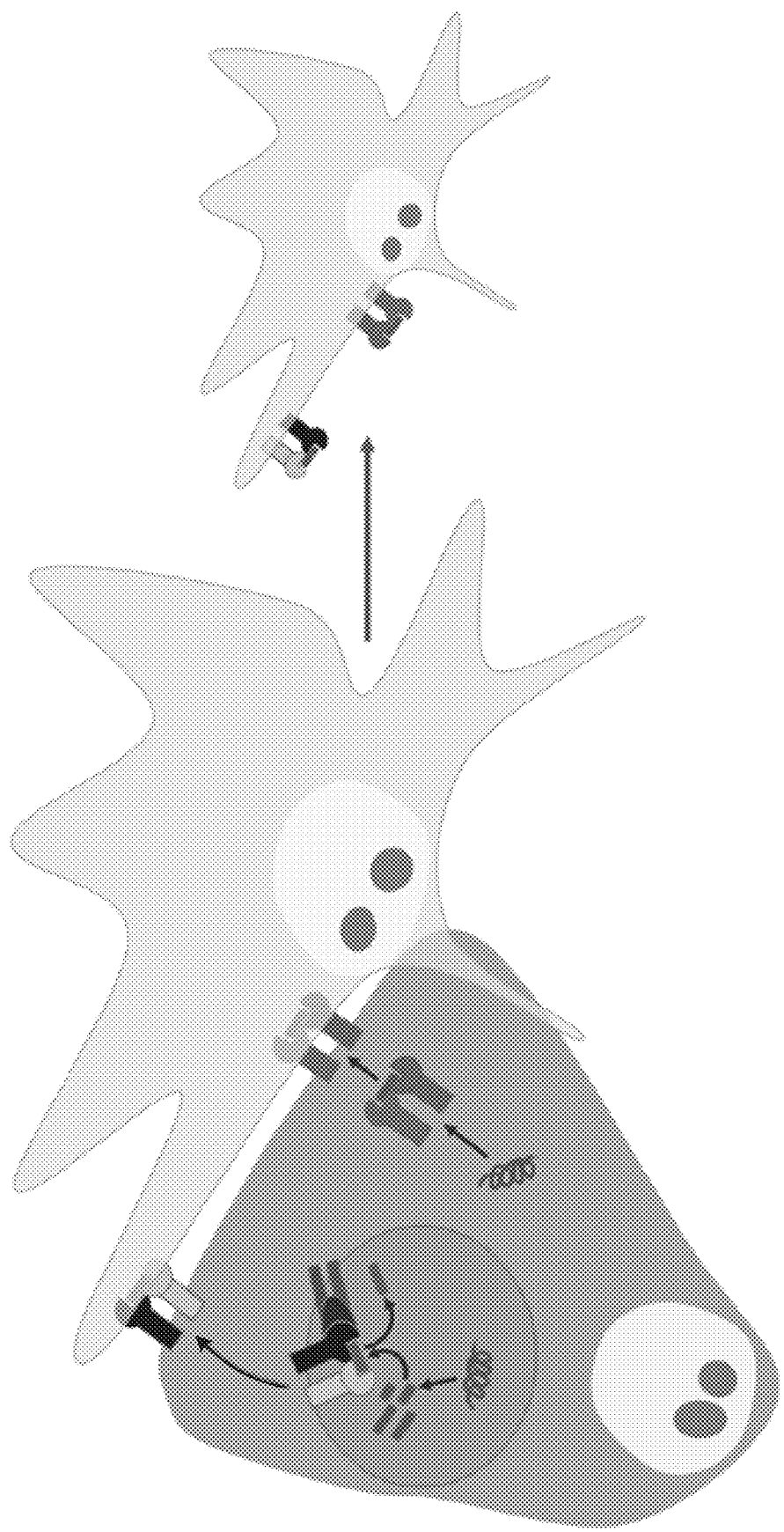
Figure 11C:
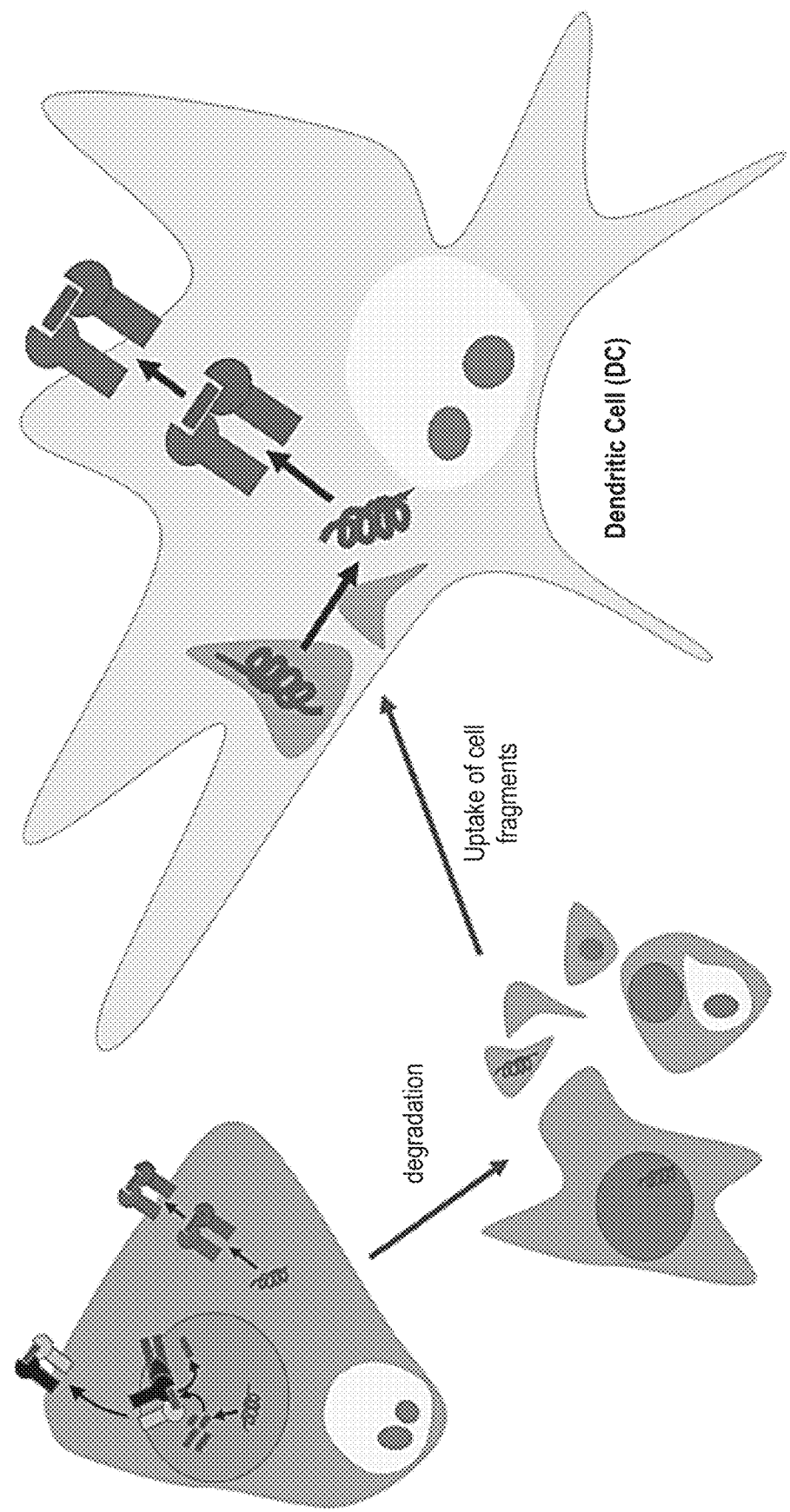

Among four clinical trial subjects (i.e., three with breast cancer and one with ovarian cancer), objective tumor regression following SV-BR-1-GM (BriaVax) inoculation was only observed in one patient (16), referred to as subject A002 in this article. In contrast to the other three subjects, subject A002 carried both HLA class I (i.e., HLA-A*11:01) and class II (i.e., HLA-DRB3*02:02) alleles that were also present in the vaccine (Table 6; FIG. 11A). Furthermore, together with a set of other genes with known immune-stimulatory roles, SV-BR-1-GM cells expressed an "immune signature" (Table 5). From a mechanistic perspective, these findings indicate that TAAs were displayed on vaccine cell surface MHCs where they could directly and/or indirectly (upon "cross-dressing", i.e., upon trogocytosis-based transfer onto APCs such as dendritic cells) activate T cells (FIG. 11B) (83-85). In addition, other mechanisms may have contributed to the immune-stimulatory effects of the vaccine. In particular, cross-presentation, whereby cellular fragments from the vaccine are endocytosed by APCs, processed, then corresponding peptide antigens loaded onto MHC molecules, may also have played a substantial role (FIG. 11C) (85, 86). Nevertheless, since only direct activation of T cells by the vaccine and cross-dressing of DCs with TAA-MHCs from the vaccine require HLA allele identity between the patient and the vaccine, and because only the patient who had both HLA class I and II allele matches with the vaccine demonstrated robust tumor regression (Table 6 and (16)), it is reasonable to speculate that either direct activation and/or cross-dressing did indeed play significant roles in the vaccine's mechanism of action.

Figure 12:
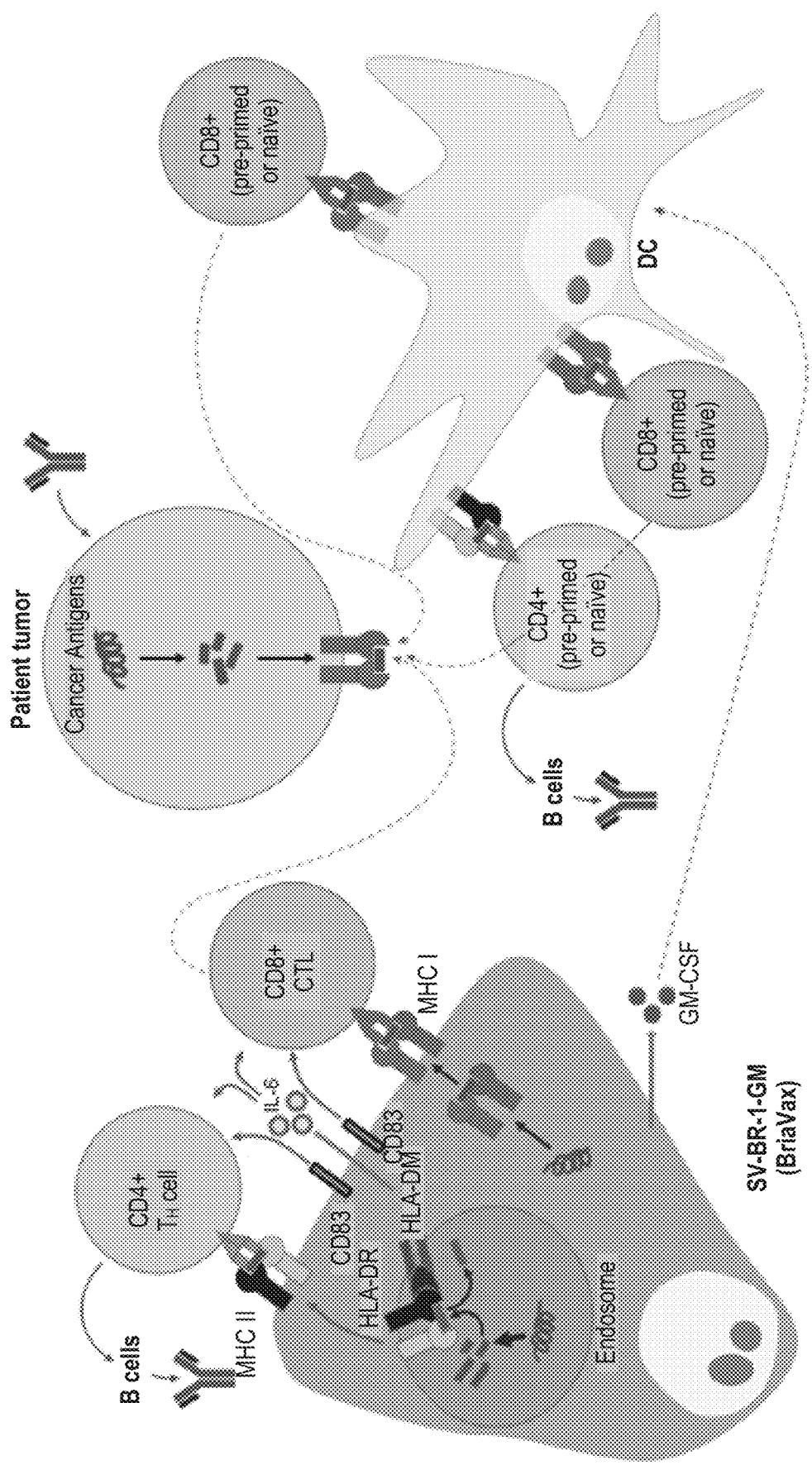
FIG. 12 depicts a mechanism of action of the BriaVax (SV-BR-1-GM) cancer vaccine. Factors expressed in SV-BR-1-GM cells (FIG. 11A) and some of their known roles as immune modulators are shown. Expression of HLA class I and II genes is consistent with a model in which the SV-BR-1-GM vaccine directly stimulates cytotoxic T lymphocytes (CD8+) and T helper cells (CD4+), and thereby induces both cytotoxic and humoral responses. Since SV-BR-1-GM cells do not express CD80 or CD86 mRNA, they unlikely act directly as antigen-presenting cells activating naïve T cells. However, DCs, displaying SV-BR-1-GM TAA peptides on MHCs obtained from SV-BR-1-GM cells (i.e., via cross-dressing (FIG. 11B) and/or on some of their own MHCs via cross-presentation (FIG. 11C)), may activate such naïve T cells. SV-BR-1-GM TAA-specific T cells recognize and kill tumor cells that co-express and present the corresponding TAAs. Additionally, tumor destruction can occur via antibodies. CTL denotes cytotoxic T lymphocyte; Tx denotes T helper cell.

Since the proposed mechanism of action of the SV-BR-1-GM vaccine (FIG. 12) is relevant to other GVAX vaccines, one may wonder whether in such programs patients with both HLA class I and II allele matches, if any, had better clinical responses to the vaccine than those without. Moreover, if HLA alleles indeed contribute to the efficacy of GVAX vaccines, high resolution HLA typing has merit as a companion diagnostic. Table 15 outlines estimated frequencies of the HLA allele combinations present in SV-BR-1-GM for different ethnic groups. As shown, allele combination frequencies range from 5.4-31.0% (i.e., the probability that a randomly selected individual carries at least one of SV-BR-1-GM's HLA class I and one of its HLA class II alleles is 5.4-31.0% depending on the ethnic group). When loosening restrictions to only consider the allele group, combination frequencies range from 12.8-37.7%.

TABLE 15

Frequencies of HLA allele combinations

| HLA Allele Matches with SV-BR-1-GM | | | | | | | | | | |
|---|---|---|---|---|---|---|---|---|---|---|
| Accuracy | Per individual | AAFA | AFB | AINDI | AMIND | CARB | CARHIS | EURCAU | FILII | JAPI |
| Allele group | ≥1 HLA I | 21.4 | 20.1 | 66.1 | 49.6 | 23.3 | 42.9 | 41.9 | 87.0 | 76.3 |
| Allele group | ≥1 HLA II | 64.7 | 63.7 | 54.1 | 53.9 | 63.1 | 55.7 | 55.2 | 29.8 | 30.7 |
| Allele group | ≥1 HLA I + II | 13.9 | 12.8 | 35.8 | 26.7 | 14.7 | 23.9 | 23.1 | 25.9 | 23.4 |

TABLE 15-continued

Frequencies of HLA allele combinations

| | | | | | | | | | | |
|---|---|---|---|---|---|---|---|---|---|---|
| Allele | ≥1 HLA I | 8.4 | 7.2 | 49.9 | 34.6 | 8.8 | 27.1 | 30.3 | 66.3 | 68.8 |
| Allele | ≥1 HLA II | 64.6 | 63.7 | 54.1 | 53.8 | 63.0 | 55.6 | 55.2 | 29.7 | 30.6 |
| Allele | ≥1 HLA I + II | 5.4 | 4.6 | 27.0 | 18.6 | 5.6 | 15.1 | 16.7 | 19.7 | 21.0 |

| | HLA Allele Matches with SV-BR-1-GM | | | | | | | | |
|---|---|---|---|---|---|---|---|---|---|
| Accuracy | Per individual | KORI | MENAFC | MSWHIS | NCHI | SCAHIS | SCSEAI | VIET |
| Allele group | ≥1 HLA I | 61.9 | 54.9 | 53.7 | 74.9 | 54.9 | 69.5 | 71.9 |
| Allele group | ≥1 HLA II | 40.1 | 68.6 | 52.1 | 46.1 | 52.0 | 52.3 | 31.1 |
| Allele group | ≥1 HLA I + II | 24.8 | 37.7 | 28.0 | 34.5 | 28.5 | 36.4 | 22.4 |
| Allele | ≥1 HLA I | 54.3 | 38.3 | 34.5 | 67.3 | 34.3 | 54.5 | 58.8 |
| Allele | ≥1 HLA II | 40.1 | 68.2 | 52.1 | 46.1 | 51.9 | 52.1 | 31.0 |
| Allele | ≥1 HLA I + II | 21.8 | 26.1 | 17.9 | 31.0 | 17.8 | 28.4 | 18.3 |

The allele frequencies disclosed in Table 15 above were reported in (87). Estimated "phenotype frequencies" were calculated indicating probabilities that an individual carries at least 1 of SV-BR-1-GM's (a) HLA class I alleles (A*11:01, HLA-A*24:02, HLA-B*35:08, and HLA-B*55:01) or allele groups (HLAA*11, HLAA*24, HLA-B*35, and HLAB*55), (b) HLA class II alleles (HLA-DRB3*01:01 and HLA-DRB3*02:02) or allele groups (HLA-DRB3*01 and HLA-DRB3*02), or (c) HLA class I and II alleles or allele groups. Shown are "phenotype frequencies" as percentage values. See the section titled "Methods" below for details on the calculations. AAFA denotes African American; AFB denotes African; AINDI denotes South Asian Indian; AMIND denotes North American Indian; CARB denotes Caribbean black; CARHIS denotes Caribbean Hispanic; EURCAU denotes European Caucasian; FILII denotes Filipino; JAPI denotes Japanese; KORI denotes Korean; MENAFC denotes Middle Eastern or N. Coast of Africa; MSWHIS denotes Mexican or Chicano; NCHI denotes Chinese; SCAHIS denotes Hispanic—South or Central American; SCSEAI denotes Southeast Asian; VIET denotes Vietnamese.

To mitigate the risk of tumor development caused by the vaccine itself, SV-BR-1-GM cells were irradiated with 200 Gy (20,000 rad) prior to their clinical application (16). Interestingly, it has been demonstrated that ex vivo gamma-irradiation may up-regulate both MHC class I and cancer/testis antigens in cancer cell lines representing different cancer types and in biopsy samples from sarcoma patients. Importantly, such gene expression changes were accompanied by increased recognition by CD8+ cells (88). This notion is also important clinically, as there is evidence suggesting that tumor irradiation could enhance the benefits of immunotherapy (89-91). Therefore, since the gene expression profiles generated in the context of this study were derived from non-irradiated cells, it would not be surprising if the 200 Gy of irradiation further increased the HLA gene expression levels.

Without being bound to any particular theory, it is plausible that, in addition to matching HLA alleles, TAAs co-expressed in the vaccine and patient tumors played a role in the favorable course of action observed in subject A002. In the molecular study presented here the identity of candidate TAAs whose overexpression in SV-BR-1-GM cells induced breakage of immunologic tolerance was sought.

Immunologic tolerance is a double-edged sword. Its underlying mechanisms prevent both autologous antigens from evoking an immune response (autoimmunity) and the recognition of tumors by the immune system. Several methods to break tolerance have been described, including the use of immune checkpoint inhibitors or monoclonal antibodies delivering co-stimulatory signals to T cells (92). In the context of GVAX, GM-CSF secreted by the vaccine has been attributed a major role in overcoming immune tolerance (9). However, given that GVAX whole-cell vaccines express a vast array of antigens co-expressed on healthy cells one would imagine that autoimmunity may accompany such treatments. Indeed, autoinflammatory responses have been observed following GVAX application as demonstrated by increased serum levels of anti-thyroglobulin antibodies. However, despite their association with autoimmunity, anti-thyroglobulin antibody levels appeared to be positively correlated with treatment efficacy (21).

Figure 10A:
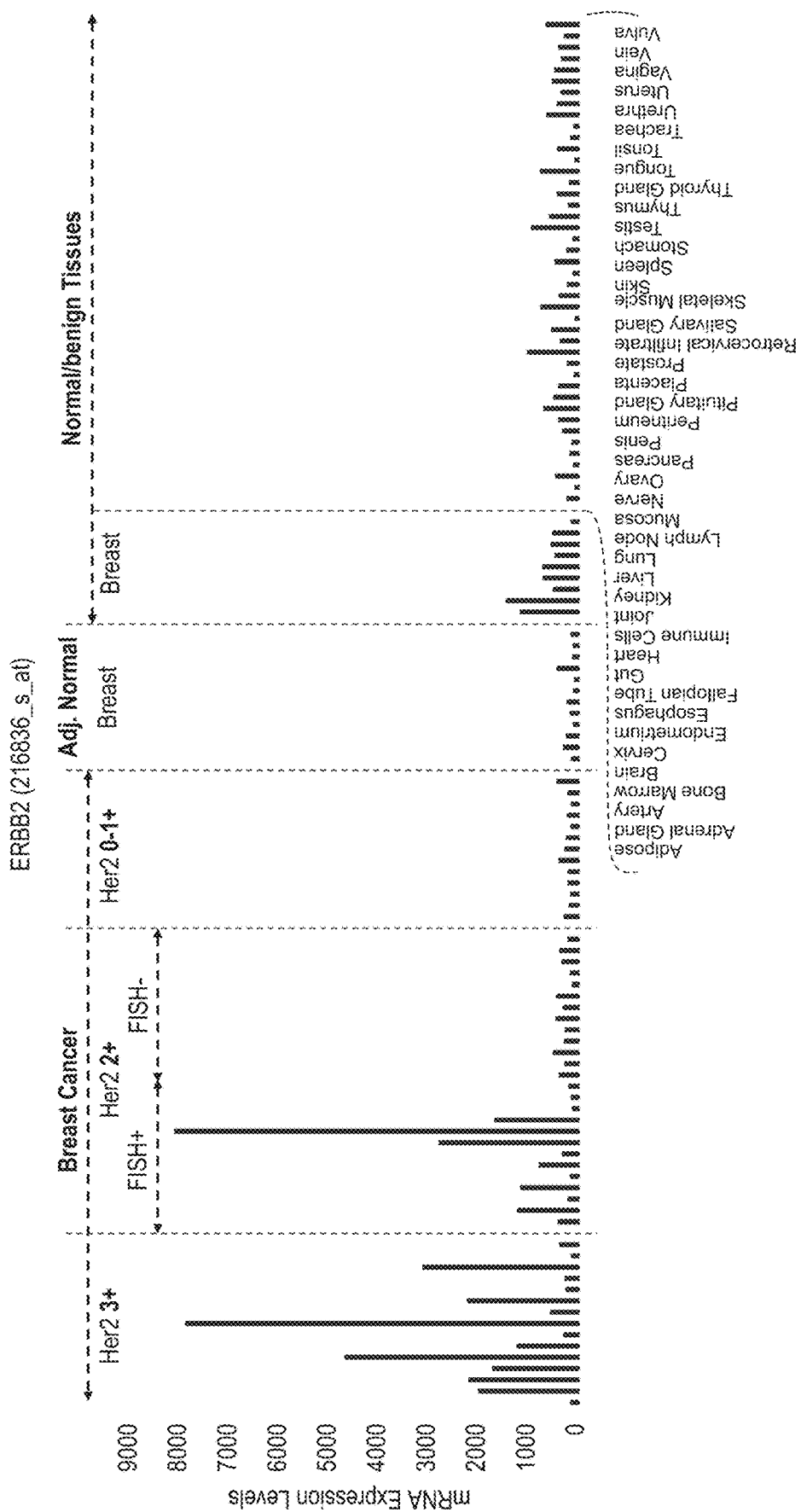

A two-tier microarray-based in silico approach was employed to examine whether TAAs responsible for the vaccine's anti-tumor effect induced an immune response due to an overexpression-mediated break of tolerance. First, genes upregulated in SV-BR-1-GM cells relative to normal breast cells were identified. This was accomplished by comparing several different lots of SV-BR-1-GM to a variety of normal human breast cell types. Second, the genes with apparently higher expression levels in SV-BR-1-GM compared with normal breast cells were subjected to a validation step for which the genes' expression levels in breast cancer were compared to those of normal tissues of various organs. Since breakage of immune tolerance by overexpression may, at least in principle, only occur for genes with no or low physiological expression at every site permissive for immune surveillance, it was reasoned that ideal candidate immunogens should be highly expressed in SV-BR-1-GM cells and breast cancer tissues but not, or only minimally, in non-immune privileged normal tissues. The bioinformatics strategy applied to validate immunogen candidates reflects this theory. Twenty genes encoding candidate TAAs were considered more highly expressed in both SV-BR-1-GM cells and breast cancer tissues than in normal tissues (Table 12). Interestingly, among these twenty genes were five located on chromosome 17 of which three mapped to 17q12 (i.e., ERBB2 (HER2/neu), MIEN1(C17ORF37), and PGAP3 (PERLD1)) (FIG. 10). This indicated that not only was ERBB2 overexpressed in a subset of breast cancers, but so were other candidate TAAs located in the vicinity of ERBB2 (93, 94).

Furthermore, the data (FIG. 10, Tables, 13, 14, and 20) presented in this example show that ERBB2, MIEN1, and PGAP3 are useful for identifying and/or differentiating HER2 positive (HER2+) patients. The microarray analyses presented herein demonstrated that ERBB2 (also known as HER2) showed poor correlation with the results of the immunohistochemistry (IHC)-based method. In particular, only 9 of 15 patients (60%) who had been diagnosed as HER2 3+ had ERBB2 mRNA levels about those of the HER2 0-1+ group. However, as shown in Table 20, if MIEN1 and/or PGAP3 were used for the analysis (either alone, in combination with each other, or in combination with ERBB2), then sensitivity was improved. MIEN1 and PGAP3 alone (i.e., instead of ERBB2) resulted in a sensitivity of 87%. Similarly, combinations of ERBB2 and MIEN1 or ERBB2 and PGAP3 resulted in sensitivities of 87%. A combination of MIEN/and PGAP3 or a combination of all three biomarkers resulted in a sensitivity of 100%. Clearly, these biomarkers afford superior sensitivity over current IHC or FISH assays, as well as ERBB2 alone when measuring mRNA levels.

Cancer/testis antigens (CTAs) are a class of tumor-associated antigens specifically expressed in cancer and germline tissues (6, 73-79). The stringent filtering approach which yielded twenty in silico validated TAA candidates did not select for CTAs. However, when gene expression profiles of a set of 279 CTAs (Table 7) were analyzed, several CTAs, most notably PRAME, were found to be selectively expressed in SV-BR-1-GM compared to normal breast cells (FIG. 9 and Table 8). Even though it was not found to be expressed in noncancerous tissues other than tissues of the testis and the endometrium, PRAME did not appear in the stringent in silico screen because of the 54 breast cancer specimens analyzed, PRAME expression was restricted to only 11 (20%) samples, of which only 2 (4%) demonstrated appreciable expression levels. Furthermore, at least some of the CTAs had low expression levels in SV-BR-1-GM cells (FIG. 9). However, as demonstrated by Groeper et al., CTA-specific tumor-infiltrating lymphocytes (TILs) could even be expanded from tumors with undetectable CTA levels (6). This indicates that minuscule (i.e., below level of detection) CTA expression levels may suffice for CTA-specific T cell retention in the tumor or that such T cells only coincidentally happened to reside in the tumor tissue as it was resected. In agreement with the latter possibility, CTA-directed cytotoxicity of TILs from tumors with undetectable CTA expression was weak (6).

In summary, the study presented here provides evidence that the tumor-directed effect observed following inoculation with the SV-BR-1-GM vaccine and reported previously (16) is mediated by the vaccine's "immune signature", which includes factors ranging from HLA class I and II components to ligands for T cell co-stimulatory receptors and chemokines known to promote attraction of immune cells, and by TAAs such as PRAME.

Conclusion

Unlike other established breast cancer cell lines, SV-BR-1-GM cells not only expressed known and putative TAAs but also a collection of factors with known roles in promoting immune responses. Most notably, in addition to HLA class I factors, class II genes such as HLA-DMA and -DMB were also expressed. Since HLA class II components are associated with bone fide antigen-presenting cells such as DCs, their expression in SV-BR-1-GM cells was surprising and points toward a unique mechanism of action. The observation that the patient who responded to the SV-BR-1-GM vaccine with tumor regression (16) also carried HLA class I and II alleles that were also found in the vaccine is consistent with the hypothesis that patients who co-express SV-BR-1-GM TAAs and possess matching HLA alleles are particularly likely to develop a strong tumor-directed immune response.

Methods

Culturing of SV-BR-1-GM (BriaVax) Cells

SV-BR-1-GM lots were manufactured in RPMI-1640 supplemented with 10% FBS and L-glutamine or Gibco® GlutaMAX™ (obtained from Thermo Fisher Scientific, Waltham, Mass.). Typically, a fraction (e.g., about 50%) of such culture medium was pre-conditioned by SV-BR-1-GM cells at the time of medium change. For early lots, SV-BR-1-GM cells were expanded from cryopreserved cell suspensions starting from T-25 flasks with sequential propagation in larger flasks and harvesting from about thirty T-150 flasks. Lots were expanded also starting from small tissue culture vessels and were scaled to and further expanded in T-225 flasks. The final expansion step was conducted in 10-STACK CellSTACK® Culture Chambers (obtained from Corning Inc., Corning, N.Y.).

Microarray Gene Expression Profiling

SV-BR-1-GM cells, obtained directly from cryogenic vials following recovery from liquid nitrogen or harvested from cultures, were lysed in Buffer RLT (obtained from Qiagen, Valencia, Calif.) with or without supplementation with β-mercaptoethanol (obtained from Bio-Rad Laboratories, Hercules, Calif.). Total RNA was isolated from lysates via RNeasy Mini Kits (obtained from Qiagen) then subjected to microarray hybridization. In short, RNA was amplified, biotin-labeled, Cy3-labeled, then hybridized onto HumanHT-12 v4 Expression BeadChip arrays (obtained from Illumina®, San Diego, Calif.). Fluorescent signal intensities were acquired on an Illumina® iScan array scanner. Average signal intensities and detection p-values were calculated using Illumina® GenomeStudio software. Thereafter, non-normalized data sets passing quality control (QC) criteria as defined below were analyzed with various modules of GenePattern software using the public server portal at www.broadinstitute.org/cancer/software/genepattern (99). If applicable, datasets to be compared were merged using the MergeColumns version 1 module. Expression levels of all Illumina® samples to be cross-compared were quantile-normalized using the IlluminaIlormalizer software version 2 (beta) module, then further processed in Microsoft Excel and/or subjected to log transformation and hierarchical clustering via the HierarchicalClustering software version 6 module (i.e., distance correlation: Pearson correlation; clustering method: Pairwise average-linkage). Heat maps and dendrograms of clustered data were generated using the HierarchicalClusteringViewer software version 11 module. To compare gene expression levels between SV-BR-1-GM and samples analyzed by others, Gene Expression Omnibus (GEO; National Center for Biotechnology Information, NCBI) datasets, also generated on the Illumina® HumanHT-12 v4 Expression BeadChip platform, were first merged with SV-BR-1-GM data sets and processed as described above. For the in silico analyses of GEO datasets generated on Affymetrix Human Genome U133 Plus 2.0 Arrays, CEL files were RMA/quantile-normalized and background-subtracted using the ExpressionFileCreator software module then filtered in Microsoft Excel as described below.

A gene was defined as being expressed if at least one corresponding probe yielded a quantile-normalized expression value above the median "expression" level among all human RNA-targeting, non-control, probes (max. 47,323 for the HumanHT-12 v4 Expression BeadChip arrays, Illumine). This background cutoff definition coincided with the rough estimate that approximately 50% of the genes in a tissue are expressed (100). However, since a tissue contains both an unknown number of different cell types and unknown relative contributions of each cell type to the overall number of cells, this definition likely overestimates the extent of actual background. Nevertheless, consequently, it reduced the probability of calling non-expressed genes expressed.

Quality Control of Non-Normalized Data Sets

The integrity of pre-amplified SV-BR-1-GM RNA was determined via Agilent's 4200 TapeStation system (obtained from Agilent, Santa Clara, Calif.). Samples with an RNA integrity Number equivalent (RIM) value of less than 7.5 were excluded from further analysis. Additionally, for SV-BR-1-GM samples as well as samples obtained via GEO (NCBI) and processed on HumanHT-12 v.4 BeadChips, non-normalized data sets were assessed for gene expression variability. Except for the analysis shown in FIG. 1C, low-variability samples were excluded from further processing. Low-variability was defined as a ratio between the expression value at the $95^{th}$ percentile and the value at the $5^{th}$ percentile of less than 10.

Sample Representation

For comparative gene expression analyses, individual genes were represented in the various SV-BR-1-GM sample types (i.e., MCB cryo, CP Lot IV culture, CP Lot IV 4p cryo, CP Lot IV 4p culture, CP Lot V cryo, CP Lot VIII cryo, CP Lot VIII culture 1d, CP Lot VIII culture 3d, and RES Lot II cryo) by their arithmetic gene expression means. For calculations requiring one representative SV-BR-1-GM gene expression value, the median value among the arithmetic means was used. Representative gene expression levels for samples other than SV-BR-1-GM, obtained from GEO, were defined as follows: breast cancer cell line samples from dataset GSE48398 and human mammary epithelial cell samples (HMECs, "early proliferating" vs. "deep senescence") from dataset GSE56718 (80) were represented by their arithmetic means. Normal breast sample types (i.e., ALDH NEG, ALDH POS, ERBB3 NEG, NCL, BASAL, and STROMAL) from dataset GSE35399 (81) were represented by their median expression values except for FIGS. 9B-9E, where arithmetic means and standard errors of the means (SEMs) are shown. For dataset GSE48398 only expression profiles from cells cultured at 37° C. were utilized. For the comparison between the breast cancer (dataset GSE2943) and normal tissues (dataset GSE7307), the $95^{th}$ percentile values among all breast cancer tissues (HER2_3+, HER2_2+, HER2_0-1+ of GSE2943) and the $95^{th}$ percentile values among the maximal expression values of each group of normal tissue (Table 11, GSE73073) were used as comparators. The $95^{th}$ percentile rather than maximal expression values were chosen to accommodate potential outliers.

In Silico Identification of Putative SV-BR-1-GM TAAs

Figure 13:
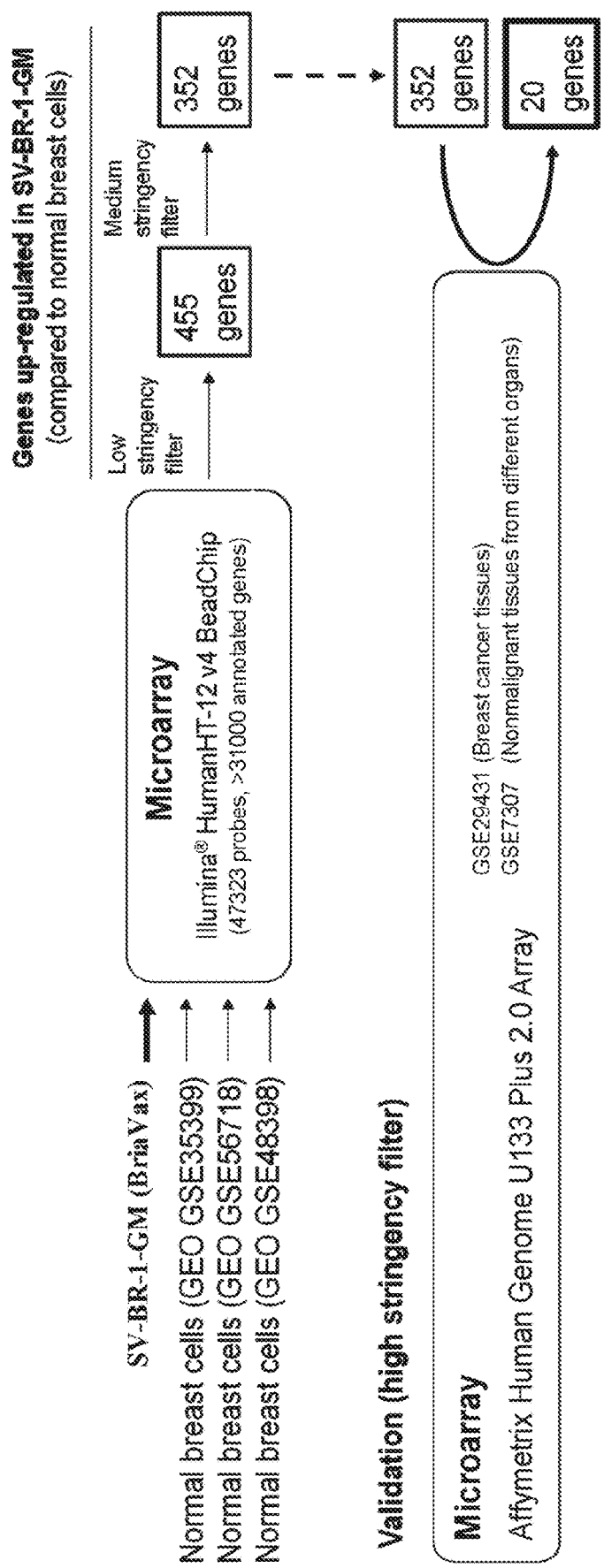
FIG. 13 depicts an overview of the filtration strategy to identify candidate TAAs. Gene expression profiles of SV-BR-1-GM cells were compared to those of normal breast cells (i.e., a subset of samples represented by GSE35399, GSE56718, GSE48398). 455 genes (NCBI Gene Symbols) were retained after applying a low-stringency filter; 352 of them were also retained after applying a medium-stringency filter. These 352 genes were then subjected to an in silico validation step aimed at identifying genes that are overexpressed both in SV-BR-1-GM cells and breast cancer tissue but lack expression in non-malignant tissues of various organs.
Figure 14:
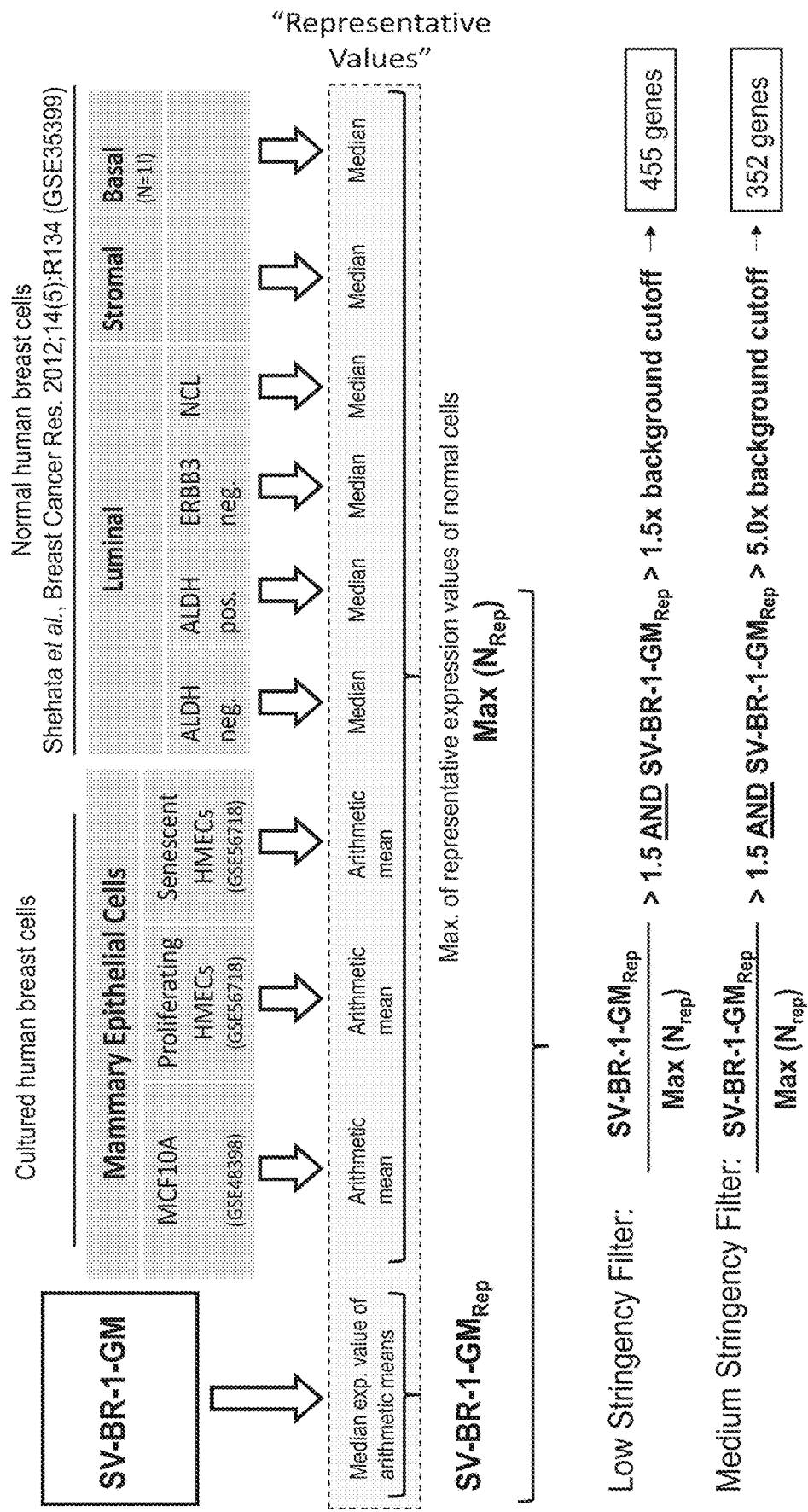
FIG. 14 depicts low- and medium-stringency filtration.

Quantile-normalized SV-BR-1-GM gene expression values were compared to those of normal human breast cells represented by the GEO datasets GSE35399 (81) and GSE56718 (80). Genes for which the representative SV-BR-1-GM expression values were both greater than 1.5 times the background cutoff value (defined above) and greater than 1.5 times higher than the maximal representative value among all groups of normal breast cells were additionally subjected to the second, medium-stringency, filtration step (i.e., expression level was greater than 5 times background cutoff value) (FIGS. 13 and 14; Tables 9 and 10). Validation of the genes retained after medium-stringency filtration was done via the quotients of the representative breast cancer samples in GSE2943 and those of the quantile-normalized and grouped normal tissues in GEO dataset GSE7307 (i.e., high-stringency filter). Groups of normal tissues are listed in Table 11 and the twenty genes retained after high-stringency filtration in Table 12. The quotient (Breast Cancer/Normal Tissues) value for the ERBB2 Affymetrix probe 216836_s_at (quotient=3.738) served as the cutoff value for high-stringency filter retention Genes of probes for which the quotient is ≥3.738 were defined as "validated".

For FIG. 3, only Cancer/Testis Antigens (CTAs) (Table 7) with a maximal representative expression value among all samples greater than 1.5 times the background cutoff value were further analyzed.

Quantitative RT-PCR

Validation of gene expression on a subset of samples by quantitative RT-PCR was conducted on an ABI 7900HT real-time PCR instrument using commercially available TaqMan® assays (Table 3) and the samples listed in Table 4.

HLA Typing and Immunohistochemistry

SV-BR-1-GM and peripheral blood cell samples were subjected to high-resolution HLA typing for HLA-A, HLA-B, and HLA-DRB3. HLA-DRB3 expression on tumor specimens was assessed on paraffin-embedded tissue by immunohistochemistry using a rabbit polyclonal antibody raised against an N-terminal region of human HLA-DRB3 (Product code: ab196601; obtained Abcam, Cambridge, Mass.).

Frequencies of HLA Allele Combinations

From the allele frequencies reported by (87), estimated "phenotype frequencies" were calculated indicating probabilities that an individual carries (a) at least one of SV-BR-1-GM's HLA class I alleles (HLA-A*11:01, HLA-A*24:02, HLA-B*35:08, or HLA-B*55:01) or allele groups (HLA-A*11, HLA-A*24, HLA-B*35, or HLA-B*55), (b) at least one of SV-BR-1-GM's HLA class II alleles (HLA-DRB3*01:01 or HLA-DRB3*02:02) or allele groups (HLA-DRB3*01 or HLA-DRB3*02), and (c) at least one of each of SV-BR-1-GM's class I and II alleles or allele groups. For the following definitions, alleles and allele groups are both referred to as "alleles", and the sums of the individual SV-BR-1-GM HLA-A, -B, and -DRB3 allele frequencies are referred to as ΣfaA, ΣfaB, and ΣfaDRB3, respectively. "Phenotype frequencies" (fp) were calculated as follows: for (a), $fp=1-(1-\Sigma faA)^2 \times (1-\Sigma faB)^2$, whereby $(1-\Sigma faA)^2$ and $(1-\Sigma faB)^2$ are the probabilities that an individual neither carries an SV-BR-1-GM HLA-A $(1-\Sigma faA)^2$ nor -B $(1-\Sigma faB)^2$ allele (exponents=2 since diploid, i.e., 2 sets of chromosomes and thus 2 HLA-A and two HLA-B loci). Conversely, $1-(\ldots)^2 \times (\ldots)^2$ is the probability that an individual carries at least one SV-BR-1-GM HLA-A or -B allele; for (b), $fp=1-(1-\Sigma faDRB3)^2$, whereby $(1-\Sigma faDRB3)^2$ is the probability that no SV-BR-1-GM HLA-DRB3 allele is present per individual, and, conversely, 1−( ... )² is the frequency that an individual carries at least one SV-BR-1-GM HLA-DRB3 allele; for (c), fp=[1−(1−ΣfaA)²×(1−ΣfaB)²]×[1−(1−ΣfaDRB3)²], whereby 1−(1−ΣfaA)²×(1−ΣfaB)² indicates the probability that an individual carries at least one SV-BR-1-GM HLA-A or -B allele and 1−(1−ΣfaDRB3)² is the probability that an individual carries at least one SV-BR-1-GM HLA-DRB3 allele. Allele frequencies used for the calculations were obtained from data 5 in (87) and included frequencies of alleles with different designations but with amino acids identical in the antigen recognition site (see, supplementary data set 1 in (87)).

Abbreviations

APC: Antigen-Presenting Cell
DC: Dendritic Cell
HGNC: Human Genome Organisation (HUGO) Gene Nomenclature Committee
HLA: Human Leukocyte Antigen
HMEC: Human Mammary Epithelial Cell
MHC: Major Histocompatibility Complex
MoA: Mechanism of Action
RT-PCR: Reverse Transcription-Polymerase Chain Reaction
TAA: Tumor-Associated Antigen

TABLE 2

Genes with known immune-stimulatory roles

| Gene Symbol (NCBI) | Positive T cell stimulation (Cell Surface Activators) | Positive T cell stimulation (Free Activators/Cytokines) | Positive APC Stimulation | Antigen Presentation |
|---|---|---|---|---|
| ADA | x | | | |
| ADGRE5 | (x) | | | |
| B2M | | | | x |
| CAV1 | x | | | |
| CCL1 | | x | | |
| CCL2 | | x | | |
| CCL3 | | x | x | |
| CCL4 | | x | x | |
| CCL5 | | x | x | |
| CCL7 | | x | x | |
| CCL8 | | x | | |
| CCL11 | | x | | |
| CCL13 | | x | | |
| CCL15 | | x | | |
| CCL16 | | x | | |
| CCL17 | | x | | |
| CCL18 | | x | | |
| CCL19 | | x | x | |
| CCL20 | | x | x | |
| CCL21 | | x | x | |
| CCL22 | | x | | |
| CCL23 | | | x | |
| CCL24 | | x | | |
| CCL25 | | x | | |
| CCL26 | | x | | |
| CCL27 | | x | | |
| CCL28 | | x | | |
| CD40 | x | | | |
| CD40LG | | | x | |
| CD48 | (x) | | | |
| CD58 | x | | | |
| CD70 | x | | | |
| CD74 | | | | x |
| CD80 | x | | | |
| CD83 | (x) | | | |
| CD86 | x | | | |
| CD209 | x | | | |
| CSF1 | | | (x) | |
| CSF2 | | | x | |
| CX3CL1 | | x | | |
| CXCL8 | | x | | |
| CXCL9 | | x | | |
| CXCL10 | | x | x | |
| CXCL11 | | x | | |
| CXCL13 | | x | | |
| CXCL16 | | | x | |
| EFNB2 | x | | | |
| FASLG | | | x | |
| FLT3LG | | | x | |
| FN1 | x | | | |
| HGF | | | x | |
| HLA-A | | | | x |
| HLA-B | | | | x |
| HLA-C | | | | x |
| HLA-DMA | | | | x |
| HLA-DMB | | | | x |
| HLA-DOA | | | | x |
| HLA-DOB | | | | x |

TABLE 2-continued

Genes with known immune-stimulatory roles

| Gene Symbol (NCBI) | Positive T cell stimulation (Cell Surface Activators) | Positive T cell stimulation (Free Activators/Cytokines) | Positive APC Stimulation | Antigen Presentation |
|---|---|---|---|---|
| HLA-DPA1 | | | | x |
| HLA-DPB1 | | | | x |
| HLA-DQA1 | | | | x |
| HLA-DQA2 | | | | x |
| HLA-DQB1 | | | | x |
| HLA-DRA | | | | x |
| HLA-DRB1 | | | | x |
| HLA-DRB3 | | | | x |
| HLA-DRB4 | | | | x |
| HLA-DRB5 | | | | x |
| HLA-F | | | | (x) |
| ICAM1 | x | | | |
| ICAM2 | x | | | |
| ICAM3 | x | | | |
| ICOSLG | x | | | |
| IFNA2 | | x | x | |
| IFNA8 | | x | x | |
| IFNA10 | | x | | |
| IFNG | | x | x | |
| IL1A | | x | x | |
| IL1B | | x | x | |
| IL2 | | x | x | |
| IL3 | | | x | |
| IL4 | | x | x | |
| IL6 | | x | (x) | |
| IL7 | | x | x | |
| IL9 | | (x) | | |
| IL10 | | (x) | | |
| IL12A | | x | | |
| IL12B | | x | | |
| IL13 | | | x | |
| IL15 | | x | x | |
| IL16 | | | (x) | |
| IL17A | | | x | |
| IL18 | | x | | |
| IL21 | | x | | |
| IL23A | | x | | |
| KITLG | | | x | |
| LAMP3 | | | | x |
| MADCAM1 | x | | | |
| MICA | x | | | |
| TNF | | x | x | |
| TNFRSF6B | x | | | |
| TNFSF4 | x | | | |
| TNFSF8 | x | | | |
| TNFSF9 | x | | | |
| TNFSF11 | | | x | |
| TNFSF14 | x | | | |
| TNFSF15 | x | | | |
| TNFSF18 | x | | | |
| VCAM1 | x | | | |
| XCL1 | | x | | |
| XCL2 | | x | | |

TABLE 3

Quantitative RT-PCR TaqMan ® reagents

| Gene Symbols | Assay Identifiers | Amplicon Lengths | Probes exon spanning | RefSeqs (NCBI) |
|---|---|---|---|---|
| CUL1 | Hs01117001_m1 | 113 | Yes | NM_003592.2 |
| HLA-DRA | Hs00219578_m1 | 129 | Yes | NM_019111.4 |
| HLA-DRB3 | Hs02339733_m1 | 74 | Yes | NM_022555.3 |
| HLA-DMA | Hs00185435_m1 | 100 | Yes | NM_006120.3 |
| HLA-DMB | Hs00157943_m1 | 148 | Yes | NM_002118.4 |
| CD74 | Hs00269961_m1 | 102 | Yes | NM_001025158.2 |
| | | | | NM_001025159.2 |
| | | | | NM_004355.3 |

Validation of gene expression on a subset of samples by quantitative RT-PCR was conducted on an ABI 7900HT real-time PCR instrument using the commercially available TaqMan® assays (obtained from Thermo Fisher Scientific, Waltham, Mass.) listed above in Table 3.

TABLE 4

Samples for quantitative RT-PCR

| Sample | RIN | [RNA] (ng/µL) | OD 260/280 | $OD_{260}/OD_{230}$ |
|---|---|---|---|---|
| MCB cryo | 7.5 | 587.1 | 1.96 | 1.97 |
| CP Lot IV cryo | 6.9 | 935.1 | 2.06 | 1.9 |
| CP Lot VIII cryo | 10 | 108.1 | 1.84 | 2.23 |
| CP Lot VIII cryo | 9.9 | 107.7 | 1.89 | 1.91 |
| CP Lot IV culture | 9.9 | 514.4 | 2 | 1.91 |
| CP Lot VIII culture | 10 | 71.24 | 1.8 | 2.41 |

Validation of gene expression on a subset of samples by quantitative RT-PCR was performed using the samples listed above in Table 4. "RIN" denotes RNA integrity number; "OD" denotes optical density.

TABLE 7

Putative CTAs

| | | | | | | | |
|---|---|---|---|---|---|---|---|
| ACRBP | ACTL8 | ADAM2 | ADAM20 | ADAM21 | ADAM22 | ADAM23 | ADAM28 |
| ADAM29 | AKAP3 | AKAP4 | ANKRD30BP2 | ANKRD45 | ARMC3 | ARX | ATAD2 |
| ATAD2B | BAGE | BAGE2 | BAGE3 | BAGE4 | BAGE5 | BRDT | CABYR |
| CAGE1 | CALR3 | CCDC110 | CCDC33 | CCDC36 | CCDC62 | CCDC83 | CCNA1 |
| CEP290 | CEP55 | CNOT9 | COX6B2 | CPXCR1 | CRISP2 | CSAG1 | CSAG2 |
| CT45A1 | CT45A2 | CT45A3 | CT45A5 | CT45A6 | CT47A1 | CT47A10 | CT47A11 |
| CT47A12 | CT47A2 | CT47A3 | CT47A4 | CT47A5 | CT47A7 | CT47A8 | |
| CT47A9 | CT47B1 | CT55 | CT62 | CT83 | CTAG1A | CTAG1B | CTAG2 |
| CTAGE1 | CTCFL | CTNNA2 | DCAF12 | DDX43 | DDX5 | DDX53 | DKKL1 |
| DMRT1 | DNAJB8 | DPPA2 | DSCR8 | ELOVL4 | EPPIN | FAM133A | FAM46D |
| FATE1 | FBXO39 | FMR1NB | FSIP1 | FTHL17 | GAGE1 | GAGE10 | GAGE12B |
| GAGE12C | GAGE12D | GAGE12E | GAGE12F | GAGE12G | GAGE12H | GAGE12I | GAGE12J |
| GAGE13 | GAGE2A | GAGE3 | GAGE4 | GAGE5 | GAGE6 | GAGE7 | GAGE8 |
| GOLGA6L2 | GPAT2 | GPATCH2 | HEMGN | HORMAD1 | HORMAD2 | HSPB9 | IGSF11 |
| IL13RA2 | IMP3 | KDM5B | KIAA0100 | KIF20B | KIF2C | KNL1 | LDHC |
| LEMD1 | LINC01192 | LINC01193 | LINC01194 | LIPI | LOC440934 | LUZP4 | LY6K |
| LYPD6B | MAEL | MAGEA1 | MAGEA10 | MAGEA11 | MAGEA12 | MAGEA2 | MAGEA2B |
| MAGEA3 | MAGEA4 | MAGEA5 | MAGEA6 | MAGEA8 | MAGEA9 | MAGEA9B | MAGEB1 |
| MAGEB10 | MAGEB16 | MAGEB17 | MAGEB18 | MAGEB2 | MAGEB3 | MAGEB4 | MAGEB5 |
| MAGEB6 | MAGEC1 | MAGEC2 | MAGEC3 | MIA2 | MORC1 | MPHOSPH10 | NLRP4 |
| NOL4 | NR6A1 | NUF2 | NXF2 | NXF2B | ODF1 | ODF2 | ODF2L |
| ODF3 | ODF3L1 | ODF3L2 | ODF4 | OIP5 | OTOA | PAGE1 | PAGE2 |
| PAGE2B | PAGE3 | PAGE4 | PAGE5 | PASD1 | PBK | PIWIL1 | PIWIL2 |
| PLAC1 | POTEA | POTEB | POTEC | POTED | POTEE | POTEG | POTEH |
| PRAME | PRAMEF1 | PRAMEF11 | PRM1 | PRM2 | PRSS50 | PRSS54 | PRSS55 |
| PTPN20 | RBM46 | REC114 | RGS22 | RHOXF2 | RNF17 | ROPN1 | ROPN1B |
| ROPN1L | SAGE1 | SEMG1 | SLCO6A1 | SPA17 | SPACA3 | SPAG1 | SPAG17 |
| SPAG4 | SPAG6 | SPAG8 | SPAG9 | SPANXA1 | SPANXA2 | SPANXB1 | SPANXC |
| SPANXD | SPANXN1 | SPANXN2 | SPANXN3 | SPANXN4 | SPANXN5 | SPATA19 | SPEF2 |
| SPO11 | SSX1 | SSX2 | SSX2B | SSX4 | SSX4B | SSX5 | SSX6 |
| SSX7 | SSX9 | SUN5 | SYCE1 | SYCE1L | SYCP1 | TAF7L | TDRD1 |
| TDRD6 | TEKT5 | TEX101 | TEX14 | TEX15 | TEX38 | TFDP3 | THEG |
| TMEFF1 | TMEFF2 | TMEM108 | TMPRSS12 | TPPP2 | TPTE | TPTE2 | TSGA10 |
| TSPY1 | TSPY2 | TSPY3 | TSSK6 | TTK | TULP2 | VENTXP1 | XAGE1B |
| XAGE1E | XAGE2 | XAGE3 | XAGE-4 | XAGE5 | ZNF165 | ZNF645 | |

TABLE 9

Genes retained after low-stringency filtration

| | | | | | | | |
|---|---|---|---|---|---|---|---|
| AARS | ABCD1 | ABHD12 | ACP1 | ACP2 | ACSF2 | ACTR1B | ADAM15 |
| ADAR | ADM2 | ADSSL1 | AFMID | AGT | AIFM1 | AKIRIN1 | AKR1B10 |
| AKR1B15 | AKR1C2 | AKR1C4 | ALDH1B1 | ALDH3A2 | ALDH3B2 | ALDH5A1 | ALDH9A1 |
| ALDOA | ALG8 | ANAPC11 | ANGPT1 | ANKRD46 | ANKRD9 | APIP | APLP1 |
| AQP11 | AR | ARHGEF19 | ARL4A | ARMCX6 | ARPC5L | ASCL2 | ASPSCR1 |
| ASS1 | ATF6 | ATG3 | ATP10B | ATP5EP2 | ATP5G1 | ATP6AP1 | ATP6V0E2 |
| ATP6V1E2 | ATP6V1G2 | ATPAF1 | ATPAF2 | AZIN1 | B9D1 | BEX1 | BLVRB |
| BMP5 | BMP7 | BOLA3 | BTF3L4 | C14orf80 | C21orf33 | C3orf38 | C7orf13 |
| CA9 | CABLES2 | CALB2 | CALCA | CALCB | CAMK2G | CAP2 | CARD16 |
| CARD17 | CASP14 | CAT | CBX2 | CCNC | CD163L1 | CD36 | CD79B |
| CD83 | CD99L2 | CDC42EP4 | CDC42SE1 | CDK5RAP1 | CDK5RAP2 | CDKN2A | CELSR3 |
| CENPB | CENPL | CENPM | CENPN | CGA | CHAC1 | CHMP2A | CKMT1A |
| CKMT1B | CKS1B | CLGN | CLNS1A | CLP1 | CNFN | CNGB1 | CNIH2 |
| CNPY2 | CNTNAP2 | COL8A1 | COX15 | COX5A | COX5B | COX7C | CPS1 |
| CPT1C | CRABP2 | CRIM1 | CRIP2 | CSMD1 | CUEDC1 | CXXC5 | CYB561 |
| DAG1 | DBP | DBT | DCAF10 | DDIT3 | DDX28 | DGCR6 | DGUOK |
| DHCR24 | DHRS11 | DHRS2 | DIO2 | DIS3L | DNAJC22 | DNASE2 | DNLZ |

TABLE 9-continued

Genes retained after low-stringency filtration

| | | | | | | | |
|---|---|---|---|---|---|---|---|
| DOLPP1 | DPM1 | DYNLL2 | E2F2 | EBAG9 | ECHS1 | EEF1A2 | EFEMP1 |
| EFNA4 | EGFL7 | EIF3H | EIF4E3 | EIF5 | ELMO1 | EPB41L1 | ERBB2 |
| ERP27 | ERP29 | EVPL | EXOSC3 | EXT1 | F8A1 | FADS2 | FAF1 |
| FAM178B | FAM188B | FAM69B | FAM71E1 | FBXO10 | FGF21 | FLAD1 | FLJ46906 |
| FLYWCH2 | FOLR1 | FOXC1 | FRMPD1 | FUCA2 | G6PD | GALK1 | GAPDH |
| GAR1 | GARS | GCHFR | GINS4 | GJA5 | GLB1 | GMDS | GMPPB |
| GNG10 | GNPTAB | GPC5 | GPNMB | GPR37 | GPS1 | GPT2 | GRAMD1B |
| GRB2 | GRB7 | GRHL2 | GRHPR | GSDMC | HAX1 | HCP5 | HEXA |
| HEXB | HIST1H2BJ | HIST1H2BK | HIST1H3F | HIST1H3G | HIST1H4H | HIST2H4A | HIST2H4B |
| HLTF | HNRNPL | HPN | HRK | IDH1 | IFI30 | IGFBP5 | ILVBL |
| IMPA2 | INTS4 | INTS7 | ITPR1 | KCTD5 | KDELR1 | KIAA2013 | KLC1 |
| KLHL13 | KRT19 | KRT81 | KRT86 | KYNU | LAGE3 | LGALS3BP | LOC728138 |
| LRPPRC | LRRC26 | LYPD3 | LYRM2 | MAL2 | MAN1B1 | MANBA | MAP7 |
| MAPK4 | MAPKAP1 | MED10 | MED19 | MED30 | MESP1 | MGAT4A | MGST3 |
| MKKS | MOCOS | MRPL16 | MRPL51 | MRPS11 | MRPS7 | MRRF | MSRB2 |
| MTHFD2 | NARS2 | NDUFA1 | NDUFA4L2 | NDUFA6 | NDUFA8 | NDUFAF3 | NDUFB10 |
| NDUFC1 | NMRAL1 | NOL3 | NOMO1 | NOV | NQO1 | OSBP | OSTC |
| P4HB | PABPC1 | PAK1 | PAQR4 | PBX3 | PCCB | PCNT | PDCD6 |
| PDE8B | PDHA1 | PDHB | PDIA6 | PDRG1 | PGAP3 | PGD | PHGDH |
| PIGK | PIR | PITX1 | PLOD1 | POLR1E | POP5 | PRAME | PRDX1 |
| PRDX2 | PRDX4 | PSAT1 | PSMB7 | PSMD10 | PTGES2 | PXDN | PYCR1 |
| RABGAP1 | RAD51C | RAP1GAP | RARS2 | RFC5 | RHOBTB3 | RNASET2 | RNF182 |
| RNF19A | ROMO1 | RP9 | RPL36A | RSF1 | S100P | SCPEP1 | SCRG1 |
| SDHA | SELENBP1 | SEPHS2 | SERPINA5 | SEZ6L2 | SHB | SHMT1 | SIVA1 |
| SLC25A10 | SLC2A8 | SLC31A1 | SLC35A2 | SLC3A2 | SLC6A9 | SLC9A3R1 | SMU1 |
| SNRPB2 | SOD1 | SPINT2 | SQSTM1 | SRXN1 | SSR4 | STARD3 | STEAP4 |
| STX3 | SUSD2 | TALDO1 | TBCD | TBL1X | TCTN1 | TESC | TFAP2C |
| TIMM10 | TK1 | TMC6 | TMED3 | TMED4 | TMEM131 | TMEM205 | TMEM9 |
| TNFRSF11B | TNPO1 | TNS3 | TOMM5 | TRIB3 | TSKU | TSPAN3 | TSPAN4 |
| TSR2 | TSTD1 | TXN | UBB | UBE2I | UBE2L6 | UBE2M | UBR5 |
| UNC50 | UQCRQ | URM1 | UST | UTP23 | VPS45 | VWA1 | WARS |
| WDR61 | ZBTB5 | ZCCHC17 | ZDHHC5 | ZNF467 | AAMDC | AARD | ADGRL1 |
| AMER1 | ARPIN | ASS1P11 | ASS1P13 | ATRAID | BRINP1 | C11orf86 | C16orf92 |
| CAMKMT | CLPSL2 | CNIH1 | CNOT11 | COA1 | COA5 | CYSRT1 | FAM206A |
| FAM217B | GAPDHP33 | GLMP | HMCES | HSPB11 | HTATSF1P2 | INIP | INTS4P2 |
| KAT14 | KRT8P47 | LINC00467 | LOC100288911 | MARC1 | MIEN1 | MSRB1 | MVB12B |
| NAA20 | NPR3 | OGFOD3 | OSGIN1 | OSTCP2 | PABPC1P4 | PRELID3B | PSAT1P3 |
| PYROXD2 | RPL35P2 | SAPCD2 | SETP14 | SLC25A51 | SLC35F6 | SLC48A1 | SMG8 |
| ST8SIA6-AS1 | SWI5 | SYBU | SYNE4 | TENM4 | THAP12 | TMED10P1 | TMEM192 |
| TMEM238 | TMEM268 | TMEM74B | TMX2 | TRMT10B | TSEN15 | XPOT | |

TABLE 10

Genes retained after medium-stringency filtration (>5.0 × Bckgr and >1.5 × Max (Normal))

| | | | | | | | |
|---|---|---|---|---|---|---|---|
| AAMDC | AARD | AARS | ACP1 | ACP2 | ACSF2 | ACTR1B | ADAM15 |
| ADAR | ADGRL1 | AIFM1 | AKR1B10 | AKR1C2 | AKR1C4 | ALDH1B1 | ALDH3A2 |
| ALDH3B2 | ALDH9A1 | ALDOA | ALG8 | ANAPC11 | ANKRD46 | ANKRD9 | APIP |
| ARL4A | ARPC5L | ASPSCR1 | ASS1 | ASS1P11 | ASS1P13 | ATF6 | ATG3 |
| ATP5EP2 | ATP6AP1 | ATP6V0E2 | ATPAF1 | ATRAID | AZIN1 | BEX1 | BLVRB |
| BOLA3 | BRINP1 | C21orf33 | CALB2 | CALCA | CAP2 | CARD17 | CAT |
| CBX2 | CD79B | CD83 | CD99L2 | CDC42EP4 | CDC42SE1 | CDK5RAP1 | CDK5RAP2 |
| CENPB | CENPM | CENPN | CGA | CKMT1A | CKMT1B | CKS1B | CLNS1A |
| CLP1 | CNFN | CNIH1 | CNOT11 | CNPY2 | COA1 | COA5 | COL8A1 |
| COX5A | COX5B | COX7C | CPS1 | CRABP2 | CRIP2 | CUEDC1 | CXXC5 |
| CYB561 | CYSRT1 | DAG1 | DBT | DCAF10 | DDIT3 | DGCR6 | DHCR24 |
| DIO2 | DIS3L | DNASE2 | DNLZ | DOLPP1 | DPM1 | DYNLL2 | E2F2 |
| ECHS1 | EEF1A2 | EIF3H | EIF4E3 | EIF5 | ERBB2 | ERP29 | EXOSC3 |
| EXT1 | F8A1 | FAF1 | FAM206A | FBXO10 | FLAD1 | FOLR1 | FOXC1 |
| FUCA2 | G6PD | GALK1 | GAPDH | GAPDHP33 | GARS | GLB1 | GLMP |
| GMDS | GMPPB | GNG10 | GPNMB | GPR37 | GPS1 | GPT2 | GRHL2 |
| GRHPR | GSDMC | HAX1 | HCP5 | HEXB | HIST1H2BJ | HIST1H2BK | HIST1H3G |
| HIST1H4H | HIST2H4A | HMCES | HNRNPL | HSPB11 | HTATSF1P2 | IDH1 | IFI30 |
| IGFBP5 | ILVBL | IMPA2 | INIP | INTS4 | INTS4P2 | INTS7 | ITPR1 |
| KAT14 | KCTD5 | KDELR1 | KIAA2013 | KLC1 | KLHL13 | KRT19 | KRT81 |
| KRT86 | KRT8P47 | KYNU | LAGE3 | LGALS3BP | LOC100288911 | LOC728138 | LRPPRC |
| LRRC26 | LYPD3 | LYRM2 | MAL2 | MAN1B1 | MANBA | MAP7 | MAPK4 |
| MAPKAP1 | MARC1 | MED10 | MED19 | MED30 | MESP1 | MGAT4A | MGST3 |
| MIEN1 | MKKS | MOCOS | MRPL16 | MRPL51 | MRPS11 | MRPS7 | MRRF |
| MSRB1 | MSRB2 | MTHFD2 | NAA20 | NARS2 | NDUFA1 | NDUFA4L2 | NDUFA6 |
| NDUFA8 | NDUFAF3 | NDUFB10 | NDUFC1 | NMRAL1 | NOL3 | NOMO1 | NOV |
| NQO1 | OGFOD3 | OSBP | OSGIN1 | OSTC | OSTCP2 | P4HB | PABPC1 |

TABLE 10-continued

Genes retained after medium-stringency filtration (>5.0 × Bckgr and >1.5 × Max (Normal))

| | | | | | | | |
|---|---|---|---|---|---|---|---|
| PABPC1P4 | PAK1 | PAQR4 | PBX3 | PCCB | PCNT | PDCD6 | PDE8B |
| PDHA1 | PDHB | PDIA6 | PDRG1 | PGAP3 | PGD | PHGDH | PIGK |
| PIR | PITX1 | PLOD1 | POLR1E | POP5 | PRAME | PRDX1 | PRDX2 |
| PRDX4 | PRELID3B | PSAT1 | PSAT1P3 | PSMB7 | PSMD10 | PTGES2 | PXDN |
| PYCR1 | RABGAP1 | RAD51C | RAP1GAP | RARS2 | RFC5 | RHOBTB3 | RNASET2 |
| RNF182 | RNF19A | ROMO1 | RP9 | RPL35P2 | RPL36A | RSF1 | S100P |
| SAPCD2 | SCPEP1 | SCRG1 | SDHA | SELENBP1 | SEPHS2 | SERPINA5 | SETP14 |
| SEZ6L2 | SHB | SHMT1 | SIVA1 | SLC25A10 | SLC25A51 | SLC2A8 | SLC31A1 |
| SLC35A2 | SLC3A2 | SLC48A1 | SLC6A9 | SLC9A3R1 | SMU1 | SNRPB2 | SOD1 |
| SPINT2 | SQSTM1 | SRXN1 | SSR4 | ST8SIA6-AS1 | STARD3 | STEAP4 | STX3 |
| SUSD2 | SWI5 | SYBU | SYNE4 | TALDO1 | TBCD | TBL1X | TCTN1 |
| TENM4 | TESC | TFAP2C | THAP12 | TIMM10 | TK1 | TMC6 | TMED10P1 |
| TMED3 | TMED4 | TMEM131 | TMEM205 | TMEM238 | TMEM268 | TMEM9 | TMX2 |
| TNFRSF11B | TNPO1 | TNS3 | TOMM5 | TRIB3 | TRMT10B | TSEN15 | TSKU |
| TSPAN3 | TSPAN4 | TSR2 | TSTD1 | TXN | UBB | UBE2I | UBE2L6 |
| UBE2M | UBR5 | UNC50 | UQCRQ | URM1 | UST | UTP23 | VPS45 |
| VWA1 | WARS | WDR61 | XPOT | ZBTB5 | ZCCHC17 | ZDHHC5 | ZNF467 |

TABLE 11

Normal tissues

| | | | | | | |
|---|---|---|---|---|---|---|
| GSM175837 | GSM176118 | GSM176121 | GSM176410 | GSM176115 | GSM176264 | GSM175906 |
| GSM175951 | GSM176300 | GSM175907 | GSM175909 | GSM175959 | GSM176030 | GSM176031 |
| GSM176033 | GSM176034 | GSM176036 | GSM176037 | GSM176073 | GSM176124 | GSM176125 |
| GSM176149 | GSM176152 | GSM176156 | GSM176160 | GSM176164 | GSM176168 | GSM176173 |
| GSM176177 | GSM176181 | GSM176185 | GSM176215 | GSM176217 | GSM176223 | GSM176233 |
| GSM176293 | GSM176372 | GSM176379 | GSM176380 | GSM176403 | GSM176404 | GSM176446 |
| GSM176448 | GSM176453 | GSM176454 | GSM175792 | GSM175795 | GSM175838 | GSM175839 |
| GSM175840 | GSM175841 | GSM176122 | GSM176231 | GSM176232 | GSM176140 | GSM176098 |
| GSM176137 | GSM176145 | GSM176392 | GSM176239 | GSM176294 | GSM175905 | GSM175947 |
| GSM175949 | GSM176123 | GSM176266 | GSM175816 | GSM175819 | GSM175935 | GSM176035 |
| GSM176005 | GSM176006 | GSM176007 | GSM176008 | GSM176009 | GSM176010 | GSM176282 |
| GSM176283 | GSM176284 | GSM176285 | GSM176286 | GSM176269 | GSM176292 | GSM175911 |
| GSM176324 | GSM176427 | GSM175910 | GSM176335 | GSM175977 | GSM175979 | GSM176434 |
| GSM175992 | GSM176388 | GSM175936 | GSM176072 | GSM176074 | GSM176075 | GSM176076 |
| GSM176077 | GSM176136 | GSM176318 | GSM175950 | GSM175881 | GSM176274 | GSM176235 |
| GSM176297 | GSM175937 | GSM175923 | GSM175938 | GSM175955 | GSM176278 | GSM176241 |
| GSM175939 | GSM176417 | GSM175884 | GSM175940 | GSM175985 | GSM176317 | GSM175948 |
| GSM175952 | GSM176267 | GSM175941 | GSM176331 | GSM175824 | GSM175943 | GSM176339 |
| GSM176343 | GSM175942 | GSM175276 | GSM176262 | GSM175954 | GSM176421 | GSM175899 |
| GSM175900 | GSM175946 | GSM175953 | GSM176114 | GSM175944 | GSM175981 | GSM176280 |
| GSM175945 | GSM176102 | GSM176138 | GSM176230 | GSM176129 | GSM176139 | GSM175880 |
| GSM176038 | GSM176299 | GSM176079 | GSM176081 | | | |

TABLE 13

95% confidence intervals of in silico validated TAA candidates in normal and breast cancer tissues (Her2 3+, 2+, and 0-1+)

| Gene Symbol (NCBI) | Probe | Normal Tissues (N = 44) 95% CI | Her2 3+ Breast Cancer N = 15 >95% CI of Normal Tissues | | Her2 2+ Breast Cancer N = 26 >95% CI of Normal Tissues | | Her2 0-1+ Breast Cancer N = 13 >95% CI of Normal Tissues | |
|---|---|---|---|---|---|---|---|---|
| | | | % all | 95% CI | % all | 95% CI | % all | 95% CI |
| ALG8 | 203545_at | 149-214 | 87% | 472-542 | 92% | 546-641 | 92% | 549-625 |
| ARPC5L | 226914_at | 76-139 | 93% | 495-574 | 92% | 631-709 | 85% | 562-723 |
| CBX2 | 226473_at | 56-68 | 40% | 172-244 | 50% | 219-266 | 62% | 156-236 |
| COL8A1 | 226237_at | 55-151 | 93% | 1157-1463 | 96% | 1093-1326 | 92% | 1122-1477 |
| DCAF10 | 226511_at | 27-34 | 73% | 68-82 | 81% | 83-105 | 85% | 103-121 |
| DCAF10 | 230679_at | 9-11 | 80% | 61-81 | 92% | 53-68 | 85% | 78-91 |
| EIF3H | 230570_at | 12-19 | 80% | 60-75 | 88% | 119-175 | 92% | 72-96 |
| ERBB2 | 216836_s_at | 313-482 | 60% | 2451-3219 | 27% | 1963-2661 | 0% | N/A |
| ERBB2 | 234354_x_at | 9-10 | 93% | 75-117 | 69% | 17-20 | 69% | 12-13 |

TABLE 13-continued

95% confidence intervals of in silico validated TAA candidates in normal and breast cancer tissues (Her2 3+, 2+, and 0-1+)

| Gene Symbol | Probe | Normal Tissues (N = 44) 95% CI | Her2 3+ Breast Cancer N = 15 >95% CI of Normal Tissues | | Her2 2+ Breast Cancer N = 26 >95% CI of Normal Tissues | | Her2 0-1+ Breast Cancer N = 13 >95% CI of Normal Tissues | |
|---|---|---|---|---|---|---|---|---|
| (NCBI) | | 95% CI | % all | 95% CI | % all | 95% CI | % all | 95% CI |
| HIST1H4H | 208180_s_at | 11-14 | 80% | 70-121 | 69% | 58-75 | 69% | 28-35 |
| HIST1H4H | 232035_at | 24-32 | 80% | 284-491 | 69% | 186-236 | 62% | 90-109 |
| IGFBP5 | 1555997_s_at | 48-97 | 33% | 307-399 | 35% | 592-854 | 15% | 430-563 |
| INTS7 | 218783_at | 31-38 | 87% | 95-111 | 77% | 106-122 | 85% | 183-229 |
| KRT19 | 228491_at | 21-24 | 53% | 49-78 | 46% | 92-115 | 77% | 136-191 |
| KRT81 | 213711_at | 58-71 | 67% | 289-554 | 54% | 295-448 | 31% | 102-119 |
| MGAT4A | 231283_at | 36-65 | 87% | 226-294 | 81% | 162-185 | 62% | 137-164 |
| MIEN1 | 224447_s_at | 356-432 | 87% | 2283-2995 | 50% | 1396-1773 | 8% | N/A |
| PGAP3 | 221811_at | 81-100 | 93% | 437-597 | 58% | 210-273 | 31% | 110-115 |
| PGAP3 | 55616_at | 150-185 | 93% | 822-1067 | 54% | 394-496 | 15% | 220-229 |
| RSF1 | 222541_at | 30-80 | 80% | 164-198 | 88% | 303-378 | 69% | 179-212 |
| RSF1 | 229885_at | 43-57 | 100% | 166-195 | 88% | 192-229 | 92% | 150-172 |
| SHB | 1557458_s_at | 61-83 | 93% | 196-229 | 81% | 251-300 | 85% | 229-277 |
| SLC35A2 | 209326_at | 90-119 | 93% | 356-420 | 92% | 435-497 | 85% | 493-602 |
| SYNE4 | 235515_at | 34-48 | 87% | 110-140 | 88% | 132-160 | 92% | 117-148 |
| TNPO1 | 225765_at | 94-134 | 93% | 521-600 | 96% | 487-571 | 92% | 432-479 |

The 95% confidence intervals (CIs) within an N=44 group of normal tissues were compared to the 95% CIs of several breast cancer groups (i.e., differing in their Her2 status), each consisting of samples with TAA expression levels higher than the upper limit of the 95% CIs of the normal tissues. GEO DataSet GSE2943 was used to establish the breast cancer expression values. 151 samples from GSE7307 were selected for the normal tissues. These 151 samples represented 44 different categories of tissues (i.e., adipose, adrenal gland, artery, bone marrow, brain, breast, cervix, endometrium, esophagus, fallopian tube, gut, heart, immune cells, joint, kidney, liver, lung, lymph node, mucosa, nerve, ovary, pancreas, penis, peritoneum, pituitary gland, placenta, prostate, retrocervical infiltrate, salivary gland, skeletal muscle, skin, spleen, stomach, testis, thymus, thyroid gland, tongue, tonsil, trachea, urethra, uterus, vagina, vein, vulva). For determining the 95% CIs within the group of normal tissues, each category was represented by its highest expression value. The 95% CIs of ERBB2, MIEN1, and PGAP3 were highest for the Her2 3+ and lowest for the Her2 0-1+ cancer groups.

TABLE 14

95% confidence intervals of in silico validated TAA candidates in normal and breast cancer tissues (FISH positive and negative Her2 2+)

| Gene Symbol | Probe | Normal Tissues N = 44 95% CI | Her2 2+ >95% CI of Normal Tissues N = 26 | | FISH+ (N = 13) | | FISH− (N = 13) | |
|---|---|---|---|---|---|---|---|---|
| (NCBI) | | 95% CI | % all | 95% CI | % all | 95% CI | % all | 95% CI |
| ALG8 | 203545_at | 149-214 | 92% | 546-641 | 85% | 416-451 | 100% | 647-812 |
| ARPC5L | 226914_at | 76-139 | 92% | 631-709 | 92% | 545-677 | 92% | 687-770 |
| CBX2 | 226473_at | 56-68 | 50% | 219-266 | 54% | 214-293 | 46% | 203-257 |
| COL8A1 | 226237_at | 55-151 | 96% | 1093-1326 | 100% | 849-1184 | 92% | 1260-1577 |
| DCAF10 | 226511_at | 27-34 | 81% | 83-105 | 69% | 87-131 | 92% | 74-90 |
| DCAF10 | 230679_at | 9-11 | 92% | 53-68 | 92% | 43-70 | 92% | 59-69 |
| EIF3H | 230570_at | 12-19 | 88% | 119-175 | 77% | 102-125 | 100% | 121-225 |
| ERBB2 | 216836_s_at | 313-482 | 27% | 1963-2661 | 46% | 2098-3128 | 8% | N/A |
| ERBB2 | 234354_x_at | 9-10 | 69% | 17-20 | 85% | 19-25 | 54% | 13-14 |
| HIST1H4H | 208180_s_at | 11-14 | 69% | 58-75 | 54% | 69-102 | 85% | 46-63 |
| HIST1H4H | 232035_at | 24-32 | 69% | 186-236 | 62% | 176-267 | 77% | 176-230 |
| IGFBP5 | 1555997_s_at | 48-97 | 35% | 592-854 | 54% | 603-1023 | 15% | 383-436 |
| INTS7 | 218783_at | 31-38 | 77% | 106-122 | 62% | 90-108 | 92% | 113-137 |
| KRT19 | 228491_at | 21-24 | 46% | 92-115 | 46% | 64-100 | 46% | 110-139 |
| KRT81 | 213711_at | 58-71 | 54% | 295-448 | 54% | 149-183 | 54% | 430-724 |
| MGAT4A | 231283_at | 36-65 | 81% | 162-185 | 77% | 156-193 | 85% | 157-187 |
| MIEN1 | 224447_s_at | 356-432 | 50% | 1396-1773 | 69% | 1642-2238 | 31% | 726-843 |
| PGAP3 | 221811_at | 81-100 | 58% | 210-273 | 62% | 264-380 | 54% | 142-159 |
| PGAP3 | 55616_at | 150-185 | 54% | 394-496 | 54% | 566-740 | 54% | 228-248 |
| RSF1 | 222541_at | 30-80 | 88% | 303-378 | 85% | 225-358 | 92% | 347-422 |
| RSF1 | 229885_at | 43-57 | 88% | 192-229 | 77% | 177-235 | 100% | 190-239 |
| SHB | 1557458_s_at | 61-83 | 81% | 251-300 | 77% | 238-313 | 85% | 243-310 |
| SLC35A2 | 209326_at | 90-119 | 92% | 435-497 | 92% | 358-444 | 92% | 486-575 |

TABLE 14-continued

95% confidence intervals of in silico validated TAA candidates in normal and breast cancer tissues (FISH positive and negative Her2 2+)

| Gene Symbol (NCBI) | Probe | Normal Tissues N = 44 | | Her2 2+ >95% CI of Normal Tissues | | | | |
|---|---|---|---|---|---|---|---|---|
| | | | | N = 26 | | FISH+ (N = 13) | | FISH− (N = 13) |
| | | 95% CI | % all | 95% CI | % all | 95% CI | % all | 95% CI |
| SYNE4 | 235515_at | 34-48 | 88% | 132-160 | 92% | 129-170 | 85% | 122-161 |
| TNPO1 | 225765_at | 94-134 | 96% | 487-571 | 100% | 484-646 | 92% | 469-512 |

The 95% confidence intervals (CIs) within an N=44 group of normal tissues were compared to the 95% CIs of several Her2 2+ breast cancer groups (i.e., overall, FISH positive, and FISH negative) each consisting of samples with TAA expression levels higher than the upper limit of the 95% CIs of the normal tissues. GEO DataSet GSE2943 was used to establish the breast cancer expression values. 151 samples from GSE7307 were selected for the normal tissues. These 151 samples represented 44 different categories of tissues (i.e., adipose, adrenal gland, artery, bone marrow, brain, breast, cervix, endometrium, esophagus, fallopian tube, gut, heart, immune cells, joint, kidney, liver, lung, lymph node, mucosa, nerve, ovary, pancreas, penis, peritoneum, pituitary gland, placenta, prostate, retrocervical infiltrate, salivary gland, skeletal muscle, skin, spleen, stomach, testis, thymus, thyroid gland, tongue, tonsil, trachea, urethra, uterus, vagina, vein, vulva). The 95% CIs of ERBB2, MIEN1, and PGAP3 were higher for the Her2 FISH+ than for the Her2 FISH− cancer group.

TABLE 20

Sensitivity analysis of select biomarkers for HER2 differentiation

| | # Her2 3+ > Max Her2 0-1+ | | |
|---|---|---|---|
| | Total # samples | Number of pos. samples | Percentage |
| Sensitivity based on single markers (at 100% Specificity) | | | |
| ERBB2 | 15 | 9 | 60% |
| MIEN1 | 15 | 13 | 87% |
| PGAP3 | 15 | 13 | 87% |
| Sensitivity based on single/double/triple markers (at 100% Specificity) | | | |
| | Sensitivity | | |
| ERBB2 | 15 | 9 | 60% |
| MIEN1 | 15 | 13 | 87% |

TABLE 20-continued

Sensitivity analysis of select biomarkers for HER2 differentiation

| | # Her2 3+ > Max Her2 0-1+ | | |
|---|---|---|---|
| | Total # samples | Number of pos. samples | Percentage |
| PGAP3 | 15 | 13 | 87% |
| ERBB2 + MIEN 1 | 15 | 13 | 87% |
| ERBB2 + PGAP3 | 15 | 13 | 87% |
| MIEN1 + PGAP3 | 15 | 15 | 100% |
| ERBB2 + MIEN1 + PGAP3 | 15 | 15 | 100% |
| Sensitivity | | | |
| ERBB2 | | | 60% |
| MIEN1 | | | 87% |
| PGAP3 | | | 87% |
| ERBB2 + MIEN 1 | | | 87% |
| ERBB2 + PGAP3 | | | 87% |
| MIEN1 + PGAP3 | | | 100% |
| ERBB2 + MIEN1 + PGAP3 | | | 100% |

(Sensitivity = % Her2 3+ patients detected as HER2 positive using RNA data; specificity = 100%, i.e., none of the Her2 0-1+ patients detected as HER2 positive)

Example 2: Overexpression of HLA-A*02:01 and HLA-DRB3*02:02 Via Stable Transfection Background As outlined in Table 16 (87), HLA-A*02:01 is a particularly prevalent HLA-A allele among 16 ethnic groups living in the U.S. (3.5-27.5%, median: 13.6%), with highest prevalence in the North American Indian group (27.8%) followed by the European Caucasian group (27.6%). Similarly, HLA-DRB3*02:02 is the most prevalent HLA-DRB3 allele among the same 16 groups (10.4-34.5%, median: 20.0%), with highest prevalence in the Middle Eastern or N. Coast of Africa group (34.5%) followed by the South Asian Indian group (27.2%). HLA-DRB3*02:02 prevalence in the North American Indian and European Caucasian groups were reported to be 14.5% and 18.2%, respectively (Table 16).

TABLE 16

HLA-A and HLA-DRB3 allele frequencies

| HLA Allele | AAFA | AFB | AINDI | AMIND | CARB | CARHIS | EURCAU | FILII | JAPI | KORI |
|---|---|---|---|---|---|---|---|---|---|---|
| A*01:01 | 4.7 | 5.1 | *15.5* | 12.0 | 4.5 | 6.7 | *16.5* | 1.2 | 1.0 | 2.1 |
| A*02:01g | 12.3 | 11.5 | 4.9 | *27.8* | 11.1 | 16.9 | *27.6* | 6.7 | 14.8 | 18.6 |
| DRB3*01:01 | 13.4 | 12.6 | 5.0 | *17.5* | 13.4 | 11.6 | *14.9* | 3.0 | 6.3 | 7.3 |

TABLE 16-continued

HLA-A and HLA-DRB3 allele frequencies

| | | | | | | | | | | |
|---|---|---|---|---|---|---|---|---|---|---|
| DRB*02:02g | 27.2 | 27.1 | 27.2 | 14.5 | 25.8 | 21.8 | 18.2 | 13.2 | 10.4 | 15.3 |
| DRB*03:01 | 9.6 | 10.8 | 6.4 | 4.0 | 9.5 | 7.8 | 4.9 | 13.9 | 7.5 | 11.6 |

| HLA Allele | MENAFC | MSWHIS | NCHI | SCAHIS | SCSEAI | VIET |
|---|---|---|---|---|---|---|
| A*01:01 | 13.5 | 7.4 | 1.4 | 7.3 | 11.5 | 3.3 |
| A*02:01g | 19.7 | 22.3 | 9.5 | 21.0 | 5.8 | 3.5 |
| DRB3*01:01 | 9.1 | 14.1 | 3.9 | 12.8 | 4.4 | 2.0 |
| DRB*02:02g | 34.5 | 16.7 | 22.7 | 17.9 | 26.4 | 14.9 |
| DRB*03:01 | 5.5 | 3.8 | 12.6 | 4.7 | 9.4 | 29.8 |

Table 16 above lists frequencies as reported by (87). AAFA denotes African American, AFB denotes African, AINDI denotes South Asian Indian, AMIND denotes North American Indian, CARB denotes Caribbean black, CARHIS denotes Caribbean Hispanic, EURCAU denotes European Caucasian, FILII, Filipino, JAPI denotes Japanese, KORI denotes Korean, MENAFC denotes Middle Eastern or N. Coast of Africa, MSWHIS denotes Mexican or Chicano, NCHI denotes Chinese, SCAHIS denotes Hispanic—South or Central American, SCSEAI denotes Southeast Asian, and VIET denotes Vietnamese. The "g" in some of the allele designations refers to the inclusion of alleles with different designations but with amino acids identical in the antigen recognition site to the alleles listed.

Phenotype frequencies, defined by the presence of at least one copy of the respective allele(s) per individual (2n), of HLA-A/HLA-DRB3 allele combinations are indicated in Table 17. With a phenotype frequency of 20.3% for the Middle Eastern or N. Coast of Africa group and of 15.7% for the European Caucasian group, HLA-A*02:01/HLA-DRB3*02:02 has the highest prevalence among the 16 ethnic groups addressed above. Thus, assuming trogocytosis (i.e., "cross-dressing") or direct antigen presentation to T cells are valid mechanisms for immune stimulation by whole cell vaccines, vaccines expressing the HLA-A*02:01/HLA-DRB3*02:02 combination have particularly broad applicability.

TABLE 17

Phenotype frequencies of HLA-A/HLA-DRB3 allele combinations

| HLA-A | DRB-3 | AAFA | AFB | AINDI | AMIND | CARB | CARHIS | EURCAU | FILII | JAPI |
|---|---|---|---|---|---|---|---|---|---|---|
| *01:01g | *01:01 | 2.3 | 2.3 | 2.8 | 7.2 | 2.2 | 2.8 | 8.3 | 0.1 | 0.2 |
| *01:01g | *02:02g | 4.3 | 4.6 | 13.4 | 6.1 | 3.9 | 5.0 | 10.0 | 0.6 | 0.4 |
| *01:01g | *03:01 | 1.7 | 2.0 | 3.5 | 1.8 | 1.6 | 1.9 | 2.9 | 0.6 | 0.3 |
| *02:01g | *01:01 | 5.8 | 5.1 | 0.9 | 15.3 | 5.2 | 6.8 | 13.1 | 0.8 | 3.3 |
| *02:01g | *02:02g | 10.9 | 10.1 | 4.5 | 12.9 | 9.4 | 12.0 | 15.7 | 3.2 | 5.4 |
| *02:01g | *03:01 | 4.3 | 4.4 | 1.2 | 3.7 | 3.8 | 4.7 | 4.6 | 3.4 | 3.9 |

| HLA-A | DRB-3 | KORI | MENAFC | MSWHIS | NCHI | SCAHIS | SCSEAI | VIET |
|---|---|---|---|---|---|---|---|---|
| *01:01g | *01:01 | 0.6 | 4.4 | 3.7 | 0.2 | 3.4 | 1.9 | 0.3 |
| *01:01g | *02:02g | 1.2 | 14.4 | 4.3 | 1.2 | 4.6 | 9.9 | 1.8 |
| *01:01g | *03:01 | 0.9 | 2.7 | 1.1 | 0.7 | 1.3 | 3.9 | 3.3 |
| *02:01g | *01:01 | 4.8 | 6.2 | 10.4 | 1.4 | 9.0 | 1.0 | 0.3 |
| *02:01g | *02:02g | 9.5 | 20.3 | 12.1 | 7.3 | 12.2 | 5.1 | 1.9 |
| *02:01g | *03:01 | 7.3 | 3.8 | 3.0 | 4.3 | 3.4 | 2.0 | 3.5 |

From the allele frequencies reported by (87), estimated "phenotype frequencies" were calculated indicating probabilities that an individual carries at least one of the indicated HLA-A and at least one of the indicated HLA-DRB3 alleles. Shown in Table 17 above are "phenotype frequencies" as percentage values. AAFA denotes African American, AFB denotes African, AINDI denotes South Asian Indian, AMIND denotes North American Indian, CARB denotes Caribbean black, CARHIS denotes Caribbean Hispanic, EURCAU denotes European Caucasian, FILII, Filipino, JAPI denotes Japanese, KORI denotes Korean, MENAFC denotes Middle Eastern or N. Coast of Africa, MSWHIS denotes Mexican or Chicano, NCHI denotes Chinese, SCAHIS denotes Hispanic—South or Central American, SCSEAI denotes Southeast Asian, and VIET denotes Vietnamese. The "g" in some of the allele designations refers to the inclusion of alleles with different designations but with amino acids identical in the antigen recognition site to the alleles listed.

Plasmid Construction

Methods for generating plasmids and performing plasmid-based transfection will be known to one of skill in the art. This example demonstrates the generation of HLA-A*02:01 and HLA-DRB3*02:02 overexpressing SV-BR-1-GM cells.

In order to maximize gene expression, the HLA-A*02:01 coding sequence is optimized in silico. As a starting point, the HLA-A*02:01 cDNA nucleic acid sequence as represented by GenBank (NCBI) accession number AY365426.1 is used (SEQ ID NO:1). Optimization is conducted using software such as the Gene Optimizer software (available from Thermo Fisher Scientific, Waltham, Mass.). User specified parameters include 1) ensuring the presence of a Kozak sequence by the addition of a "GCCACC" sequence immediately upstream of the translational start codon, 2) a 5' BamHI restriction site sequence (GGATCC) and a 3' ClaI (ATCGAT) restriction site sequence for straightforward transfer of the insert to another vector, and 3) optimization for Homo sapiens. Methods of gene synthesis, transfer into a suitable vector such as the pcDNA™ 3.4-TOPO® vector (available from Thermo Fisher Scientific), plasmid amplification (e.g., using bacterial cells such as E. coli) and purification will be known to one of skill in the art. The DNA sequence of the optimized HLA-A*02:01 ORF is set forth in SEQ ID NO:2 and the entire pcDNA3.4-A0201 construct sequence is set forth in SEQ ID NO:3.

Methods of achieving expression of the HLA-A gene (e.g., in mammalian cells) will be known to one of skill in the art. Particularly relevant for the current invention is that SV-BR-1-GM cells (see, e.g., U.S. Pat. No. 7,674,456 and U.S. patent application Ser. No. 10/868,094, both of which are incorporated fully herein for all purposes), despite numerous months of culturing, have not lost expression of the CMV promoter-driven CSF2 gene, encoding GM-CSF. Nevertheless, an alternative promoter can be used, such as the EF-1α promoter, which is less prone to silencing than a CMV promoter (101).

A preferred aspect of the current invention comprises cancer cells engineered to express two ectopic HLA genes. To accomplish such dual expression using a single plasmid with two separate transcription units, the pVITRO2-neo-mcs (available from Invivogen, San Diego, Calif.) is utilized. The pVITRO2-neo-mcs plasmid comprises two multiple cloning sites (i.e., MCS1 and MCS2). Whereas MCS1 permits ectopic expression via a promoter containing human ferritin heavy chain and mouse EF-1α regulatory elements, MCS2 inserts are expressed by means of a composite promoter comprising human ferritin light chain and chimpanzee EF-1α regulatory elements. Furthermore, expression of the MCS1 transcription unit results in a bicistronic messenger RNA comprising mRNA encoding the MCS1 insert, an internal ribosome entry site (IRES), and an mRNA encoding a neomycin/G418 resistance marker. One of skill in the art will recognize that the latter feature is particularly important for the selection of mammalian cells with stably integrated DNA derived from pVITRO2-neo-mcs, as neomycin/G418 resistant cells also express the transgene cloned into the MCS1.

To transfer the HLA-A*02:01 ORF from pcDNA3.4-A0201 into the MCS1 of the pVITRO2-neo-mcs vector, both plasmids are double-digested with BamHI and ScaI Thereafter, the BamHI[HLA-A*02:01]-ScaI fragment from pcDNA3.4-A0201 is ligated into the BamHI and ScaI sites of the pVITRO2-neo-mcs vector. Thereafter, the resulting plasmid, referred to as pVITRO2-A0201, is amplified in E. coli under kanamycin selective pressure, then purified. Standard techniques known to one of skill in the art are employed for the above steps. The purified pVITRO2-A0201 plasmid can be utilized to transiently or stably (via G418 selection) transfect mammalian cells, and/or can be further engineered for expression of a second ectopic gene, inserted into the MCS2. pVITRO2-A0201 contains a single ApaLI restriction (GTGCAC) site in the ori region (for plasmid replication in E. coli), i.e., outside of mammalian regulatory regions or in the ORFs of the neomycin-resistance marker or of HLA-A*02:01. Thus, prior to transfection into mammalian cells, pVITRO2-A0201 can be digested with ApaLI to promote chromosomal integration without functional inactivation of any of these critical elements.

To facilitate co-expression of ectopic HLA-A*02:01 and HLA-DRB3*02:02, the HLA-DRB3*02:02 ORF is inserted into the MCB2 of pVITRO2-A0201. To accomplish this, the ApaLI site (GTGCAC) in the HLA-DRB3*02:02 ORF sequence, as available via The European Bioinformatics Institute as IMGT/HLA Acc No. HLA00895 (SEQ ID NO:4), is first removed by altering the last "C" through an "A". Through this alteration, a CGG codon is replaced with an AGG codon, both encoding arginine. The frequencies of both codons are similar (i.e., 11.4/1000 for CGG and 12.0/1000 for AGG). The HLA-DRB3*02:02 ORF (SEQ ID NO:4), after inclusion of the synonymous mutation, is shown as SEQ ID NO:5. The latter sequence is thereafter optimized using the Gene Optimizer software (Thermo Fisher Scientific). User specified parameters include those described above. After optimization, this temporary ApaLI site is removed from the sequence. Subsequent steps for synthesis, transfer into a vector, amplification, and purification are as described above. The DNA sequence of the optimized HLA-DRB3*02:02 ORF is set forth in SEQ ID NO:6 and the sequence of the entire pcDNA3.4-DRB30202 construct is set forth in SEQ ID NO:7.

To transfer the HLA-DRB3*02:02 ORF from pcDNA3.4-DRB30202 into the MCS2 of the pVITRO2-A0201 vector, both plasmids are double-digested with XhoI and NheI. Thereafter, the XhoI-[HLA-DRB3*02:02]-NheI fragment from pcDNA3.4-DRB30202 is ligated into the XhoI and NheI sites of the pVITRO2-A0201 vector. Thereafter, the resulting plasmid, referred to as pVITRO2-A0201-DRB30202, is amplified in E. coli under kanamycin selective pressure, then purified. Standard techniques known to one of skill in the art are employed for the above steps. The purified pVITRO2-A0201-DRB30202 plasmid can be utilized to transiently or stably transfect mammalian cells. The sequence of pVITRO2-A0202-DRB30202 is set forth in SEQ ID NO:8.

Introduction of Plasmids into Mammalian Cells

Methods to stably transfect the pcDNA3.4-A0201, pcDNA3.4-DRB30202, and/or pVITRO2-A0201-DRB30202 plasmids into appropriate cells (e.g., mammalian cells) will be known to one of skill in the art. For pcDNA3.4-A0201 and pcDNA-DRB30202, PvuI is a suitable restriction endonuclease cutting in the ORF of the ampicillin resistance marker. For pVITRO2-A0201-DRB30202, ApaLI, cutting in the origin of replication (ori) region, is the most preferred restriction enzyme.

After linearization, the plasmids are purified using methods known to one of skill in the art. Subsequent steps, including the culturing of SV-BR-1-GM cells, preparation of the transfection reagent (TR)-DNA complexes, enzymatic detachment of the cells and resuspension in culture medium, seeding of cells and incubation with TR-DNA complexes, replacement of medium with fresh culture medium, short-term culturing antibiotic-selection of stably transfected cells, and cloning of stably transfected cells, will also be known to one of skill in the art. It will also be known to one of skill in the art that methods similar to those employed for the transfection of suspended cells can be applied to the transfection of adherent cells.

While the method outlined here is exemplified using SV-BR-1-GM cells as an example, one of skill in the art will recognize that as ectopic expression of HLA alleles facilitates antigen presentation on a variety of mammalian cells, including other whole-cell cancer vaccines, the methods described herein are useful for any number of cells in addition to SV-BR-1-GM cells. Furthermore, although SV-BR-1-GM does express endogenous HLA-DRB3*02:02, ectopic expression via strong promoters further improves HLA-DRB3 based antigen presentation.

Example 3: Assessing Immunogenicity of SV-BR-1-GM Cells Engineered to Overexpress HLA-A*02:01 and HLA-DRB3*02:02

In Vitro Assessment of HLA-A*02:01-Specific Immune Effects

To assess the immunogenic potential of SV-BR-1-GM cells engineered to overexpress HLA-A*02:01, alone or in combination with HLA-DRB3*02:02, T cells specific for MHCs comprising HLA-A*02:01 proteins are co-incubated with HLA-A*02:01+ SV-BR-1-GM cells, then assayed for activation.

First, T cells from SV-BR-1-GM vaccinated or unvaccinated donors carrying the HLA-A*02:01 allele are in vitro expanded via antibody-mediated stimulation of CD28 and CD3, and optionally CD2. As a non-limiting example, the T Cell Activation/Expansion Kit (available from Miltenyi Biotec GmbH, Bergisch Gladbach, Germany) in combination with unsorted PBMCs or selected CD8+ T cells is employed. Second, T cells specific for MHCs comprising HLA-A*02:01 proteins are isolated from the total population of donor-derived cells. This enrichment step is conducted by FACS using fluorescently labelled MHC tetramers or pentamers comprising HLA-A*02:01 and antigenic peptides representing tumor-associated antigens that are expressed in SV-BR-1-GM cells such as PRAME or ERBB2 (HER2). Third, to assess whether and to what extent the effector T cells become activated following stimulation by target cells, peptide-specific effector T cells and target cells are co-incubated. Thereafter, the effector T cells are retrieved and analyzed for activation. As a non-limiting example, staining for the activation marker CD137 (4-1BB) can be performed, followed by flow cytometry-based quantification and assessment of the cells' proliferative behavior. Such assessment, can be performed, as a non-limiting example, in a CFSE dye dilution assay by employing, for instance, the CellTrace™ CFSE Cell Proliferation Kit (available from Thermo Fisher Scientific). For the latter assay, T cells are stained with carboxyfluorescein succinimidyl ester (CFSE), a cell permeable and fluorescent dye whose intracellular concentrations decrease with each cell division. Accordingly, the per-cell fluorescent signal also decreases in a population of dividing cells. To address the cytotoxic potential of the effector T cells, target cells are seeded in 96-well plates and then incubated with effector cells. Following removal of the effector T cells, cell viability of the target cells is measured.

Methods and reagents required to conduct this study are known to those of skill in the art. For instance, pentamers comprising HLA-A*02:01 proteins and peptides representing PRAME (VLDGLDVLL or ALYVDSLFFL) or ERBB2/HER2 (RLLQETELV) are available from ProImmune (ProImmune Ltd., Oxford, UK; ProImmune Inc., Sarasota, Fla.).

In Vitro Assessment of HLA-DRB3*02:02-Specific Immune Effects

To assess whether SV-BR-1-GM cells overexpressing HLA-DRB3*02:02, alone or in combination with HLA-A*02:01, can activate T helper cells, methods known to those of skill in the art can be employed. One non-limiting example of a suitable method is described in (102), which is hereby incorporated by reference herein for all purposes. In the context of engineered SV-BR-1-GM cells, peripheral blood mononuclear cells (PBMCs) from donors carrying the HLA-DRB3*02:02 allele are stimulated with tetanus toxin (TT) peptides (e.g., MSLLTEVETYVLSIIPSGPL, TYVLSIIPSGPLKAEIAQRL, and/or GLQRRRFVQNALNGNGDPNN) that interact with HLA-DRB3*02:02 tetramers (102). After about 14 days of stimulation, CD4+ T cells (i.e., enriched with TT-HLA-DRB3*02:02-specific T cells) are isolated and then co-incubated with SV-BR-1-GM cells overexpressing HLA-DRB3*02:02, which have, or have not, been pre-incubated with TT peptides. Thereafter, the T cells are retrieved and analyzed for production of cytokines such as interferon-gamma or IL-2 by ELISpot and/or flow cytometry, and for their proliferative behavior, for instance, by a CSFE dye dilution assay.

Functional contribution of the ectopic HLA-DRB3*02:02 allele to T helper cell activation is given if TT peptide-stimulated SV-BR-1-GM cells induce higher levels of T helper cell-associated cytokines and/or a more substantial T cell proliferation rate than SV-BR-1-GM cells not pre-incubated with TT peptides.

In Vivo Assessment of MHC Match Contribution to Whole-Cell Immunogenicity

To assess the functional links between the HLA/MHC type of a whole-cell vaccine and a variety of effector immune cells in vivo, a mouse vaccine cell line is generated and tested on different mouse strains with diverse MHC haplotypes. However, it is imperative that the preclinical model also permits the testing of the vaccine in combination with immune checkpoint inhibitors such as anti-PD-1, anti-PD-L1, or anti-CTLA4 antibodies.

NF639 cells (ATCC: CRL-3090) are mouse breast tumor cells with FVB/N background expressing Erbb2/neu and thus resemble SV-BR-1-GM cells. To also overexpress granulocyte-macrophage colony-stimulating factor (GMCSF), cells are engineered to stably express the mouse Csf2 gene using techniques that will be known to one of skill in the art, resulting in a cell line referred to as NF639-GM.

FVB/N mice carry the "q" alleles at the MHC I loci H-2K, H-2D, and H-2L, and the MHC II loci I-A and I-E. In contrast, Balb/c mice carry the "d" alleles at these MHC I and II loci. To obtain MHC I or MHC I and II matches between NF639-GM (FVB/N background) and Balb/c effector cells, NF639-GM cells are further engineered, using techniques that will be known to one of skill in the art, to express the (Balb/c) "d" MHC I and II alleles outlined in Table 18.

TABLE 18

MHC alleles

| Vaccine No. | Ectopic MHC I "d" alleles | Ectopic MHC I "d" alleles | Comments |
|---|---|---|---|
| 1 | — | — | Unmodified NF639-GM 0x MHC I, 0x MHC II match to Balb/c |
| 2 | H-2K | — | 1x MHC I, 0x MHC II match to Balb/c |
| 3 | H-2D | — | 1x MHC I, 0x MHC II match to Balb/c |
| 4 | H-2L | — | 1x MHC I, 0x MHC II match to Balb/c |
| 5 | H-2K | I-A | 1x MHC I, 0x MHC II match to Balb/c |
| 6 | H-2K | I-E | 1x MHC I, 1x MHC II match to Balb/c |
| 7 | H-2D | I-A | 1x MHC I, 1x MHC II match to Balb/c |
| 8 | H-2D | I-E | 1x MHC I, 1x MHC II match to Balb/c |
| 9 | H-2L | I-A | 1x MHC I, 1x MHC II match to Balb/c |
| 10 | H-2L | I-E | 1x MHC I, 1x MHC II match to Balb/c |

Generation of allogeneic tumors in Balb/c mice with Balb/c-derived syngeneic breast cancer cell lines such as the isogenic lines 67NR, 168FARN, 4TO7, and 4T1, addressed by (103), permits the testing of the HLA/MHC allele-match hypothesis by using all or a subset of the 10 engineered NF639-derived cell lines indicated (Table 18) as vaccines. Tumor shrinkage or growth kinetics serve as the main endpoint. One of skill in the art will readily be familiar with methods to assess tumor volume, a non-limiting example of which being caliper-based measurement at several time points before and after vaccination.

Example 4: Overexpression of HLA-A*02:01 and HLA-DRB3*02:02 Via Zinc Finger Nuclease-Based Engineering Cell line engineering using zinc finger nucleases (ZFNs) is an alternative approach to plasmid-based transfection. In contrast to plasmid-based stable transfections, chromosomal integration of the ectopic expression cassette is directed to a defined locus. For overexpression studies using human cells, the adeno-associated virus integration site 1 (AAVS1) on chromosome 19 is a preferred integration site. A commercially available kit, referred to as CompoZr Targeted Integration Kit—AAVS1 (available from Sigma-Aldrich, St. Louis, Mo.), permits customized integration into this site. The method employed by the kit utilizes a plasmid, pZDonor, into which the ORF to be expressed is cloned. The multiple cloning site (MCS) into which the ORF is inserted is flanked by DNA elements also found in the AAVS1 integration site. Cotransfection (as a non-limiting example, by nucleofection (i.e., an electroporation approach)) of the pZDonor plasmid carrying the ORF with mRNA encoding the AAVS1-specific ZFN permits integration of the ORF into the AAVS1 locus. Given the high efficacy of the method it is possible to integrate ORFs into the AAVS1 loci of both copies of chromosome 19 that are present in diploid cells. Thereby, for instance, both HLA-A*0201 and HLA-DRB3*02:02 can be overexpressed in the same cell.

It should be noted that the pcDNA3.4-A0201 and pcDNA3.4-DRB30202 plasmids described above in Example 2, carrying HLA-A*02:01 and HLA-DRB3*02:02 ORFs, respectively, permit straightforward transfer of the HLA inserts into the MCS of the pZDonor plasmid. Both ORFs can be transferred as XbaI-EcoRV fragments and cloned into the XbaI and PmeI sites of pZDonor.

Example 5: Assessing Correlative Relationship Between Patient and Vaccine HLA Types, and Vaccine Effectivity To assess the extent of the correlation between SV-BR-1-GM vaccine effectivity and vaccine-patient HLA allele identity, HLA types of clinical trial subjects enrolled in a Phase I/IIa study (BB-IND 10312) are determined.

Background

The clinical study comprises a series of vaccine cycles, whereby each vaccine administration comprises four intradermal injections of the vaccine (i.e., at four different locations with about five million irradiated SV-BR-1-GM cells per location). Each vaccine cycle includes four study events: 1) pre-vaccine cyclophosphamide, 2) vaccine inoculation, 3) interferon-alpha-2b (available from Merck) administration at about 48 hours post-vaccine, and 4) interferon-alpha-2b administration at about about 96 hours post-vaccine (e.g., performed at a physician's office). The evaluation of safety and clinical developments is assessed at every study visit after starting the vaccine therapy cycles.

As outlined in Table 19, the first three cycles occur over one month at 0, 2, and 4 weeks. This is followed by monthly cycles for a total of 6 months, with optional treatments extending out to one year. Imaging and restaging occurs after the fifth inoculation. In the absence of progressive disease (defined below) or major safety issues, the patient continues with additional vaccine therapy cycles to complete 6 months of experimental vaccine administration, with restaging every 3 months at approximately 3 weeks following the last treatment. If the patient remains non-progressive and desires to continue treatment after six months, an additional three months of treatment are offered, followed by restaging at nine months. Again, if the patient has non-progressive disease and desires to continue treatment, an additional 3 months of treatment are offered, with completion at 12 months.

TABLE 19

Study design

| Vaccine Cycle | | Comments |
|---|---|---|
| Week # | | |
| 0, 2, 4 | 1, 2, 3 | |
| Month # | | |
| 2, 3 | 4, 5 | Restaging about 1-2 weeks prior to initiation of next cycle (#6) |
| 4, 5, 6, | 6, 7, 8 | Restaging about 1-2 weeks prior to initiation of next cycle (#9) |
| Optional Treatment Cycles | | Patient may continue if they show non-progressive response |
| 7, 8, 9 | 9, 10, 11 | Restaging about 1-2 weeks prior to initiation of next cycle (#12) |

TABLE 19-continued

Study design

| | Vaccine Cycle | Comments |
|---|---|---|
| Optional Treatment Cycles | | Patient may continue if they show non-progressive response |
| 10, 11, 12 | 12, 13, 14 | Off-vaccine evaluation about 6-8 weeks after last inoculation cycle |

Flexibility between cycles can be +/− within one week under special circumstances as approved by Principal Investigator To boost the immune response, patients are pretreated with low-dose cyclophosphamide that downregulates T regulatory-cell mechanisms 48-72 hours prior to each vaccine inoculation. Low-dose Interferon-alpha-2b serves as an adjuvant and is given by intradermal injection to the inoculation site about 48 hours and about 96 hours after vaccine inoculation. Biological samples are collected at regular intervals per protocol, and stored in a repository.

Study participants are closely monitored for adverse events (e.g., toxicity) using the common terminology criteria for adverse events (i.e., CTCAE v 4.03) scale. Development of a new or progressive tumor, or treatment-related Grade III allergy/hypersensitivity, truncates further inoculations to any particular subject.

Success Measures

While the core success measure is safety and lack of toxicity, any of the following may be applied as success measures: 1) objective clinical response as defined by irRC RECIST 1.1 criteria in 25% of patients, 2) improvement in quality of life in 50% or more patients as evidenced by significant change in one or more scales in the SF-36 questionnaire (quality of life), 3) prolongation of disease-free and overall survival as compared with historical controls from reports of other salvage therapies in the published literature, 4) evidence of development or amplification of immune responses, especially if correlating with prolongation of survival.

Objective clinical response is primarily assessed by radiographic assessment of tumor burden. This may be conducted, as non-limiting examples, by computed tomography (CT), magnetic resonance imaging (MRI), and/or positron emission tomography (PET). See, (16). To assess whether objective tumor regression is particularly pronounced in patients with HLA alleles also found in SV-BR-1-GM cells, HLA types from, as non-limiting examples, buccal cells or blood cells of clinical trial subjects are determined. Several methods known to one of skill in the art are suitable to determine HLA alleles. For non-limiting examples, see (104).

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications, and sequence accession numbers cited herein are hereby incorporated by reference in their entirety for all purposes.

V. References

All references are incorporated herein in their entirety, for all purposes.

1. Maude S L, Frey N, Shaw P A, Aplenc R, Barrett D M, Bunin N J, et al. Chimeric antigen receptor T cells for sustained remissions in leukemia. N Engl J Med. 2014; 371(16):1507-17.
2. Maus M V, Grupp S A, Porter D L, June C H. Antibody-modified T cells: CARs take the front seat for hematologic malignancies. Blood. 2014; 123(17):2625-35.
3. Kontermann R E, Brinkmann U. Bispecific antibodies. Drug Discov Today. 2015; 20(7):838-47.
4. Robbins P F, Kassim S H, Tran T L, Crystal J S, Morgan R A, Feldman S A, et al. A pilot trial using lymphocytes genetically engineered with an N Y-ESO-1-reactive T-cell receptor: long-term follow-up and correlates with response. Clin Cancer Res. 2015; 21(5):1019-27.
5. Prickett T D, Crystal J S, Cohen C J, Pasetto A, Parkhurst M R, Gartner J J, et al. Durable Complete Response from Metastatic Melanoma after Transfer of Autologous T Cells Recognizing 10 Mutated Tumor Antigens. Cancer Immunol Res. 2016; 4(8):669-78.
6. Groeper C, Gambazzi F, Zajac P, Bubendorf L, Adamina M, Rosenthal R, et al. Cancer/testis antigen expression and specific cytotoxic T lymphocyte responses in non small cell lung cancer. Int J Cancer. 2007; 120(2):337-43.
7. Chen G, Gupta R, Petrik S, Laiko M, Leatherman J M, Asquith J M, et al. A feasibility study of cyclophosphamide, trastuzumab, and an allogeneic GM-CSF-secreting breast tumor vaccine for HER2+ metastatic breast cancer. Cancer Immunol Res. 2014; 2(10):949-61.
8. Creelan B C, Antonia S, Noyes D, Hunter T B, Simon G R, Bepler G, et al. Phase II trial of a GM-CSF-producing and CD40L-expressing bystander cell line combined with an allogeneic tumor cell-based vaccine for refractory lung adenocarcinoma. J Immunother. 2013; 36(8):442-50.
9. Gupta R, Emens L A. GM-CSF-secreting vaccines for solid tumors: moving forward. Discov Med. 2010; 10(50):52-60.
10. Le D T, Wang-Gillam A, Picozzi V, Greten T F, Crocenzi T, Springett G, et al. Safety and survival with GVAX pancreas prime and *Listeria Monocytogenes*-expressing mesothelin (CRS-207) boost vaccines for metastatic pancreatic cancer. J Clin Oncol. 2015; 33(12):1325-33.
11. Lipson E J, Sharfman W H, Chen S, McMiller T L, Pritchard T S, Salas J T, et al. Safety and immunologic correlates of Melanoma GVAX, a GM-CSF secreting allogeneic melanoma cell vaccine administered in the adjuvant setting. J Transl Med. 2015; 13:214.
12. Lollini P L, Cavallo F, Nanni P, Quaglino E. The Promise of Preventive Cancer Vaccines. Vaccines (Basel). 2015; 3(2):467-89.
13. Mittendorf E A, Clifton G T, Holmes J P, Schneble E, van Echo D, Ponniah S, et al. Final report of the phase I/II clinical trial of the E75 (nelipepimut-S) vaccine with booster inoculations to prevent disease recurrence in high-risk breast cancer patients. Ann Oncol. 2014; 25(9): 1735-42.
14. Santegoets S J, Stam A G, Lougheed S M, Gall H, Jooss K, Sacks N, et al. Myeloid derived suppressor and dendritic cell subsets are related to clinical outcome in prostate cancer patients treated with prostate GVAX and ipilimumab. J Immunother Cancer. 2014; 2:31.
15. Srivatsan S, Patel J M, Bozeman E N, Imasuen I E, He S, Daniels D, et al. Allogeneic tumor cell vaccines: the promise and limitations in clinical trials. Hum Vaccin Immunother. 2014; 10(1):52-63.
16. Wiseman C L, Kharazi A. Objective clinical regression of metastatic breast cancer in disparate sites after use of whole-cell vaccine genetically modified to release sargramostim. Breast J. 2006; 12(5):475-80.
17. Wiseman C L, Kharazi A. Phase I Study with SV-BR-1 Breast Cancer Cell Line Vaccine and GM-CSF: Clinical Experience in 14 Patients. The Open Breast Cancer Journal (discontinued). 2010; 2:4-11.
18. Silvestri I, Cattarino S, Agliano A M, Collalti G, Sciarra A. Beyond the Immune Suppression: The Immunotherapy in Prostate Cancer. Biomed Res Int. 2015; 2015:794968.
19. Villadolid J, Amin A. Immune checkpoint inhibitors in clinical practice: update on management of immune-related toxicities. Transl Lung Cancer Res. 2015; 4(5): 560-75.
20. Keenan B P, Jaffee E M. Whole cell vaccines—past progress and future strategies. Semin Oncol. 2012; 39(3): 276-86.
21. De Remigis A, de Gruijl T D, Uram J N, Tzou S C, Iwama S, Talor M V, et al. Development of thyroglobulin antibodies after GVAX immunotherapy is associated with prolonged survival. Int J Cancer. 2015; 136(1):127-37.
22. Soares K C, Rucki A A, Kim V, Foley K, Solt S, Wolfgang C L, et al. TGF-beta blockade depletes T regulatory cells from metastatic pancreatic tumors in a vaccine dependent manner. Oncotarget. 2015; 6(40): 43005-15.
23. Borrello I M, Levitsky H I, Stock W, Sher D, Qin L, DeAngelo D J, et al. Granulocyte-macrophage colony-stimulating factor (GM-CSF)-secreting cellular immunotherapy in combination with autologous stem cell transplantation (ASCT) as postremission therapy for acute myeloid leukemia (AML). Blood. 2009; 114(9):1736-45.
24. Emens L A, Asquith J M, Leatherman J M, Kobrin B J, Petrik S, Laiko M, et al. Timed sequential treatment with cyclophosphamide, doxorubicin, and an allogeneic granulocyte-macrophage colony-stimulating factor-secreting breast tumor vaccine: a chemotherapy dose-ranging factorial study of safety and immune activation. J Clin Oncol. 2009; 27(35):5911-8.
25. Ogawa T, Kusumoto M, Mizumoto K, Sato N, Tanaka M. Adenoviral GM-CSF Gene Transduction into Breast Cancer Cells Induced Long-Lasting Antitumor Immunity in Mice. Breast Cancer. 1999; 6(4):301-4.
26. Broughton S E, Hercus T R, Nero T L, Dottore M, McClure B J, Dhagat U, et al. Conformational Changes in the GM-CSF Receptor Suggest a Molecular Mechanism for Affinity Conversion and Receptor Signaling. Structure. 2016; 24(8):1271-81.
27. Brown C B, Pihl C E, Kaushansky K. Mapping of human granulocyte-macrophage-colony-stimulating-factor domains interacting with the human granulocyte-macrophage-colony-stimulating-factor-receptor alpha-subunit. Eur J Biochem. 1994; 225(3):873-80.
28. Hu Z B, Ma W, Zaborski M, MacLeod R, Quentmeier H, Drexler H G. Establishment and characterization of two novel cytokine-responsive acute myeloid and monocytic leukemia cell lines, MUTZ-2 and MUTZ-3. Leukemia. 1996; 10(6):1025-40.
29. Arruda L B, Sim D, Chikhlikar P R, Maciel M, Jr., Akasaki K, August J T, et al. Dendritic cell-lysosomal-associated membrane protein (LAMP) and LAMP-1-HIV-1 gag chimeras have distinct cellular trafficking pathways and prime T and B cell responses to a diverse repertoire of epitopes. J Immunol. 2006; 177(4):2265-75.
30. Bates J M, Flanagan K, Mo L, Ota N, Ding J, Ho S, et al. Dendritic cell CD83 homotypic interactions regulate inflammation and promote mucosal homeostasis. Mucosal Immunol. 2015; 8(2):414-28.
31. Caux C, Massacrier C, Vanbervliet B, Dubois B, Van Kooten C, Durand I, et al. Activation of human dendritic cells through CD40 cross-linking. J Exp Med. 1994; 180(4): 1263-72.
32. Lee S, Margolin K. Cytokines in cancer immunotherapy. Cancers (Basel). 2011; 3(4):3856-93.
33. Leitner J. The role of costimulatory pathways during the activation of human T cells. Dissertation (Ph.D. Thesis). University of Vienna, Austria. URL: othes.univie.ac.at/15063/1/2011-03-07 0107588.pdf. 2011.
34. Ohshima Y, Tanaka Y, Tozawa H, Takahashi Y, Maliszewski C, Delespesse G. Expression and function of OX40 ligand on human dendritic cells. J Immunol. 1997; 159 (8):3838-48.
35. Rescigno M, Piguet V, Valzasina B, Lens S, Zubler R, French L, et al. Fas engagement induces the maturation of dendritic cells (DCs), the release of interleukin (IL)-1beta, and the production of interferon gamma in the absence of IL-12 during DC-T cell cognate interaction: a new role for Fas ligand in inflammatory responses. J Exp Med. 2000; 192(11): 1661-8.
36. Wong B R, Josien R, Lee S Y, Sauter B, Li H L, Steinman R M, et al. TRANCE (tumor necrosis factor [TNF]-related activation-induced cytokine), a new TNF family member predominantly expressed in T cells, is a dendritic cell-specific survival factor. J Exp Med. 1997; 186(12): 2075-80.
37. Zou G M, Tam Y K. Cytokines in the generation and maturation of dendritic cells: recent advances. Eur Cytokine Netw. 2002; 13(2):186-99.
38. Bleijs D A, de Waal-Malefyt R, Figdor C G, van Kooyk Y. Co-stimulation of T cells results in distinct IL-10 and TNF-alpha cytokine profiles dependent on binding to ICAM-1, ICAM-2 or ICAM-3. Eur J Immunol. 1999; 29(7):2248-58.
39. Damle N K, Aruffo A. Vascular cell adhesion molecule 1 induces T-cell antigen receptor-dependent activation of CD4+T lymphocytes. Proc Natl Acad Sci USA. 1991; 88(15):6403-7.
40. Dieu M C, Vanbervliet B, Vicari A, Bridon J M, Oldham E, Ait-Yahia S, et al. Selective recruitment of immature and mature dendritic cells by distinct chemokines expressed in different anatomic sites. J Exp Med. 1998; 188(2):373-86.
41. Gokhale A, Kanthala S, Latendresse J, Taneja V, Satyanarayanajois S. Immunosuppression by co-stimulatory molecules: inhibition of CD2-CD48/CD58 interaction by peptides from CD2 to suppress progression of collagen-induced arthritis in mice. Chem Biol Drug Des. 2013; 82(1):106-18.
42. He S, Wang L, Wu Y, Li D, Zhang Y. CCL3 and CCL20-recruited dendritic cells modified by melanoma antigen gene-1 induce anti-tumor immunity against gastric cancer ex vivo and in vivo. J Exp Clin Cancer Res. 2010; 29:37.
43. Leitner J, Grabmeier-Pfistershammer K, Steinberger P. Receptors and ligands implicated in human T cell costimulatory processes. Immunol Lett. 2010; 128(2):89-97.
44. Sutavani R V, Bradley R G, Ramage J M, Jackson A M, Durrant L G, Spendlove I. CD55 costimulation induces differentiation of a discrete T regulatory type 1 cell population with a stable phenotype. J Immunol. 2013; 191(12):5895-903.
45. Arango Duque G, Descoteaux A. Macrophage cytokines: involvement in immunity and infectious diseases. Front Immunol. 2014; 5:491.
46. Goswami R, Kaplan M H. A brief history of IL-9. J Immunol. 2011; 186(6):3283-8.
47. Hirano N, Butler M O, Xia Z, Ansen S, von Bergwelt-Baildon M S, Neuberg D, et al. Engagement of CD83 ligand induces prolonged expansion of CD8+ T cells and preferential enrichment for antigen specificity. Blood. 2006; 107(4):1528-36.
48. Imai T, Baba M, Nishimura M, Kakizaki M, Takagi S, Yoshie O. The T cell-directed C C chemokine TARC is a highly specific biological ligand for C C chemokine receptor 4. J Biol Chem. 1997; 272(23):15036-42.
49. Luo H, Yu G, Wu Y, Wu J. EphB6 crosslinking results in costimulation of T cells. J Clin Invest. 2002; 110(8): 1141-50.
50. Mandapathil M, Szczepanski M, Harasymczuk M, Ren J, Cheng D, Jackson E K, et al. CD26 expression and adenosine deaminase activity in regulatory T cells (Treg) and CD4(+) T effector cells in patients with head and neck squamous cell carcinoma. Oncoimmunology. 2012; 1(5): 659-69.
51. Prazma C M, Tedder T F. Dendritic cell CD83: a therapeutic target or innocent bystander? Immunol Lett. 2008; 115(1):1-8.
52. Rodriguez R M, Pitzalis C, Kingsley G H, Henderson E, Humphries M J, Panayi G S. T lymphocyte adhesion to fibronectin (FN): a possible mechanism for T cell accumulation in the rheumatoid joint. Clin Exp Immunol. 1992; 89(3):439-45.
53. Shimizu Y, van Seventer G A, Horgan K J, Shaw S. Costimulation of proliferative responses of resting CD4+ T cells by the interaction of VLA-4 and VLA-5 with fibronectin or VLA-6 with laminin. J Immunol. 1990; 145(1):59-67.
54. Turner M D, Nedjai B, Hurst T, Pennington D J. Cytokines and chemokines: At the crossroads of cell signalling and inflammatory disease. Biochim Biophys Acta. 2014; 1843(11):2563-82.
55. Gibbert K, Schlaak J F, Yang D, Dittmer U. IFN-alpha subtypes: distinct biological activities in anti-viral therapy. Br J Pharmacol. 2013; 168(5):1048-58.
56. Oft M. IL-10: master switch from tumor-promoting inflammation to antitumor immunity. Cancer Immunol Res. 2014; 2(3):194-9.
57. Geijtenbeek T B, Torensma R, van Vliet S J, van Duijnhoven G C, Adema G J, van Kooyk Y, et al. Identification of DC-SIGN, a novel dendritic cell-specific ICAM-3 receptor that supports primary immune responses. Cell. 2000; 100(5):575-85.
58. Le Y, Zhou Y, Iribarren P, Wang J. Chemokines and chemokine receptors: their manifold roles in homeostasis and disease. Cell Mol Immunol. 2004; 1(2):95-104.
59. Lebre M C, Burwell T, Vieira P L, Lora J, Coyle A J, Kapsenberg M L, et al. Differential expression of inflammatory chemokines by Th1- and Th2-cell promoting dendritic cells: a role for different mature dendritic cell populations in attracting appropriate effector cells to peripheral sites of inflammation. Immunol Cell Biol. 2005; 83(5):525-35.
60. Ray P, Krishnamoorthy N, Ray A. Emerging functions of c-kit and its ligand stem cell factor in dendritic cells: regulators of T cell differentiation. Cell Cycle. 2008; 7(18):2826-32.
61. Dorak M T, Lawson T, Machulla H K, Mills K I, Burnett A K. Increased heterozygosity for MEW class II lineages in newborn males. Genes Immun. 2002; 3(5):263-9.
62. Foroni I, Couto A R, Bettencourt B F, Santos M, Lima M, Bruges-Armas J. HLA-E, HLA-F and HLA-G—The Non-Classical Side of the MHC Cluster. Chapter 3 of HLA and Associated Important Diseases, book edited by Yongzhi Xi, ISBN 978-953-51-1230-3, Published: Mar. 19, 2014 under CC BY 30 license http://dxdoiorg/105772/57507. 2014.
63. Fortin J S, Cloutier M, Thibodeau J. Exposing the Specific Roles of the Invariant Chain Isoforms in Shaping the MHC Class II Peptidome. Front Immunol. 2013; 4:443.
64. Shiina T, Hosomichi K, Inoko H, Kulski J K. The HLA genomic loci map: expression, interaction, diversity and disease. J Hum Genet. 2009; 54(1):15-39.
65. Yang J, Yi Q. Killing tumor cells through their surface beta(2)-microglobulin or major histocompatibility complex class I molecules. Cancer. 2010; 116(7):1638-45.
66. Ezinne C C, Yoshimitsu M, White Y, Arima N. HTLV-1 specific CD8+ T cell function augmented by blockade of 2B4/CD48 interaction in HTLV-1 infection. PLoS One. 2014; 9(2):e87631.
67. Ma D Y, Clark E A. The role of CD40 and CD154/CD40L in dendritic cells. Semin Immunol. 2009; 21(5): 265-72.
68. Ohnuma K, Uchiyama M, Yamochi T, Nishibashi K, Hosono O, Takahashi N, et al. Caveolin-1 triggers T-cell activation via CD26 in association with CARMA1. J Biol Chem. 2007; 282(13): 10117-31.
69. Gessani S, Conti L, Del Corno M, Belardelli F. Type I interferons as regulators of human antigen presenting cell functions. Toxins (Basel). 2014; 6(6):1696-723.
70. Hillyer P, Raviv N, Gold D M, Dougherty D, Liu J, Johnson T R, et al. Subtypes of type I IFN differentially enhance cytokine expression by suboptimally stimulated CD4(+) T cells. Eur J Immunol. 2013; 43(12):3197-208.
71. Guce A I, Mortimer S E, Yoon T, Painter C A, Jiang W, Mellins E D, et al. HLA-DO acts as a substrate mimic to inhibit HLA-DM by a competitive mechanism. Nat Struct Mol Biol. 2013; 20(1):90-8.
72. Edgecombe A D. HLA class II expression on breast cancer cells (Ph.D. Thesis). Faculty of Medicine, Memorial University of Newfoundland, Canada. URL: http://research.library.mun.ca/9160/. 2002.
73. Suri A, Jagadish N, Saini S, Gupta N. Targeting cancer testis antigens for biomarkers and immunotherapy in colorectal cancer: Current status and challenges. World J Gastrointest Oncol. 2015; 7(12):492-502.
74. Fratta E, Coral S, Covre A, Parisi G, Colizzi F, Danielli R, et al. The biology of cancer testis antigens: putative function, regulation and therapeutic potential. Mol Oncol. 2011; 5(2): 164-82.
75. Gjerstorff M F, Andersen M H, Ditzel H J. Oncogenic cancer/testis antigens: prime candidates for immunotherapy. Oncotarget. 2015; 6(18):15772-87.
76. LaVoy E C, Bollard C M, Hanley P J, Blaney J W, O'Connor D P, Bosch J A, et al. A single bout of dynamic exercise enhances the expansion of MAGE-A4 and PRAME-specific cytotoxic T-cells from healthy adults. Exerc Immunol Rev. 2015; 21:144-53.
77. Almeida L G, Sakabe N J, deOliveira A R, Silva M C, Mundstein A S, Cohen T, et al. CTdatabase: a knowledgebase of high-throughput and curated data on cancer-testis antigens. Nucleic Acids Res. 2009; 37(Database issue): D816-9.
78. Chapman K B, Prendes M J, Kidd J L, Sternberg H, West M D, Wagner J. Elevated expression of cancer/testis antigen FSIP1 in ER-positive breast tumors. Biomark Med. 2013; 7(4):601-11.
79. Dobrynin P, Matyunina E, Malov S V, Kozlov A P. The novelty of human cancer/testis antigen encoding genes in evolution. Int J Genomics. 2013; 2013:105108.

80. Lowe R, Overhoff M G, Ramagopalan S V, Garbe J C, Koh J, Stampfer M R, et al. The senescent methylome and its relationship with cancer, ageing and germline genetic variation in humans. Genome Biol. 2015; 16:194.
81. Shehata M, Teschendorff A, Sharp G, Novcic N, Russell I A, Avril S, et al. Phenotypic and functional characterisation of the luminal cell hierarchy of the mammary gland. Breast Cancer Res. 2012; 14(5):R134.
82. Marchini C, Kalogris C, Garulli C, Pietrella L, Gabrielli F, Curcio C, et al. Tailoring DNA Vaccines: Designing Strategies Against HER2-Positive Cancers. Front Oncol. 2013; 3:122.
83. Bonaccorsi I, Pezzino G, Morandi B, Ferlazzo G. Drag cells in immunity (Plasmacytoid DCs dress up as cancer cells). OncoImmunology. 2014; 3:e27897.
84. Nakayama M. Antigen Presentation by MHC-Dressed Cells. Front Immunol. 2014; 5:672.
85. Smyth L A, Harker N, Turnbull W, El-Doueik H, Klavinskis L, Kioussis D, et al. The relative efficiency of acquisition of MHC:peptide complexes and cross-presentation depends on dendritic cell type. J Immunol. 2008; 181(5):3212-20.
86. Mantegazza A R, Magalhaes J G, Amigorena S, Marks M S. Presentation of phagocytosed antigens by MHC class I and II. Traffic. 2013; 14(2):135-52.
87. Gragert L, Madbouly A, Freeman J, Maiers M. Six-locus high resolution HLA haplotype frequencies derived from mixed-resolution DNA typing for the entire US donor registry. Hum Immunol. 2013; 74(10):1313-20.
88. Sharma A, Bode B, Wenger R H, Lehmann K, Sartori A A, Moch H, et al. gamma-Radiation promotes immunological recognition of cancer cells through increased expression of cancer-testis antigens in vitro and in vivo. PLoS One. 2011; 6(11):e28217.
89. Safi S, Beckhove P, Warth A, Benner A, Roeder F, Rieken S, et al. A randomized phase II study of radiation induced immune boost in operable non-small cell lung cancer (RadImmune trial). BMC Cancer. 2015; 15:988.
90. Finkelstein S E, Salenius S, Mantz C A, Shore N D, Fernandez E B, Shulman J, et al. Combining immunotherapy and radiation for prostate cancer. Clin Genitourin Cancer. 2015; 13(1):1-9.
91. Reynders K, Illidge T, Siva S, Chang J Y, De Ruysscher D. The abscopal effect of local radiotherapy: using immunotherapy to make a rare event clinically relevant. Cancer Treat Rev. 2015; 41(6):503-10.
92. Makkouk A, Weiner G J. Cancer immunotherapy and breaking immune tolerance: new approaches to an old challenge. Cancer Res. 2015; 75(1):5-10.
93. Hongisto V, Aure M R, Makela R, Sahlberg K K. The HER2 amplicon includes several genes required for the growth and survival of HER2 positive breast cancer cells—A data description. Genom Data. 2014; 2:249-53.
94. Sahlberg K K, Hongisto V, Edgren H, Makela R, Hellstrom K, Due E U, et al. The HER2 amplicon includes several genes required for the growth and survival of HER2 positive breast cancer cells. Mol Oncol. 2013; 7(3):392-401.
95. Evans E E, Henn A D, Jonason A, Paris M J, Schiffhauer L M, Borrello M A, et al. C35 (C17orf37) is a novel tumor biomarker abundantly expressed in breast cancer. Mol Cancer Ther. 2006; 5(11):2919-30.
96. Katz E, Dubois-Marshall S, Sims A H, Faratian D, Li J, Smith E S, et al. A gene on the HER2 amplicon, C35, is an oncogene in breast cancer whose actions are prevented by inhibition of Syk. Br J Cancer. 2010; 103(3):401-10.
97. Kpetemey M, Chaudhary P, Van Treuren T, Vishwanatha J K. MIEN1 drives breast tumor cell migration by regulating cytoskeletal-focal adhesion dynamics. Oncotarget. 2016; 7(34): 54913-24.
98. Knaus A, Awaya T, Helbig I, Afawi Z, Pendziwiat M, Abu-Rachma J, et al. Rare Noncoding Mutations Extend the Mutational Spectrum in the PGAP3 Subtype of Hyperphosphatasia with Mental Retardation Syndrome. Hum Mutat. 2016; 37(8):737-44.
99. Reich M, Liefeld T, Gould J, Lerner J, Tamayo P, Mesirov J P. GenePattern 2.0. Nat Genet. 2006; 38(5): 500-1.
100. Jongeneel C V, Delorenzi M, Iseli C, Zhou D, Haudenschild C D, Khrebtukova I, et al. An atlas of human gene expression from massively parallel signature sequencing (MPSS). Genome Res. 2005; 15(7):1007-14.
101. Norrman K, Fischer Y, Bonnamy B, Wolfhagen Sand F, Ravassard P, Semb H. Quantitative comparison of constitutive promoters in human ES cells. PLoS One. 2010; 5(8):e12413.
102. Faner R, James E, Huston L, Pujol-Borrel R, Kwok W W, Juan M. Reassessing the role of HLA-DRB3 T-cell responses: evidence for significant expression and complementary antigen presentation. Eur J Immunol. 2010; 40(1):91-102.
103. Dykxhoorn D M, Wu Y, Xie H, Yu F, Lal A, Petrocca F, et al. miR-200 enhances mouse breast cancer cell colonization to form distant metastases. PLoS One. 2009; 4(9):e7181.
104. Wittig M, Anmarkrud J A, Kassens J C, Koch S, Forster M, Ellinghaus E, et al. Development of a high-resolution NGS-based HLA-typing and analysis pipeline. Nucleic Acids Res. 2015; 43(11):e70.

VI. Exemplary Embodiments

Exemplary embodiments provided in accordance with the presently disclosed subject matter include, but are not limited to, the claims and the following embodiments:

1. A modified human cancer cell comprising a recombinant polynucleotide encoding an allele of a human leukocyte antigen (HLA) class I gene.
2. The modified human cancer cell of embodiment 1, further comprising a recombinant polynucleotide encoding an allele of an HLA class II gene.
3. A modified human cancer cell comprising a recombinant polynucleotide encoding an allele of an HLA class II gene.
4. The modified human cancer cell of embodiment 3, further comprising a recombinant polynucleotide encoding an allele of an HLA class I gene.
5. The modified human cancer cell of any one of embodiments 1 to 4, wherein the recombinant polynucleotide is present on a vector in the cell.
6. The modified human cancer cell of any one of embodiments 1 to 4, wherein the recombinant polynucleotide is integrated into the genome of the cell.
7. The modified human cancer cell of any one of embodiments 1 to 6, wherein the HLA class I gene is selected from the group consisting of an HLA-A gene, an HLA-B gene, an HLA-C gene, an HLA-E gene, an HLA-F gene, an HLA-G gene, a beta-2-microglobulin (B2M) gene, and a combination thereof.
8. The modified human cancer cell of embodiment 7, wherein the allele of the HLA-A gene is an allele selected from the group consisting of HLA-A*11:01, HLA-A*01:01, HLA-A*02:01, HLA-A*03:01, HLA-A*26:01, HLA-A*29:

02, HLA-A*32:01, HLA-A*24:02, HLA-A*33:03, HLA-A*68:01, HLA-A*31:01, HLA-A*02:06, and a combination thereof.

9. The modified human cancer cell of embodiment 7, wherein the allele of the HLA-B gene is an allele selected from the group consisting of HLA-B*13:02, HLA-B*41:01, HLA-B*18:03, HLA-B*44:02, HLA-B*07:02, HLA-B*35:01, HLA-B*40:01, HLA-B*35:08, HLA-B*55:01, HLA-B*51:01, HLA-B*44:03, HLA-B*58:01, HLA-B*08:01, HLA-B*18:01, HLA-B*15:01, HLA-B*52:01, and a combination thereof.

10. The modified human cancer cell of embodiment 7, wherein the allele of the HLA-C gene is an allele selected from the group consisting of HLA-C*04:01, HLA-C*07:02, HLA-C*07:01, HLA-C*06:02, HLA-C*03:04, HLA-C*01:02, HLA-C*02:02, HLA-C*08:02, HLA-C*15:02, HLA-C*03:03, HLA-C*05:01, HLA-C*08:01, HLA-C*16:01, HLA-C*12:03, HLA-C*14:02, and a combination thereof.

11. The modified human cancer cell of any one of embodiments 2 to 10, wherein the HLA class II gene is selected from the group consisting of an HLA class II alpha subunit gene, an HLA class II beta subunit gene, and a combination thereof.

12. The modified human cancer cell of any one of embodiments 2 to 10, wherein the HLA class II gene is selected from the group consisting of an HLA-DP gene, an HLA-DM gene, an HLA-DOA gene, an HLA-DOB gene, an HLA-DQ gene, an HLA-DR gene, and a combination thereof.

13. The modified human cancer cell of embodiment 12, wherein the HLA-DM gene is selected from the group consisting of an HLA-DMA gene, an HLA-DMB gene, and a combination thereof.

14. The modified human cancer cell of embodiment 12, wherein the HLA-DR gene is selected from the group consisting of an HLA-DRA gene, an HLA-DRB1 gene, an HLA-DRB3 gene, an HLA-DRB4 gene, an HLA-DRB5 gene, and a combination thereof.

15. The modified human cancer cell of embodiment 14, wherein the allele of the HLA-DRB3 gene is an allele selected from the group consisting of HLA-DRB3*02:02, HLA-DRB3*01:01, HLA-DRB3*03:01, and a combination thereof.

16. The modified human cancer cell of any one of embodiments 2 to 15, wherein the allele of the HLA class I gene is HLA-A*11:01 or HLA-A*24:02 and the allele of the HLA class II gene is HLA-DRB3*02:02 or HLA-DRB3*01:01.

17. The modified human cancer cell of any one of embodiments 1 to 16, further comprising a recombinant polynucleotide encoding granulocyte-macrophage colony-stimulating factor (GM-CSF).

18. The modified human cancer cell of any one of embodiments 1 to 17, further comprising a recombinant polynucleotide encoding interferon alpha (IFNa).

19. The modified human cancer cell of any one of embodiments 1 to 18, further comprising a recombinant polynucleotide encoding adenosine deaminase (ADA), adhesion G protein-coupled receptor E5 (ADGRE5), caveolin 1 (CAV1), CD58 molecule (CD58), CD74 molecule (CD74), CD83 molecule (CD83), C-X-C motif chemokine ligand 8 (CXCL8), C-X-C motif chemokine ligand 16 (CXCL16), intracellular adhesion molecule 3 (ICAM3), interleukin 6 (IL6), interleukin 10 (IL10), interleukin 15 (IL15), interleukin 18 (IL18), KIT ligand (KITLG), tumor necrosis factor superfamily member 14 (TNFSF14), preferentially expressed antigen in melanoma (PRAME), PDZ binding kinase (PBK), centrosomal protein 55 (CEP55), kinesin family member 2C (KIF2C), placenta-specific protein 1 (PLAC1), Opa interacting protein 5 (OIP5), calcium binding tyrosine phosphorylation regulated (CABYR), sperm-associated antigen 1 (SPAG1), or a combination thereof.

20. The modified human cancer cell of any one of embodiments 1 to 19, wherein the human cancer cell is a human cancer cell line.

21. The modified human cancer cell of embodiment 20, wherein the human cancer cell line is an SV-BR-1 breast cancer cell line.

22. A method for selecting a whole-cell cancer vaccine for a subject having cancer, the method comprising:
(a) detecting the presence or absence of one or more alleles of one or more human leukocyte antigen (HLA) genes in a sample obtained from the subject to generate an HLA allele profile of the subject;
(b) comparing the HLA allele profile of the subject to an HLA allele profile of the whole-cell cancer vaccine based on the presence or absence of the one or more alleles of one or more of the HLA genes in the whole-cell cancer vaccine; and
(c) selecting the whole-cell cancer vaccine for the subject when the HLA allele profile of the subject matches the HLA allele profile of the whole-cell cancer vaccine.

23. The method of embodiment 22, wherein the one or more HLA genes comprise an HLA class I gene, an HLA class II gene, or a combination thereof.

24. The method of embodiment 23, wherein the HLA class I gene is selected from the group consisting of an HLA-A gene, an HLA-B gene, an HLA-C gene, an HLA-E gene, an HLA-F gene, an HLA-G gene, a beta-2-microglobulin (B2M) gene, and a combination thereof.

25. The method of embodiment 24, wherein the allele of the HLA-A gene is an allele selected from the group consisting of HLA-A*11:01, HLA-A*01:01, HLA-A*02:01, HLA-A*03:01, HLA-A*26:01, HLA-A*29:02, HLA-A*32:01, HLA-A*24:02, HLA-A*33:03, HLA-A*68:01, HLA-A*31:01, HLA-A*02:06, and a combination thereof.

26. The method of embodiment 24, wherein the allele of the HLA-B gene is an allele selected from the group consisting of HLA-B*13:02, HLA-B*41:01, HLA-B*18:03, HLA-B*44:02, HLA-B*07:02, HLA-B*35:01, HLA-B*40:01, HLA-B*35:08, HLA-B*55:01, HLA-B*51:01, HLA-B*44:03, HLA-B*58:01, HLA-B*08:01, HLA-B*18:01, HLA-B*15:01, HLA-B*52:01, and a combination thereof.

27. The method of embodiment 24, wherein the allele of the HLA-C gene is an allele selected from the group consisting of HLA-C*04:01, HLA-C*07:02, HLA-C*07:01, HLA-C*06:02, HLA-C*03:04, HLA-C*01:02, HLA-C*02:02, HLA-C*08:02, HLA-C*15:02, HLA-C*03:03, HLA-C*05:01, HLA-C*08:01, HLA-C*16:01, HLA-C*12:03, HLA-C*14:02, and a combination thereof.

28. The method of embodiment 23, wherein the HLA class II gene is selected from the group consisting of an HLA class II alpha subunit gene, an HLA class II beta subunit gene, and a combination thereof.

29. The method of embodiment 23, wherein the HLA class II gene is selected from the group consisting of an HLA-DP gene, an HLA-DM gene, an HLA-DOA gene, an HLA-DOB gene, an HLA-DQ gene, an HLA-DR gene, and a combination thereof.

30. The method of embodiment 29, wherein the HLA-DM gene is selected from the group consisting of an HLA-DMA gene, an HLA-DMB gene, and a combination thereof.

31. The method of embodiment 29, wherein the HLA-DR gene is selected from the group consisting of an HLA-DRA gene, an HLA-DRB1 gene, an HLA-DRB3 gene, an HLA-DRB4 gene, an HLA-DRB5 gene, and a combination thereof.

32. The method of embodiment 31, wherein the allele of the HLA-DRB3 gene is an allele selected from the group consisting of HLA-DRB3*02:02, HLA-DRB3*01:01, HLA-DRB3*03:01, and a combination thereof.

33. The method of any one of embodiments 23 to 32, wherein the allele of the HLA class I gene is HLA-A*11:01 or HLA-A*24:02 and the allele of the HLA class II gene is HLA-DRB3*02:02 or HLA-DRB3*01:01.

34. The method of any one of embodiments 22 to 33, wherein the whole-cell cancer vaccine is selected for the subject when one or more alleles in the HLA allele profile of the subject match the HLA allele profile of the whole-cell cancer vaccine.

35. The method of embodiment 34, wherein the whole-cell cancer vaccine is selected for the subject when two or more alleles in the HLA allele profile of the subject match the HLA allele profile of the whole-cell cancer vaccine.

36. A method for selecting a whole-cell cancer vaccine for a subject having cancer, the method comprising:
(a)(i) detecting the presence or level of one or more biomarkers in a sample obtained from the subject; and/or
(a)(ii) measuring the level of activity and/or number of one or more immune cells obtained from the subject;
(b) comparing the presence or level of the one or more biomarkers detected in step (a)(i) and/or the level of activity and/or number of the one or more immune cells measured in step (a)(ii) to the presence or level of the one or more biomarkers and/or the level of activity and/or number of one or more immune cells in a control sample; and
(c) selecting the whole-cell cancer vaccine for the subject based on the comparison in step (b), wherein the whole-cell cancer vaccine is derived from a breast cancer cell line or a breast cancer cell.

37. The method of embodiment 36, wherein the breast cancer cell line is an SV-BR-1 breast cancer cell line.

38. The method of embodiment 36 or 37, wherein the one or more biomarkers is selected from the group consisting of preferentially expressed antigen in melanoma (PRAME), PDZ binding kinase (PBK), centrosomal protein 55 (CEP55), kinesin family member 2C (KIF2C), placenta-specific protein 1 (PLAC1), Opa interacting protein 5 (OIP5), calcium binding tyrosine phosphorylation regulated (CABYR), sperm-associated antigen 1 (SPAG1), alpha-1,3-glucosyltransferase (ALG8), actin-related protein 2/3 complex, subunit 5-like (ARPC5L), chromobox homolog 2 (CBX2), collagen type VIII alpha 1 chain (COL8A1), DDB1 and CUL4 associated factor 10, (DCAF10), eukaryotic translation initiation factor 3 subunit H (EIF3H), erb-b2 receptor tyrosine kinase 2 (ERBB2), histone cluster 1 H4 family member h (HIST1H4H), insulin like growth factor binding protein 5 (IGFBP5), integrator complex subunit 7 (INTS7), keratin 19 (KRT19), keratin 81 (KRT81), mannosyl (alpha-1,3-)-glycoprotein beta-1,4-N-acetylglucosaminyltransferase, isozyme A (MGAT4A), migration and invasion enhancer 1 (MIEN1), post-GPI attachment to proteins 3 (PGAP3), remodeling and spacing factor 1 (RSF1), SH2 domain containing adaptor protein B (SHB), soluble carrier family 35, member A2 (SLC35A2), spectrin repeat containing nuclear envelope family member 4 (SYNE4), transportin 1 (TNPO1), and a combination thereof.

39. The method of any one of embodiments 36 to 38, wherein the one or more biomarkers is selected from the group consisting of PRAME, PBK, CEP55, KIF2C, ERBB2, MIEN1, PGAP3, and a combination thereof.

40. The method of embodiment 39, wherein the one or more biomarkers is PRAME.

41. The method of embodiment 39, wherein the one or more biomarkers is selected from the group consisting of ERBB2, MIEN1, PGAP3, and a combination thereof.

42. The method of any one of embodiments 36 to 41, wherein the vaccine is selected for the subject when the level of at least one of the one or more biomarkers is overexpressed in the sample obtained from the subject compared to the control sample, wherein the control sample comprises a normal cell or tissue obtained from the subject, from a different subject, or from a population of subjects.

43. The method of embodiment 42, wherein the vaccine is selected for the subject when the level of at least one of the one or more biomarkers is overexpressed at least about 1.5-fold compared to the control sample.

44. The method of any one of embodiments 36 to 43, wherein the vaccine is selected for the subject when the level of activity and/or number of the one or more immune cells obtained from the subject is higher compared to the control sample, wherein the control sample comprises one or more immune cells obtained from a different subject or population of subjects who do not have cancer.

45. The method of embodiment 44, wherein the level of activity and/or number of the one or more immune cells obtained from the subject is at least about 1.5-fold higher compared to the control sample.

46. The method of any one of embodiments 36 to 45, wherein the one or more immune cells in which the level of activity and/or number is measured is selected from the group consisting of a peripheral blood mononuclear cell (PBMC), a lymphocyte, a monocyte, a natural killer (NK) cell, a dendritic cell, a macrophage, a myeloid-derived suppressor cell (MDSC), and a combination thereof.

47. The method of embodiment 46, wherein the one or more immune cells in which the level of activity and/or number is measured is selected from the group consisting of a PBMC, a lymphocyte, a dendritic cell, and a combination thereof.

48. The method of any one of embodiments 36 to 47, wherein the presence or level of the one or more biomarkers is detected using a method selected from the group consisting of an ELISA, a multiplex assay, measuring the RNA transcript level of a gene encoding an antigen, immunohistochemistry, a Western blot, a bead-based method, and a combination thereof.

49. The method of any one of embodiments 36 to 48, wherein the level of activity and/or number of the one or more immune cells is measured using a method selected from the group consisting of an ELISA, an ELISPOT assay, a Western blot, a cytotoxic T lymphocyte (CTL) activity assay, a cytotoxicity assay, a proliferation assay, a cytokine production assay, an MEW multimer assay, a flow cytometry assay, and a combination thereof.

50. The method of any one of embodiments 36 to 49, wherein the level of activity and/or number of the one or more immune cells is measured following stimulation with an antigen.

51. The method of any one of embodiments 36 to 50, wherein the one or more biomarkers comprise one or more alleles of one or more human leukocyte antigen (HLA) genes.

52. The method of embodiment 51, wherein the one or more HLA genes comprise an HLA class I gene, an HLA class II gene, or a combination thereof.

53. The method of embodiment 52, wherein the HLA class I gene is selected from the group consisting of an HLA-A gene, an HLA-B gene, an HLA-C gene, an HLA-E gene, an HLA-F gene, an HLA-G gene, a beta-2-microglobulin (B2M) gene, and a combination thereof.

54. The method of embodiment 53, wherein the allele of the HLA-A gene is an allele selected from the group consisting of HLA-A*11:01, HLA-A*01:01, HLA-A*02:01, HLA-A*03:01, HLA-A*26:01, HLA-A*29:02, HLA-A*32:01, HLA-A*24:02, HLA-A*33:03, HLA-A*68:01, HLA-A*31:01, HLA-A*02:06, and a combination thereof.

55. The method of embodiment 53, wherein the allele of the HLA-B gene is an allele selected from the group consisting of HLA-B*13:02, HLA-B*41:01, HLA-B*18:03, HLA-B*44:02, HLA-B*07:02, HLA-B*35:01, HLA-B*40:01, HLA-B*35:08, HLA-B*55:01, HLA-B*51:01, HLA-B*44:03, HLA-B*58:01, HLA-B*08:01, HLA-B*18:01, HLA-B*15:01, HLA-B*52:01, and a combination thereof.

56. The method of embodiment 53, wherein the allele of the HLA-C gene is an allele selected from the group consisting of HLA-C*04:01, HLA-C*07:02, HLA-C*07:01, HLA-C*06:02, HLA-C*03:04, HLA-C*01:02, HLA-C*02:02, HLA-C*08:02, HLA-C*15:02, HLA-C*03:03, HLA-C*05:01, HLA-C*08:01, HLA-C*16:01, HLA-C*12:03, HLA-C*14:02, and a combination thereof.

57. The method of embodiment 52, wherein the HLA class II gene is selected from the group consisting of an HLA class II alpha subunit gene, an HLA class II beta subunit gene, and a combination thereof.

58. The method of embodiment 52, wherein the HLA class II gene is selected from the group consisting of an HLA-DP gene, an HLA-DM gene, an HLA-DOA gene, an HLA-DOB gene, an HLA-DQ gene, an HLA-DR gene, and a combination thereof.

59. The method of embodiment 58, wherein the HLA-DM gene is selected from the group consisting of an HLA-DMA gene, an HLA-DMB gene, and a combination thereof.

60. The method of embodiment 58, wherein the HLA-DR gene is selected from the group consisting of an HLA-DRA gene, an HLA-DRB1 gene, an HLA-DRB3 gene, an HLA-DRB4 gene, an HLA-DRB5 gene, and a combination thereof.

61. The method of embodiment 60, wherein the allele of the HLA-DRB3 gene is an allele selected from the group consisting of HLA-DRB3*02:02, HLA-DRB3*01:01, HLA-DRB3*03:01, and a combination thereof.

62. The method of any one of embodiments 52 to 61, wherein the allele of the HLA class I gene is HLA-A*11:01 or HLA-A*24:02 and the allele of the HLA class II gene is HLA-DRB3*02:02 or HLA-DRB3*01:01.

63. The method of any one of embodiments 51 to 62, wherein the vaccine is selected for the subject when one or more alleles of one or more human leukocyte antigen (HLA) genes in the sample obtained from the subject match one or more alleles of one or more human leukocyte antigen (HLA) genes in the vaccine.

64. The method of any one of embodiments 36 to 63, wherein the sample obtained from the subject is a whole blood sample, a plasma sample, a serum sample, a buccal swab sample, a tumor tissue sample, a biofluid sample, a pleural effusion sample, a urine sample, a hair sample, a skin sample, or a combination thereof.

65. The method of any one of embodiments 36 to 64, wherein the sample is obtained from a biopsy, from a surgical resection, as a fine needle aspirate (FNA), or a combination thereof.

66. The method of any one of embodiments 36 to 65, wherein the sample comprises tumor tissue, a tumor cell, a circulating tumor cell (CTC), or a combination thereof.

67. A composition comprising a modified human cancer cell comprising a recombinant polynucleotide encoding an allele of a human leukocyte antigen (HLA) class I gene.

68. The composition of embodiment 67, wherein the modified human cancer cell further comprises a recombinant polynucleotide encoding an allele of an HLA class II gene.

69. A composition comprising a modified human cancer cell comprising a recombinant polynucleotide encoding an allele of an HLA class II gene.

70. The composition of embodiment 69, wherein the modified human cancer cell further comprises a recombinant polynucleotide encoding an allele of an HLA class I gene.

71. The composition of any one of embodiments 67 to 70, wherein the recombinant polynucleotide is present on a vector in the cell.

72. The composition of any one of embodiments 67 to 70, wherein the recombinant polynucleotide is integrated into the genome of the cell.

73. The composition of any one of embodiments 67 to 72, wherein the HLA class I gene is selected from the group consisting of an HLA-A gene, an HLA-B gene, an HLA-C gene, an HLA-E gene, an HLA-F gene, an HLA-G gene, a beta-2-microglobulin (B2M) gene, and a combination thereof.

74. The composition of embodiment 73, wherein the allele of the HLA-A*11:01, HLA-A*01:01, HLA-A*02:01, HLA-A*03:01, HLA-A*26:01, HLA-A*29:02, HLA-A*32:01, HLA-A*24:02, HLA-A*33:03, HLA-A*68:01, HLA-A*31:01, HLA-A*02:06, and a combination thereof.

75. The composition of embodiment 73, wherein the allele of the HLA-B gene is an allele selected from the group consisting of HLA-B*13:02, HLA-B*41:01, HLA-B*18:03, HLA-B*44:02, HLA-B*07:02, HLA-B*35:01, HLA-B*40:01, HLA-B*35:08, HLA-B*55:01, HLA-B*51:01, HLA-B*44:03, HLA-B*58:01, HLA-B*08:01, HLA-B*18:01, HLA-B*15:01, HLA-B*52:01, and a combination thereof.

76. The composition of embodiment 73, wherein the allele of the HLA-C gene is an allele selected from the group consisting of HLA-C*04:01, HLA-C*07:02, HLA-C*07:01, HLA-C*06:02, HLA-C*03:04, HLA-C*01:02, HLA-C*02:02, HLA-C*08:02, HLA-C*15:02, HLA-C*03:03, HLA-C*05:01, HLA-C*08:01, HLA-C*16:01, HLA-C*12:03, HLA-C*14:02, and a combination thereof.

77. The composition of any one of embodiments 68 to 76, wherein the HLA class II gene is selected from the group consisting of an HLA class II alpha subunit gene, an HLA class II beta subunit gene, and a combination thereof.

78. The composition of any one of embodiments 68 to 76, wherein the HLA class II gene is selected from the group consisting of an HLA-DP gene, an HLA-DM gene, an HLA-DOA gene, an HLA-DOB gene, an HLA-DQ gene, an HLA-DR gene, and a combination thereof.

79. The composition of embodiment 78, wherein the HLA-DM gene is selected from the group consisting of an HLA-DMA gene, an HLA-DMB gene, and a combination thereof.

80. The composition of embodiment 78, wherein the HLA-DR gene is selected from the group consisting of an HLA-DRA gene, an HLA-DRB1 gene, an HLA-DRB3 gene, an HLA-DRB4 gene, an HLA-DRB5 gene, and a combination thereof.

81. The composition of embodiment 80, wherein the allele of the HLA-DRB3 gene is an allele selected from the group consisting of HLA-DRB3*02:02, HLA-DRB3*01:01, HLA-DRB3*03:01, and a combination thereof.

82. The composition of any one of embodiments 68 to 81, wherein the allele of the HLA class I gene is HLA-A*11:01 or HLA-A*24:02 and the allele of the HLA class II gene is HLA-DRB3*02:02 or HLA-DRB3*01:01.

83. The composition of any one of embodiments 67 to 82, wherein the modified human cancer cell further comprises a recombinant polynucleotide encoding adenosine deaminase (ADA), adhesion G protein-coupled receptor E5 (ADGRE5), caveolin 1 (CAV1), CD58 molecule (CD58), CD74 molecule (CD74), CD83 molecule (CD83), C-X-C motif chemokine ligand 8 (CXCL8), C-X-C motif chemokine ligand 16 (CXCL16), intracellular adhesion molecule 3 (ICAM3), interleukin 6 (IL6), interleukin 10 (IL10), interleukin 15 (IL15), interleukin 18 (IL18), KIT ligand (KITLG), tumor necrosis factor superfamily member 14 (TNFSF14), or a combination thereof.

84. The composition of any one of embodiments 67 to 83, further comprising granulocyte-macrophage colony-stimulating factor (GM-CSF).

85. The composition of embodiment 84, wherein the GM-CSF is encoded by a recombinant polynucleotide and expressed by a modified cell.

86. The composition of embodiment 85, wherein the GM-CSF is expressed by the same modified cell that comprises the recombinant polynucleotide encoding an allele of a human leukocyte antigen (HLA) class I and/or class II gene.

87. The composition of embodiment 85, wherein the GM-CSF is not expressed by the same modified cell that comprises the recombinant polynucleotide encoding an allele of a human leukocyte antigen (HLA) class I and/or class II gene.

88. The composition of embodiment 84, wherein the GM-CSF is present in a soluble form.

89. The composition of any one of embodiments 67 to 88, further comprising interferon alpha (IFNa).

90. The composition of embodiment 89, wherein the IFNa is expressed by the same modified cell that comprises the recombinant polynucleotide encoding an allele of a human leukocyte antigen (HLA) class I and/or class II gene.

91. The composition of embodiment 89, wherein the IFNa is present in a soluble form.

92. The composition of any one of embodiments 67 to 91, wherein the human cancer cell is a human cancer cell line.

93. The composition of embodiment 92, wherein the human cancer cell line is an SV-BR-1 breast cancer cell line.

94. A pharmaceutical composition comprising the composition of any one of embodiments 67 to 93 and a pharmaceutically acceptable carrier.

95. A method for treating cancer in a subject, the method comprising administering to the subject a therapeutically effective amount of the pharmaceutical composition of embodiment 94.

96. The method of embodiment 95, further comprising treating the subject with a therapy selected from the group consisting of chemotherapy, immunotherapy, radiotherapy, hormone therapy, a differentiating agent, a small-molecule drug, and a combination thereof.

97. The method of embodiment 96, wherein the immunotherapy comprises an agent selected from the group consisting of an immune checkpoint inhibitor, a monoclonal antibody, a small-molecule drug, and a combination thereof.

98. The method of embodiment 96, wherein the chemotherapy comprises an agent selected from the group consisting of an alkylating agent, an antimetabolite, an antitumor antibiotic, a topoisomerase inhibitor, a mitotic inhibitor, a corticosteroid, and a combination thereof.

99. The method of any one of embodiments 95 to 98, further comprising selecting a whole-cell cancer vaccine for the subject according to the method of any one of embodiments 22 to 66.

100. The method of any one of embodiments 95 to 99, wherein the subject has stage I, stage II, stage III, or stage IV cancer.

101. The method of any one of embodiments 95 to 100, wherein the cancer is selected from the group consisting of breast cancer, ovarian cancer, cervical cancer, prostate cancer, pancreatic cancer, colorectal cancer, gastric cancer, lung cancer, skin cancer, liver cancer, brain cancer, eye cancer, soft tissue cancer, renal cancer, bladder cancer, head and neck cancer, mesothelioma, acute leukemia, chronic leukemia, medulloblastoma, multiple myeloma, sarcoma, and a combination thereof.

102. The method of any one of embodiments 95 to 101, wherein the pharmaceutical composition is administered by injection.

103. The method of 102, wherein the injection is an intradermal and/or intralymphatic injection.

104. The method of any one of embodiments 95 to 103, wherein treating the subject produces a decrease in tumor volume.

105. The method of any one of embodiments 95 to 104, wherein treating the subject ameliorates or eliminates one or more signs or symptoms of cancer.

106. The method of any one of embodiments 95 to 105, wherein treating the subject results in an increase in the activity and/or number of one or more immune cells.

107. The method of embodiment 106, wherein the one or immune cells in which the level of activity and/or number is increased is selected from the group consisting of a peripheral blood mononuclear cell (PBMC), a lymphocyte, a monocyte, a natural killer (NK) cell, a dendritic cell, a macrophage, a myeloid-derived suppressor cell (MDSC), and a combination thereof.

108. The method of embodiment 107, wherein the one or more immune cells in which the level of activity and/or number is increased is selected from the group consisting of a PBMC, a lymphocyte, a dendritic cell, and a combination thereof.

109. The method of any one of embodiments 106 to 108, wherein the level of activity and/or number of the one or more immune cells is measured using a method selected from the group consisting of an ELISA, an ELISPOT assay, a Western blot, a cytotoxic T lymphocyte (CTL) activity assay, a cytotoxicity assay, a proliferation assay, a cytokine production assay, an MEW multimer assay, a flow cytometry assay, and a combination thereof.

110. The method of any one of embodiments 106 to 109, wherein the level of activity and/or number of the one or more immune cells is measured following stimulation with an antigen.

111. The method of any one of embodiments 106 to 110, wherein an increase in immune cell activity and/or number indicates that the subject should be administered one or more additional doses of the pharmaceutical composition.

112. The method of any one of embodiments 95 to 111, wherein treating the subject results in an increased survival time.

113. A kit for treating a subject with cancer comprising the pharmaceutical composition of embodiment 94.

114. The kit of embodiment 113, further comprising instructions for use.

115. The kit of embodiment 113 or 114, further comprising one or more reagents.

116. The kit of embodiment 115, wherein the one or more reagents are for isolating a sample from the subject having cancer, detecting the presence or absence of one or more alleles of one or more human leukocyte antigen (HLA)

genes, detecting the presence or level of one or more biomarkers, and/or measuring the activity and/or number of one or more immune cells.

117. A method for determining the HER2 status of a sample cell, the method comprising:
(a) detecting the presence or level of one or more biomarkers in the sample cell, wherein the one or more biomarkers comprise:
    (i) MIEN1,
    (ii) PGAP3,
    (iii) ERBB2 and MIEN1,
    (iv) ERBB2 and PGAP3,
    (v) MIEN1 and PGAP3, or
    (vi) ERBB2, MIEN1, and PGAP3;
(b) comparing the presence or level of the one or more biomarkers detected in step (a) to the presence or level of the one or more biomarkers in a reference cell; and
(c) determining the HER2 status of the sample cell based upon the comparison performed in step (b).

118. The method of embodiment 117, wherein the sample cell is a cancer cell or is a cell obtained from a subject who has cancer.

119. The method of embodiment 117 or 118, wherein the sample cell is determined to be HER2 positive when the one or more biomarkers is expressed at a higher level in the sample cell compared to the reference cell.

120. The method of embodiment 119, wherein the reference cell is a non-cancer cell obtained from the same subject as the sample cell or is a non-cancer cell obtained from a different subject or population of subjects.

121. The method of any one of embodiments 117 to 120, wherein the level of the one or more biomarkers is higher in a HER2 3+ cell than in a HER2 2+ cell.

122. The method of any one of embodiments 117 to 121, wherein the level of the one or more biomarkers is higher in a HER2 2+ cell than in a HER2 1+ or a HER2 0 cell.

123. The method of any one of embodiments 117 to 122, wherein detecting the presence or level of the one or more biomarkers comprises measuring mRNA expression, protein abundance, or a combination thereof.

124. The method of any one of embodiments 117 to 123, wherein the determination is made with a sensitivity of at least about 60%.

125. The method of embodiment 124, wherein the determination is made with a sensitivity of at least about 87%.

126. The method of embodiment 125, wherein the determination is made with a sensitivity of at least about 100%.

127. The method of any one of embodiments 117 to 126, wherein the steps of (a), (b), and/or (c) are automated.

```
INFORMAL SEQUENCE LISTING

HLA-A*02:01 ORF before optimization (1098 bp) (SEQ ID NO: 1)
Sequence as represented by GenBank (NCBI) accession number
AY365426.1.
ATGGCCGTCATGGCGCCCCGAACCCTCGTCCTGCTACTCTCGGGGGCTCTGGCCCTGACCCA

GACCTGGGCGGGCTCTCACTCCATGAGGTATTTCTTCACATCCGTGTCCCGGCCCGGCCGCG

GGGAGCCCCGCTTCATCGCAGTGGGCTACGTGGACGACACGCAGTTCGTGCGGTTCGACAGC

GACGCCGCGAGCCAGAGGATGGAGCCGCGGGCGCCGTGGATAGAGCAGGAGGGTCCGGAGTA

TTGGGACGGGGAGACACGGAAAGTGAAGGCCCACTCACAGACTCACCGAGTGGACCTGGGGA

CCCTGCGCGGCTACTACAACCAGAGCGAGGCCGGTTCTCACACCGTCCAGAGGATGTATGGC

TGCGACGTGGGGTCGGACTGGCGCTTCCTCCGCGGGTACCACCAGTACGCCTACGACGGCAA

GGATTACATCGCCCTGAAAGAGGACCTGCGCTCTTGGACCGCGGCGGACATGGCAGCTCAGA

CCACCAAGCACAAGTGGGAGGCGGCCCATGTGGCGGAGCAGTTGAGAGCCTACCTGGAGGGC

ACGTGCGTGGAGTGGCTCCGCAGATACCTGGAGAACGGGAAGGAGACGCTGCAGCGCACGGA

CGCCCCCAAAACGCATATGACTCACCACGCTGTCTCTGACCATGAAGCCACCCTGAGGTGCT

GGGCCCTGAGCTTCTACCCTGCGGAGATCACACTGACCTGGCAGCGGGATGGGGAGGACCAG

ACCCAGGACACGGAGCTCGTGGAGACCAGGCCTGCAGGGGATGGAACCTTCCAGAAGTGGGC

GGCTGTGGTGGTGCCTTCTGGACAGGAGCAGAGATACACCTGCCATGTGCAGCATGAGGGTT

TGCCCAAGCCCCTCACCCTGAGATGGGAGCCGTCTTCCCAGCCCACCATCCCCATCGTGGGC

ATCATTGCTGGCCTGGTTCTCTTTGGAGCTGTGATCACTGGAGCTGTGGTCGCTGCTGTGAT

GTGGAGGAGGAAGAGCTCAGATAGAAAAGGAGGGAGCTACTCTCAGGCTGCAAGCAGTGACA

GTGCCCAGGGCTCTGATGTGTCTCTCACAGCTTGTAAAGTGTGA

HLA-A*02:01 ORF after optimization (1098 bp) (SEQ ID NO: 2)
ATGGCTGTTATGGCCCCTAGAACACTGGTGCTGCTGCTGTCTGGTGCCCTGGCTCTGACACA

AACATGGGCCGGCAGCCACAGCATGCGGTACTTTTTCACCAGCGTGTCCAGACCTGGCAGAG

GCGAGCCTAGATTCATTGCCGTGGGCTACGTGGACGACACCCAGTTCGTCAGATTCGATTCC

GATGCCGCCAGCCAGCGGATGGAACCTAGAGCACCTTGGATCGAGCAAGAGGGCCCCGAGTA
```

-continued

INFORMAL SEQUENCE LISTING

TTGGGACGGCGAGACAAGAAAAGTGAAGGCCCACAGCCAGACACACAGAGTGGATCTGGGAA

CCCTGCGGGGCTACTACAATCAGTCTGAGGCCGGCTCTCACACCGTGCAGAGGATGTATGGC

TGTGACGTGGGCAGCGATTGGCGGTTCCTGAGAGGCTATCACCAGTACGCCTACGACGGCAA

GGACTATATCGCCCTGAAAGAGGACCTGCGGTCTTGGACAGCCGCCGATATGGCTGCCCAGA

CCACAAAGCACAAGTGGGAAGCCGCTCACGTGGCCGAACAGCTGAGAGCTTATCTGGAAGGC

ACCTGTGTGGAATGGCTGCGGAGATACCTGGAAAACGGCAAAGAGACACTGCAGCGGACAGA

CGCCCCTAAGACACACATGACACACCACGCCGTGTCCGACCACGAAGCCACACTTAGATGTT

GGGCCCTGAGCTTCTACCCCGCCGAGATCACACTGACATGGCAGAGAGATGGCGAGGATCAG

ACCCAGGATACCGAGCTGGTGGAAACAAGACCTGCCGGCGACGGCACCTTCCAGAAATGGGC

TGCTGTGGTGGTGCCTAGCGGCCAAGAGCAGAGATACACCTGTCACGTGCAGCACGAGGGCC

TGCCTAAGCCTCTTACACTGAGATGGGAGCCCAGCAGCCAGCCTACAATCCCCATCGTGGGA

ATCATTGCCGGCCTGGTGCTGTTTGGCGCCGTGATTACAGGTGCAGTGGTGGCCGCTGTTAT

GTGGCGGAGAAAGAGCAGCGACAGAAAAGGCGGCAGCTACTCTCAGGCCGCCAGCTCTGATT

CTGCCCAGGGCTCTGATGTGTCTCTGACCGCCTGCAAAGTGTGA

Sequence of pcDNA3.4-A0201 (7126 bp) (SEQ ID NO. 3)
Optimized HLA-A*02:01 sequence in pcDNA3.4-TOPO. 5'-BamHI
restriction site (GGATCC), start codon (ATG), stop codon
(TGA), and 3'-ClaI restriction site (ATCGAT) are
underlined. Also underlined is the single PvuI restriction
site (CGATCG), useful for linearization of the plasmid prior
to stable transfection.
GTTAGGCGTTTTGCGCTGCTTCGCGATGTACGGGCCAGATATACGCGTTGACATTGATTATT

GACTAGTTATTAATAGTAATCAATTACGGGGTCATTAGTTCATAGCCCATATATGGAGTTCC

GCGTTACATAACTTACGGTAAATGGCCCGCCTGGCTGACCGCCCAACGACCCCCGCCCATTG

ACGTCAATAATGACGTATGTTCCCATAGTAACGCCAATAGGGACTTTCCATTGACGTCAATG

GGTGGAGTATTTACGGTAAACTGCCCACTTGGCAGTACATCAAGTGTATCATATGCCAAGTA

CGCCCCCTATTGACGTCAATGACGGTAAATGGCCCGCCTGGCATTATGCCCAGTACATGACC

TTATGGGACTTTCCTACTTGGCAGTACATCTACGTATTAGTCATCGCTATTACCATGGTGAT

GCGGTTTTGGCAGTACATCAATGGGCGTGGATAGCGGTTTGACTCACGGGGATTTCCAAGTC

TCCACCCCATTGACGTCAATGGGAGTTTGTTTTGGCACCAAAATCAACGGGACTTTCCAAAA

TGTCGTAACAACTCCGCCCCATTGACGCAAATGGGCGGTAGGCGTGTACGGTGGGAGGTCTA

TATAAGCAGAGCTCGTTTAGTGAACCGTCAGATCGCCTGGAGACGCCATCCACGCTGTTTTG

ACCTCCATAGAAGACACCGGGACCGATCCAGCCTCCGGACTCTAGAGGATCGAACCCTT<u>GGA

TCCGCCACCATG</u>GCTGTTATGGCCCCTAGAACACTGGTGCTGCTGCTGTCTGGTGCCCTGGC

TCTGACACAAACATGGGCCGGCAGCCACAGCATGCGGTACTTTTTCACCAGCGTGTCCAGAC

CTGGCAGAGGCGAGCCTAGATTCATTGCCGTGGGCTACGTGGACGACACCCAGTTCGTCAGA

TTCGATTCCGATGCCGCCAGCCAGCGGATGGAACCTAGAGCACCTTGGATCGAGCAAGAGGG

CCCCGAGTATTGGGACGGCGAGACAAGAAAAGTGAAGGCCCACAGCCAGACACACAGAGTGG

ATCTGGGAACCCTGCGGGGCTACTACAATCAGTCTGAGGCCGGCTCTCACACCGTGCAGAGG

ATGTATGGCTGTGACGTGGGCAGCGATTGGCGGTTCCTGAGAGGCTATCACCAGTACGCCTA

CGACGGCAAGGACTATATCGCCCTGAAAGAGGACCTGCGGTCTTGGACAGCCGCCGATATGG

CTGCCCAGACCACAAAGCACAAGTGGGAAGCCGCTCACGTGGCCGAACAGCTGAGAGCTTAT

INFORMAL SEQUENCE LISTING

CTGGAAGGCACCTGTGTGGAATGGCTGCGGAGATACCTGGAAAACGGCAAAGAGACACTGCA

GCGGACAGACGCCCCTAAGACACACATGACACACCACGCCGTGTCCGACCACGAAGCCACAC

TTAGATGTTGGGCCCTGAGCTTCTACCCCGCCGAGATCACACTGACATGGCAGAGAGATGGC

GAGGATCAGACCCAGGATACCGAGCTGGTGGAAACAAGACCTGCCGGCGACGGCACCTTCCA

GAAATGGGCTGCTGTGGTGGTGCCTAGCGGCCAAGAGCAGAGATACACCTGTCACGTGCAGC

ACGAGGGCCTGCCTAAGCCTCTTACACTGAGATGGGAGCCCAGCAGCCAGCCTACAATCCCC

ATCGTGGGAATCATTGCCGGCCTGGTGCTGTTTGGCGCCGTGATTACAGGTGCAGTGGTGGC

CGCTGTTATGTGGCGGAGAAAGAGCAGCGACAGAAAAGGCGGCAGCTACTCTCAGGCCGCCA

GCTCTGATTCTGCCCAGGGCTCTGATGTGTCTCTGACCGCCTGCAAAGTGTGAATCGATAAG

GGTTCGATCCCTACCGGTTAGTAATGAGTTTGATATCTCGACAATCAACCTCTGGATTACAA

AATTTGTGAAAGATTGACTGGTATTCTTAACTATGTTGCTCCTTTTACGCTATGTGGATACG

CTGCTTTAATGCCTTTGTATCATGCTATTGCTTCCCGTATGGCTTTCATTTTCTCCTCCTTG

TATAAATCCTGGTTGCTGTCTCTTTATGAGGAGTTGTGGCCCGTTGTCAGGCAACGTGGCGT

GGTGTGCACTGTGTTTGCTGACGCAACCCCCACTGGTTGGGGCATTGCCACCACCTGTCAGC

TCCTTTCCGGGACTTTCGCTTTCCCCCTCCCTATTGCCACGGCGGAACTCATCGCCGCCTGC

CTTGCCCGCTGCTGGACAGGGGCTCGGCTGTTGGGCACTGACAATTCCGTGGTGTTGTCGGG

GAAGCTGACGTCCTTTCCATGGCTGCTCGCCTGTGTTGCCACCTGGATTCTGCGCGGGACGT

CCTTCTGCTACGTCCCTTCGGCCCTCAATCCAGCGGACCTTCCTTCCCGCGGCCTGCTGCCG

GCTCTGCGGCCTCTTCCGCGTCTTCGCCTTCGCCCTCAGACGAGTCGGATCTCCCTTTGGGC

CGCCTCCCCGCCTGGAACGGGGGAGGCTAACTGAAACACGGAAGGAGACAATACCGGAAGGA

ACCCGCGCTATGACGGCAATAAAAAGACAGAATAAAACGCACGGGTGTTGGGTCGTTTGTTC

ATAAACGCGGGGTTCGGTCCCAGGGCTGGCACTCTGTCGATACCCCACCGAGACCCCATTGG

GGCCAATACGCCCGCGTTTCTTCCTTTTCCCCACCCCACCCCCCAAGTTCGGGTGAAGGCCC

AGGGCTCGCAGCCAACGTCGGGGCGGCAGGCCCTGCCATAGCAGATCTGCGCAGCTGGGGCT

CTAGGGGGTATCCCCACGCGCCCTGTAGCGGCGCATTAAGCGCGGCGGGTGTGGTGGTTACG

CGCAGCGTGACCGCTACACTTGCCAGCGCCCTAGCGCCCGCTCCTTTCGCTTTCTTCCCTTC

CTTTCTCGCCACGTTCGCCGGCTTTCCCCGTCAAGCTCTAAATCGGGGGCTCCCTTTAGGGT

TCCGATTTAGTGCTTTACGGCACCTCGACCCCAAAAAACTTGATTAGGGTGATGGTTCACGT

AGTGGGCCATCGCCCTGATAGACGGTTTTTCGCCCTTTGACGTTGGAGTCCACGTTCTTTAA

TAGTGGACTCTTGTTCCAAACTGGAACAACACTCAACCCTATCTCGGTCTATTCTTTTGATT

TATAAGGGATTTTGCCGATTTCGGCCTATTGGTTAAAAAATGAGCTGATTTAACAAAAATTT

AACGCGAATTAATTCTGTGGAATGTGTGTCAGTTAGGGTGTGGAAAGTCCCCAGGCTCCCCA

GCAGGCAGAAGTATGCAAAGCATGCATCTCAATTAGTCAGCAACCAGGTGTGGAAAGTCCCC

AGGCTCCCCAGCAGGCAGAAGTATGCAAAGCATGCATCTCAATTAGTCAGCAACCATAGTCC

CGCCCCTAACTCCGCCCATCCCGCCCCTAACTCCGCCCAGTTCCGCCCATTCTCCGCCCCAT

GGCTGACTAATTTTTTTTATTTATGCAGAGGCCGAGGCCGCCTCTGCCTCTGAGCTATTCCA

GAAGTAGTGAGGAGGCTTTTTTGGAGGCCTAGGCTTTTGCAAAAAGCTCCCGGGAGCTTGTA

TATCCATTTTCGGATCTGATCAAGAGACAGGATGAGGATCGTTTCGCATGATTGAACAAGAT

| INFORMAL SEQUENCE LISTING |
|---|
| GGATTGCACGCAGGTTCTCCGGCCGCTTGGGTGGAGAGGCTATTCGGCTATGACTGGGCACA |
| ACAGACAATCGGCTGCTCTGATGCCGCCGTGTTCCGGCTGTCAGCGCAGGGGCGCCCGGTTC |
| TTTTTGTCAAGACCGACCTGTCCGGTGCCCTGAATGAACTGCAGGACGAGGCAGCGCGGCTA |
| TCGTGGCTGGCCACGACGGGCGTTCCTTGCGCAGCTGTGCTCGACGTTGTCACTGAAGCGGG |
| AAGGGACTGGCTGCTATTGGGCGAAGTGCCGGGCAGGATCTCCTGTCATCTCACCTTGCTC |
| CTGCCGAGAAAGTATCCATCATGGCTGATGCAATGCGGCGGCTGCATACGCTTGATCCGGCT |
| ACCTGCCCATTCGACCACCAAGCGAAACATCGCATCGAGCGAGCACGTACTCGGATGGAAGC |
| CGGTCTTGTCGATCAGGATGATCTGGACGAAGAGCATCAGGGGCTCGCGCCAGCCGAACTGT |
| TCGCCAGGCTCAAGGCGCGCATGCCCGACGGCGAGGATCTCGTCGTGACCCATGGCGATGCC |
| TGCTTGCCGAATATCATGGTGGAAAATGGCCGCTTTTCTGGATTCATCGACTGTGGCCGGCT |
| GGGTGTGGCGGACCGCTATCAGGACATAGCGTTGGCTACCCGTGATATTGCTGAAGAGCTTG |
| GCGGCGAATGGGCTGACCGCTTCCTCGTGCTTTACGGTATCGCCGCTCCCGATTCGCAGCGC |
| ATCGCCTTCTATCGCCTTCTTGACGAGTTCTTCTGAGCGGGACTCTGGGGTTCGCGAAATGA |
| CCGACCAAGCGACGCCCAACCTGCCATCACGAGATTTCGATTCCACCGCCGCCTTCTATGAA |
| AGGTTGGGCTTCGGAATCGTTTTCCGGGACGCCGGCTGGATGATCCTCCAGCGCGGGGATCT |
| CATGCTGGAGTTCTTCGCCCACCCCAACTTGTTTATTGCAGCTTATAATGGTTACAAATAAA |
| GCAATAGCATCACAAATTTCACAAATAAAGCATTTTTTTCACTGCATTCTAGTTGTGGTTTG |
| TCCAAACTCATCAATGTATCTTATCATGTCTGTATACCGTCGACCTCTAGCTAGAGCTTGGC |
| GTAATCATGGTCATAGCTGTTTCCTGTGTGAAATTGTTATCCGCTCACAATTCCACACAACA |
| TACGAGCCGGAAGCATAAAGTGTAAAGCCTGGGGTGCCTAATGAGTGAGCTAACTCACATTA |
| ATTGCGTTGCGCTCACTGCCCGCTTTCCAGTCGGGAAACCTGTCGTGCCAGCTGCATTAATG |
| AATCGGCCAACGCGCGGGGAGAGGCGGTTTGCGTATTGGGCGCTCTTCCGCTTCCTCGCTCA |
| CTGACTCGCTGCGCTCGGTCGTTCGGCTGCGGCGAGCGGTATCAGCTCACTCAAAGGCGGTA |
| ATACGGTTATCCACAGAATCAGGGGATAACGCAGGAAAGAACATGTGAGCAAAAGGCCAGCA |
| AAAGGCCAGGAACCGTAAAAAGGCCGCGTTGCTGGCGTTTTTCCATAGGCTCCGCCCCCCTG |
| ACGAGCATCACAAAAATCGACGCTCAAGTCAGAGGTGGCGAAACCCGACAGGACTATAAAGA |
| TACCAGGCGTTTCCCCCTGGAAGCTCCCTCGTGCGCTCTCCTGTTCCGACCCTGCCGCTTAC |
| CGGATACCTGTCCGCCTTTCTCCCTTCGGGAAGCGTGGCGCTTTCTCATAGCTCACGCTGTA |
| GGTATCTCAGTTCGGTGTAGGTCGTTCGCTCCAAGCTGGGCTGTGTGCACGAACCCCCCGTT |
| CAGCCCGACCGCTGCGCCTTATCCGGTAACTATCGTCTTGAGTCCAACCCGGTAAGACACGA |
| CTTATCGCCACTGGCAGCAGCCACTGGTAACAGGATTAGCAGAGCGAGGTATGTAGGCGGTG |
| CTACAGAGTTCTTGAAGTGGTGGCCTAACTACGGCTACACTAGAAGAACAGTATTTGGTATC |
| TGCGCTCTGCTGAAGCCAGTTACCTTCGGAAAAAGAGTTGGTAGCTCTTGATCCGGCAAACA |
| AACCACCGCTGGTAGCGGTGGTTTTTTTGTTTGCAAGCAGCAGATTACGCGCAGAAAAAAAG |
| GATCTCAAGAAGATCCTTTGATCTTTTCTACGGGGTCTGACGCTCAGTGGAACGAAAACTCA |
| CGTTAAGGGATTTTGGTCATGAGATTATCAAAAAGGATCTTCACCTAGATCCTTTTAAATTA |
| AAAATGAAGTTTTAAATCAATCTAAAGTATATATGAGTAAACTTGGTCTGACAGTTACCAAT |
| GCTTAATCAGTGAGGCACCTATCTCAGCGATCTGTCTATTTCGTTCATCCATAGTTGCCTGA |
| CTCCCCGTCGTGTAGATAACTACGATACGGGAGGGCTTACCATCTGGCCCCAGTGCTGCAAT |

-continued

INFORMAL SEQUENCE LISTING

GATACCGCGAGACCCACGCTCACCGGCTCCAGATTTATCAGCAATAAACCAGCCAGCCGGAA

GGGCCGAGCGCAGAAGTGGTCCTGCAACTTTATCCGCCTCCATCCAGTCTATTAATTGTTGC

CGGGAAGCTAGAGTAAGTAGTTCGCCAGTTAATAGTTTGCGCAACGTTGTTGCCATTGCTAC

AGGCATCGTGGTGTCACGCTCGTCGTTTGGTATGGCTTCATTCAGCTCCGGTTCCCAACGAT

CAAGGCGAGTTACATGATCCCCATGTTGTGCAAAAAAGCGGTTAGCTCCTTCGGTCCTC<u>CG</u>

<u>ATCG</u>TTGTCAGAAGTAAGTTGGCCGCAGTGTTATCACTCATGGTTATGGCAGCACTGCATAA

TTCTCTTACTGTCATGCCATCCGTAAGATGCTTTTCTGTGACTGGTGAGTACTCAACCAAGT

CATTCTGAGAATAGTGTATGCGGCGACCGAGTTGCTCTTGCCCGGCGTCAATACGGGATAAT

ACCGCGCCACATAGCAGAACTTTAAAAGTGCTCATCATTGGAAAACGTTCTTCGGGGCGAAA

ACTCTCAAGGATCTTACCGCTGTTGAGATCCAGTTCGATGTAACCCACTCGTGCACCCAACT

GATCTTCAGCATCTTTTACTTTCACCAGCGTTTCTGGGTGAGCAAAAACAGGAAGGCAAAAT

GCCGCAAAAAAGGGAATAAGGGCGACACGGAAATGTTGAATACTCATACTCTTCCTTTTTCA

ATATTATTGAAGCATTTATCAGGGTTATTGTCTCATGAGCGGATACATATTTGAATGTATTT

AGAAAAATAAACAAATAGGGGTTCCGCGCACATTTCCCCGAAAAGTGCCACCTGACGTCGAC

GGATCGGGAGATCTCCCGATCCCCTATGGTCGACTCTCAGTACAATCTGCTCTGATGCCGCA

TAGTTAAGCCAGTATCTGCTCCCTGCTTGTGTGTTGGAGGTCGCTGAGTAGTGCGCGAGCAA

AATTTAAGCTACAACAAGGCAAGGCTTGACCGACAATTGCATGAAGAATCTGCTTAGG

HLA-DRB3*02:02 ORF before optimization (801 bp) (SEQ ID NO: 4)
Sequence as represented by IMGT/HLA Acc No. HLA00895. ApaLI
restriction site (GTGCAC) is underlined.
ATGGTGTGTCTGAAGCTCCCTGGAGGCTCCAGCTTGGCAGCGTTGACAGTGACACTGATGGT

GCTGAGCTCCCGACTGGCTTTCGCTGGGGACACCCGACCACGTTTCTTGGAGCTGCTTAAGT

CTGAGTGTCATTTCTTCAATGGGACGGAGCGGGTGCGGTTCCTGGAGAGACACTTCCATAAC

CAGGAGGAGTACGCGCGCTTCGACAGCGACGTGGGGGAGTACCGGGCGGTGAGGGAGCTGGG

GCGGCCTGATGCCGAGTACTGGAACAGCCAGAAGGACCTCCTGGAGCAGAAGCGGGGCCAGG

TGGACAATTACTGCAGACACAACTACGGGGTTGGTGAGAGCTTCACAGTGCAGCGGCGAGTC

CATCCTCAGGTGACTGTGTATCCTGCAAAGACCCAGCCCCTGCAGCACCACAACCTCCTGGT

CTGCTCTGTGAGTGGTTTCTATCCAGGCAGCATTGAAGTCAGGTGGTTCCGGAACGGCCAGG

AAGAGAAGGCTGGGGTGGTGTCCACGGGCCTGATCCAGAATGGAGACTGGACCTTCCAGACC

CTGGTGATGCTAGAAACAGTTCCTCGGAGTGGAGAGGTTTACACCTGCCAAGTGGAGCACCC

AAGCGTAACGAGCCCTCTCACAGTGGAATGGA<u>GTGCAC</u>GGTCTGAATCTGCACAGAGCAAGA

TGCTGAGTGGAGTCGGGGGCTTTGTGCTGGGCCTGCTCTTCCTTGGGGCCGGGCTGTTCATC

TACTTCAGGAATCAGAAAGGACACTCTGGACTTCAGCCAACAGGATTCCTGAGCTGA

HLA-DRB3*02:02 ORF before optimization, with removed ApaLI
site (801 bp) (SEQ ID NO: 5)
Mutation introduced in ApaLI restriction site (GTGCAC),
leading to GTGCAA (underlined).
ATGGTGTGTCTGAAGCTCCCTGGAGGCTCCAGCTTGGCAGCGTTGACAGTGACACTGATGGT

GCTGAGCTCCCGACTGGCTTTCGCTGGGGACACCCGACCACGTTTCTTGGAGCTGCTTAAGT

CTGAGTGTCATTTCTTCAATGGGACGGAGCGGGTGCGGTTCCTGGAGAGACACTTCCATAAC

CAGGAGGAGTACGCGCGCTTCGACAGCGACGTGGGGGAGTACCGGGCGGTGAGGGAGCTGGG

GCGGCCTGATGCCGAGTACTGGAACAGCCAGAAGGACCTCCTGGAGCAGAAGCGGGGCCAGG

TGGACAATTACTGCAGACACAACTACGGGGTTGGTGAGAGCTTCACAGTGCAGCGGCGAGTC

CATCCTCAGGTGACTGTGTATCCTGCAAAGACCCAGCCCCTGCAGCACCACAACCTCCTGGT

CTGCTCTGTGAGTGGTTTCTATCCAGGCAGCATTGAAGTCAGGTGGTTCCGGAACGGCCAGG

AAGAGAAGGCTGGGGTGGTGTCCACGGGCCTGATCCAGAATGGAGACTGGACCTTCCAGACC

CTGGTGATGCTAGAAACAGTTCCTCGGAGTGGAGAGGTTTACACCTGCCAAGTGGAGCACCC

AAGCGTAACGAGCCCTCTCACAGTGGAATGGA<u>GTGCAA</u>GGTCTGAATCTGCACAGAGCAAGA

TGCTGAGTGGAGTCGGGGGCTTTGTGCTGGGCCTGCTCTTCCTTGGGGCCGGGCTGTTCATC

TACTTCAGGAATCAGAAAGGACACTCTGGACTTCAGCCAACAGGATTCCTGAGCTGA

HLA-DRB3*02:02 ORF after optimization (801 bp) (SEQ ID NO: 6)
ATGGTTTGCCTTAAACTGCCTGGCGGCAGCTCTCTGGCTGCCCTGACAGTTACACTGATGGT

GCTGAGCAGCAGACTGGCCTTTGCCGGCGATACCCGGCCTAGATTTCTGGAACTGCTGAAGT

CCGAGTGCCACTTCTTCAACGGAACCGAGAGAGTGCGGTTCCTGGAAAGGCACTTCCACAAT

CAAGAGGAATACGCCAGATTCGACAGCGACGTGGGCGAGTACAGAGCCGTCAGAGAACTGGG

CAGACCCGATGCCGAGTACTGGAACAGCCAGAAGGACCTGCTGGAACAGAAGAGAGGCCAGG

TCGACAACTACTGCCGGCACAATTATGGCGTGGGCGAAAGCTTCACCGTGCAGAGAAGAGTG

CATCCCCAAGTGACAGTGTACCCCGCCAAGACACAGCCTCTGCAGCACCACAATCTGCTCGT

GTGTAGCGTGTCCGGCTTCTACCCTGGCTCTATCGAAGTGCGGTGGTTCAGAAACGGCCAAG

AGGAAAAGGCCGGCGTCGTCAGCACAGGCCTGATCCAAAATGGCGACTGGACCTTTCAGACC

CTGGTCATGCTGGAAACCGTGCCTAGAAGCGGCGAGGTGTACACATGCCAGGTGGAACACCC

TAGCGTGACAAGCCCTCTGACAGTCGAGTGGAGCGCCAGATCTGAAAGCGCCCAGAGCAAGA

TGCTGTCTGGCGTTGGCGGATTTGTGCTGGGCCTGCTGTTTCTTGGAGCCGGCCTGTTCATC

TACTTCCGGAACCAGAAGGGCCACAGCGGCTTGCAGCCAACAGGCTTTCTGAGCTGA

Sequence of pcDNA3.4-DRB30202 (6829 bp) (SEQ ID NO: 7)
Optimized HLA-DRB3*02:02 sequence in pcDNA3.4-TOPO. 5'-XhoI
restriction site (CTCGAG), start codon (ATG), stop codon
(TGA), and 3'-NheI restriction site (GCTAGC) are
underlined. Also underlined is the single PvuI restriction
site (CGATCG), useful for linearization of the plasmid prior
to stable transfection.
GTTAGGCGTTTTGCGCTGCTTCGCGATGTACGGGCCAGATATACGCGTTGACATTGATTATT

GACTAGTTATTAATAGTAATCAATTACGGGGTCATTAGTTCATAGCCCATATATGGAGTTCC

GCGTTACATAACTTACGGTAAATGGCCCGCCTGGCTGACCGCCCAACGACCCCCGCCCATTG

ACGTCAATAATGACGTATGTTCCCATAGTAACGCCAATAGGGACTTTCCATTGACGTCAATG

GGTGGAGTATTTACGGTAAACTGCCCACTTGGCAGTACATCAAGTGTATCATATGCCAAGTA

CGCCCCCTATTGACGTCAATGACGGTAAATGGCCCGCCTGGCATTATGCCCAGTACATGACC

TTATGGGACTTTCCTACTTGGCAGTACATCTACGTATTAGTCATCGCTATTACCATGGTGAT

GCGGTTTTGGCAGTACATCAATGGGCGTGGATAGCGGTTTGACTCACGGGGATTTCCAAGTC

TCCACCCCATTGACGTCAATGGGAGTTTGTTTTGGCACCAAAATCAACGGGACTTTCCAAAA

TGTCGTAACAACTCCGCCCCATTGACGCAAATGGGCGGTAGGCGTGTACGGTGGGAGGTCTA

TATAAGCAGAGCTCGTTTAGTGAACCGTCAGATCGCCTGGAGACGCCATCCACGCTGTTTTG

ACCTCCATAGAAGACACCGGGACCGATCCAGCCTCCGGACTCTAGAGGATCGAACCCTT<u>CTC

GAG</u>GCCACC<u>ATG</u>GTTTGCCTTAAACTGCCTGGCGGCAGCTCTCTGGCTGCCCTGACAGTTAC

| INFORMAL SEQUENCE LISTING |
|---|
| ACTGATGGTGCTGAGCAGCAGACTGGCCTTTGCCGGCGATACCCGGCCTAGATTTCTGGAAC |
| TGCTGAAGTCCGAGTGCCACTTCTTCAACGGAACCGAGAGAGTGCGGTTCCTGGAAAGGCAC |
| TTCCACAATCAAGAGGAATACGCCAGATTCGACAGCGACGTGGGCGAGTACAGAGCCGTCAG |
| AGAACTGGGCAGACCCGATGCCGAGTACTGGAACAGCCAGAAGGACCTGCTGGAACAGAAGA |
| GAGGCCAGGTCGACAACTACTGCCGGCACAATTATGGCGTGGGCGAAAGCTTCACCGTGCAG |
| AGAAGAGTGCATCCCCAAGTGACAGTGTACCCCGCCAAGACACAGCCTCTGCAGCACCACAA |
| TCTGCTCGTGTGTAGCGTGTCCGGCTTCTACCCTGGCTCTATCGAAGTGCGGTGGTTCAGAA |
| ACGGCCAAGAGGAAAAGGCCGGCGTCGTCAGCACAGGCCTGATCCAAAATGGCGACTGGACC |
| TTTCAGACCCTGGTCATGCTGGAAACCGTGCCTAGAAGCGGCGAGGTGTACACATGCCAGGT |
| GGAACACCCTAGCGTGACAAGCCCTCTGACAGTCGAGTGGAGCGCCAGATCTGAAAGCGCCC |
| AGAGCAAGATGCTGTCTGGCGTTGGCGGATTTGTGCTGGGCCTGCTGTTTCTTGGAGCCGGC |
| CTGTTCATCTACTTCCGGAACCAGAAGGGCCACAGCGGCTTGCAGCCAACAGGCTTTCTGAG |
| CTGAGCTAGCAAGGGTTCGATCCCTACCGGTTAGTAATGAGTTTGATATCTCGACAATCAAC |
| CTCTGGATTACAAAATTTGTGAAAGATTGACTGGTATTCTTAACTATGTTGCTCCTTTTACG |
| CTATGTGGATACGCTGCTTTAATGCCTTTGTATCATGCTATTGCTTCCCGTATGGCTTTCAT |
| TTTCTCCTCCTTGTATAAATCCTGGTTGCTGTCTCTTTATGAGGAGTTGTGGCCCGTTGTCA |
| GGCAACGTGGCGTGGTGTGCACTGTGTTTGCTGACGCAACCCCCACTGGTTGGGCATTGCC |
| ACCACCTGTCAGCTCCTTTCCGGGACTTTCGCTTTCCCCCTCCCTATTGCCACGGCGGAACT |
| CATCGCCGCCTGCCTTGCCCGCTGCTGGACAGGGGCTCGGCTGTTGGGCACTGACAATTCCG |
| TGGTGTTGTCGGGGAAGCTGACGTCCTTTCCATGGCTGCTCGCCTGTGTTGCCACCTGGATT |
| CTGCGCGGGACGTCCTTCTGCTACGTCCCTTCGGCCCTCAATCCAGCGGACCTTCCTTCCCG |
| CGGCCTGCTGCCGGCTCTGCGGCCTCTTCCGCGTCTTCGCCTTCGCCCTCAGACGAGTCGGA |
| TCTCCCTTTGGGCCGCCTCCCCGCCTGGAACGGGGGAGGCTAACTGAAACACGGAAGGAGAC |
| AATACCGGAAGGAACCCGCGCTATGACGGCAATAAAAAGACAGAATAAAACGCACGGGTGTT |
| GGGTCGTTTGTTCATAAACGCGGGGTTCGGTCCCAGGGCTGGCACTCTGTCGATACCCCACC |
| GAGACCCCATTGGGGCCAATACGCCCGCGTTTCTTCCTTTTCCCCACCCCACCCCCCAAGTT |
| CGGGTGAAGGCCCAGGGCTCGCAGCCAACGTCGGGGCGGCAGGCCCTGCCATAGCAGATCTG |
| CGCAGCTGGGGCTCTAGGGGGTATCCCCACGCGCCCTGTAGCGGCGCATTAAGCGCGGCGGG |
| TGTGGTGGTTACGCGCAGCGTGACCGCTACACTTGCCAGCGCCCTAGCGCCCGCTCCTTTCG |
| CTTTCTTCCCTTCCTTTCTCGCCACGTTCGCCGGCTTTCCCCGTCAAGCTCTAAATCGGGGG |
| CTCCCTTTAGGGTTCCGATTTAGTGCTTTACGGCACCTCGACCCCAAAAAACTTGATTAGGG |
| TGATGGTTCACGTAGTGGGCCATCGCCCTGATAGACGGTTTTTCGCCCTTTGACGTTGGAGT |
| CCACGTTCTTTAATAGTGGACTCTTGTTCCAAACTGGAACAACACTCAACCCTATCTCGGTC |
| TATTCTTTTGATTTATAAGGGATTTTGCCGATTTCGGCCTATTGGTTAAAAAATGAGCTGAT |
| TTAACAAAAATTTAACGCGAATTAATTCTGTGGAATGTGTGTCAGTTAGGGTGTGGAAAGTC |
| CCCAGGCTCCCCAGCAGGCAGAAGTATGCAAAGCATGCATCTCAATTAGTCAGCAACCAGGT |
| GTGGAAAGTCCCCAGGCTCCCCAGCAGGCAGAAGTATGCAAAGCATGCATCTCAATTAGTCA |
| GCAACCATAGTCCCGCCCCTAACTCCGCCCATCCCGCCCCTAACTCCGCCCAGTTCCGCCCA |
| TTCTCCGCCCCATGGCTGACTAATTTTTTTTATTTATGCAGAGGCCGAGGCCGCCTCTGCCT |

INFORMAL SEQUENCE LISTING

```
CTGAGCTATTCCAGAAGTAGTGAGGAGGCTTTTTTGGAGGCCTAGGCTTTTGCAAAAAGCTC

CCGGGAGCTTGTATATCCATTTTCGGATCTGATCAAGAGACAGGATGAGGATCGTTTCGCAT

GATTGAACAAGATGGATTGCACGCAGGTTCTCCGGCCGCTTGGGTGGAGAGGCTATTCGGCT

ATGACTGGGCACAACAGACAATCGGCTGCTCTGATGCCGCCGTGTTCCGGCTGTCAGCGCAG

GGGCGCCCGGTTCTTTTTGTCAAGACCGACCTGTCCGGTGCCCTGAATGAACTGCAGGACGA

GGCAGCGCGGCTATCGTGGCTGGCCACGACGGGCGTTCCTTGCGCAGCTGTGCTCGACGTTG

TCACTGAAGCGGGAAGGGACTGGCTGCTATTGGGCGAAGTGCCGGGGCAGGATCTCCTGTCA

TCTCACCTTGCTCCTGCCGAGAAAGTATCCATCATGGCTGATGCAATGCGGCGGCTGCATAC

GCTTGATCCGGCTACCTGCCCATTCGACCACCAAGCGAAACATCGCATCGAGCGAGCACGTA

CTCGGATGGAAGCCGGTCTTGTCGATCAGGATGATCTGGACGAAGAGCATCAGGGGCTCGCG

CCAGCCGAACTGTTCGCCAGGCTCAAGGCGCGCATGCCCGACGGCGAGGATCTCGTCGTGAC

CCATGGCGATGCCTGCTTGCCGAATATCATGGTGGAAAATGGCCGCTTTTCTGGATTCATCG

ACTGTGGCCGGCTGGGTGTGGCGGACCGCTATCAGGACATAGCGTTGGCTACCCGTGATATT

GCTGAAGAGCTTGGCGGCGAATGGGCTGACCGCTTCCTCGTGCTTTACGGTATCGCCGCTCC

CGATTCGCAGCGCATCGCCTTCTATCGCCTTCTTGACGAGTTCTTCTGAGCGGGACTCTGGG

GTTCGCGAAATGACCGACCAAGCGACGCCCAACCTGCCATCACGAGATTTCGATTCCACCGC

CGCCTTCTATGAAAGGTTGGGCTTCGGAATCGTTTTCCGGGACGCCGGCTGGATGATCCTCC

AGCGCGGGGATCTCATGCTGGAGTTCTTCGCCCACCCCAACTTGTTTATTGCAGCTTATAAT

GGTTACAAATAAAGCAATAGCATCACAAATTTCACAAATAAAGCATTTTTTTCACTGCATTC

TAGTTGTGGTTTGTCCAAACTCATCAATGTATCTTATCATGTCTGTATACCGTCGACCTCTA

GCTAGAGCTTGGCGTAATCATGGTCATAGCTGTTTCCTGTGTGAAATTGTTATCCGCTCACA

ATTCCACACAACATACGAGCCGGAAGCATAAAGTGTAAAGCCTGGGGTGCCTAATGAGTGAG

CTAACTCACATTAATTGCGTTGCGCTCACTGCCCGCTTTCCAGTCGGGAAACCTGTCGTGCC

AGCTGCATTAATGAATCGGCCAACGCGCGGGGAGAGGCGGTTTGCGTATTGGGCGCTCTTCC

GCTTCCTCGCTCACTGACTCGCTGCGCTCGGTCGTTCGGCTGCGGCGAGCGGTATCAGCTCA

CTCAAAGGCGGTAATACGGTTATCCACAGAATCAGGGGATAACGCAGGAAAGAACATGTGAG

CAAAAGGCCAGCAAAAGGCCAGGAACCGTAAAAAGGCCGCGTTGCTGGCGTTTTTCCATAGG

CTCCGCCCCCCTGACGAGCATCACAAAAATCGACGCTCAAGTCAGAGGTGGCGAAACCCGAC

AGGACTATAAAGATACCAGGCGTTTCCCCCTGGAAGCTCCCTCGTGCGCTCTCCTGTTCCGA

CCCTGCCGCTTACCGGATACCTGTCCGCCTTTCTCCCTTCGGGAAGCGTGGCGCTTTCTCAT

AGCTCACGCTGTAGGTATCTCAGTTCGGTGTAGGTCGTTCGCTCCAAGCTGGGCTGTGTGCA

CGAACCCCCCGTTCAGCCCGACCGCTGCGCCTTATCCGGTAACTATCGTCTTGAGTCCAACC

CGGTAAGACACGACTTATCGCCACTGGCAGCAGCCACTGGTAACAGGATTAGCAGAGCGAGG

TATGTAGGCGGTGCTACAGAGTTCTTGAAGTGGTGGCCTAACTACGGCTACACTAGAAGAAC

AGTATTTGGTATCTGCGCTCTGCTGAAGCCAGTTACCTTCGGAAAAAGAGTTGGTAGCTCTT

GATCCGGCAAACAAACCACCGCTGGTAGCGGTGGTTTTTTTGTTTGCAAGCAGCAGATTACG

CGCAGAAAAAAAGGATCTCAAGAAGATCCTTTGATCTTTTCTACGGGGTCTGACGCTCAGTG

GAACGAAAACTCACGTTAAGGGATTTTGGTCATGAGATTATCAAAAAGGATCTTCACCTAGA
```

| INFORMAL SEQUENCE LISTING |
|---|
| TCCTTTTAAATTAAAAATGAAGTTTTAAATCAATCTAAAGTATATATGAGTAAACTTGGTCT |
| GACAGTTACCAATGCTTAATCAGTGAGGCACCTATCTCAGCGATCTGTCTATTTCGTTCATC |
| CATAGTTGCCTGACTCCCCGTCGTGTAGATAACTACGATACGGGAGGGCTTACCATCTGGCC |
| CCAGTGCTGCAATGATACCGCGAGACCCACGCTCACCGGCTCCAGATTTATCAGCAATAAAC |
| CAGCCAGCCGGAAGGGCCGAGCGCAGAAGTGGTCCTGCAACTTTATCCGCCTCCATCCAGTC |
| TATTAATTGTTGCCGGGAAGCTAGAGTAAGTAGTTCGCCAGTTAATAGTTTGCGCAACGTTG |
| TTGCCATTGCTACAGGCATCGTGGTGTCACGCTCGTCGTTTGGTATGGCTTCATTCAGCTCC |
| GGTTCCCAACGATCAAGGCGAGTTACATGATCCCCCATGTTGTGCAAAAAAGCGGTTAGCTC |
| CTTCGGTCCTCCGATCGTTGTCAGAAGTAAGTTGGCCGCAGTGTTATCACTCATGGTTATGG |
| CAGCACTGCATAATTCTCTTACTGTCATGCCATCCGTAAGATGCTTTTCTGTGACTGGTGAG |
| TACTCAACCAAGTCATTCTGAGAATAGTGTATGCGGCGACCGAGTTGCTCTTGCCCGGCGTC |
| AATACGGGATAATACCGCGCCACATAGCAGAACTTTAAAAGTGCTCATCATTGGAAAACGTT |
| CTTCGGGGCGAAAACTCTCAAGGATCTTACCGCTGTTGAGATCCAGTTCGATGTAACCCACT |
| CGTGCACCCAACTGATCTTCAGCATCTTTTACTTTCACCAGCGTTTCTGGGTGAGCAAAAAC |
| AGGAAGGCAAAATGCCGCAAAAAAGGGAATAAGGGCGACACGGAAATGTTGAATACTCATAC |
| TCTTCCTTTTTCAATATTATTGAAGCATTTATCAGGGTTATTGTCTCATGAGCGGATACATA |
| TTTGAATGTATTTAGAAAAATAAACAAATAGGGGTTCCGCGCACATTTCCCCGAAAAGTGCC |
| ACCTGACGTCGACGGATCGGGAGATCTCCCGATCCCCTATGGTCGACTCTCAGTACAATCTG |
| CTCTGATGCCGCATAGTTAAGCCAGTATCTGCTCCCTGCTTGTGTGTTGGAGGTCGCTGAGT |
| AGTGCGCGAGCAAAATTTAAGCTACAACAAGGCAAGGCTTGACCGACAATTGCATGAAGAAT |
| CTGCTTAGG |
| Sequence of pVITRO2-A0201-DRB30202 (8030 bp) (SEQ ID NO. 8) For the HLA-A*02:01 insert, 5'-BamHI restriction site (GGATCC), start codon (ATG), stop codon (TGA), and 3'-ClaI restriction site (ATCGAT) are underlined. For the HLA-DRB3*02:02 insert, 5'-XhoI restriction site (CTCGAG), start codon (ATG), stop codon (TGA), and 3'-NheI restriction site (GCTAGC) are underlined. Also underlined is the single ApaLI restriction site (GTGCAC), useful for linearization of the plasmid prior to stable transfection. |
| CCTGCAGGCGTTACATAACTTACGGTAAATGGCCCGCCTGGCTGACCGCCCAACGACCCCCG |
| CCCATTGACGTCAATAATGACGTATGTTCCCATAGTAACGCCAATAGGGACTTTCCATTGAC |
| GTCAATGGGTGGAGTATTTACGGTAAACTGCCCACTTGGCAGTACATCAAGTGTATCATATG |
| CCAAGTACGCCCCCTATTGACGTCAATGACGGTAAATGGCCCGCCTGGCATTATGCCCAGTA |
| CATGACCTTATGGGACTTTCCTACTTGGCAGTACATCTACGTATTAGTCATCGCTATTACCA |
| TGATGATGCGGTTTTGGCAGTACATCAATGGGCGTGGATAGCGGTTTGACTCACGGGGATTT |
| CCAAGTCTCCACCCCATTGACGTCAATGGGAGTTTGTTTTGACTAGTCAGGGCCCCAACCCC |
| CCCAAGCCCCCATTTCACAACACGCTGGCGCTACAGGCGCGTGACTTCCCCTTGCTTTGGGG |
| CGGGGGGCTGAGACTCCTATGTGCTCCCGGATTGGTCAGGCACGGCCTTCGGCCCCGCCTCCT |
| GCCACCGCAGATTGGCCGCTAGGCCTCCCCGAGCGCCCTGCCTCCGAGGGCCGGCGCACCAT |
| AAAAGAAGCCGCCCTAGCCACGTCCCCTCGCAGTTCGGCGGTCCCGCGGGTCTGTCTCAAGC |
| TTGCCGCCAGAACACAGGTAAGTGCCGTGTGTGGTTCCCGCGGGCCTGGCCTCTTTACGGGT |
| TATGGCCCTTGCGTGCCTTGAATTACTTCCATGCCCCTGGCTGCAGTACGTGATTCTTGATC |

| INFORMAL SEQUENCE LISTING |
| --- |
| CCGAGCTTCGGGTTGGAAGTGGGTGGGAGAGTTCGAGGCCTTGCGCTTAAGGAGCCCCTTCG |
| CCTCGTGCTTGAGTTGAGGCCTGGCTTGGGCGCTGGGGCCGCCGCGTGCTAATCTGGTGGCA |
| CCTTCGCGCCTGTCTCGCTGCTTTCGCTAAGTCTCTAGCCATTTAAAATTTTTGATAACCAG |
| CTGCGACGCTTTTTTTCTGGCGAGATAGTCTTGTAAATGCGGGCCAGGATCTGCACACTGGT |
| ATTTCGGTTTTTGGGGCCGCGGGCGGCGACGGGGCCCGTGCGTCCCAGCGCACATGTTCGGC |
| GAGGCGGGGCCTGCGAGCGCGGCCACCGAGAATCGGACGGGGGTAGTCTCAAACTGGCCGGC |
| CTGCTCTGGTGCCTGGCCTCGCGCCGCCGTGTATCGCCCCGCCCTGGGCGGCAAGGCTGGCC |
| CGGTCGGCACCAGTTGCGTGAGCGGAAAGATGGCCGCTTCCCGGCCCTGCTGCAGGGAGCTC |
| AAAATGGAGGACGCGGCGCCCGGGAGAGCGGGCGGGTGAGTCACCCACACAAAGGAAAAGGG |
| CCTTTCCTTCCTCATCCGTCGCTTCATGTGACTCCACGGAGTACCGGGCGCCGTCCAGGCAC |
| CTCGATTAGTTGTCGAGCTTTTGGAGTACGTCGTCTTTAGGTTGGGGGGAGGGGTTTTATGC |
| GATGGAGTTTCCCCACACTGAGTGGGTGGAGACTGAAGAGTTAGGCCAGCTTGGCACTTGAT |
| GTAATTCTCCTTGGAATTTGCCCTTTTTGAGTTTGGATCTTGCCTCATTCTCAAGCCTCAGA |
| CAGTGGTTCAAAGTTTTTTTCTTCCATTTCAGGTGTCGTGAAAACTACCCCTAAAAGCCACC |
| GGCGTGCGCAAGATCTGAATTCTTCGAA<u>CTCGAGG</u>CCACC<b>ATG</b>GTTTGCCTTAAACTGCCTG |
| GCGGCAGCTCTCTGGCTGCCCTGACAGTTACACTGATGGTGCTGAGCAGCAGACTGGCCTTT |
| GCCGGCGATACCCGGCCTAGATTTCTGGAACTGCTGAAGTCCGAGTGCCACTTCTTCAACGG |
| AACCGAGAGAGTGCGGTTCCTGGAAAGGCACTTCCACAATCAAGAGGAATACGCCAGATTCG |
| ACAGCGACGTGGGCGAGTACAGAGCCGTCAGAGAACTGGGCAGACCCGATGCCGAGTACTGG |
| AACAGCCAGAAGGACCTGCTGGAACAGAAGAGAGGCCAGGTCGACAACTACTGCCGGCACAA |
| TTATGGCGTGGGCGAAAGCTTCACCGTGCAGAGAAGAGTGCATCCCCAAGTGACAGTGTACC |
| CCGCCAAGACACAGCCTCTGCAGCACCACAATCTGCTCGTGTGTAGCGTGTCCGGCTTCTAC |
| CCTGGCTCTATCGAAGTGCGGTGGTTCAGAAACGGCCAAGAGGAAAAGGCCGGCGTCGTCAG |
| CACAGGCCTGATCCAAAATGGCGACTGGACCTTTCAGACCCTGGTCATGCTGGAAACCGTGC |
| CTAGAAGCGGCGAGGTGTACACATGCCAGGTGGAACACCCTAGCGTGACAAGCCCTCTGACA |
| GTCGAGTGGAGCGCCAGATCTGAAAGCGCCCAGAGCAAGATGCTGTCTGGCGTTGGCGGATT |
| TGTGCTGGGCCTGCTGTTTCTTGGAGCCGGCCTGTTCATCTACTTCCGGAACCAGAAGGGCC |
| ACAGCGGCTTGCAGCCAACAGGCTTTCTGAGC<b>TGA</b>GCTAGCTGGCCAGACATGATAAGATAC |
| ATTGATGAGTTTGGACAAACCACAACTAGAATGCAGTGAAAAAAATGCTTTATTTGTGAAAT |
| TTGTGATGCTATTGCTTTATTTGTAACCATTATAAGCTGCAATAAACAAGTTAACAACAACA |
| ATTGCATTCATTTTATGTTTCAGGTTCAGGGGGAGGTGTGGGAGGTTTTTTAAAGCAAGTAA |
| AACCTCTACAAATGTGGTATGAAATGTTAATTAACTAGCCATGACCAAAATCCCTTAACGT |
| GAGTTTTCGTTCCACTGAGCGTCAGACCCCGTAGAAAAGATCAAAGGATCTTCTTGAGATCC |
| TTTTTTTCTGCGCGTAATCTGCTGCTTGCAAACAAAAAAACCACCGCTACCAGCGGTGGTTT |
| GTTTGCCGGATCAAGAGCTACCAACTCTTTTTCCGAAGGTAACTGGCTTCAGCAGAGCGCAG |
| ATACCAAATACTGTTCTTCTAGTGTAGCCGTAGTTAGGCCACCACTTCAAGAACTCTGTAGC |
| ACCGCCTACATACCTCGCTCTGCTAATCCTGTTACCAGTGGCTGCTGCCAGTGGCGATAAGT |
| CGTGTCTTACCGGGTTGGACTCAAGACGATAGTTACCGGATAAGGCGCAGCGGTCGGGCTGA |
| ACGGGGGGTTC<b><u>GTGCAC</u></b>ACAGCCCAGCTTGGAGCGAACGACCTACACCGAACTGAGATACCT |

INFORMAL SEQUENCE LISTING

```
ACAGCGTGAGCTATGAGAAAGCGCCACGCTTCCCGAAGGGAGAAAGGCGGACAGGTATCCGG
TAAGCGGCAGGGTCGGAACAGGAGAGCGCACGAGGGAGCTTCCAGGGGGAAACGCCTGGTAT
CTTTATAGTCCTGTCGGGTTTCGCCACCTCTGACTTGAGCGTCGATTTTTGTGATGCTCGTC
AGGGGGGCGGAGCCTATGGAAAAACGCCAGCAACGCGGCCTTTTTACGGTTCCTGGCCTTTT
GCTGGCCTTTTGCTCACATGTTCTTAATTAACCTGCAGGGCCTGAAATAACCTCTGAAAGAG
GAACTTGGTTAGGTACCTTCTGAGGCTGAAAGAACCAGCTGTGGAATGTGTGTCAGTTAGGG
TGTGGAAAGTCCCCAGGCTCCCCAGCAGGCAGAAGTATGCAAAGCATGCATCTCAATTAGTC
AGCAACCAGGTGTGGAAAGTCCCCAGGCTCCCCAGCAGGCAGAAGTATGCAAAGCATGCATC
TCAATTAGTCAGCAACCATAGTCCCACTAGTTCCGCCAGAGCGCGCGAGGGCCTCCAGCGGC
CGCCCCTCCCCCACAGCAGGGGCGGGTCCCGCGCCCACCGGAAGGAGCGGGCTCGGGGCGG
GCGGCGCTGATTGGCCGGGGCGGGCCTGACGCCGACGCGGCTATAAGAGACCACAAGCGACC
CGCAGGGCCAGACGTTCTTCGCCGAAGCTTGCCGTCAGAACGCAGGTGAGGGCGGGTGTGG
CTTCCGCGGGCCGCCGAGCTGGAGGTCCTGCTCCGAGCGGGCCGGGCCCCGCTGTCGTCGGC
GGGGATTAGCTGCGAGCATTCCCGCTTCGAGTTGCGGGCGGCGCGGGAGGCAGAGTGCGAGG
CCTAGCGGCAACCCCGTAGCCTCGCCTCGTGTCCGGCTTGAGGCCTAGCGTGGTGTCCGCGC
CGCCGCCGCGTGCTACTCCGGCCGCACTCTGGTCTTTTTTTTTTTGTTGTTGTTGCCCTGC
TGCCTTCGATTGCCGTTCAGCAATAGGGGCTAACAAAGGGAGGGTGCGGGGCTTGCTCGCCC
GGAGCCCGGAGAGGTCATGGTTGGGGAGGAATGGAGGGACAGGAGTGGCGGCTGGGGCCCGC
CCGCCTTCGGAGCACATGTCCGACGCCACCTGGATGGGGCGAGGCCTGGGGTTTTTCCCGAA
GCAACCAGGCTGGGGTTAGCGTGCCGAGGCCATGTGGCCCCAGCACCCGGCACGATCTGGCT
TGGCGGCGCCGCGTTGCCCTGCCTCCCTAACTAGGGTGAGGCCATCCCGTCCGGCACCAGTT
GCGTGCGTGGAAAGATGGCCGCTCCCGGGCCCTGTTGCAAGGAGCTCAAAATGGAGGACGCG
GCAGCCCGGTGGAGCGGGCGGGTGAGTCACCCACACAAAGGAAGAGGGCCTGGTCCCTCACC
GGCTGCTGCTTCCTGTGACCCCGTGGTCCTATCGGCCGCAATAGTCACCTCGGGCTTTTGAG
CACGGCTAGTCGCGGCGGGGGAGGGGATGTAATGGCGTTGGAGTTTGTTCACATTTGGTGG
GTGGAGACTAGTCAGGCCAGCCTGGCGCTGGAAGTCATTTTTGGAATTTGTCCCCTTGAGTT
TTGAGCGGAGCTAATTCTCGGGCTTCTTAGCGGTTCAAAGGTATCTTTTAAACCCTTTTTA
GGTGTTGTGAAAACCACCGCTAATTCAAAGCAACCGGTGATATCGGATCCGCCACCATGGCT
GTTATGGCCCCTAGAACACTGGTGCTGCTGCTGTCTGGTGCCCTGGCTCTGACACAAACATG
GGCCGGCAGCCACAGCATGCGGTACTTTTTCACCAGCGTGTCCAGACCTGGCAGAGGCGAGC
CTAGATTCATTGCCGTGGGCTACGTGGACGACACCCAGTTCGTCAGATTCGATTCCGATGCC
GCCAGCCAGCGGATGGAACCTAGAGCACCTTGGATCGAGCAAGAGGGCCCCGAGTATTGGGA
CGGCGAGACAAGAAAAGTGAAGGCCCACAGCCAGACACACAGAGTGGATCTGGGAACCCTGC
GGGGCTACTACAATCAGTCTGAGGCCGGCTCTCACACCGTGCAGAGGATGTATGGCTGTGAC
GTGGGCAGCGATTGGCGGTTCCTGAGAGGCTATCACCAGTACGCCTACGACGGCAAGGACTA
TATCGCCCTGAAAGAGGACCTGCGGTCTTGGACAGCCGCCGATATGGCTGCCCAGACCACAA
AGCACAAGTGGGAAGCCGCTCACGTGGCCGAACAGCTGAGAGCTTATCTGGAAGGCACCTGT
GTGGAATGGCTGCGGAGATACCTGGAAAACGGCAAAGAGACACTGCAGCGGACAGACGCCCC
```

INFORMAL SEQUENCE LISTING

TAAGACACACATGACACCACGCCGTGTCCGACCACGAAGCCACACTTAGATGTTGGGCCC

TGAGCTTCTACCCCGCCGAGATCACACTGACATGGCAGAGAGATGGCGAGGATCAGACCCAG

GATACCGAGCTGGTGGAAACAAGACCTGCCGGCGACGGCACCTTCCAGAAATGGGCTGCTGT

GGTGGTGCCTAGCGGCCAAGAGCAGAGATACACCTGTCACGTGCAGCACGAGGGCCTGCCTA

AGCCTCTTACACTGAGATGGGAGCCCAGCAGCCAGCCTACAATCCCCATCGTGGGAATCATT

GCCGGCCTGGTGCTGTTTGGCGCCGTGATTACAGGTGCAGTGGTGGCCGCTGTTATGTGGCG

GAGAAAGAGCAGCGACAGAAAAGGCGGCAGCTACTCTCAGGCCGCCAGCTCTGATTCTGCCC

AGGGCTCTGATGTGTCTCTGACCGCCTGCAAAGTGTGAATCGATTGTCGACCCTAGGAGCAG

GTTTCCCCAATGACACAAAACGTGCAACTTGAAACTCCGCCTGGTCTTTCCAGGTCTAGAGG

GGTAACACTTTGTACTGCGTTTGGCTCCACGCTCGATCCACTGGCGAGTGTTAGTAACAGCA

CTGTTGCTTCGTAGCGGAGCATGACGGCCGTGGGAACTCCTCCTTGGTAACAAGGACCCACG

GGGCCAAAAGCCACGCCCACACGGGCCCGTCATGTGTGCAACCCCAGCACGGCGACTTTACT

GCGAAACCCACTTTAAAGTGACATTGAAACTGGTACCCACACACTGGTGACAGGCTAAGGAT

GCCCTTCAGGTACCCCGAGGTAACACGCGACACTCGGGATCTGAGAAGGGGACTGGGGCTTC

TATAAAAGCGCTCGGTTTAAAAAGCTTCTATGCCTGAATAGGTGACCGGAGGTCGGCACCTT

TCCTTTGCAATTACTGACCCTATGAATACAACTGACTGTTTGACAATTAATCATCGGCATAG

TATATCGGCATAGTATAATACGACTCACTATAGGAGGGCCACCATGATTGAACAAGATGGAT

TGCACGCAGGTTCTCCGGCCGCTTGGGTGGAGAGGCTATTCGGCTATGACTGGGCACAACAG

ACAATCGGCTGCTCTGATGCCGCCGTGTTCCGGCTGTCAGCGCAGGGGCGCCCGGTTCTTTT

TGTCAAGACCGACCTGTCCGGTGCCCTGAATGAACTGCAAGACGAGGCAGCGCGGCTATCGT

GGCTGGCCACGACGGGCGTTCCTTGCGCAGCTGTGCTCGACGTTGTCACTGAAGCGGGAAGG

GACTGGCTGCTATTGGGCGAAGTGCCGGGGCAGGATCTCCTGTCATCTCACCTTGCTCCTGC

CGAGAAAGTATCCATCATGGCTGATGCAATGCGGCGGCTGCATACGCTTGATCCGGCTACCT

GCCCATTCGACCACCAAGCGAAACATCGCATCGAGCGAGCACGTACTCGGATGGAAGCCGGT

CTTGTCGATCAGGATGATCTGGACGAAGAGCATCAGGGGCTCGCGCCAGCCGAACTGTTCGC

CAGGCTCAAGGCGAGCATGCCCGACGGCGAGGATCTCGTCGTGACACATGGCGATGCCTGCT

TGCCGAATATCATGGTGGAAAATGGCCGCTTTTCTGGATTCATCGACTGTGGCCGGCTGGGT

GTGGCGGACCGCTATCAGGACATAGCGTTGGCTACCCGTGATATTGCTGAAGAGCTTGGCGG

CGAATGGGCTGACCGCTTCCTCGTGCTTTACGGTATCGCCGCTCCCGATTCGCAGCGCATCG

CCTTCTATCGCCTTCTTGACGAGTTCTTCTGAGCGGGACTCTGGGGTTCGAAATGACCGACC

AAGCGAATTCGCTAGGATTATCCCTAATACCTGCCACCCCACTCTTAATCAGTGGTGGAAGA

ACGGTCTCAGAACTGTTTGTTTCAATTGGCCATTTAAGTTTAGTAGTAAAAGACTGGTTAAT

GATAACAATGCATCGTAAAACCTTCAGAAGGAAAGGAGAATGTTTTGTGGACCACTTTGGTT

TTCTTTTTTGCGTGTGGCAGTTTTAAGTTATTAGTTTTTAAAATCAGTACTTTTTAATGGAA

ACAACTTGACCAAAAATTTGTCACAGAATTTTGAGACCCATTAAAAAAGTTAAATGAGAAAC

CTGTGTGTTCCTTTGGTCAACACCGAGACATTTAGGTGAAAGACATCTAATTCTGGTTTTAC

GAATCTGGAAACTTCTTGAAAATGTAATTCTTGAGTTAACACTTCTGGGTGGAGAATAGGGT

INFORMAL SEQUENCE LISTING

TGTTTTCCCCCCACATAATTGGAAGGGGAAGGAATATCATTTAAAGCTATGGGAGGGTTGCT

TTGATTACAACACTGGAGAGAAATGCAGCATGTTGCTGATTGCCTGTCACTAAAACAGGCCA

AAAACTGAGTCCTTGGGTTGCATAGAAAGCTG

What is claimed is:

1. A modified human cancer cell comprising:
   (a) a recombinant polynucleotide encoding an allele of a human leukocyte antigen (HLA) class II gene, wherein the HLA class II gene comprises an HLA-DRB3 gene, an HLA-DRB4 gene, an HLA-DRB5 gene, or a combination thereof, and wherein the allele of the HLA-DRB3 gene comprises HLA-DRB3*02:02, HLA-DRB3*01:01, HLA-DRB3*03:01, or a combination thereof;
   (b) a recombinant polynucleotide encoding an allele of an HLA class I gene, wherein the allele of the HLA class I gene comprises HLA-A*11:01, HLA-A*01:01, HLA-A*02:01, HLA-A*03:01, HLA-A*26:01, HLA-A*29:02, HLA-A*32:01, HLA-A*24:02, HLA-A*33:03, HLA-A*68:01, HLA-A*31:01, HLA-A*02:06, or a combination thereof; and
   (c) a recombinant polynucleotide encoding granulocyte-macrophage colony-stimulating factor (GM-CSF).

2. The modified human cancer cell of claim 1, wherein the recombinant polynucleotides are present on one or more vectors in the cell.

3. The modified human cancer cell of claim 1, wherein one or more of the recombinant polynucleotides is integrated into the genome of the cell.

4. The modified human cancer cell of claim 1, further comprising a recombinant polynucleotide encoding an allele of an HLA-B gene, an HLA-C gene, an HLA-E gene, an HLA-F gene, an HLA-G gene, a beta-2-microglobulin (B2M) gene, or a combination thereof.

5. The modified human cancer cell of claim 1, further comprising a recombinant polynucleotide encoding an allele of an HLA-DP gene, an HLA-DM gene, an HLA-DOA gene, an HLA-DOB gene, an HLA-DQ gene, an HLA-DRA gene, or a combination thereof.

6. The modified human cancer cell of claim 1, further comprising a recombinant polynucleotide encoding interferon alpha (IFN-α).

7. The modified human cancer cell of claim 1, wherein the modified human cancer cell is derived from a human cancer cell line.

8. The modified human cancer cell of claim 7, wherein the human cancer cell line is a breast, skin, prostate, or lung cancer cell line.

9. The modified human cancer cell of claim 8, wherein:
   (a) the human cancer cell line is an SV-BR-1, MDA-MB-231, or MDA-MB-157 breast cancer cell line;
   (b) the human cancer cell line is an A375-C6 skin cancer cell line;
   (c) the human cancer cell line is an LNCaP clone FGC or PC-3 prostate cancer cell line; or (d) the human cancer cell line is a COR-L23/R, COR-L23/5010, or SHP-77 lung cancer cell line.

10. A composition comprising a modified human cancer cell comprising:
(a) a recombinant polynucleotide encoding an allele of a human leukocyte antigen (HLA) class II gene,
wherein the HLA class II gene comprises an HLA-DRB3 gene, an HLA-DRB4 gene, an HLA-DRB5 gene, or a combination thereof, and
wherein the allele of the HLA-DRB3 gene comprises HLA-DRB3*02:02, HLA-DRB3*01:01, HLA-DRB3*03:01, or a combination thereof; and
(b) a recombinant polynucleotide encoding an allele of an HLA class I gene,
wherein the allele of the HLA class I gene comprises HLA-A*11:01, HLA-A*01:01, HLA-A*02:01, HLA-A*03:01, HLA-A*26:01, HLA-A*29:02, HLA-A*32:01, HLA-A*24:02, HLA-A*33:03, HLA-A*68:01, HLA-A*31:01, HLA-A*02:06, or a combination thereof,
wherein the composition further comprises granulocyte-macrophage colony-stimulating factor (GM-CSF).

11. The composition of claim 10, wherein the recombinant polynucleotides are present on one or more vectors in the cell.

12. The composition of claim 10, wherein one or more of the recombinant polynucleotides is integrated into the genome of the cell.

13. The composition of claim 10, wherein the cell further comprises a recombinant polynucleotide encoding an allele of an HLA-B gene, an HLA-C gene, an HLA-E gene, an HLA-F gene, an HLA-G gene, a beta-2-microglobulin (B2M) gene, or a combination thereof.

14. The composition of claim 10, wherein the cell further comprises a recombinant polynucleotide encoding an allele of an HLA-DP gene, an HLA-DM gene, an HLA-DOA gene, an HLA-DOB gene, an HLA-DQ gene, an HLA-DRA gene, or a combination thereof.

15. The composition of claim 10, wherein the GM-CSF is encoded by a recombinant polynucleotide and expressed by the modified human cancer cell.

16. The composition of claim 10, wherein the GM-CSF is present in a soluble form.

17. The composition of claim 10, further comprising interferon alpha (IFN-α).

18. The composition of claim 17, wherein the IFN-α is expressed by the modified human cancer cell.

19. The composition of claim 17, wherein the IFN-α is present in a soluble form.

20. The composition of claim 10, wherein the modified human cancer cell is derived from a human cancer cell line.

21. The composition of claim 20, wherein the human cancer cell line is a breast, skin, prostate, or lung cancer cell line.

22. The composition of claim 21, wherein:
(a) the human cancer cell line is an SV-BR-1, MDA-MB-231, or MDA-MB-157 breast cancer cell line;
(b) the human cancer cell line is an A375-C6 skin cancer cell line;
(c) the human cancer cell line is an LNCaP clone FGC or PC-3 prostate cancer cell line; or
(d) the human cancer cell line is a COR-L23/R, COR-L23/5010, or SHP-77 lung cancer cell line.

23. A pharmaceutical composition comprising the composition of claim 10 and a pharmaceutically acceptable carrier.

24. A method for treating cancer in a subject, the method comprising administering to the subject a therapeutically effective amount of the pharmaceutical composition of claim 23.

25. The method of claim 24, further comprising treating the subject with a therapy selected from the group consisting of chemotherapy, immunotherapy, radiotherapy, hormone therapy, a differentiating agent, a small-molecule drug, and a combination thereof.

26. The method of claim 25, wherein the immunotherapy comprises an agent selected from the group consisting of an immune checkpoint inhibitor, a monoclonal antibody, a small-molecule drug, and a combination thereof.

27. The method of claim 25, wherein the chemotherapy comprises an agent selected from the group consisting of an alkylating agent, an antimetabolite, an anti-tumor antibiotic, a topoisomerase inhibitor, a mitotic inhibitor, a corticosteroid, and a combination thereof.

28. The method of claim 24, wherein the pharmaceutical composition is administered by injection.

29. The method of claim 28, wherein the injection is an intradermal and/or intralymphatic injection.

30. A modified human cancer cell comprising:
(a) a recombinant polynucleotide encoding an allele of a human leukocyte antigen (HLA) class I gene; and
(b) a recombinant polynucleotide encoding an allele of an HLA class II gene,
wherein the allele of the HLA class I gene comprises an HLA-A*02:01 allele and an HLA-A*11:01 allele.

31. The modified human cancer cell of claim 30, wherein the allele of the HLA class II gene comprises an allele of an HLA-DRB3 gene and an allele of an HLA-DRB4 gene.

32. The modified human cancer cell of claim 31, wherein the allele of the HLA-DRB3 gene comprises an HLA-DRB3 *03:01 allele or an HLA-DRB3 *01:01 allele.

33. The modified human cancer cell of claim 32, further comprising a recombinant polynucleotide encoding granulocyte-macrophage colony-stimulating factor (GM-CSF).

34. The modified human cancer cell of claim 33, further comprising a recombinant polynucleotide encoding interferon alpha (IFN-α).

35. The modified human cancer cell of claim 34, wherein the modified human cancer cell is derived from a human cancer cell line.

36. The modified human cancer cell of claim 35, wherein the human cancer cell line is a breast, skin, prostate, or lung cancer cell line.

37. A modified human cancer cell comprising:
(a) a recombinant polynucleotide encoding an allele of a human leukocyte antigen (HLA) class I gene; and
(b) a recombinant polynucleotide encoding an allele of an HLA class II gene,
wherein the allele of the HLA class I gene comprises an HLA-A*01:01 allele and an HLA-A*68:01 allele.

38. The modified human cancer cell of claim 37, wherein the allele of the HLA class II gene comprises (i) an allele of an HLA-DRB3 gene and an allele of an HLA-DRB4 gene or (ii) an allele of an HLA-DRB3 gene and an allele of an HLA-DRB5 gene.

39. The modified human cancer cell of claim 38, wherein the allele of the HLA-DRB3 gene comprises an HLA-DRB3*02:02 allele.

40. The modified human cancer cell of claim 39, further comprising a recombinant polynucleotide encoding GM-CSF.

41. The modified human cancer cell of claim 40, further comprising a recombinant polynucleotide encoding IFN-α.

42. The modified human cancer cell of claim 41, wherein the modified human cancer cell is derived from a human cancer cell line.

43. The modified human cancer cell of claim 42, wherein the human cancer cell line is a breast, skin, prostate, or lung cancer cell line.

44. A modified human cancer cell comprising:
(a) a recombinant polynucleotide encoding an allele of a human leukocyte antigen (HLA) class I gene; and
(b) a recombinant polynucleotide encoding an allele of an HLA class II gene,
wherein the allele of the HLA class I gene comprises an HLA-A*03:01 allele, and wherein the allele of the HLA class II gene comprises an allele of an HLA-DRB3 gene and an allele of an HLA-DRB5 gene.

45. The modified human cancer cell of claim 44, wherein the allele of the HLA-DRB3 gene comprises an HLA-DRB3 *01:01 allele or an HLA-DRB3*03:01 allele.

46. The modified human cancer cell of claim 45, further comprising a recombinant polynucleotide encoding GM-CSF.

47. The modified human cancer cell of claim 46, further comprising a recombinant polynucleotide encoding IFN-α.

48. The modified human cancer cell of claim 47, wherein the modified human cancer cell is derived from a human cancer cell line.

49. The modified human cancer cell of claim 48, wherein the human cancer cell line is a breast, skin, prostate, or lung cancer cell line.

50. A modified human cancer cell comprising:
(a) a recombinant polynucleotide encoding an allele of a human leukocyte antigen (HLA) class I gene; and
(b) a recombinant polynucleotide encoding an allele of an HLA class II gene,
wherein the allele of the HLA class I gene comprises an HLA-A*24:02 allele and an HLA-A*33:03 allele.

51. The modified human cancer cell of claim 50, wherein the allele of the HLA class II gene comprises (i) an allele of an HLA-DRB5 gene or (ii) an allele of an HLA-DRB3 gene and an allele of an HLA-DRB5 gene.

52. The modified human cancer cell of claim 51, further comprising a recombinant polynucleotide encoding GM-CSF.

53. The modified human cancer cell of claim 52, further comprising a recombinant polynucleotide encoding IFN-α.

54. The modified human cancer cell of claim 53, wherein the modified human cancer cell is derived from a human cancer cell line.

55. The modified human cancer cell of claim 54, wherein the human cancer cell line is a breast, skin, prostate, or lung cancer cell line.

56. The modified human cancer cell of claim 36, wherein:
(a) the human cancer cell line is an SV-BR-1, MDA-MB-231, or MDA-MB-157 breast cancer cell line;
(b) the human cancer cell line is an A375-C6 skin cancer cell line;
(c) the human cancer cell line is an LNCaP clone FGC or PC-3 prostate cancer cell line; or
(d) the human cancer cell line is a COR-L23/R, COR-L23/5010, or SHP-77 lung cancer cell line.

57. The modified human cancer cell of claim 43, wherein:
(a) the human cancer cell line is an SV-BR-1, MDA-MB-231, or MDA-MB-157 breast cancer cell line;
(b) the human cancer cell line is an A375-C6 skin cancer cell line;
(c) the human cancer cell line is an LNCaP clone FGC or PC-3 prostate cancer cell line; or
(d) the human cancer cell line is a COR-L23/R, COR-L23/5010, or SHP-77 lung cancer cell line.

58. The modified human cancer cell of claim 49, wherein:
(a) the human cancer cell line is an SV-BR-1, MDA-MB-231, or MDA-MB-157 breast cancer cell line;
(b) the human cancer cell line is an A375-C6 skin cancer cell line;
(c) the human cancer cell line is an LNCaP clone FGC or PC-3 prostate cancer cell line; or
(d) the human cancer cell line is a COR-L23/R, COR-L23/5010, or SHP-77 lung cancer cell line.

59. The modified human cancer cell of claim 55, wherein:
(a) the human cancer cell line is an SV-BR-1, MDA-MB-231, or MDA-MB-157 breast cancer cell line;
(b) the human cancer cell line is an A375-C6 skin cancer cell line;
(c) the human cancer cell line is an LNCaP clone FGC or PC-3 prostate cancer cell line; or
(d) the human cancer cell line is a COR-L23/R, COR-L23/5010, or SHP-77 lung cancer cell line.

60. The modified human cancer cell of claim 1, wherein the modified human cancer cell is derived from a cancer cell obtained from a tumor biopsy.

61. The modified human cancer cell of claim 60, wherein the cancer cell is a breast, skin, prostate, or lung cancer cell.

62. The composition of claim 10, wherein the modified human cancer cell is derived from a cancer cell obtained from a tumor biopsy.

63. The composition of claim 62, wherein the cancer cell is a breast, skin, prostate, or lung cancer cell.

64. The modified human cancer cell of claim 34, wherein the modified human cancer cell is derived from a cancer cell obtained from a tumor biopsy.

65. The modified human cancer cell of claim 64, wherein the cancer cell is a breast, skin, prostate, or lung cancer cell.

66. The modified human cancer cell of claim 41, wherein the modified human cancer cell is derived from a cancer cell obtained from a tumor biopsy.

67. The modified human cancer cell of claim 66, wherein the cancer cell is a breast, skin, prostate, or lung cancer cell.

68. The modified human cancer cell of claim 47, wherein the modified human cancer cell is derived from a cancer cell obtained from a tumor biopsy.

69. The modified human cancer cell of claim 68, wherein the cancer cell is a breast, skin, prostate, or lung cancer cell.

70. The modified human cancer cell of claim 53, wherein the modified human cancer cell is derived from a cancer cell obtained from a tumor biopsy.

71. The modified human cancer cell of claim 70, wherein the cancer cell is a breast, skin, prostate, or lung cancer cell.

72. The modified human cancer cell of claim 30, wherein the recombinant polynucleotides are present on one or more vectors in the cell.

73. The modified human cancer cell of claim 37, wherein the recombinant polynucleotides are present on one or more vectors in the cell.

74. The modified human cancer cell of claim 44, wherein the recombinant polynucleotides are present on one or more vectors in the cell.

75. The modified human cancer cell of claim 50, wherein the recombinant polynucleotides are present on one or more vectors in the cell.

76. A modified human cancer cell comprising:
(a) a recombinant polynucleotide encoding an allele of a human leukocyte antigen (HLA) class I gene; and
(b) a recombinant polynucleotide encoding an allele of an HLA class II gene, wherein the allele of the HLA class II gene comprises HLA-DRB3*02:02, HLA-DRB3*01:01, HLA-DRB3*03:01, or a combination thereof.

77. The modified human cancer cell of claim 76, wherein the recombinant polynucleotides are present on one or more vectors in the cell.

78. The modified human cancer cell of claim 76, wherein the HLA class I gene is selected from the group consisting of an HLA-A gene, an HLA-B gene, an HLA-C gene, an HLA-E gene, an HLA-F gene, an HLA-G gene, a beta-2-microglobulin (B2M) gene, and a combination thereof.

79. The modified human cancer cell of claim 76, further comprising a recombinant polynucleotide encoding an allele of an HLA-DP gene, an HLA-DM gene, an HLA-DOA gene, an HLA-DOB gene, an HLA-DQ gene, an HLA-DRA gene, an HLA-DRB1 gene, an HLA-DRB4 gene, an HLA-DRB5 gene, or a combination thereof.

80. The modified human cancer cell of claim 76, further comprising a recombinant polynucleotide encoding granulocyte-macrophage colony-stimulating factor (GM-CSF).

81. The modified human cancer cell of claim 76, further comprising a recombinant polynucleotide encoding interferon alpha (IFN-α).

* * * * *

SEQUENCE LISTING

<160> NUMBER OF SEQ ID NOS: 14

<210> SEQ ID NO 1
<211> LENGTH: 1098
<212> TYPE: DNA
<213> ORGANISM: Homo sapiens

<400> SEQUENCE: 1

| | | | | | |
|---|---|---|---|---|---|
| atggccgtca | tggcgccccg | aaccctcgtc | ctgctactct | cggggctct | ggccctgacc | 60 |
| cagacctggg | cgggctctca | ctccatgagg | tatttcttca | catccgtgtc | ccggcccggc | 120 |
| cgcggggagc | cccgcttcat | cgcagtgggc | tacgtggacg | acacgcagtt | cgtgcggttc | 180 |
| gacagcgacg | ccgcgagcca | gaggatggag | ccgcgggcgc | cgtggataga | gcaggagggt | 240 |
| ccggagtatt | gggacgggga | gacacggaaa | gtgaaggccc | actcacagac | tcaccgagtg | 300 |
| gacctgggga | ccctgcgcgg | ctactacaac | cagagcgagg | ccggttctca | caccgtccag | 360 |
| aggatgtatg | gctgcgacgt | ggggtcggac | tggcgcttcc | tccgcgggta | ccaccagtac | 420 |
| gcctacgacg | gcaaggatta | catcgccctg | aaagaggacc | tgcgctcttg | gaccgcggcg | 480 |
| gacatggcag | ctcagaccac | caagcacaag | tgggaggcgg | cccatgtggc | ggagcagttg | 540 |
| agagcctacc | tggagggcac | gtgcgtggag | tggctccgca | gatacctgga | gaacgggaag | 600 |
| gagacgctgc | agcgcacgga | cgcccccaaa | acgcatatga | ctcaccacgc | tgtctctgac | 660 |
| catgaagcca | ccctgaggtg | ctgggccctg | agcttctacc | ctgcggagat | cacactgacc | 720 |
| tggcagcggg | atggggagga | ccagacccag | gacacggagc | tcgtggagac | caggcctgca | 780 |
| ggggatggaa | ccttccagaa | gtgggcggct | gtggtggtgc | ttctggaca | ggagcagaga | 840 |
| tacacctgcc | atgtgcagca | tgagggtttg | cccaagcccc | tcaccctgag | atgggagccg | 900 |
| tcttcccagc | ccaccatccc | catcgtgggc | atcattgctg | gcctggttct | ctttggagct | 960 |
| gtgatcactg | gagctgtggt | cgctgctgtg | atgtggagga | ggaagagctc | agatagaaaa | 1020 |
| ggagggagct | actctcaggc | tgcaagcagt | gacagtgccc | agggctctga | tgtgtctctc | 1080 |
| acagcttgta | aagtgtga | | | | | 1098 |

<210> SEQ ID NO 2
<211> LENGTH: 1098
<212> TYPE: DNA
<213> ORGANISM: Artificial Sequence
<220> FEATURE:
<223> OTHER INFORMATION: Synthetic Construct

<400> SEQUENCE: 2

| | | | | | |
|---|---|---|---|---|---|
| atggctgtta | tggcccctag | aacactggtg | ctgctgctgt | ctggtgccct | ggctctgaca | 60 |
| caaacatggg | ccggcagcca | cagcatgcgg | tacttttca | ccagcgtgtc | cagacctggc | 120 |
| agaggcgagc | ctagattcat | tgccgtgggc | tacgtggacg | acacccagtt | cgtcagattc | 180 |
| gattccgatg | ccgccagcca | gcggatggaa | cctagagcac | cttggatcga | gcaagagggc | 240 |

```
cccgagtatt gggacggcga gacaagaaaa gtgaaggccc acagccagac acacagagtg      300
gatctgggaa ccctgcgggg ctactacaat cagtctgagg ccggctctca caccgtgcag      360
aggatgtatg gctgtgacgt gggcagcgat tggcggttcc tgagaggcta tcaccagtac      420
gcctacgacg gcaaggacta tatcgccctg aaagaggacc tgcggtcttg acagccgcc       480 gatatggctg cccagaccac aaagcacaag tgggaagccg ctcacgtggc cgaacagctg      540
agagcttatc tggaaggcac ctgtgtggaa tggctgcgga gatacctgga aaacggcaaa      600
gagacactgc agcggacaga cgcccctaag acacacatga caccacgc cgtgtccgac        660 cacgaagcca cacttagatg ttgggccctg agcttctacc ccgccgagat cacactgaca      720
tggcagagag atggcgagga tcagacccag gataccgagc tggtggaaac aagacctgcc      780
ggcgacggca ccttccagaa atgggctgct gtggtggtgc ctagcggcca agagcagaga      840
tacacctgtc acgtgcagca cgagggcctg cctaagcctc ttacactgag atgggagccc      900
agcagccagc ctacaatccc catcgtggga atcattgccg gcctggtgct gtttggcgcc      960
gtgattacag gtgcagtggt ggccgctgtt atgtggcgga gaaagagcag cgacagaaaa     1020
ggcggcagct actctcaggc cgccagctct gattctgccc agggctctga tgtgtctctg     1080
accgcctgca aagtgtga                                                   1098

<210> SEQ ID NO 3
<211> LENGTH: 7126
<212> TYPE: DNA
<213> ORGANISM: Artificial Sequence
<220> FEATURE:
<223> OTHER INFORMATION: Synthetic Constrcut

<400> SEQUENCE: 3
gttaggcgtt ttgcgctgct tcgcgatgta cgggccagat atacgcgttg acattgatta       60
ttgactagtt attaatagta atcaattacg gggtcattag ttcatagccc atatatggag      120
ttccgcgtta cataacttac ggtaaatggc ccgcctggct gaccgcccaa cgacccccgc      180
ccattgacgt caataatgac gtatgttccc atagtaacgc caatagggac tttccattga      240
cgtcaatggg tggagtattt acggtaaact gcccacttgg cagtacatca agtgtatcat      300
atgccaagta cgccccctat tgacgtcaat gacggtaaat ggcccgcctg gcattatgcc      360
cagtacatga ccttatggga ctttcctact tggcagtaca tctacgtatt agtcatcgct      420
attaccatgg tgatgcggtt ttggcagtac atcaatgggc gtggatagcg gtttgactca      480
cggggatttc caagtctcca ccccattgac gtcaatggga gtttgttttg gcaccaaaat      540
caacgggact ttccaaaatg tcgtaacaac tccgccccat tgacgcaaat gggcggtagg      600
cgtgtacggt gggaggtcta taagcagag ctcgtttag tgaaccgtca gatcgcctgg       660
agacgccatc cacgctgttt tgacctccat agaagacacc gggaccgatc cagcctccgg      720
actctagagg atcgaaccct tggatccgcc accatggctg ttatggcccc tagaacactg      780
gtgctgctgc tgtctggtgc cctggctctg acacaaacat gggccggcag ccacagcatg      840
cggtactttt tcaccagcgt gtccagacct ggcagaggcg agcctagatt cattgccgtg      900
ggctacgtgg acgacaccca gttcgtcaga ttcgattccg atgccgccag ccagcggatg      960
gaacctagag caccttggat cgagcaagag ggccccgagt attgggacgg cgagacaaga     1020
aaagtgaagg cccacagcca gacacacaga gtggatctgg aaccctgcg gggctactac      1080 aatcagtctg aggccggctc tcacaccgtg cagaggatgt atggctgtga cgtgggcagc     1140
```

```
gattggcggt tcctgagagg ctatcaccag tacgcctacg acggcaagga ctatatcgcc    1200
ctgaaagagg acctgcggtc ttggacagcc gccgatatgg ctgcccagac cacaaagcac    1260
aagtgggaag ccgctcacgt ggccgaacag ctgagagctt atctggaagg cacctgtgtg    1320
gaatggctgc ggagatacct ggaaaacggc aaagagacac tgcagcggac agacgcccct    1380
aagacacaca tgacacacca cgccgtgtcc gaccacgaag ccacacttag atgttgggcc    1440
ctgagcttct accccgccga gatcacactg acatggcaga gagatggcga ggatcagacc    1500
caggataccg agctggtgga aacaagacct gccggcgacg gcaccttcca gaaatgggct    1560
gctgtggtgg tgcctagcgg ccaagagcag agatacacct gtcacgtgca gcacgagggc    1620
ctgcctaagc ctcttacact gagatgggag cccagcagcc agcctacaat ccccatcgtg    1680
ggaatcattg ccggcctggt gctgtttggc gccgtgatta caggtgcagt ggtggccgct    1740
gttatgtggc ggagaaagag cagcgacaga aaaggcggca gctactctca ggccgccagc    1800
tctgattctg cccagggctc tgatgtgtct ctgaccgcct gcaaagtgtg aatcgataag    1860
ggttcgatcc ctaccggtta gtaatgagtt tgatatctcg acaatcaacc tctgattac    1920 aaaatttgtg aaagattgac tggtattctt aactatgttg ctccttttac gctatgtgga    1980
tacgctgctt taatgccttt gtatcatgct attgcttccc gtatggcttt cattttctcc    2040
tccttgtata atcctggtt gctgtctctt tatgaggagt tgtggcccgt tgtcaggcaa    2100
cgtggcgtgg tgtgcactgt gtttgctgac gcaaccccca ctggttgggg cattgccacc    2160
acctgtcagc tcctttccgg actttcgct ttccccctcc ctattgccac ggcggaactc    2220
atcgccgcct gccttgcccg ctgctggaca ggggctcggc tgttgggcac tgacaattcc    2280
gtggtgttgt cggggaagct gacgtccttt ccatggctgc tcgcctgtgt tgccacctgg    2340
attctgcgcg gacgtccttt ctgctacgtc ccttcggccc tcaatccagc ggaccttcct    2400
tcccgcggcc tgctgccggc tctgcggcct cttccgcgtc ttcgcctttcg ccctcagacg    2460 agtcggatct ccctttgggc cgcctccccg cctggaacgg gggaggctaa ctgaaacacg    2520
gaaggagaca ataccggaag gaacccgcgc tatgacggca ataaaaagac agaataaaac    2580
gcacgggtgt tgggtcgttt gttcataaac gcggggttcg gtcccagggc tggcactctg    2640 tcgataccc accgagaccc cattggggcc aatacgcccg cgtttcttcc ttttccccac    2700
cccacccccc aagttcgggt gaaggcccag ggctcgcagc caacgtcggg gcggcaggcc    2760
ctgccatagc agatctgcgc agctggggct ctaggggta tccccacgcg ccctgtagcg    2820
gcgcattaag cgcggcgggt gtggtggtta cgcgcagcgt gaccgctaca cttgccagcg    2880
ccctagcgcc cgctcctttc gctttcttcc cttcctttct cgccacgttc gccggctttc    2940
cccgtcaagc tctaaatcgg gggctccctt tagggttccg atttagtgct ttacggcacc    3000
tcgaccccaa aaaacttgat tagggtgatg gttcacgtag tgggccatcg ccctgataga    3060 cggttttcg ccctttgacg ttggagtcca cgttctttaa tagtggactc ttgttccaaa    3120
ctggaacaac actcaaccct atctcggtct attcttttga tttataaggg attttgccga    3180
tttcggccta ttggttaaaa aatgagctga tttaacaaaa atttaacgcg aattaattct    3240
gtggaatgtg tgtcagttag ggtgtggaaa gtccccaggc tccccagcag gcagaagtat    3300
gcaaagcatg catctcaatt agtcagcaac caggtgtgga aagtccccag gctccccagc    3360
aggcagaagt atgcaaagca tgcatctcaa ttagtcagca accatagtcc cgcccctaac    3420
tccgcccatc ccgcccctaa ctccgcccag ttccgcccat tctccgcccc atggctgact    3480
aatttttttt atttatgcag aggccgaggc cgcctctgcc tctgagctat tccagaagta    3540
```

```
gtgaggaggc ttttttggag gcctaggctt ttgcaaaaag ctcccgggag cttgtatatc    3600
cattttcgga tctgatcaag agacaggatg aggatcgttt cgcatgattg aacaagatgg    3660
attgcacgca ggttctccgg ccgcttgggt ggagaggcta ttcggctatg actgggcaca    3720
acagacaatc ggctgctctg atgccgccgt gttccggctg tcagcgcagg gcgcccggt     3780 tcttttttgtc aagaccgacc tgtccggtgc cctgaatgaa ctgcaggacg aggcagcgcg    3840
gctatcgtgg ctggccacga cgggcgttcc ttgcgcagct gtgctcgacg ttgtcactga    3900
agcgggaagg gactggctgc tattgggcga agtgccgggg caggatctcc tgtcatctca    3960
ccttgctcct gccgagaaag tatccatcat ggctgatgca atgcggcggc tgcatacgct    4020
tgatccggct acctgcccat tcgaccacca agcgaaacat cgcatcgagc gagcacgtac    4080
tcggatggaa gccggtcttg tcgatcagga tgatctggac gaagagcatc aggggctcgc    4140
gccagccgaa ctgttcgcca ggctcaaggc gcgcatgccc gacggcgagg atctcgtcgt    4200
gacccatggc gatgcctgct tgccgaatat catggtggaa aatggccgct tttctggatt    4260
catcgactgt ggccggctgg gtgtggcgga ccgctatcag acatagcgt tggctacccg     4320 tgatattgct gaagagcttg gcggcgaatg ggctgaccgc ttcctcgtgc tttacggtat    4380
cgccgctccc gattcgcagc gcatcgcctt ctatcgcctt cttgacgagt tcttctgagc    4440
gggactctgg ggttcgcgaa atgaccgacc aagcgacgcc caacctgcca tcacgagatt    4500
tcgattccac cgccgccttc tatgaaaggt tgggcttcgg aatcgttttc cgggacgccg    4560
gctggatgat cctccagcgc ggggatctca tgctggagtt cttcgcccac ccaaacttgt    4620
ttattgcagc ttataatggt tacaaataaa gcaatagcat cacaaatttc acaaataaag    4680 cattttttc actgcattct agttgtggtt tgtccaaact catcaatgta tcttatcatg      4740
tctgtatacc gtcgacctct agctagagct tggcgtaatc atggtcatag ctgtttcctg    4800
tgtgaaattg ttatccgctc acaattccac acaacatacg agccgaagc ataaagtgta     4860 aagcctgggg tgcctaatga gtgagctaac tcacattaat tgcgttgcgc tcactgcccg    4920
ctttccagtc gggaaacctg tcgtgccagc tgcattaatg aatcggccaa cgcgcgggga    4980
gaggcggttt gcgtattggg cgctcttccg cttcctcgct cactgactcg ctgcgctcgg    5040
tcgttcggct gcggcgagcg gtatcagctc actcaaaggc ggtaatacgg ttatccacag    5100
aatcagggga taacgcagga aagaacatgt gagcaaaagg ccagcaaaag gccaggaacc    5160
gtaaaaaggc cgcgttgctg gcgtttttcc ataggctccg cccccctgac gagcatcaca    5220
aaaatcgacg ctcaagtcag aggtggcgaa acccgacagg actataaaga taccaggcgt    5280
ttccccctgg aagctccctc gtgcgctctc ctgttccgac cctgccgctt accggatacc    5340
tgtccgcctt tctcccttcg ggaagcgtgg cgctttctca tagctcacgc tgtaggtatc    5400
tcagttcggt gtaggtcgtt cgctccaagc tgggctgtgt gcacgaaccc cccgttcagc    5460
ccgaccgctg cgccttatcc ggtaactatc gtcttgagtc aacccggta agacacgact     5520 tatcgccact ggcagcagcc actggtaaca ggattagcag agcgaggtat gtaggcggtg    5580
ctacagagtt cttgaagtgg tggcctaact acggctacac tagaagaaca gtatttggta    5640
tctgcgctct gctgaagcca gttaccttcg gaaaaagagt tggtagctct tgatccggca    5700
aacaaaccac cgctggtagc ggtggttttt tgtttgcaa gcagcagatt acgcgcagaa    5760
aaaaaggatc tcaagaagat cctttgatct tttctacggg gtctgacgct cagtggaacg    5820
aaaactcacg ttaagggatt ttggtcatga gattatcaaa aaggatcttc acctagatcc    5880
```

-continued

| | |
|---|---|
| ttttaaatta aaaatgaagt tttaaatcaa tctaaagtat atatgagtaa acttggtctg | 5940 |
| acagttacca atgcttaatc agtgaggcac ctatctcagc gatctgtcta tttcgttcat | 6000 |
| ccatagttgc ctgactcccc gtcgtgtaga taactacgat acgggagggc ttaccatctg | 6060 |
| gccccagtgc tgcaatgata ccgcgagacc cacgctcacc ggctccagat ttatcagcaa | 6120 |
| taaaccagcc agccggaagg gccgagcgca gaagtggtcc tgcaacttta ccgcctcca | 6180 |
| tccagtctat taattgttgc cgggaagcta gagtaagtag ttcgccagtt aatagtttgc | 6240 |
| gcaacgttgt tgccattgct acaggcatcg tggtgtcacg ctcgtcgttt ggtatggctt | 6300 |
| cattcagctc cggttcccaa cgatcaaggc gagttacatg atcccccatg ttgtgcaaaa | 6360 |
| aagcggttag ctccttcggt cctccgatcg ttgtcagaag taagttggcc gcagtgttat | 6420 |
| cactcatggt tatggcagca ctgcataatt ctcttactgt catgccatcc gtaagatgct | 6480 |
| tttctgtgac tggtgagtac tcaaccaagt cattctgaga atagtgtatg cggcgaccga | 6540 |
| gttgctcttg cccggcgtca atacgggata taccgcgcc acatagcaga actttaaaag | 6600 |
| tgctcatcat tggaaaacgt tcttcggggc gaaaactctc aaggatctta ccgctgttga | 6660 |
| gatccagttc gatgtaaccc actcgtgcac ccaactgatc ttcagcatct tttactttca | 6720 |
| ccagcgtttc tgggtgagca aaaacaggaa ggcaaaatgc cgcaaaaaag gaataagggg | 6780 |
| cgacacggaa atgttgaata ctcatactct tcctttttca atattattga agcatttatc | 6840 |
| agggttattg tctcatgagc ggatacatat ttgaatgtat ttagaaaaat aaacaaatag | 6900 |
| gggttccgcg cacatttccc cgaaaagtgc cacctgacgt cgacggatcg ggagatctcc | 6960 |
| cgatccccta tggtcgactc tcagtacaat ctgctctgat gccgcatagt taagccagta | 7020 |
| tctgctccct gcttgtgtgt tggaggtcgc tgagtagtgc gcgagcaaaa tttaagctac | 7080 |
| aacaaggcaa ggcttgaccg acaattgcat gaagaatctg cttagg | 7126 |

<210> SEQ ID NO 4
<211> LENGTH: 801
<212> TYPE: DNA
<213> ORGANISM: Homo sapiens

<400> SEQUENCE: 4

| | |
|---|---|
| atggtgtgtc tgaagctccc tggaggctcc agcttggcag cgttgacagt gacactgatg | 60 |
| gtgctgagct cccgactggc tttcgctggg gacacccgac cacgtttctt ggagctgctt | 120 |
| aagtctgagt gtcatttctt caatgggacg gagcgggtgc ggttcctgga gagacacttc | 180 |
| cataaccagg aggagtacgc gcgcttcgac agcgacgtgg gggagtaccg ggcggtgagg | 240 |
| gagctggggc ggcctgatgc cgagtactgg aacagccaga aggacctcct ggagcagaag | 300 |
| cggggccagt ggacaattac tgcagacac aactacgggg ttggtgagag cttcacagtg | 360 |
| cagcggcgag tccatcctca ggtgactgtg tatcctgcaa agacccagcc cctgcagcac | 420 |
| cacaacctcc tggtctgctc tgtgagtggt ttctatccag gcagcattga agtcaggtgg | 480 |
| ttccggaacg gccaggaaga gaaggctggg gtggtgtcca cgggcctgat ccagaatgga | 540 |
| gactggacct tccagaccct ggtgatgcta gaaacagttc ctcggagtgg agaggtttac | 600 |
| acctgccaag tggagcaccc aagcgtaacg agccctctca cagtggaatg gagtgcacgg | 660 |
| tctgaatctg cacagagcaa gatgctgagt ggagtcgggg gctttgtgct gggcctgctc | 720 |
| ttccttgggg ccgggctgtt catctacttc aggaatcaga aggacactc tggacttcag | 780 |
| ccaacaggat tcctgagctg a | 801 |

<210> SEQ ID NO 5
<211> LENGTH: 801
<212> TYPE: DNA
<213> ORGANISM: Artificial Sequence
<220> FEATURE:
<223> OTHER INFORMATION: Synthetic Construct

<400> SEQUENCE: 5

```
atggtgtgtc tgaagctccc tggaggctcc agcttggcag cgttgacagt gacactgatg      60
gtgctgagct cccgactggc tttcgctggg gacacccgac acgtttctt ggagctgctt      120
aagtctgagt gtcatttctt caatgggacg gagcgggtgc ggttcctgga gagacacttc     180
cataaccagg aggagtacgc gcgcttcgac agcgacgtgg gggagtaccg ggcggtgagg     240
gagctggggc ggcctgatgc cgagtactgg aacagccaga aggacctcct ggagcagaag     300
cggggccagg tggacaatta ctgcagacac aactacgggg ttggtgagag cttcacagtg     360
cagcggcgag tccatcctca ggtgactgtg tatcctgcaa agacccagcc cctgcagcac     420
cacaacctcc tggtctgctc tgtgagtggt ttctatccag gcagcattga agtcaggtgg     480
ttccggaacg gccaggaaga aaggctgggg gtggtgtcca cgggcctgat ccagaatgga     540
gactggacct tccagaccct ggtgatgcta gaaacagttc ctcggagtgg agaggtttac     600
acctgccaag tggagcaccc aagcgtaacg agccctctca cagtggaatg gagtgcaagg     660
tctgaatctg cacagagcaa gatgctgagt ggagtcgggg gctttgtgct gggcctgctc     720
ttccttgggg ccgggctgtt catctacttc aggaatcaga aggacactc tggacttcag     780
ccaacaggat tcctgagctg a                                                801
```

<210> SEQ ID NO 6
<211> LENGTH: 801
<212> TYPE: DNA
<213> ORGANISM: Artificial Sequence
<220> FEATURE:
<223> OTHER INFORMATION: Synthetic Construct

<400> SEQUENCE: 6

```
atggttttgcc ttaaactgcc tggcggcagc tctctggctg ccctgacagt tacactgatg     60
gtgctgagca gcagactggc cttttgccggc gatacccggc ctagatttct ggaactgctg    120
aagtccgagt gccacttctt caacggaacc gagagagtgc ggttcctgga aggcacttc     180
cacaatcaag aggaatacgc cagattcgac agcgacgtgg gcgagtacag agccgtcaga    240
gaactgggca gacccgatgc cgagtactgg aacagccaga aggacctgct ggaacagaag    300
agaggccagg tcgacaacta ctgccggcac aattatggcg tgggcgaaag cttcaccgtg    360
cagagaagag tgcatcccca agtgacagtg taccccgcca agacacagcc tctgcagcac    420
cacaatctgc tcgtgtgtag cgtgtccggc ttctaccctg gctctatcga agtgcggtgg    480
ttcagaaacg gccaagagga aaaggccggc gtcgtcagca caggcctgat ccaaaatggc    540
gactggacct tcagaccct ggtcatgctg gaaaccgtgc ctagaagcgg cgaggtgtac   600
acatgccagg tggaacaccc tagcgtgaca agccctctga cagtcgagtg gagcgccaga   660
tctgaaagcg cccagagcaa gatgctgtct ggcgttggcg gatttgtgct gggcctgctg   720
tttcttggag ccggcctgtt catctacttc cggaaccaga agggccacag cggcttgcag   780
ccaacaggct ttctgagctg a                                              801
```

<210> SEQ ID NO 7
<211> LENGTH: 6829
<212> TYPE: DNA

<213> ORGANISM: Artificial Sequence
<220> FEATURE:
<223> OTHER INFORMATION: Synthetic Construct

<400> SEQUENCE: 7

```
gttaggcgtt ttgcgctgct tcgcgatgta cgggccagat atacgcgttg acattgatta    60
ttgactagtt attaatagta atcaattacg gggtcattag ttcatagccc atatatggag   120
ttccgcgtta cataacttac ggtaaatggc ccgcctggct gaccgcccaa cgaccccgc    180
ccattgacgt caataatgac gtatgttccc atagtaacgc caatagggac tttccattga   240
cgtcaatggg tggagtattt acggtaaact gcccacttgg cagtacatca agtgtatcat   300
atgccaagta cgccccctat tgacgtcaat gacggtaaat ggcccgcctg gcattatgcc   360
cagtacatga ccttatggga ctttcctact tggcagtaca tctacgtatt agtcatcgct   420
attaccatgg tgatgcggtt ttggcagtac atcaatgggc gtggatagcg gtttgactca   480
cggggatttc caagtctcca ccccattgac gtcaatggga gtttgttttg gcaccaaaat   540
caacgggact ttccaaaatg tcgtaacaac tccgccccat tgacgcaaat gggcggtagg   600
cgtgtacggt gggaggtcta tataagcaga gctcgtttag tgaaccgtca gatcgcctgg   660
agacgccatc cacgctgttt tgacctccat agaagacacc gggaccgatc cagcctccgg   720
actctagagg atcgaaccct tctcgaggcc accatggttt gccttaaact gcctggcggc   780
agctctctgg ctgccctgac agttacactg atggtgctga gcagcagact ggcctttgcc   840
ggcgataccc ggcctagatt tctggaactg ctgaagtccg agtgccactt cttcaacgga   900
accgagagag tgcggttcct ggaaaggcac ttcacaatc aagaggaata cgccagattc   960
gacagcgacg tgggcgagta cagagccgtc agagaactgg gcagacccga tgccgagtac  1020
tggaacagcc agaaggacct gctggaacag aagagaggcc aggtcgacaa ctactgccgg  1080
cacaattatg gcgtgggcga aagcttcacc gtgcagagaa gagtgcatcc ccaagtgaca  1140
gtgtaccccg ccaagacaca gcctctgcag caccacaatc tgctcgtgtg tagcgtgtcc  1200
ggcttctacc ctggctctat cgaagtgcgg tggttcagaa acggccaaga ggaaaaggcc  1260
ggcgtcgtca gcacaggcct gatccaaaat ggcgactgga cctttcagac cctggtcatg  1320
ctggaaaccg tgcctagaag cggcgaggtg tacacatgcc aggtggaaca ccctagcgtg  1380
acaagccctc tgacagtcga gtggagcgcc agatctgaaa gcgcccagag caagatgctg  1440
tctggcgttg gcggatttgt gctgggcctg ctgtttcttg gagccggcct gttcatctac  1500
ttccggaacc agaagggcca cagcggcttg cagccaacag gctttctgag ctgagctagc  1560
aagggttcga tccctaccgg ttagtaatga gtttgatatc tcgacaatca acctctggat  1620
tacaaaattt gtgaaagatt gactggtatt cttaactatg ttgctccttt tacgctatgt  1680
ggatacgctg ctttaatgcc tttgtatcat gctattgctt cccgtatggc tttcattttc  1740
tcctccttgt ataaatcctg gttgctgtct ctttatgagg agttgtggcc cgttgtcagg  1800
caacgtggcg tggtgtgcac tgtgtttgct gacgcaaccc ccactggttg ggcattgcc   1860
accacctgtc agctcctttc cgggactttc gctttccccc tccctattgc cacggcggaa  1920
ctcatcgccg cctgccttgc ccgctgctgg acagggctc ggctgttggg cactgacaat  1980
tccgtggtgt tgtcggggaa gctgacgtcc tttccatggc tgctcgcctg tgttgccacc  2040
tggattctgc gcgggacgtc cttctgctac gtcccttcgg ccctcaatcc agcggacctt  2100
ccttcccgcg gcctgctgcc ggctctgcgg cctcttccgc gtcttcgcct tcgccctcag  2160
acgagtcgga tctcccttg ggccgcctcc ccgcctggaa cggggaggc taactgaaac  2220
```

```
acggaaggag acaataccgg aaggaacccg cgctatgacg gcaataaaaa gacagaataa    2280
aacgcacggg tgttgggtcg tttgttcata aacgcggggt tcggtcccag ggctggcact    2340
ctgtcgatac cccaccgaga ccccattggg gccaatacgc ccgcgtttct tccttttccc    2400
caccccaccc cccaagttcg ggtgaaggcc cagggctcgc agccaacgtc ggggcggcag    2460
gccctgccat agcagatctg cgcagctggg gctctagggg gtatcccccac gcgccctgta   2520 gcggcgcatt aagcgcggcg ggtgtggtgg ttacgcgcag cgtgaccgct acacttgcca    2580
gcgccctagc gcccgctcct ttcgctttct tcccttcctt tctcgccacg ttcgccggct    2640
ttccccgtca agctctaaat cggggctcc ctttagggtt ccgatttagt gctttacggc     2700
acctcgaccc caaaaaactt gattaggggtg atggttcacg tagtgggcca tcgccctgat   2760
agacggtttt tcgccctttg acgttggagt ccacgttctt taatagtgga ctcttgttcc    2820
aaactggaac aacactcaac cctatctcgg tctattcttt tgatttataa gggattttgc    2880
cgatttcggc ctattggtta aaaaatgagc tgatttaaca aaaatttaac gcgaattaat    2940
tctgtggaat gtgtgtcagt tagggtgtgg aaagtcccca ggctcccaag caggcagaag    3000
tatgcaaagc atgcatctca attagtcagc aaccaggtgt ggaaagtccc caggctcccc    3060
agcaggcaga agtatgcaaa gcatgcatct caattagtca gcaaccatag tcccgcccct    3120
aactccgccc atcccgcccc taactccgcc cagttccgcc cattctccgc cccatggctg    3180
actaattttt tttatttatg cagaggccga ggccgcctct gcctctgagc tattccagaa    3240
gtagtgagga ggctttttg gaggcctagg cttttgcaaa aagctcccgg gagcttgtat     3300
atccattttc ggatctgatc aagagacagg atgaggatcg tttcgcatga ttgaacaaga    3360
tggattgcac gcaggttctc cggccgcttg ggtggagagg ctattcggct atgactgggc    3420
acaacagaca atcggctgct ctgatgccgc cgtgttccgg ctgtcagcgc aggggcgccc    3480
ggttcttttt gtcaagaccg acctgtccgg tgccctgaat gaactgcagg acgaggcagc    3540
gcggctatcg tggctggcca cgacgggcgt tccttgcgca gctgtgctcg acgttgtcac    3600
tgaagcggga agggactggc tgctattggg cgaagtgccg gggcaggatc tcctgtcatc    3660
tcaccttgct cctgccgaga aagtatccat catggctgat gcaatgcggc ggctgcatac    3720
gcttgatccg gctacctgcc cattcgacca ccaagcgaaa catcgcatcg agcgagcacg    3780
tactcggatg aagccggtc ttgtcgatca ggatgatctg gacgaagagc atcagggggct    3840 cgcgccagcc gaactgttcg ccaggctcaa ggcgcgcatg cccgacggcg aggatctcgt    3900
cgtgacccat ggcgatgcct gcttgccgaa tatcatggtg gaaaatggcc gcttttctgg    3960
attcatcgac tgtggccggc tgggtgtggc ggaccgctat caggacatag cgttggctac    4020
ccgtgatatt gctgaagagc ttggcggcga atgggctgac cgcttcctcg tgctttacgg    4080
tatcgccgct cccgattcgc agcgcatcgc cttctatcgc cttcttgacg agttcttctg    4140
agcgggactc tggggttcgc gaaatgaccg accaagcgac gcccaacctg ccatcacgag    4200
atttcgattc caccgccgcc ttctatgaaa ggttgggctt cggaatcgtt ttccgggacg    4260
ccggctggat gatcctccag cgcggggatc tcatgctgga gttcttcgcc cacccccaact   4320 tgtttattgc agcttataat ggttacaaat aaagcaatag catcacaaat ttcacaaata    4380
aagcattttt ttcactgcat tctagttgtg gtttgtccaa actcatcaat gtatcttatc    4440
atgtctgtat accgtcgacc tctagctaga gcttggcgta atcatggtca tagctgtttc    4500
ctgtgtgaaa ttgttatccg ctcacaattc cacacaacat acgagccgga agcataaagt    4560
```

```
gtaaagcctg gggtgcctaa tgagtgagct aactcacatt aattgcgttg cgctcactgc   4620
ccgctttcca gtcgggaaac ctgtcgtgcc agctgcatta atgaatcggc caacgcgcgg   4680
ggagaggcgg tttgcgtatt gggcgctctt ccgcttcctc gctcactgac tcgctgcgct   4740
cggtcgttcg gctgcggcga gcggtatcag ctcactcaaa ggcggtaata cggttatcca   4800
cagaatcagg ggataacgca ggaaagaaca tgtgagcaaa aggccagcaa aaggccagga   4860
accgtaaaaa ggccgcgttg ctggcgtttt tccataggct ccgcccccct gacgagcatc   4920
acaaaaatcg acgctcaagt cagaggtggc gaaacccgac aggactataa agataccagg   4980
cgtttccccc tggaagctcc ctcgtgcgct ctcctgttcc gaccctgccg cttaccggat   5040
acctgtccgc ctttctccct tcgggaagcg tggcgctttc tcatagctca cgctgtaggt   5100
atctcagttc ggtgtaggtc gttcgctcca agctgggctg tgtgcacgaa ccccccgttc   5160
agcccgaccg ctgcgcctta tccggtaact atcgtcttga gtccaacccg gtaagacacg   5220
acttatcgcc actggcagca gccactggta acaggattag cagagcgagg tatgtaggcg   5280
gtgctacaga gttcttgaag tggtggccta actacggcta cactagaaga acagtatttg   5340
gtatctgcgc tctgctgaag ccagttacct tcggaaaaag agttggtagc tcttgatccg   5400
gcaaacaaac caccgctggt agcggtggtt tttttgtttg caagcagcag attacgcgca   5460
gaaaaaaagg atctcaagaa gatcctttga tcttttctac ggggtctgac gctcagtgga   5520
acgaaaactc acgttaaggg attttggtca tgagattatc aaaaaggatc ttcacctaga   5580
tccttttaaa ttaaaaatga agttttaaat caatctaaag tatatatgag taaacttggt   5640
ctgacagtta ccaatgctta atcagtgagg cacctatctc agcgatctgt ctatttcgtt   5700
catccatagt tgcctgactc cccgtcgtgt agataactac gatacgggag ggcttaccat   5760
ctggccccag tgctgcaatg ataccgcgag acccacgctc accggctcca gatttatcag   5820
caataaacca gccagccgga agggccgagc gcagaagtgg tcctgcaact ttatccgcct   5880
ccatccagtc tattaattgt tgccgggaag ctagagtaag tagttcgcca gttaatagtt   5940
tgcgcaacgt tgttgccatt gctacaggca tcgtggtgtc acgctcgtcg tttggtatgg   6000
cttcattcag ctccggttcc caacgatcaa ggcgagttac atgatccccc atgttgtgca   6060
aaaaagcggt tagctccttc ggtcctccga tcgttgtcag aagtaagttg gccgcagtgt   6120
tatcactcat ggttatggca gcactgcata attctcttac tgtcatgcca tccgtaagat   6180
gcttttctgt gactggtgag tactcaacca agtcattctg agaatagtgt atgcggcgac   6240
cgagttgctc ttgcccggcg tcaatacggg ataataccgc gccacatagc agaactttaa   6300
aagtgctcat cattggaaaa cgttcttcgg ggcgaaaact ctcaaggatc ttaccgctgt   6360
tgagatccag ttcgatgtaa cccactcgtg cacccaactg atcttcagca tcttttactt   6420
tcaccagcgt ttctgggtga gcaaaaacag gaaggcaaaa tgccgcaaaa aagggaataa   6480
gggcgacacg gaaatgttga atactcatac tcttcctttt tcaatattat tgaagcattt   6540
atcagggtta ttgtctcatg agcggataca tatttgaatg tatttagaaa aataaacaaa   6600
taggggttcc gcgcacattt ccccgaaaag tgccacctga cgtcgacgga tcgggagatc   6660
tcccgatccc ctatggtcga ctctcagtac aatctgctct gatgccgcat agttaagcca   6720
gtatctgctc cctgcttgtg tgttggaggt cgctgagtag tgcgcgagca aaatttaagc   6780
tacaacaagg caaggcttga ccgacaattg catgaagaat ctgcttagg    6829
```

<210> SEQ ID NO 8
<211> LENGTH: 8030

<212> TYPE: DNA
<213> ORGANISM: Artificial Sequence
<220> FEATURE:
<223> OTHER INFORMATION: Synthetic Construct

<400> SEQUENCE: 8

```
cctgcaggcg ttacataact tacggtaaat ggcccgcctg gctgaccgcc caacgacccc    60
cgcccattga cgtcaataat gacgtatgtt cccatagtaa cgccaatagg gactttccat   120
tgacgtcaat gggtggagta tttacggtaa actgcccact tggcagtaca tcaagtgtat   180
catatgccaa gtacgccccc tattgacgtc aatgacggta aatggcccgc ctggcattat   240
gcccagtaca tgaccttatg gactttcct  acttggcagt acatctacgt attagtcatc   300
gctattacca tgatgatgcg gttttggcag tacatcaatg ggcgtggata gcggtttgac   360
tcacggggat ttccaagtct ccaccccatt gacgtcaatg ggagtttgtt ttgactagtc   420
agggccccaa ccccccaag  ccccatttc  acaacacgct ggcgctacag gcgcgtgact   480
tccccttgct ttgggcggg  gggctgagac tcctatgtgc tccggattgg tcaggcacgg   540
ccttcggccc cgcctcctgc caccgcagat tggccgctag gcctccccga gcgccctgcc   600
tccgagggcc ggcgcaccat aaaagaagcc gccctagcca cgtcccctcg cagttcggcg   660
gtcccgcggg tctgtctcaa gcttgccgcc agaacacagg taagtgccgt gtgtggttcc   720
cgcgggcctg gcctctttac gggttatggc ccttgcgtgc cttgaattac ttccatgccc   780
ctggctgcag tacgtgattc ttgatcccga gcttcgggtt ggaagtgggt gggagagttc   840
gaggccttgc gcttaaggag ccccttcgcc tcgtgcttga gttgaggcct ggcttgggcg   900
ctggggccgc cgcgtgctaa tctggtggca ccttcgcgcc tgtctcgctg ctttcgctaa   960
gtctctagcc atttaaaatt tttgataacc agctgcgacg cttttttctt ggcgagatag  1020
tcttgtaaat gcgggccagg atctgcacac tggtatttcg gtttttgggg ccgcgggcgg  1080
cgacggggcc cgtgcgtccc agcgcacatg ttcggcgagg cggggcctgc gagcgcggcc  1140
accgagaatc ggacgggggt agtctcaaac tggccggcct gctctggtgc ctggcctcgc  1200
gccgccgtgt atcgccccgc cctgggcggc aaggctggcc cggtcggcac cagttgcgtg  1260
agcggaaaga tggccgcttc ccggccctgc tgcagggagc tcaaaatgga ggacgcggcg  1320
cccgggagag cgggcgggtg agtcacccac acaaaggaaa agggcctttc cttcctcatc  1380
cgtcgcttca tgtgactcca cggagtaccg ggcgccgtcc aggcacctcg attagttgtc  1440
gagcttttgg agtacgtcgt ctttaggttg ggggagggg  ttttatgcga tggagtttcc  1500
ccacactgag tgggtggaga ctgaagagtt aggccagctt ggcacttgat gtaattctcc  1560
ttggaatttg cccttttga  gtttggatct tgcctcattc tcaagcctca gacagtggtt  1620
caaagttttt ttcttccatt tcaggtgtcg tgaaaactac ccctaaaagc caccggcgtg  1680
cgcaagatct gaattcttcg aactcgaggc caccatggtt tgccttaaac tgcctggcgg  1740
cagctctctg gctgccctga cagttacact gatggtgctg agcagcagac tggcctttgc  1800
cggcgatacc cggcctagat ttctggaact gctgaagtcc gagtgccact tcttcaacgg  1860
aaccgagaga gtgcggttcc tggaaaggca cttccacaat caagaggaat acgccagatt  1920
cgacagcgac gtgggcgagt acagagccgt cagagaactg gcagacccg  atgccgagta  1980
ctggaacagc cagaaggacc tgctggaaca aagagaggc  caggtcgaca actactgccg  2040
gcacaattat ggcgtgggcg aaagcttcac cgtgcagaga agagtgcatc cccaagtgac  2100
agtgtacccc gccaagacac agcctctgca gcaccacaat ctgctcgtgt gtagcgtgtc  2160
```

```
cggcttctac cctggctcta tcgaagtgcg gtggttcaga aacggccaag aggaaaaggc   2220
cggcgtcgtc agcacaggcc tgatccaaaa tggcgactgg acctttcaga ccctggtcat   2280
gctggaaacc gtgcctagaa gcggcgaggt gtacacatgc caggtggaac ccctagcgt    2340 gacaagccct ctgacagtcg agtggagcgc cagatctgaa agcgcccaga gcaagatgct   2400
gtctggcgtt ggcggatttg tgctgggcct gctgtttctt ggagccggcc tgttcatcta   2460
cttccggaac cagaagggcc acagcggctt gcagccaaca ggctttctga gctgagctag   2520
ctggccagac atgataagat acattgatga gtttggacaa accacaacta gaatgcagtg   2580
aaaaaaatgc tttatttgtg aaatttgtga tgctattgct ttatttgtaa ccattataag   2640
ctgcaataaa caagttaaca acaacaattg cattcatttt atgtttcagg ttcaggggga   2700
ggtgtgggag gtttttttaaa gcaagtaaaa cctctacaaa tgtggtatgg aaatgttaat   2760
taactagcca tgaccaaaat cccttaacgt gagttttcgt tccactgagc gtcagacccc   2820
gtagaaaaga tcaaaggatc ttcttgagat cctttttttc tgcgcgtaat ctgctgcttg   2880
caaacaaaaa aaccaccgct accagcggtg gtttgtttgc cggatcaaga gctaccaact   2940 cttttttccga aggtaactgg cttcagcaga gcgcagatac caaatactgt tcttctagtg   3000
tagccgtagt taggccacca cttcaagaac tctgtagcac cgcctacata cctcgctctg   3060
ctaatcctgt taccagtggc tgctgccagt ggcgataagt cgtgtcttac cgggttggac   3120
tcaagacgat agttaccgga taaggcgcag cggtcgggct gaacgggggg ttcgtgcaca   3180
cagcccagct tggagcgaac gacctacacc gaactgagat acctacagcg tgagctatga   3240
gaaagcgcca cgcttcccga agggagaaag gcggacaggt atccggtaag cggcagggtc   3300
ggaacaggag agcgcacgag ggagcttcca gggggaaacg cctggtatct ttatagtcct   3360
gtcgggtttc gccacctctg acttgagcgt cgatttttgt gatgctcgtc aggggggcgg   3420
agcctatgga aaaacgccag caacgcggcc ttttacggt tcctggcctt ttgctggcct   3480
tttgctcaca tgttcttaat taacctgcag ggcctgaaat aacctctgaa agaggaactt   3540
ggttaggtac cttctgaggc tgaaagaacc agctgtggaa tgtgtgtcag ttagggtgtg   3600
gaaagtcccc aggctcccca gcaggcagaa gtatgcaaag catgcatctc aattagtcag   3660
caaccaggtg tggaaagtcc ccaggctccc cagcaggcag aagtatgcaa agcatgcatc   3720
tcaattagtc agcaaccata gtcccactag ttccgccaga gcgcgcgagg gcctccagcg   3780
gccgcccctc ccccacagca ggggcgggt cccgcgccca ccggaaggag cgggctcggg   3840
gcgggcggcg ctgattggcc ggggcgggcc tgacgccgac gcggctataa gagaccacaa   3900
gcgacccgca gggccagacg ttcttcgccg aagcttgccg tcagaacgca ggtgaggggc   3960
gggtgtggct tccgcgggcc gccgagctgg aggtcctgct ccgagcgggc cgggccccgc   4020
tgtcgtcggc ggggattagc tgcgagcatt cccgcttcga gttgcgggcg gcgcgggagg   4080
cagagtgcga ggcctagcgg caaccccgta gcctcgcctc gtgtccggct tgaggcctag   4140
cgtggtgtcc gcgccgccgc gcgtgctac tccgccgca ctctggtctt ttttttttt     4200 gttgttgttg ccctgctgcc ttcgattgcc gttcagcaat aggggctaac aaagggaggg   4260 tgcgggctt gctcgcccgg agcccggaga ggtcatggtt ggggaggaat ggagggacag    4320
gagtggcggc tggggcccgc ccgccttcgg agcacatgtc cgacgccacc tggatggggc   4380
gaggcctggg gttttccccg aagcaaccag gctggggtta gcgtgccgag gccatgtggc   4440
cccagcaccc ggcacgatct ggcttggcgg cgccgcgttg ccctgcctcc ctaactaggg   4500
tgaggccatc ccgtccggca ccagttgcgt gcgtggaaag atggccgctc ccgggccctg   4560
```

```
ttgcaaggag ctcaaaatgg aggacgcggc agcccggtgg agcggcgggt gagtcaccc   4620 acacaaagga agagggcctg gtccctcacc ggctgctgct tcctgtgacc ccgtggtcct   4680
atcggccgca atagtcacct cgggcttttg agcacggcta gtcgcggcgg ggggagggga   4740
tgtaatggcg ttggagtttg ttcacatttg gtgggtggag actagtcagg ccagcctggc   4800
gctggaagtc attttttggaa tttgtcccct tgagttttga gcggagctaa ttctcgggct   4860
tcttagcggt tcaaaggtat cttttaaacc ctttttttagg tgttgtgaaa accaccgcta   4920
attcaaagca accggtgata tcggatccgc caccatggct gttatggccc ctagaacact   4980
ggtgctgctg ctgtctggtg ccctggctct gacacaaaca tgggccggca gccacagcat   5040
gcggtacttt ttcaccagcg tgtccagacc tggcagaggc gagcctagat tcattgccgt   5100
gggctacgtg gacgacaccc agttcgtcag attcgattcc gatgccgcca gccagcggat   5160
ggaacctaga gcaccttgga tcgagcaaga gggccccgag tattgggacg gcgagacaag   5220
aaaagtgaag gcccacagcc agacacacag agtggatctg ggaacccctgc ggggctacta   5280 caatcagtct gaggccggct ctcacaccgt gcagaggatg tatggctgtg acgtgggcag   5340
cgattggcgg ttcctgagag gctatcacca gtacgcctac gacggcaagg actatatcgc   5400
cctgaaagag gacctgcggt cttggacagc cgccgatatg gctgcccaga ccacaaagca   5460
caagtgggaa gccgctcacg tggccgaaca gctgagagct tatctggaag gcacctgtgt   5520
ggaatggctg cggagatacc tggaaaacgg caaagagaca ctgcagcgga cagacgcccc   5580
taagacacac atgacacacc acgccgtgtc cgaccacgaa gccacactta gatgttgggc   5640
cctgagcttc taccccgccg agatcacact gacatggcag agagatggcg aggatcagac   5700
ccaggatacc gagctggtgg aaacaagacc tgccggcgac ggcaccttcc agaaatgggc   5760
tgctgtggtg gtgcctagcg gccaagagca gagatacacc tgtcacgtgc agcacgaggg   5820
cctgcctaag cctcttacac tgagatggga gcccagcagc cagcctacaa tccccatcgt   5880
gggaatcatt gccggcctgg tgctgtttgg cgccgtgatt acaggtgcag tggtggccgc   5940
tgttatgtgg cggagaaaga gcagcgacag aaaaggcggc agctactctc aggccgccag   6000
ctctgattct gcccagggct ctgatgtgtc tctgaccgcc tgcaaagtgt gaatcgattg   6060
tcgaccctag gagcaggttt ccccaatgac acaaaacgtg caacttgaaa ctccgcctgg   6120
tctttccagg tctagagggg taacactttg tactgcgttt ggctccacgc tcgatccact   6180
ggcgagtgtt agtaacagca ctgttgcttc gtagcggagc atgacggccg tgggaactcc   6240
tccttggtaa caaggaccca cggggccaaa agccacgccc acgggccc gtcatgtgtg   6300 caacccagc acggcgactt tactgcgaaa cccactttaa agtgacattg aaactggtac   6360
ccacacactg gtgacaggct aaggatgccc ttcaggtacc ccgaggtaac acgcgacact   6420
cgggatctga aaggggact ggggcttcta taaaagcgct cggtttaaaa agcttctatg   6480
cctgaatagg tgaccggagg tcggcacctt tcctttgcaa ttactgaccc tatgaataca   6540
actgactgtt tgacaattaa tcatcggcat agtatatcgg catagtataa tacgactcac   6600
tataggaggg ccaccatgat tgaacaagat ggattgcacg caggttctcc ggccgcttgg   6660
gtggagaggc tattcggcta tgactgggca caacagacaa tcggctgctc tgatgccgcc   6720
gtgttccggc tgtcagcgca ggggcgcccg gttcttttttg tcaagaccga cctgtccggt   6780
gccctgaatg aactgcaaga cgaggcagcg cggctatcgt ggctggccac gacgggcgtt   6840
ccttgcgcag ctgtgctcga cgttgtcact gaagcgggaa gggactggct gctattgggc   6900
```

```
gaagtgccgg ggcaggatct cctgtcatct caccttgctc ctgccgagaa agtatccatc    6960
atggctgatg caatgcggcg gctgcatacg cttgatccgg ctacctgccc attcgaccac    7020
caagcgaaac atcgcatcga gcgagcacgt actcggatgg aagccggtct tgtcgatcag    7080
gatgatctgg acgaagagca tcaggggctc gcgccagccg aactgttcgc caggctcaag    7140
gcgagcatgc ccgacggcga ggatctcgtc gtgacacatg gcgatgcctg cttgccgaat    7200
atcatggtgg aaaatggccg ctttctgga ttcatcgact gtggccggct gggtgtggcg    7260
gaccgctatc aggacatagc gttggctacc cgtgatattg ctgaagagct ggcggcgaa    7320 tgggctgacc gcttcctcgt gctttacggt atcgccgctc ccgattcgca gcgcatcgcc    7380
ttctatcgcc ttcttgacga gttcttctga gcgggactct ggggttcgaa atgaccgacc    7440
aagcgaattc gctaggatta tccctaatac ctgccacccc actcttaatc agtggtggaa    7500
gaacggtctc agaactgttt gtttcaattg gccatttaag tttagtagta aaagactggt    7560
taatgataac aatgcatcgt aaaaccttca gaaggaaagg agaatgtttt gtggaccact    7620 ttggtttttct ttttgcgtg tggcagtttt aagttattag ttttttaaaat cagtactttt    7680 taatggaaac aacttgacca aaaatttgtc acagaatttt gagacccatt aaaaaagtta    7740
aatgagaaac ctgtgtgttc ctttggtcaa caccgagaca tttaggtgaa agacatctaa    7800
ttctggtttt acgaatctgg aaacttcttg aaaatgtaat tcttgagtta acacttctgg    7860
gtggagaata gggttgtttt cccccacat aattggaagg ggaaggaata tcatttaaag    7920
ctatgggagg gttgctttga ttacaacact ggagagaaat gcagcatgtt gctgattgcc    7980
tgtcactaaa acaggccaaa aactgagtcc ttgggttgca tagaaagctg                8030
```

<210> SEQ ID NO 9
<211> LENGTH: 9
<212> TYPE: PRT
<213> ORGANISM: Artificial Sequence
<220> FEATURE:
<223> OTHER INFORMATION: Synthetic Construct

<400> SEQUENCE: 9

Val Leu Asp Gly Leu Asp Val Leu Leu
1               5

<210> SEQ ID NO 10
<211> LENGTH: 10
<212> TYPE: PRT
<213> ORGANISM: Artificial Sequence
<220> FEATURE:
<223> OTHER INFORMATION: Synthetic Construct

<400> SEQUENCE: 10

Ala Leu Tyr Val Asp Ser Leu Phe Phe Leu
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Synthetic Construct

<400> SEQUENCE: 11

Arg Leu Leu Gln Glu Thr Glu Leu Val
1               5

<210> SEQ ID NO 12

```
<211> LENGTH: 20
<212> TYPE: PRT
<213> ORGANISM: Artificial Sequence
<220> FEATURE:
<223> OTHER INFORMATION: Synthetic Construct

<400> SEQUENCE: 12

Met Ser Leu Leu Thr Glu Val Glu Thr Tyr Val Leu Ser Ile Ile Pro
1               5                   10                  15

Ser Gly Pro Leu
            20

<210> SEQ ID NO 13
<211> LENGTH: 20
<212> TYPE: PRT
<213> ORGANISM: Artificial Sequence
<220> FEATURE:
<223> OTHER INFORMATION: Synthetic Construct

<400> SEQUENCE: 13

Thr Tyr Val Leu Ser Ile Ile Pro Ser Gly Pro Leu Lys Ala Glu Ile
1               5                   10                  15

Ala Gln Arg Leu
            20

<210> SEQ ID NO 14
<211> LENGTH: 20
<212> TYPE: PRT
<213> ORGANISM: Artificial Sequence
<220> FEATURE:
<223> OTHER INFORMATION: Synthetic Construct

<400> SEQUENCE: 14

Gly Leu Gln Arg Arg Arg Phe Val Gln Asn Ala Leu Asn Gly Asn Gly
1               5                   10                  15

Asp Pro Asn Asn
            20
```